United States Patent
King et al.

(10) Patent No.: US 9,221,796 B2
(45) Date of Patent: Dec. 29, 2015

(54) SELECTIVE NR2B ANTAGONISTS

(71) Applicant: BRISTOL-MYERS SQUIBB COMPANY, Princeton, NJ (US)

(72) Inventors: Dalton King, Hamden, CT (US); Lorin A. Thompson, III, Higganum, CT (US); Jianliang Shi, Madison, CT (US); Srinivasan Thangathirupathy, Hosur (IN); Jayakumar Sankara Warrier, Bangalore (IN); Imadul Islam, Richmond, CA (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/589,205

(22) Filed: Jan. 5, 2015

(65) Prior Publication Data

US 2015/0191452 A1 Jul. 9, 2015

Related U.S. Application Data

(60) Provisional application No. 61/925,636, filed on Jan. 9, 2014.

(51) Int. Cl.
*C07D 403/04* (2006.01)
*C07D 401/04* (2006.01)

(52) U.S. Cl.
CPC ............ *C07D 403/04* (2013.01); *C07D 401/04* (2013.01)

(58) Field of Classification Search
None
See application file for complete search history.

(56) References Cited

FOREIGN PATENT DOCUMENTS

| EP | 1 988 077 A1 | 11/2008 |
|---|---|---|
| WO | WO 01/32615 | 5/2001 |
| WO | WO 01/81295 | 11/2001 |
| WO | WO 03/035641 | 5/2003 |
| WO | WO 2005/035523 | 4/2005 |

OTHER PUBLICATIONS

Thompson III et al., U.S. Appl. No. 14/591,372, filed Jan. 7, 2015.
CAS Registry No. 1385072-30-9, Entered STN: Aug. 1, 2012.
CAS Registry No. 1623322-96-2, Entered STN: Sep. 18, 2014.

*Primary Examiner* — Timothy R Rozof
(74) *Attorney, Agent, or Firm* — James Epperson

(57) ABSTRACT

The disclosure generally relates to compounds of formula I, including their salts, as well as compositions and methods of using the compounds. The compounds are ligands of the NR2B receptor and may be useful for the treatment of various disorders of the central nervous system.

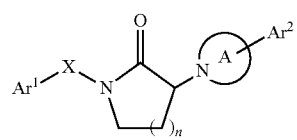

12 Claims, No Drawings

SELECTIVE NR2B ANTAGONISTS

CROSS-REFERENCE TO RELATED APPLICATIONS

This application claims priority to Provisional Patent Application U.S. Ser. No. 61/925,363 filed Jan. 9, 2014, hereby incorporated by reference in its entirety.

BACKGROUND OF THE INVENTION

The disclosure generally relates to compounds of formula I, including their salts, as well as compositions and methods of using the compounds. The compounds are ligands for the NR2B NMDA receptor and may be useful for the treatment of various disorders of the central nervous system.

N-Methyl-D-aspartate (NMDA) receptors are ion channels which are gated by the binding of glutamate, an excitatory neurotransmitter in the central nervous system. They are thought to play a key role in the development of a number of neurological diseases, including depression, neuropathic pain, Alzheimer's disease, and Parkinson's disease. Functional NMDA receptors are tetrameric structures primarily composed of two NR1 and two NR2 subunits. The NR2 subunit is further subdivided into four individual subtypes: NR2A, NR2B, NR2C, and NR2D, which are differentially distributed throughout the brain. Antagonists or allosteric modulators of NMDA receptors, in particular NR2B subunit-containing channels, have been investigated as therapeutic agents for the treatment of major depressive disorder (G. Sanacora, 2008, Nature Rev. Drug Disc. 7: 426-437).

The NR2B receptor contains additional ligand binding sites in addition to that for glutamate. Non-selective NMDA antagonists such as Ketamine are pore blockers, interfering with the transport of $Ca^{++}$ through the channel. Ketamine has demonstrated rapid and enduring antidepressant properties in human clinical trials as an i.v. drug. Additionally, efficacy was maintained with repeated, intermittent infusions of Ketamine (Zarate et al., 2006, Arch. Gen. Psychiatry 63: 856-864). This class of drugs, though, has limited therapeutic value because of its CNS side effects, including dissociative effects.

An allosteric, non-competitive binding site has also been identified in the N-terminal domain of NR2B. Agents which bind selectively at this site, such as Traxoprodil, exhibited a sustained antidepressant response and improved side effect profile in human clinical trials as an i.v. drug (Preskorn et al., 2008, J. Clin. Psychopharmacol., 28: 631-637, and F. S. Menniti, et al., 1998, CNS Drug Reviews, 4, 4, 307-322). However, development of drugs from this class has been hindered by low bioavailability, poor pharmacokinetics, and lack of selectivity against other pharmacological targets including the hERG ion channel. Blockade of the hERG ion channel can lead to cardiac arrythmias, including the potentially fatal Torsades de pointe, thus selectivity against this channel is critical. Thus, in the treatment of major depressive disorder, there remains an unmet clinical need for the development of effective NR2B-selective negative allosteric modulators which have a favorable tolerability profile.

NR2B receptor antagonists have been disclosed in PCT publication WO 2009/006437.

The invention provides technical advantages, for example, the compounds are novel and are ligands for the NR2B receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders related to levels of tachykinins or serotonin or both.

One aspect of the invention is a compound of formula I

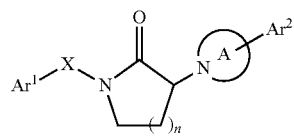

where:
$Ar^1$ is phenyl or indanyl and is substituted with 0-3 substituents selected from cyano, halo, alkyl, haloalkyl, and haloalkoxy;
$Ar^2$ is phenyl substituted with 1 OH substituent and also substituted with 0-3 substituents selected from cyano, halo, alkyl, haloalkyl, and haloalkoxy;
X is a bond or $C_1$-$C_3$ alkylene;
n is 1 or 2; and
ring A is azetidinyl, pyrrolidinyl, piperidinyl, piperazinyl, homopiperidinyl, or homopiperazinyl and is substituted with 0-4 substituents selected from halo, alkyl, hydroxy, or alkoxy; or a pharmaceutically acceptable salt thereof.

Another aspect of the invention is a compound of formula I where n is 1 and ring A is piperidinyl substituted with 0-2 halo substituents.

Another aspect of the invention is a compound of formula I where $Ar^1$ is phenyl substituted with 0-3 substituents selected from cyano, halo, alkyl, haloalkyl, and haloalkoxy.

Another aspect of the invention is a compound of formula I where $Ar^2$ is p-hydroxyphenyl.

Another aspect of the invention is a compound of formula I where X is methylene.

Another aspect of the invention is the compound of formula I: (R)-3-((3S,4S)-3-fluoro-4-(4-hydroxyphenyl)piperidin-1-yl)-1-(4-methylbenzyl)pyrrolidin-2-one or a pharmaceutically acceptable salt thereof

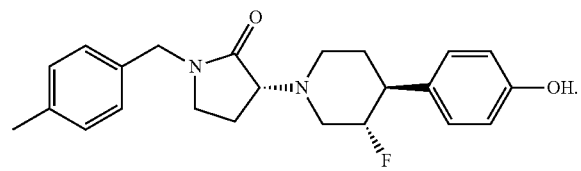 [SMILES: Cc1ccc(CN2CC[C@@H](N3CC[C@@H](c4ccc(O)cc4)[C@H](F)C3)C2=O)cc1]

For a compound of formula I, the scope of any instance of a variable substituent, including $Ar^1$, $Ar^2$, $Ar^3$ X, and n can be used independently with the scope of any other instance of a variable substituent. As such, the invention includes combinations of the different aspects.

Unless specified otherwise, these terms have the following meanings "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art. The compounds include all tautomeric forms.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

Synthesis of the desired compounds I may begin with the condensation of anilines/benzyl amines I with α,ω-dibromoalkanoyl chlorides III to yield amides/anilides IV, which may be cyclized to 1-phenyl/benzyl-3-bromo-pyrrolidinones/piperidinones V, as shown in synthetic scheme 1.

Synthetic Scheme 1

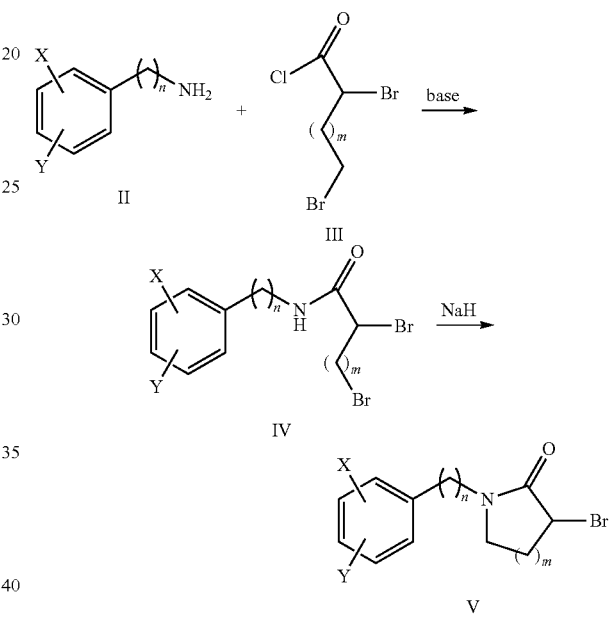

The 1-phenyl/benzyl-3-bromo-pyrrolidinones/piperidinones V may be reacted with (4-oxy-phenyl)cyclic amines VI in the presence of base to produce protected products VII, which may be subjected to cleavage conditions appropriate for the protecting group (PG$_1$) to generate final products I, which may be separated into individual enantiomers/diastereomers I*, as shown in synthetic scheme 2.

Synthetic Scheme 2

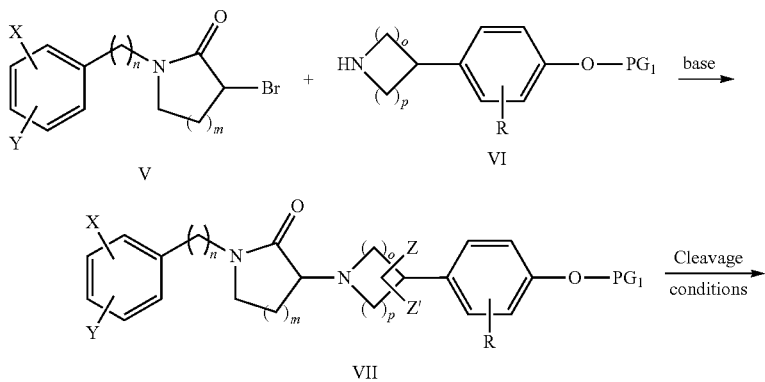

-continued

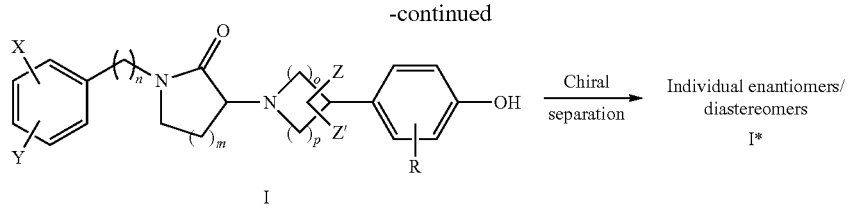

I

Compounds Ia may be prepared by condensing 1-phenyl/benzyl-3-bromo-pyrroli-dinones/piperidinones V with substituted 4(4-oxyphenyl)piperidines VIIIa-c to generate protected intermediates IX, which may be subjected to cleavage conditions appropriate for the protecting group ($PG_1$) to generate final products Ia, which may be separated into individual enantiomers/diastereomers Ia*, as shown in synthetic scheme 3.

dropiperidine X, which can be hydroxylated via hydroboration/oxidation to give the protected hydroxypiperidine XI, which may be either directly transformed into the protected fluoropiperidine XII by treatment with DAST or oxidized into the protected 3-oxopiperidine XIII, which may be further transformed into protected 3,3-difluoropiperidines XIV via treatment with DAST. XI, XII, and XIV may be transformed into VIIIa, VIIIb, and VIIIc, respectively, by employing Synthetic Scheme 3

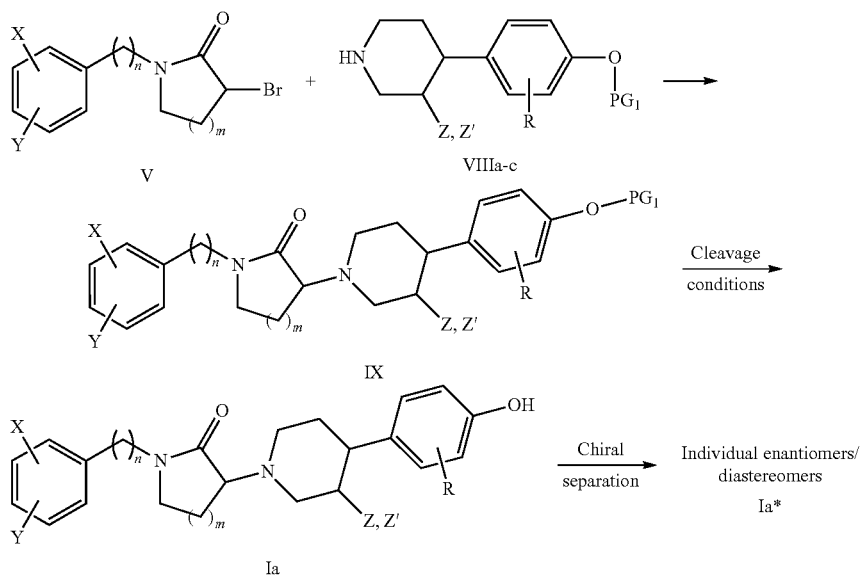

The 4(4-oxyphenyl)piperidines VIIIa-c may be synthesized in turn by a sequence starting with a protected tetrahydropiperidine X, cleaving conditions appropriate for the protecting group ($PG_2$), as shown in synthetic scheme 3a.

Synthetic scheme 3a

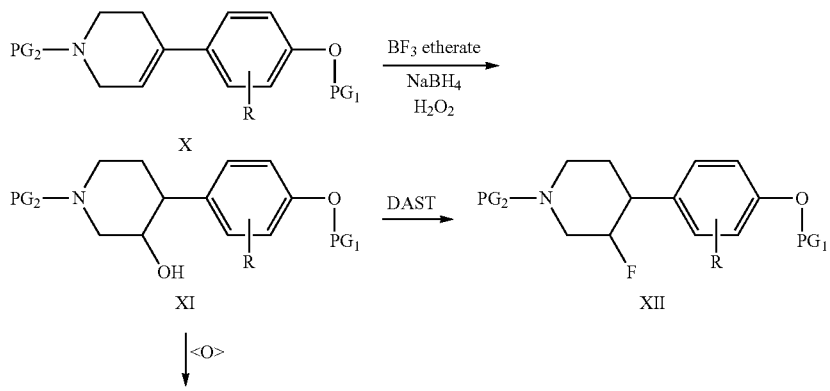

-continued

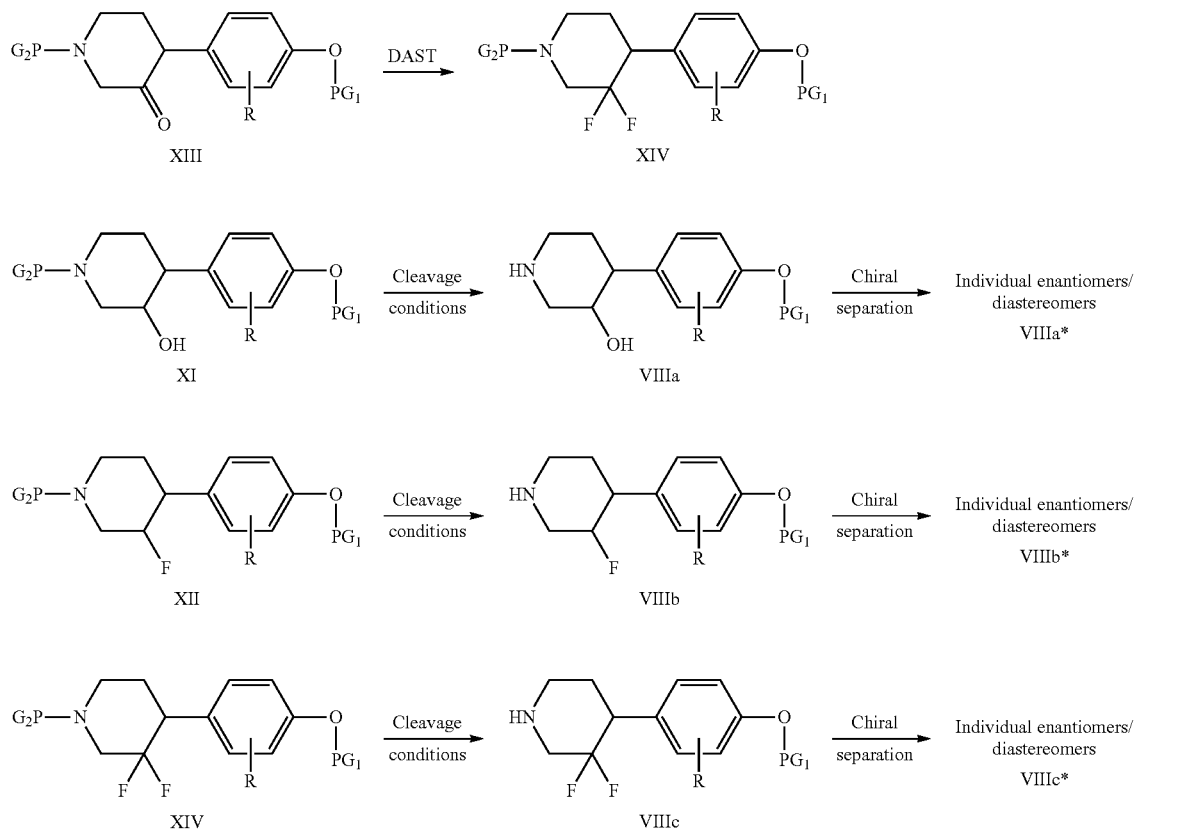

For tetrahydropyridines X which are not commercially available may be synthesized by coupling protected bromophenols XV with protected unsaturated piperidineboronic acids XVI, as shown in synthetic scheme 4a.

Synthetic scheme 4a:

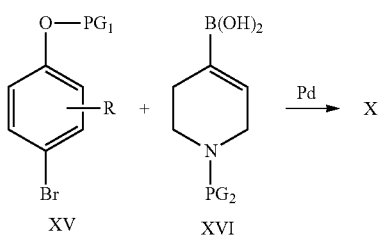

For tetrahydropyridines X which are not commercially available may be synthesized by adding the anion generated from protected bromophenols XV to a protected 4-piperidinone XVII to yield 4-phenyl-4-piperidinol XVIII, which may be dehydrated under acid conditions to yield the desired X, as shown in synthetic scheme 4b.

Synthetic scheme 4b:

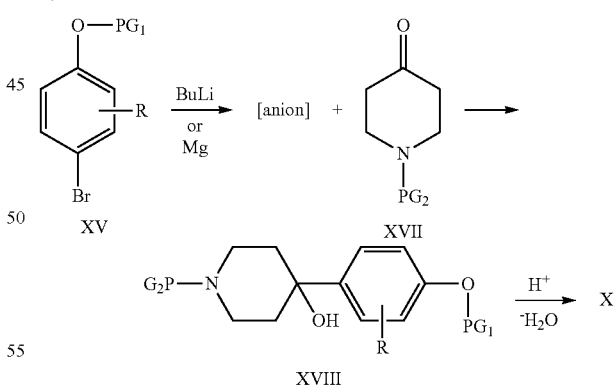

1-Phenyl/benzyl-3-bromo-pyrroli-dinones/piperidinones V may be condensed with isolated individual enantiomers VIIIa-c*, which results in diastereomers 1-phenyl/benzyl-3-bromo-pyrroli-dinones/piperidinones IX*, which may be deprotected and separated to give final products Ia*, as shown in scheme 5.

Scheme 5

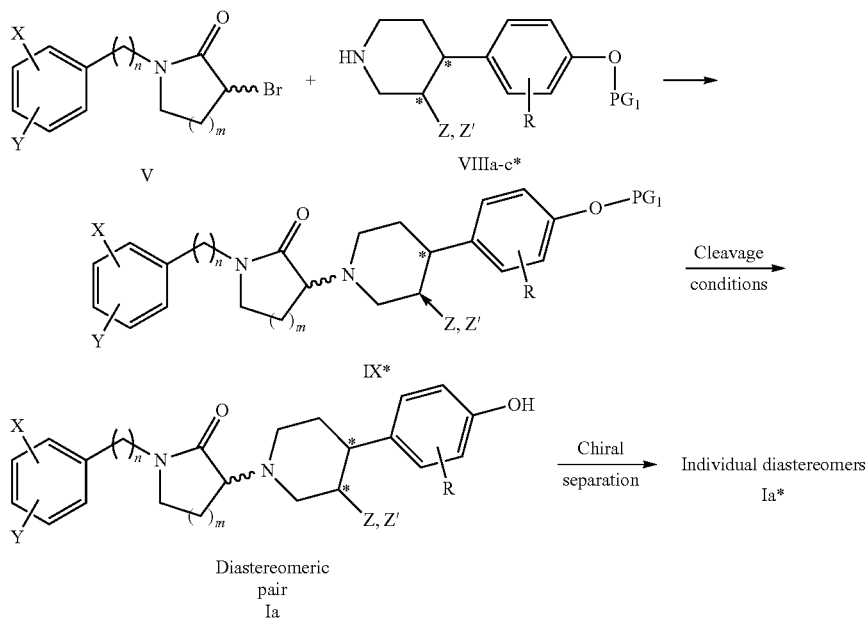

Alternatively, the backbone scaffold may be synthesized by condensing 1-phenyl/benzyl-3-bromo-pyrroli-dinones/piperidinones V with hydroxypiperidines VIIIa to yield the protected 3-fluoropiperidines IXa, which may themselves be converted to the protected 3-fluoropiperidines IXb or oxidized to the ketones XIX, which may be converted to the 3,3-difluoropiperidines Ixc, as shown in scheme 6. The final compounds can then be isolated after the deprotection of IXa-c.

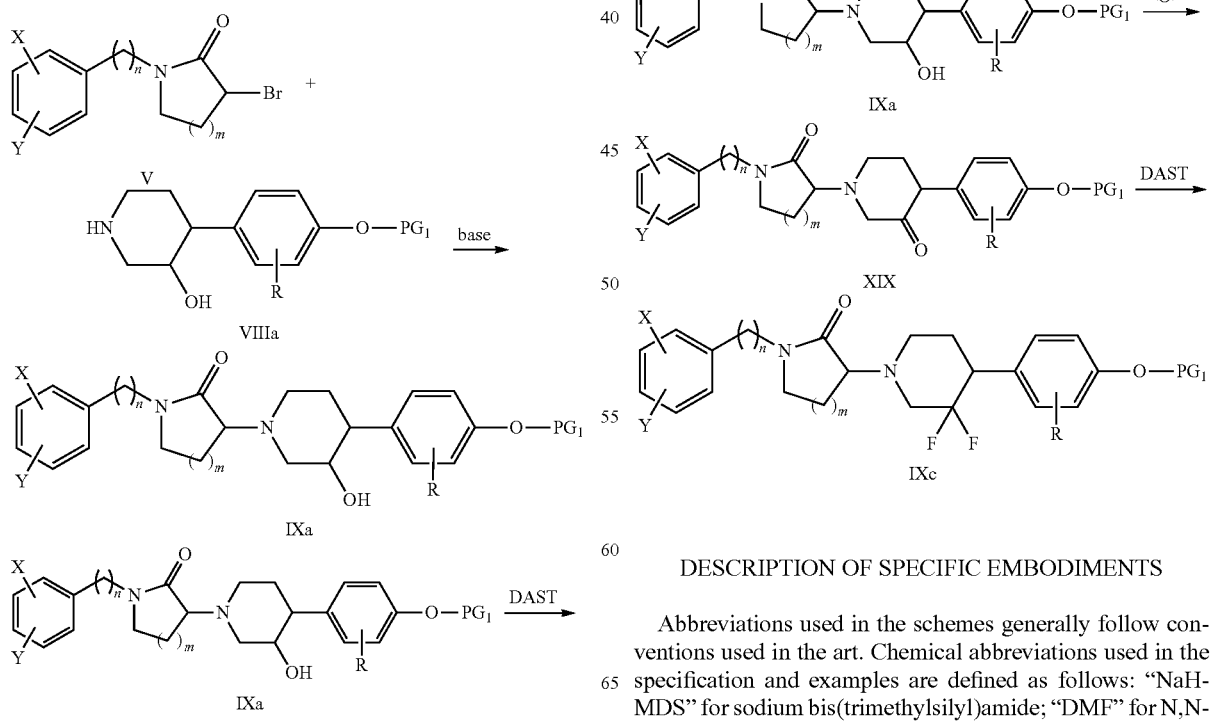

DESCRIPTION OF SPECIFIC EMBODIMENTS

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "DCM" for dichloromethane; "LAH" for lithium aluminum hydride; "BOC" for t-butoxycarbonyl, "DMSO" for dimethylsulfoxide; "h" for hours; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "satd." for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "SFC" for supercritical fluid chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "R", "S", "E", and "Z" are stereochemical designations familiar to one skilled in the art.

LC-MS methods:

Method A:
Column: XBridge Phe 8, 4.6×30 mm, 5 μm; Solvent A=2% AcCN: 98% H2O: 10 mM NH$_4$COOH; Solvent B=98% AcCN: 2% H2O: 10 mM NH$_4$COOH; gradient 0-100% B over 1.5 min; 3.2 min run time.

Method B:
Column: ZORBAX SB C18, 4.6×50 mm, 5 μm; Solvent A=10% MeOH: 90% H2O: 0.1% TFA; Solvent B=90% AcCN: 10% H2O: 0.1% TFA; gradient 0-100% B over 2 min; 3 min run time.

Method C:
Column: ZORBAX SB AQ, 4.6×50 mm, 3.5 m; Solvent A=10% MeOH: 90% H2O: 0.1% TFA; Solvent B=90% AcCN: 10% H2O: 0.1% TFA; gradient 0-100% B over 2 min; 3 min run time.

Method D:
Column: Purospher@star RP-18, 4×55 mm, 3 μm; Solvent A=10% AcCN: 90% H2O: 20 mM NH4OAc; Solvent B=90% AcCN: 10% H2O: 20 mM NH4COOH; gradient 0-100% B over 1.5 min; 3.2 min run time.

Method E:
Column: Ascentis Express C18, 50×4.6 mm, 5 μm; Solvent A=2% AcCN: 98% H2O: 10 mM NH4COOH; Solvent B=98% AcCN: 2% H2O: 10 mM NH4COOH; gradient 0-100% B over 1.5 min.

Method F:
Column: Ascentis Express C18, 50×2.1 mm, 2.7 μm; Solvent A=2% AcCN: 98% H2O: 10 mM NH4COOH; Solvent B=98% AcCN: 2% H2O: 10 mM NH4COOH; gradient 0-100% B over 1.5 min.

Method G:
Column: XBridge Phenyl, 4.6×150 mm, 3.5 μm; Solvent A=5% AcCN: 95% H2O: 0.05 TFA pH=2.5; Solvent B=95 AcCN: 5% H2O: 0.05 TFA pH=2.5; gradient 0-100% B.

Method H:
Column: Sunfire C18, 4.6×150 mm, 3.5 μm; Solvent A=5% AcCN: 95% H2O: 0.05% TFA pH=2.5; Solvent B=95% AcCN: 5% H2O: 0.05% TFA pH=2.5; gradient 0-100% B.

Method I:
Column: Eclipse XDB C18, 4.6×150 mm, 3.5 μm; Solvent A=20 mM NH4Oac in water; Solvent B=AcCN: Gradient 0-100%.

Method J:
Column: Acquity UPLC BEH C18, 50×2.1 mm, 1.7 μm; Solvent A=0.1% TFA in water; Solvent B: 0.1% TFA in AcCN; gradient 2-98% B over 1.6 min.

Method K:
Column: Ascentis Express C8, 50×2.1 mm, 2.7 μm; Solvent A=2% AcCN: 98% H2O: 10 mM NH4COOH; Solvent B=98% AcCN: 2% H2O: 10 mM NH4COOH; gradient 0-100% B over 1.5 min).

Method L:
Column: ACE Excel 2 C18, (50×3.0 mm-2 μm); Solvent A=2% ACN-98% H2O: 10 mM NH4COOH; Solvent B=98% ACN: 2% H2O: 10 mM NH4COOH; gradient 0-100% B over 1.8 min) Flow=1.2 mL/min T=40 C Method M:
Column: X-Bridge BEH C18; 50×2.1 mm, 2.5 u; Solvent A: 2% ACN-98% H2O-0.1% TFA; Solvent B: 98% ACN-2% H2O-0.1% TFA Flow: 1.2 ml/min; T=50 C Time (min.); gradient 0-100% B over 2.6 min Method N:
Column: Ascentis Express C18 4.6×50 mm, 2.7 μm; Solvent A: 5:95 Acetonitrile:water with 10 mM NH4OAc; Solvent B: 95:5 Acetonitrile:water with 10 mM NH4OAc; Temperature: 50° C.; Gradient: 0-100% B over 4 minutes; Flow: 4.0 ml/min.

Method O:
Column: Ascentis Express C18 4.6×50 mm, 2.7 μm; Solvent A: 5:95 Acetonitrile:water with 0.05% TFA; Solvent B: 95:5 Acetonitrile:water with 0.05% TFA; Temperature: 50° C.; Gradient: 0-100% B over 4 minutes; Flow: 4.0 ml/min Method P:
Column: Acquity BEH C18 (2.1×50 mm) 1.7 u; Buffer: 10 mM Ammonium Acetate pH 5 adjusted with HCOOH; Solvent A: Buffer:ACN (95:5); Solvent B:Buffer:ACN (5:95); Gradient: % B: 0 min-5%:1.1 min-95%:1.7 min-95%

Method Q:
Column: Ascentis Express C18 2.1×50 mm, 2.7 μm; Solvent A: 5:95 Acetonitrile:water with 0.1% TFA; Solvent B: 95:5 Acetonitrile:water with 0.05% TFA; Temperature: 50° C.; Gradient: 0-100% B over 3 minutes; Flow: 1.1 ml/min Method S:
Column: Xbridge C18 (50×2.1 mm) 2.5 u; Solvent A: 10 mM NH4COOH; Solvent B Acetonitrile, gradient 0-100% B over 1.7 minutes, 100% B for 1.5 minutes Method T:
Column: Phenomenex LUNA C18, 50×2, 3 um; Solvent A: 5% ACN: 95% Water: 10 mM Ammonium Actetate; Solvent B: 95% ACN: 5% Water: 10 mM Ammonium Actetate; Gradient: 0-100% B over 4 min Method U:
Column: PHENOMENEX-LUNA 2.0×50 mm 3 um; Solvent A: 95% Water: 5% methanol: 0.1% TFA; Solvent B=5% Water: 95% methanol: 0.1% TFA; Gradient 0-100% B over 4 min Method V Column: Xbridge BEH C18 (2.1×50 mm), 2.5 µm; Solvent A: 0.1% HCOOH/water; Solvent B: 0.07% HCOOH/acetonitrile; Gradient 0-100% B over 1.5 min, stop time 4 min Method 100:

Column: Xbridge $C_{18}$ 4.6×50 mm, 5 µm; Solvent A: water with 10 mM $NH_4OAc$; Solvent B: methanol; Gradient: 5-95% B over 4 minutes; Flow: 4.0 ml/min.

Method 107

Column: Xbridge $C_{18}$ 2.1×50 mm, 2.5 µm; Solvent A: water with 10 mM $NH_4HCO_3$; Solvent B: Acetonitrile; Gradient: 0-100% B over 1.7 minutes; then 100% B for 1.5 min.

Method 109

Column: Kinetex $C_{18}$ 2.1×50 mm, 2.6 µm; Solvent A: 2:98 acetonitrile/water with 10 mM ammonium formate; Solvent B: 98:2 acetonitrile/water with 10 mM ammonium formate; Gradient: 0-100% B over 1.7 minutes; then 100% B for 1.5 min.

CZ-1:

Column: Waters Aquity UPLC BEH $C_{18}$ 2.1×50 mm 1.7 µm; Solvent A: 100% water: 0.05% TFA; Solvent B: 100% acetonitrile: 0.05% TFA; Gradient: 2 to 98% B over 1.5 minutes

CZ-2

Column: X-BRIDGE $C_{18}$ 2.1×50 mm, 3.5 um; Solvent A: 5% Water: 95% methanol: 0.1% TFA; Solvent B: 95% Water: 5% methanol: 0.1% TFA; Gradient: 0 to 100% B over 4 minutes Chiral HPLC Methods:

Method A:

Column: CHIRALPAK AD-H (250×4.6) mm 5 µm; Mob. Phase: 0.2% DEA in n-hexane: IPA (80:20)

Method A-2:

Column: CHIRALPAK AD-H (250×21), 5 µm; Mob. Phase: 0.2% DEA in n-hexane: IPA (70:30)

Method A-3:

Column: CHIRALPAK AD-H (250×4.6) mm, 5 µm; Mob. Phase: 0.2% DEA in n-hexane: IPA (70:30)

Method A-4:

Column: CHIRALPAK AD-H (250×4.6) mm, 5 µm; Mob. Phase: 0.2% DEA in n-hexane: IPA (50:50)

Method B:

Column: CHIRALPAK-ASH (250×4.6) mm, 5 µm; Mob. Phase: 0.2% DEA in n-hexane: ethanol (70:30)

Method C:

Column: CHIRALPAK IC (250×4.6) mm, 5 µm; Mob. Phase: 0.1% TFA in n-hexane: ethanol (40:60)

Method D:

Column: CHIRALPAK IA (250×4.6) mm, 5 µm; Mob. Phase: 0.1% TFA in hexane: ethanol (50:50)

Method E:

Column: CHIRALPAK IC (250×4.6) mm, 5 µm; Mob. Phase: 0.05% TFA in $H_2O$: acetonitrile (80:20)

Method F:

Column: CHIRALCEL ODH (250×4.6) mm, 5 µm; Mob. phase: 0.2% DEA in n-hexane: ethanol (30:70)

Method G (SFC):

Column: Lux Cellulose-2, (4.6×250) mm, 5 µm; co-solvent 0.3% DEA in methanol; flow rate 2.55 g/min, 15% co-solvent, back pressure 100 bar Method G-2 (SFC):

Column: Lux Cellulose-2, (4.6×250) mm, 5 µm; co-solvent 0.3% DEA in methanol, flow rate 2.55 g/min, 10% co-solvent, back pressure 100 bar Method H:

Column: Chiralcel OJ (21×250 mm) 10 µm; Mob.Phase 0.1% diethylamine/heptane: ethanol (40:60)

Method H-2:

Column: Chiralcel OJ (4.6×100 mm) 10 µm; Mob.Phase 0.1% diethylamine/heptane: ethanol (40:60)

Method H-3:

Column: Chiralcel OJ (4.6×250 mm) 5 µm; Mob.Phase 0.1% diethylamine/hexane: ethanol (50:50)

Method H-4:

Column: Chiralcel OJ (4.6×250 mm) 5 µm; Mob.Phase 0.2% diethylamine/hexane: ethanol (50:50)

Chiral SFC methods:

Method A1:

Column: CHIRALPAK IC; Co Solvent: 0.5% DEA in methanol; Co Solvent %: 50; Total flow: 3 g/min; Back pressure: 93 bar.

Method A2:

Column: CHIRALPAK IC; Co Solvent: 0.5% DEA in methanol; Co Solvent %: 50; Total flow: 3 g/min; Back pressure: 100 bar;

Method A3:

Column: CHIRALPAK IC; Co Solvent: 0.5% DEA in methanol; Co Solvent %: 40; Total flow: 3 g/min; Back pressure: 101 bar Method A4:

Column: CHIRALPAK IC; Co Solvent: 0.5% DEA in methanol; Co Solvent %: 40; Total flow: 3 g/min; Back pressure: 101 bar Method A5:

Column: CHIRALPAK IC; Co Solvent: 0.5% DEA in methanol; Co Solvent %: 20; Total flow: 3 g/min; Back pressure: 101 bar Method B1:

Column: CHIRALCEL OD H; Co Solvent: 0.5% DEA in methanol; Co Solvent %: 30; Total flow: 3 g/min; Back pressure: 100 bar Method C1:

Column: CHIRALPAK AD H; Co Solvent: 0.5% DEA in methanol; Co Solvent %: 20; Total flow: 3 g/min; Back pressure: 100 bar Method C2:

Column: CHIRALPAK AD H; Co Solvent: 0.5% DEA in methanol; Co Solvent %: 20; Total flow: 3 g/min; Back pressure: 99 bar Method C3:

Column: CHIRALPAK AD H; Co Solvent: 0.5% DEA in methanol; Co Solvent %: 40; Total flow: 3 g/min; Back pressure: 97 bar Method C4:

Column: CHIRALPAK AD H; Co Solvent: 0.5% DEA in methanol; Co Solvent %: 30; Total flow: 3 g/min; Back pressure: 102 bar Method C5:

Column: CHIRALPAK AD H (250×4.6 mm, 5 u); Co Solvent: 0.3% DEA in methanol; Co Solvent %: 30; Total flow: 3 g/min; Back pressure: 102 bar Method C6:

Column: CHIRALPAK AD H (250×4.6 mm, 5 u); Co Solvent: 0.3% DEA in methanol; Co Solvent %: 45; Total flow: 3 g/min; Back pressure: 102 bar Method C7:

Column: CHIRALPAK AD H (250×21 mm, 5 u); Co Solvent: 0.3% DEA in methanol; Co Solvent %: 45; Total flow: 60 g/min; Back pressure: 102 bar.

Method C8:

Column: CHIRALPAK AD H (250×21 mm, 5 u); Co Solvent: 0.3% DEA in methanol; Co Solvent %: 30; Total flow: 60 g/min; Back pressure: 102 bar.

Method D:
Column: Lux Cellulose-2 (250×21.2) mm, 5 u; Co Solvent: 0.3% DEA in methanol; Co Solvent %: 20; Total flow: 60 g/min; Back pressure: 100 bar.

Method E:
Column: CHIRALPAK AS H (250×4.6 mm, 5 u); Co Solvent: 0.3% DEA in methanol; Co Solvent %: 60; Total flow: 3 g/min; Back pressure: 102 bar.

Method F:
Column: CHIRALPAK AS H (250×4.6 mm, 5 u); Co Solvent: 0.3% DEA in methanol; Co Solvent 30%; Total flow: 3 g/min; Back pressure: 102 bar.

Method G:
Column: Whelk Ol (R,R), 250×4.6 mm, 5 u; Co-solvent 0.3% DEA in methanol, cosolvent 35%; total flow 4 g/min, backpressure 102 bar Method H:
Column: Whelk Ol (R,R), 250×4.6 mm, 5 u; Co-solvent 0.3% DEA in methanol, cosolvent 30%; total flow 4 g/min, backpressure 102 bar Method H-1:
Column: Whelk Ol (R,R), 250×30 mm, 5 u; Co-solvent 0.3% DEA in methanol, cosolvent 25%; total flow 120 g/min, backpressure 102 bar Method I:
Column: CHIRALPAK AS H (250×4.6 mm, 5 u); Co Solvent: 0.3% DEA in methanol; Co Solvent 35%: Total flow: 3 g/min; Back pressure: 102 bar.

Method J:
Column: CHIRALPAK AS H (250×4.6 mm, 5 u); Co Solvent: 0.3% DEA in methanol; Co Solvent 20%; Total flow: 3 g/min; Back pressure: 102 bar.

Method K:
Column: CHIRALPAK AS H (250×4.6 mm, 5 u); Co Solvent: 0.3% DEA in methanol; Co Solvent 40%; Total flow: 80 g/min; Back pressure: 102 bar.

Method L:
Column: CHIRALPAK AS H (250×4.6 mm, 5 u); Co Solvent: 0.3% DEA in methanol; Co Solvent 25%; Total flow: 100 g/min; Back pressure: 102 bar.

Method 101:
Column: Lux Cellulose-2 (250×21.2) mm, 5 u; Co Solvent: 0.3% DEA in methanol; Co Solvent %: 40; Total flow: 70 g/min; Back pressure: 100 bar.

Method 104:
Column: CHIRALPAK AD H (250×30 mm, 5 μm); Co Solvent: 0.3% DEA in methanol; Co Solvent %: 40; Total flow: 70 g/min; Back pressure: 100 bar.

Method 105:
Column: CHIRALPAK AD H (250×4.6 mm, 5 u); Co Solvent: 0.3% DEA in methanol; Co Solvent %: 45; Total flow: 3 g/min; Back pressure: 100 bar.

Method 106:
Column: CHIRALPAK AD H (250×4.6 mm, 5 u); Co Solvent: 0.3% DEA in methanol; Co Solvent %: 40; Total flow: 4 g/min; Back pressure: 100 bar.

Method 108:
Column: CHIRALPAK AS H (250×4.6 mm, 5 u); Co Solvent: 0.3% DEA in methanol; Co Solvent %: 30; Total flow: 3 g/min; Back pressure: 100 bar.

Analytical HPLC Methods:
Method A:
Column: Waters analytical C18 Sunfire (4.6×150 mm, 3.5 μm); Mobile phase: Buffer: 0.05% TFA in $H_2O$ pH=2.5 adjusted with ammonia; Solvent A=buffer and acetonitrile (95:5), Solvent B=acetonitrile and buffer (95:5); 0-15 min, 0% B→50% B; 15-18 min, 50% B→100% B; 18-23 min, 100% B; flow rate=1 mL/min; run time=28 min.

Method B:
Column: Waters analytical phenyl Xbridge column (4.6×150 mm, 3.5 μm); Mobile phase: Buffer: 0.05% TFA in $H_2O$ pH=2.5 adjusted with ammonia; Solvent A=buffer and acetonitrile (95:5), Solvent B=acetonitrile and buffer (95:5); 0-15 min, 0% B→50% B; 15-18 min, 50% B→100% B; 18-23 min, 100% B; flow rate=1 mL/min; run time=28 min.

Method C:
Column: Waters analytical C18 Sunfire (4.6×150 mm, 3.5 μm); Mobile phase: Buffer: 0.05% TFA in $H_2O$ pH=2.5 adjusted with ammonia; Solvent A=buffer and acetonitrile (95:5), Solvent B=acetonitrile and buffer (95:5); 0-12 min, 10% B→100% B; 12-15 min, 100% B; flow rate=1 mL/min; run time=17 min.

Method D:
Column: Waters analytical phenyl Xbridge column (4.6×150 mm, 3.5 μm), mobile phase: Buffer: 0.05% TFA in $H_2O$ pH=2.5 adjusted with ammonia; solvent A=buffer and acetonitrile (95:5), Solvent B=acetonitrile and buffer (95:5); 0-12 min, 10% B→100% B; 12-15 min, B→100% B; flow rate=1 mL/min; run time=17 min.

Method E:
Column: Waters analytical phenyl Xbridge (4.6×150 mm, 3.5 μm), Mobile phase: Solvent A=10 m M $NH_4HCO_3$ in $H_2O$, pH=9.5 adjusted with ammonia, Solvent B=methanol; 0-12 min, 10% B→100% B; 12-20 min, B→100% B; flow rate=1 mL/min; run time=23 min.

Method F:
Column: Waters analytical C18 Sunfire (4.6×150 mm, 3.5 μm); Mobile phase: Buffer: 0.05% TFA in $H_2O$ pH=2.5 adjusted with ammonia, Solvent A=buffer and acetonitrile (95:5), Solvent B=acetonitrile and buffer (95:5); 0-25 min, 10% B→100% B; 25-30 min, 100% B; flow rate=1 mL/min; run time=32 min.

Method G:
Column: ECLIPSE XDB C18 (4.6×150 mm, 3.5 μm); Mobile phase; Solvent A=20 mM $NH_4OAc$ in $H_2O$, Solvent B=acetonitrile; 0-12 min, 10% B→100% B; 12-15 min, 100% B; flow rate=1 mL/min; run time=18 min.

Method H:
Column: Waters analytical phenyl Xbridge (4.6×150 mm, 3.5 μm); Mobile phase: Buffer: 0.05% TFA in $H_2O$ pH=2.5 adjusted with ammonia, solvent A=buffer and acetonitrile (95:5), Solvent B=acetonitrile and buffer (95:5); 0-25 min, 10% B→100% B; 25-30 min, 100% B; flow rate=1 mL/min; run time=32 min.

Method I:
Column: Waters analytical phenyl Xbridge (4.6×150 mm, 3.5 μm), Mobile phase: A=10 m M $NH_4HCO_3$ in $H_2O$ pH=9.5 adjusted with ammonia, B=methanol; 0-25 min, 10% B→100% B; 25-30 min, B→100% B; flow rate=1 mL/min; run time=30 min.

Method J:
Column: ECLIPSE XDB $C_{18}$ (4.6×150 mm, 5 μm); Mobile phase: A=20 mM $NH_4OAc$ in $H_2O$, B=acetonitrile; 0-25 min, 10% B→100% B; 25-30 min, 100% B; flow rate=1 mL/min; run time=30 min.

Method K:
Column: Waters analytical phenyl Xbridge (4.6×150 mm, 3.5 μm), Mobile phase: A=10 m M $NH_4HCO_3$ in $H_2O$ pH=9.5 adjusted with ammonia, B=methanol; 0-15 min, 0% B→50% B; 15-18 min, 50%→100% B; 18-23 min, 100% B; flow rate=1 mL/min; run time=25 min.

Method L:

Column: ECLIPSE XDB $C_{18}$ (4.6×150 mm, 5 µm); mobile phase: A=20 mM $NH_4OAc$ in $H_2O$, B=acetonitrile; 0-15 min, 0% B→50% B; 15-18 min, 50%→100% B; 18-23 min, 100% B; flow rate=1 mL/min; run time=25 min.

Method M:

Column: Waters analytical phenyl Xbridge $C_{18}$ (4.6×150 mm, 3.5 µm), Mobile phase: A=20 m M $NH_4OAc$ in $H_2O$, B=acetonitrile; 0-25 min, 10% B→100% B; 25-30 min, B→100% B; flow rate=1 mL/min; run time=30 min.

Method N:

Column: Waters analytical phenyl Xbridge $C_{18}$ column (4.6×150 mm, 3.5 µm), Mobile phase: A=20 mM $NH_4OAc$ in $H_2O$, B=acetonitrile; 0-12 min, 10% B→100% B; 12-15 min, B→100% B; flow rate=1 mL/min; run time=20 min.

Method O:

Column: Ascentis Express $C_{18}$ (50×2.1 mm-2.7 µM); Solvent A: 2% ACN-98% H20-10 mM $NH_4COOH$, Solvent B: 98% ACN-2% H20-10 mM $NH_4COOH$; Gradient 0-100% B over 1.7 min, stop time 3.4 min.

Method P:

Column: XBridge Phenyl (150×4.6 mm) 3.5 µM; Mobile phase A: 0.05% TFA in water:Acetonitrile (95:5), Mobile phase B:Acetonitrile: 0.05% TFA in water (95:5); Gradient 10-100% B over 12 min, stop time 15 min.

Method 102

Column:Ascentis Express c 18 (50×2.1 mm-2.7 µM); Solvent A: 5% ACN-95% H20-10 mM $NH_4COOH$, Solvent B: 95% ACN-5% H20-10 mM $NH_4COOH$, Gradient from 0-100% B over 3 minutes.

Preparative HPLC Methods:

Method A:

Column: Symmetry $C_8$ (300×19 mm×7µ); Mobile phase A: 10 mM aqueous ammonium acetate, mobile phase B: methanol; Isocratic run with 25% B in A; run time=20 minutes Method B:

Column: Waters Xbridge $C_{18}$, 19×150 mm, 5 µm; Guard Column: Waters XBridge $C_{18}$, 19×10 mm, 5 µm; Mobile Phase A: 5:95 acetonitrile:water with 10 mM $NH_4OAc$; Mobile Phase B: 95:5 Acetonitrile:water with 10 mM $NH_4OAc$; Gradient: 10-40% B over 25 minutes, followed by a 10 minute hold at 40% B and 5 minute hold at 100% B;

Method C:

Column: ODS (250×4.6 mm), 3.5 u; Mobile phase A: 10 mM ammonium acetate/water; Mobile phase B acetonitrile; gradient 50-100% B in A over 25 min Method D:

Column: Waters Xbridge $C_{18}$, 19×150 mm, 5 µm; Guard Column: Waters XBridge $C_{18}$, 19×10 mm, 5 µm; Mobile Phase A: 5:95 methanol:water with 0.1% TFA; Mobile Phase B: 95:5 methanol:water with 0.1% TFA; Gradient: 10-30% B over 25 minutes, followed by a 10 minute hold at 30% B and 5 minute hold at 100% B;

Method E:

Column: Symmetry C18(300×19 mm×7 u); Mobile phase A 10 mM aqueous ammonium acetate, mobile phase B acetonitrile; flow rate=16 mL/min, gradient run 20-55% B in A over 10 min; λ=220 nm; run time=20 minutes Method F:

Column: Xterra $RP_{18}$ (250×19 mm, 5 u); Mobile phase A: 10 mM ammonium acetate pH 4.5, Mobile phase B: acetonitrile. Flow 15 ml/min Method 103:

Column: Sunfire C18(150×4.6 mm×5 u); Mobile phase A 10 mM aqueous ammonium acetate, Mobile phase B acetonitrile; Gradient 0-100% B over 18 minutes; run time=20 minutes.

General Intermediates

1-Benzyl-3-bromopyrrolidin-2-ones/1-benzyl-3-bromopiperidin-2-ones

The synthetic intermediates in Table 1 were synthesized by a procedure analogous to that reported in A. Kamal, et. al., *Tetrahedron: Asymmetry*, 2003, 14, 2587-2594, using substituted benzylamines and the appropriate dibromo-alkanoyl chloride.

Representative Procedure (Intermediate 6)

Intermediate 6, 3-Bromo-1-(3-fluoro-4-methyl-benzyl)pyrrolidin-2-one

Step A

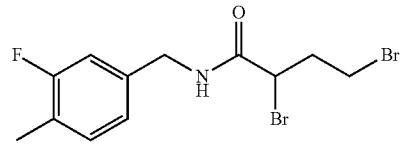 [SMILES: Cc1ccc(CNC(=O)C(Br)CCBr)cc1F]

To a stirring 0° C. solution of 3-fluoro-4-methylbenzyl amine (2.0 g, 14 mmol) and N-ethyl-N-isopropylpropan-2-amine (3.5 mL, 20 mmol) in dichloromethane (30 mL) was added dropwise a solution of 2,4-dibromobutanoyl chloride (3.98 g, 15 mmol) in dichloromethane (5 mL). After completion of the addition, the reaction was stirred in the ice bath until all of the ice had melted, then it was partitioned between ethyl acetate and water. The layers were separated, the organic layer was washed with brine, and it was then dried over magnesium sulfate. The drying agent was filtered off, the solvent was evaporated, and the residue was dissolved in ethyl acetate and subjected to silica gel chromatography in 10→25→100% ethyl acetate/hexane, collecting the main component to yield 4.5 g (85%) 2,4-dibromo-N-(3-fluoro-4-methylbenzyl)butanamide. LCMS (method CZ-1): RT 1.21 min, m/z 367.9 ($MH^+$); $^1H$ NMR (500 MHz, chloroform-d) δ 7.17 (t, J=7.7 Hz, 1H), 7.01-6.91 (m, 2H), 6.70 (br. s., 1H), 4.59 (dd, J=9.0, 4.9 Hz, 1H), 4.51-4.37 (m, 2H), 3.64-3.51 (m, 2H), 2.71 (dddd, J=15.0, 8.5, 6.1, 4.9 Hz, 1H), 2.51 (ddt, J=15.0, 9.2, 5.5 Hz, 1H), 2.27 (d, J=1.4 Hz, 3H).

Step B

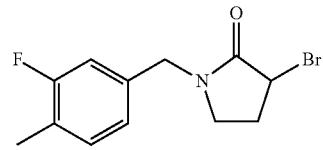 [SMILES: Cc1ccc(CN2CCC(Br)C2=O)cc1F]

To a stirring suspension of NaH (0.76 g, 19 mmol) in tetrahydrofuran (50 mL) was added dropwise over ~½ hour a solution of 2,4-dibromo-N-(3-fluoro-4-methylbenzyl)butanamide (4.5 g, 12.2 mmol) in tetrahydrofuran (30 mL) and the resulting mixture was stirred at room temperature overnight. The reaction mixture was then filtered and the solvent evaporated.

The residue was subjected to silica gel chromatography in 10-50% ethyl acetate/hexane, collecting 949 mg recovered starting material and 2.28 g 3-bromo-1-(3-fluoro-4-methyl-benzyl)pyrrolidin-2-one (Intermediate #6) as a white solid.

TABLE 1

Substituted 1-benzyl-3-bromo-pyrrolidin-2-ones/ 1-benzyl-3-bromopiperidin-2-ones

| Int. No. | Structure | LCMS (Method) RT (min) | LCMS [M + H]+ | 1H NMR |
|---|---|---|---|---|
| 1 | 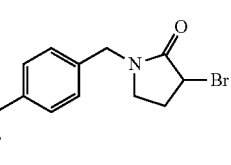 | (P) 0.85 | 272.4/ 274.3 | 1H NMR (400 MHz, DMSO-d6) δ ppm 2.12-2.27 (m, 1 H) 2.56-2.68 (m, 1 H) 3.27 (dd, J = 7.78, 3.26 Hz, 2 H) 4.29-4.38 (m, 1 H) 4.40-4.57 (m, 1 H) 4.73 (dd, J = 7.03, 3.01 Hz, 1 H) 7.04-7.35 (m, 4 H) |
| 2 | 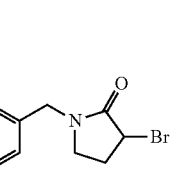 | (V) 2.30 | 268/ 270 | 1H NMR (400 MHz, chloroform-d) δ ppm 2.20-2.30 (m, 1 H) 2.34 (s, 3 H) 2.54 (s, 1 H) 3.19 (s, 1 H) 3.36-3.45 (m, 1 H) 4.36-4.54 (m, 3 H) 7.15 (s, 4 H) |
| 2a | 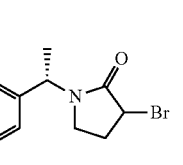 | (K) 1.89 | 304/ 306 | 1H NMR (400 MHz, DMSO-d6) δ ppm 7.58 (d, J = 8.03 Hz, 2 H) 7.40 (d, J = 8.53 Hz, 2 H) 7.03 (m, 1 H) 4.75 (dd, J = 7.53, 3.01 Hz, 1 H) 4.52-4.59 (m, 1 H) 4.41-4.47 (m, 1 H) 3.33-3.39 (m, 1 H) 3.25-3.32 (m, 1 H) 2.65 (dq, J = 14.62, 7.34 Hz, 1 H) 2.21 (ddt, J = 14.43, 6.65, 3.26, 3.26 Hz, 1 H) |
| 3 | 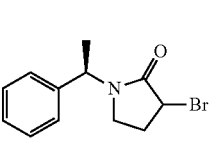 | (P) 0.90 | 254.0/ 256.0 | 300 MHz, DMSO-d6: δ 2.15-2.24 (m, 1H), 2.49-2.52 (m, 1H), 3.23-3.28 (m, 2H), 4.35 (d, J = 15.00 Hz, 1H), 4.51 (d, J = 15.00 Hz, 1H), 4.74 (dd, J = 3.00, 7.20 Hz, 1H), 7.23-7.40 (m, 5H) |
| 4 | 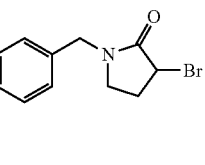 | | | 300 MHz, DMSO-d6: δ 1.49 (dd, J = 3.30, 7.20 Hz, 3H), 2.11-2.18 (m, 1H), 2.49-2.63 (m, 1H), 2.95-3.03 (m, 1H), 3.38-3.41 (m, 1H), 4.71 (dd, J = 3.00, 7.20 Hz, 1H), 5.22-5.24 (m, 1H), 7.28-7.41 (m, 5H), |
| 5 | 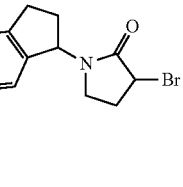 | | | 300 MHz, DMSO-d6: δ 1.49 (d, J = 7.20 Hz, 3H), 2.11-2.18 (m, 1H), 2.53-2.63 (m, 1H), 2.95-3.03 (m, 1H), 3.35-3.41 (m, 1H), 4.70 (dd, J = 3.0, 7.20 Hz, 1H), 5.22-5.24 (m, 1H), 7.28-7.41 (m, 5H) |
| 6 | 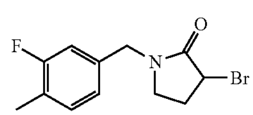 [SMILES: Cc1ccc(CN2CCC(Br)C2=O)cc1F] | (P) 0.90 | 286.3/ 288.3 | 1H NMR (400 MHz, chloroform-d) δ ppm 2.26 (d, J = 2.01 Hz, 5 H) 2.48-2.64 (m, 1 H) 3.20 (s, 1 H) 3.38-3.49 (m, 1 H) 4.29-4.55 (m, 3 H) 6.92 (s, 2 H) 7.15 (s, 1 H) |
| 7 | 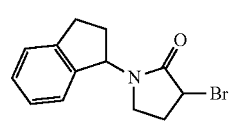 [SMILES: O=C1C(Br)CCN1C1CCc2ccccc21] | | | 300 MHz, DMSO-d6: δ 1.90-2.18 (m, 1H), 2.20-2.29 (m, 1H), 2.32-2.33 (m, 1H), 2.59-2.62 (m, 1H), 2.88-3.01 (m, 3H), 3.21-3.25 (m, 1H), 4.74 (dd, J = 2.70, 6.90 Hz, 1H), 5.57 (t, J = 7.80 Hz, 1H), 7.08-7.11 (m, 1H), 7.23-7.32 (m, 3H) |

TABLE 1-continued

Substituted 1-benzyl-3-bromo-pyrrolidin-2-ones/
1-benzyl-3-bromopiperidin-2-ones

| Int. No. | Structure | LCMS (Method) RT (min) | LCMS [M + H]+ | 1H NMR |
|---|---|---|---|---|
| 8 | 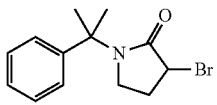 [SMILES: CC(C)(c1ccccc1)N1CCC(Br)C1=O] | (J) 0.92 | 282.0/ 284.0 | |
| 9 | 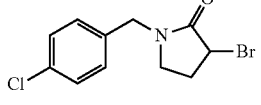 | (P) 0.97 | 288.4/ 290.3 | 1H NMR (400 MHz, chloroform-d) δ ppm 7.32 (d, J = 8.4, 2H), 7.20 (d, J = 8.4, 2H), 4.54 (d, J = 14, 1H), 4.48 (m, 1H), 4.74 (d, J = 14, 1H), 3.45-3.39 (m, 1H), 3.22-3.17 (m, 1H), 2.59-2.54 (m, 1H), 2.33-2.27 (m, 1H), |
| 10 | 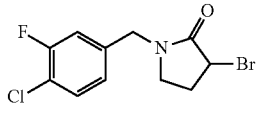 [SMILES: O=C1C(Br)CCN1Cc1ccc(Cl)c(F)c1] | (V) 1.94 | 306.0/ 307.9 | 400 MHz, MeOD: δ 2.34-2.29 (m, 1H), 2.67-2.72 (m, 1H), 3.39-3.32 (m, 1H), 3.52-3.46 (m, 1H), 4.42 (d, J = −15.20 Hz, 1H), 4.61 (d, J = −24.80 Hz, 2H), 7.17 (dd, J = −41.60, Hz, 2H), 7.48 (t, J = −15.60 Hz, 1H) |
| 11 | 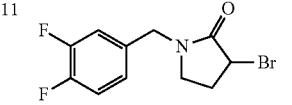 | (S) 1.85 | 289.9/ 291.9 | 400 MHz, DMSO-d6: δ 7.41-7.48 (m, 1H), 7.28-7.34 (m, 1H), 7.10-7.13 (m, 1H), 4.73-4.76 (m, 1H), 4.36-4.50 (m, 2H), 3.27-3.31 (m, 2H), 3.36-3.39 (m, 1H), 2.62-2.68 (m, 1H), 2.18-2.23 (m, 1H) |
| 12 | 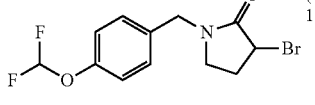 | (K) 1.96 | 320.0/ 322.0 | 400 MHz, DMSO-d6: δ 6.98-7.47 (m, 4H), 4.73 (dd, J = 14.00, Hz, 1H), 4.49 (d, J = 19.60 Hz, 1H), 4.35 (d, J = 20.00 Hz, 1H), 3.22-3.29 (m, 2H), 2.56-2.68 (m, 1H), 2.15-2.23 (m, 1H) |
| 13 | 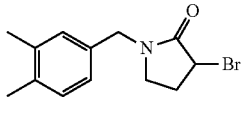 [SMILES: Cc1ccc(CN2CCC(Br)C2=O)cc1C] | (V) 3.14 | 282.0/ 284.0 | 1H NMR (400 MHz, chloroform -d) δ ppm 2.26 (d, J = 2.01 Hz, 5 H) 2.48-2.64 (m, 1 H) 3.20 (s, 1 H) 3.38-3.49 (m, 1 H) 4.29-4.55 (m, 3 H) 6.92 (s, 2 H) 7.15 (s, 1 H) |
| 14 | 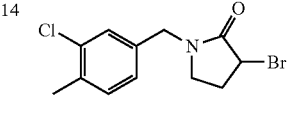 | (V) 2.02 | 302.0/ 304.0 | |
| 15 | 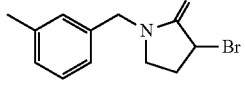 | (F) 1.97 | 268.3/ 270.2 | 1H NMR 400 MHz, MeOD: δ ppm 7.26-7.21 (m, 1H), 7.13-7.05 (m, 2H), 4.62-4.53 (m, 2H), 4.35 (d, J = 14.7, 1H), 3.47-3.38 (m, 1H), 3.31-3.25 (m, 1H), 2.70-2.58 (m, 1H), 2.33-2.18 (m, 4H) |
| 16 | 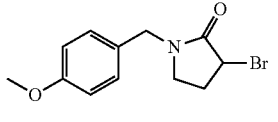 [SMILES: COc1ccc(CN2CCC(Br)C2=O)cc1] | (V) 1.73 | 284.0/ 286.1 | 1H NMR 400 MHz, MeOD: δ ppm 7.22 (d, J = 6.6, 2H), 6.91 (d, J = 6.6, 2H), 4.60 (m, 1H), 4.54 (d, J = 15, 1H), 4.34 (d, J = 15, 1H), 3.78 (s, 3H), 3.46-3.38 (m, 1H), 3.31-3.26 (m, 1H), 2.70-2.58 (m, 1H), 2.31-2.23 (m, 1H) |

TABLE 1-continued

Substituted 1-benzyl-3-bromo-pyrrolidin-2-ones/
1-benzyl-3-bromopiperidin-2-ones

| Int. No. | Structure | LCMS (Method) RT (min) | LCMS [M + H]+ | 1H NMR |
|---|---|---|---|---|
| 17 | 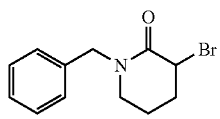 [SMILES: O=C1C(Br)CCCN1Cc1ccccc1] | (P) 0.82/ 0.84 | 268.3/ 270.3 | 1H NMR (300 MHz, DMSO-d6) δ ppm 1.67-1.86 (m, 1 H) 1.90-2.19 (m, 2 H) 2.25-2.42 (m, 1 H) 3.23-3.32 (m, 2 H) 4.41 (s, 1 H) 4.61 (s, 1 H) 4.73-4.85 (m, 1 H) 7.12-7.44 (m, 5 H) |
| 18 | 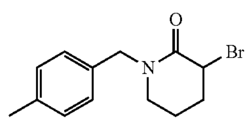 [SMILES: Cc1ccc(CN2CCCC(Br)C2=O)cc1] | (P) 0.92 | 282.3/ 284.3 | 1H NMR (400 MHz, DMSO-d6) δ ppm 1.67-1.84 (m, 1 H) 1.92-2.04 (m, 1 H) 2.04-2.17 (m, 1 H) 2.29 (s, 4 H) 3.19-3.28 (m, 2 H) 4.24-4.37 (m, 1 H) 4.53-4.64 (m, 1 H) 4.72-4.82 (m, 1 H) 7.14 (d, J = 4.02 Hz, 4 H) |
| 19 | 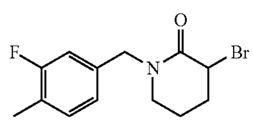 [SMILES: Cc1ccc(CN2CCCC(Br)C2=O)cc1F] | (P) 0.96 | 300.0/ 302.0 | 1H NMR (400 MHz, DMSO-d6) δ ppm 1.65-1.85 (m, 1 H) 1.99 (s, 1 H) 2.21 (d, J = 1.51 Hz, 1 H) 2.27-2.40 (m, 3 H) 2.59-2.26 (s, 1 H) 3.24-3.32 (m, 2H) 4.36 (d, J = 15.06 Hz, 1 H) 4.57 (d, J = 15.06 Hz, 1 H) 4.79 (s, 1 H) 6.91-7.05 (m, 2 H) 7.25 (s, 1 H) |
| 20 | 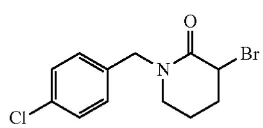 [SMILES: O=C1C(Br)CCCN1Cc1ccc(Cl)cc1] | (P) 0.99 | 302.3/ 304.3 | 1H NMR (300 MHz, DMSO-d6) δ ppm 1.68-1.87 (m, 1 H) 1.92-2.18 (m, 2 H) 2.22-2.39 (m, 1 H) 3.20-3.29 (m, 2 H) 4.33-4.45 (m, 1 H) 4.53-4.64 (m, 1 H) 4.74-4.83 (m, 1 H) 7.25-7.33 (m, 2 H) 7.35-7.47 (m, 2 H) |

Substituted (4-methoxyphenyl)cycloalkylamines

Intermediate 21: 4-(4-Methoxyphenyl)azepane

Step A tert-Butyl 4-hydroxy-4-(4-methoxyphenyl)azepane-1-carboxylate

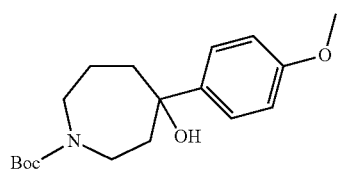 [SMILES: COc1ccc(C2(O)CCCN(C(=O)OC(C)(C)C)CC2)cc1]

To a solution of 1-bromo-4-methoxybenzene (0.88 g, 4.7 mmol) in THF (50 mL) was added n-butyllithium (2.9 mL, 4.7 mmol) at −78° C. The reaction mixture was stirred at −78° C. for 2 h, then added to a flask containing tert-butyl 4-oxoazepane-1-carboxylate (1 g, 4.7 mmol) in THF, cooled to −78° C. The reaction mixture was stirred at −78° C. for 30 min and then at 0° C. for 15 min. It was then quenched with saturated ammonium chloride solution and extracted with ethyl acetate. The organic phase was dried over sodium sulfate, filtered, and concentrated. The crude product was purified by flash chromatography on silica gel using hexane/ethyl acetate as the eluant to yield tert-butyl 4-hydroxy-4-(4-methoxyphenyl)azepane-1-carboxylate (0.68 g, 45%). LCMS: R.T. 0.96 min. LCMS (ES-API), m/z 320 (M−H).

Step B 5-(4-Methoxyphenyl)-2,3,4,7-tetrahydro-1H-azepine hydrochloride

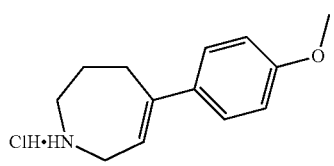

A mixture of HCl in dioxane (10 mL, 40 mmol) and tert-butyl 4-hydroxy-4-(4-methoxyphenyl)azepane-1-carboxylate (0.68 g, 2.1 mmol) was stirred at room temperature for 3 h. The reaction mixture was concentrated and washed with diethyl ether and dried over sodium sulfate to yield 0.36 g 5-(4-methoxyphenyl)-2,3,4,7-tetrahydro-1H-azepine hydrochloride. LCMS: R.T. 0.61 min. LCMS (ES-API), m/z 204.0 (M+H).

Step C 4-(4-Methoxyphenyl)azepane

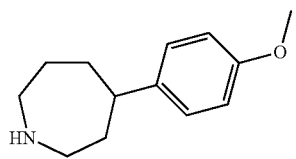

A mixture of 5-(4-methoxyphenyl)-2,3,4,7-tetrahydro-1H-azepine hydrochloride (0.35 g, 1.5 mmol) and 10% palladium on carbon (0.2 g) in methanol (10 mL) was stirred overnight under balloon pressure of hydrogen. The reaction mixture was filtered through Celite and concentrated to yield 4-(4-methoxyphenyl)azepane (0.26 g, 1.2 mmol, 79%). LCMS: R.T. 0.60 min. LCMS (ES-API), m/z 206.0 (M+H).

Intermediate 22: 3-(4-Methoxyphenyl)azepane

Step A tert-Butyl 3-hydroxy-3-(4-methoxyphenyl)azepane-1-carboxylate

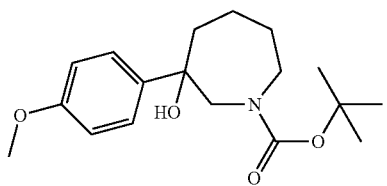 [SMILES: COc1ccc(C2(O)CCCCN(C(=O)OC(C)(C)C)C2)cc1]

To a stirred solution of 1-bromo-4-methoxybenzene (0.67 mL, 5.4 mmol) in THF (50 mL) at −78° C. was added n-butyllithium (5 mL, 8 mmol) and the reaction mixture was stirred at −78° C. for 2 h. Then was added tert-butyl 3-oxoazepane-1-carboxylate (1.14 g, 5.4 mmol) at −78° C. and the reaction mixture was warmed to room temperature over 12 h. It was then quenched with saturated NH$_4$Cl at 0° C., and extracted with ethyl acetate. The combined organic layers were washed with brine, dried over anhydrous sodium sulfate, filtered, and concentrated. The crude product was purified by flash chromatography on silica gel (24 g) using 10% ethyl acetate in hexane to yield tert-butyl 3-hydroxy-3-(4-methoxyphenyl)azepane-1-carboxylate (1.2 g, 57%) as a colorless gum. LCMS: R.T. 1.03 min. LCMS (ES-API), m/z 204 (M-117).

Step B 6-(4-Methoxyphenyl)-2,3,4,5-tetrahydro-1H-azepine hydrochloride

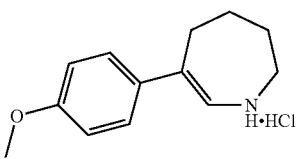

A solution of tert-butyl 3-hydroxy-3-(4-methoxyphenyl) azepane-1-carboxylate (0.25 g, 0.78 mmol) in HCl (4M solution in dioxane) (3 mL, 12 mmol) was stirred at room temperature for 5 h. The reaction mixture was concentrated and the residue was titurated with diethyl ether to yield 6-(4-methoxyphenyl)-2,3,4,5-tetrahydro-1H-azepine hydrochloride (0.18 g, 62%) as a black gum. LCMS: R.T. 0.60 min. LCMS (ES-API), m/z 204 (M+1).

Step C 3-(4-Methoxyphenyl)azepane hydrochloride

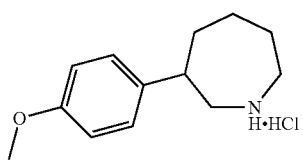

A mixture of 6-(4-methoxyphenyl)-2,3,4,5-tetrahydro-1H-azepine hydrochloride (0.3 g, 1.251 mmol) and 10% Pd-C (0.133 g, 1.251 mmol) in methanol (5 mL), was hydrogenated at 50 psi for 12 h. The reaction mixture was filtered through Celite and and concentrated to yield crude 3-(4-methoxyphenyl)azepane hydrochloride (0.2 g, 57%) as a black gum, used without further purification. LCMS: RT 0.62 min. LCMS (ES-API), m/z 206.1 (M+1).

Intermediate 24: 4-(4-Methoxyphenyl)piperidine hydrochloride

Step A tert-Butyl 4-hydroxy-4-(4-methoxyphenyl) piperidine-1-carboxylate

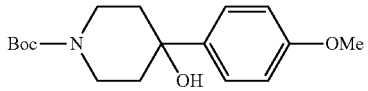 [SMILES: COc1ccc(C2(O)CCN(C(=O)OC(C)(C)C)CC2)cc1]

A mixture of tert-butyl 4-oxopiperidine-1-carboxylate (2 g, 10.04 mmol) and diethyl ether (30 ml) was cooled to 0° C., followed by the dropwise addition of (4-methoxyphenyl) magnesium bromide (0.5 M in diethyl ether, 30 ml, 15 mmol). The reaction mixture was allowed to warm to rt and stirred for 2 h. It was then slowly quenched with 150 ml of ice cold water and then the resulting mixture was extracted with 3×150 ml of DCM. The organic layers were combined, dried, filtered, and concentrated under vacuum. The crude product was purified by silica gel chromatography eluting with 30:70 ethyl acetate: hexane to provide 3 g tert-butyl 4-hydroxy-4-(4-methoxyphenyl)piperidine-1-carboxylate (100%). LCMS: RT 1.950 min. LCMS (ES-API), m/z 305.5 (M−H). $^1$H NMR (400 MHz, DMSO-d$_6$) δ 7.37 (q, J=1.0 Hz, 2H), 6.86 (q, J=1.0 Hz, 2H), 4.94 (s, 1H), 3.82 (d, J=11.5 Hz, 2H), 3.73 (s, 3H), 3.13 (br. s, 2H), 1.75 (td, J=12.9, 4.8 Hz, 2H), 1.56 (d, J=12.3 Hz, 2H), 1.41 (s, 9H).

Step B 4-(4-Methoxyphenyl)-1,2,3,6-tetrahydropyridine hydrochloride

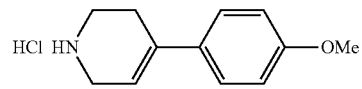 [SMILES: Cl ; COc1ccc(C2=CCNCC2)cc1]

A mixture of tert-butyl 4-hydroxy-4-(4-methoxyphenyl) piperidine-1-carboxylate (700 mg, 2.27 mmol) from Step A and HCl in dioxane (4 ml, 16 mmol) was stirred at rt for 3 h.

The crude mass was concentrated under vacuum and the solid residue was washed with 3×10 ml of DCM to remove non-polar impurities. The desired salt was collected as a fine solid (480 mg, 93%). LCMS: RT 1.27 min. LCMS (ES-API), m/z 190.2 (M+H). NMR: $^1$H NMR (400 MHz, DMSO-d$_6$) δ 7.37 (d, J=9.0 Hz, 2H), 6.98 (d, J=9.0 Hz, 2H), 6.08-5.98 (m, 1H), 5.11 (s, 1H), 3.97 (br. s., 1H), 3.52 (s, 1H), 3.32 (s, 3H), 2.47-2.37 (m, 1H).

Step C 4-(4-Methoxyphenyl)piperidine hydrochloride

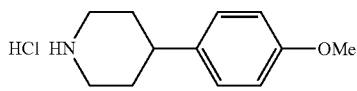

To a stirred solution of 4-(4-methoxyphenyl)-1,2,3,6-tetrahydropyridine, HCl (3 g, 13.3 mmol) (from step B) in methanol (20 mL) was added 10% palladium on carbon (1.4 g) and the reaction mixture was stirred at 20 psi of hydrogen for 12 h. The reaction mixture was filtered through a pad of celite, which was washed with ethyl acetate, and the combined organic fractions were concentrated to obtain a white solid (2 g, 70% yield). LCMS (ES-API), m/z 192.1 (M+H); $^1$H NMR (300 MHz, DMSO-d$_6$) δ 9.13-8.36 (m, 2H), 7.14 (d, J=8.7 Hz, 2H), 6.90 (d, J=8.7 Hz, 2H), 3.73 (s, 3H), 3.07-2.87 (m, 4H), 2.87-2.65 (m, 4H).

Intermediate 24
trans-4-(4-Methoxyphenyl)piperidin-3-ol

Step A:
trans-1-Benzyl-4-(4-methoxyphenyl)piperidin-3-ol

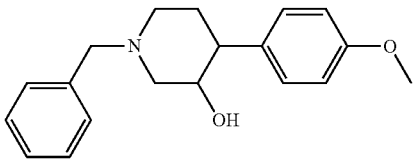 [SMILES: COc1ccc(C2CCN(Cc3ccccc3)CC2O)cc1]

To a suspension of sodium tetrahydroborate (2.7 g, 72 mmol) in THF (200 mL) 0° C. was added dropwise boron trifluoride etherate (8.8 mL, 70 mmol) under a nitrogen atmosphere and the resulting mixture was stirred for 30 minutes. Then was added 1-benzyl-4-(4-methoxyphenyl)-1,2,3,6-tetrahydropyridine (10 g, 36 mmol) (from S. Halazy et al WO 97/28140 (8/7/97)) dissolved in 100 mL of tetrahydrofuran. Stirring was continued at rt for 2 hours. The reaction was then quenched by the dropwise addition of 100 mL water. Next were added sequentially 100 mL ethanol, 100 mL 10% aqueous sodium hydroxide, and hydrogen peroxide (18 mL, 18 mmol) and the temperature was raised to reflux overnight. The reaction mixture was diluted with saturated aqueous ammonium chloride (200 mL), and extracted with ethyl acetate (500 mL). The organic layer was dried over Na$_2$SO$_4$, filtered, and evaporated under reduced pressure to give trans-1-benzyl-4-(4-methoxyphenyl)piperidin-3-ol (8.5 g, 24.6 mmol, 69% yield). LCMS (Method K) RT 1.99 min; m/z 298.0 (MH$^+$).

Step B: trans-4-(4-Methoxyphenyl)piperidin-3-ol

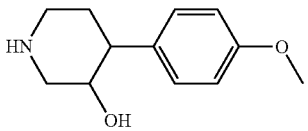

To a solution of trans-1-benzyl-4-(4-methoxyphenyl)piperidin-3-ol (9 g, 30 mmol) in methanol (150 mL) was added 10% Pd/C (4.8 g) and the reaction was stirred overnight under a hydrogen atmosphere. The catalyst was then removed by filtration through Celite and the solvent was evaporated under reduced pressure to give (+/−) trans-4-(4-methoxyphenyl)-piperidin-3-ol (5.1 g, 24.6 mmol, 81% yield). $^1$H NMR (400 MHz, DMSO-d$_6$) δ ppm 7.10-7.15 (m, 2H) 6.80-6.86 (m, 2H) 4.30 (d, J=5.27 Hz, 1H) 3.37-3.43 (m, 1H) 3.04 (dd, J=11.58, 4.36 Hz, 1H) 2.86 (d, J=12.17 Hz, 1H) 2.43 (td, J=12.09, 2.67 Hz, 1H) 2.22-2.35 (m, 2H) 1.57-1.63 (m, 1H) 1.43-1.54 (m, 1H).

Intermediate 25. 3-(4-Methoxyphenyl)piperidine

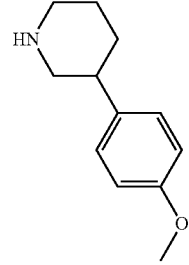

Step A: 1-Benzyl-3-(4-methoxyphenyl)piperidin-3-ol

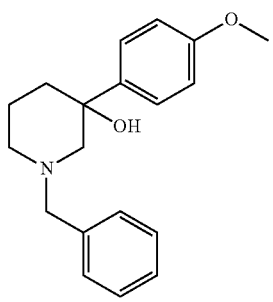 [SMILES: COc1ccc(C2(O)CCCN(Cc3ccccc3)C2)cc1]

To a solution of 1-benzylpiperidin-3-one (5 g, 26 mmol) in THF (30 mL) was added (4-methoxyphenyl)magnesium bromide (0.5 M in ether) (66 mL, 33 mmol) at rt under a nitrogen atmosphere. The reaction was stirred for 2 h and then diluted with sat. ammonium chloride solution and extracted with ethyl acetate (200 mL). The organic layer was dried over Na2SO4 and evaporated under reduced pressure to give crude 1-benzyl-3-(4-methoxyphenyl)piperidin-3-ol (5.1 g, 10.29 mmol, 38.9% yield) with was used in the next step without further purification. LCMS (Method 107): (ES-API), m/z 298.2 (M+H) RT=1.703 min.

Step B: 1-Benzyl-5-(4-methoxyphenyl)-1,2,3,6-tetrahydropyridine

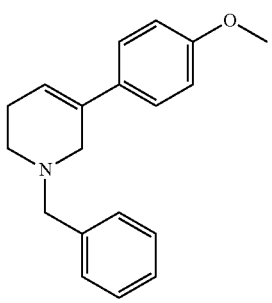 [SMILES: COc1ccc(C2=CCCN(Cc3ccccc3)C2)cc1]

To a solution of 1-benzyl-3-(4-methoxyphenyl)piperidin-3-ol (3.5 g, 11.8 mmol) in dioxane (20 mL) was added concentrated HCl (3.6 mL, 43 mmol) and the reaction mixture was stirred overnight. The solvents were evaporated under reduced pressure and the residue was diluted with sat. bicarbonate solution (200 mL) and extracted with ethyl acetate (200 mL). The organic layer was dried over $Na_2SO_4$ and evaporated under reduced pressure to give the crude product which was purified via silica gel chromatography eluting with 30% ethyl acetate in hexane to give 1-benzyl-5-(4-methoxyphenyl)-1,2,3,6-tetrahydropyridine (1.5 g, 4.2 mmol, 35.6% yield). LCMS (Method 107): (ES-API), m/z 280.2 (M+H) RT=2.263 min; $^1$H NMR (300 MHz, DMSO-$d_6$) δ 7.42-7.32 (m, 4H), 7.29-7.19 (m, 3H), 6.91-6.82 (m, 2H), 6.16-5.97 (m, 1H), 3.73 (s, 3H), 3.65 (d, J=2.6 Hz, 3H), 3.23 (d, J=1.9 Hz, 2H), 2.55 (s, 1H), 2.24 (d, J=3.8 Hz, 2H).

Step C: 3-(4-Methoxyphenyl)piperidine

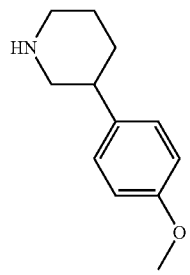

To a solution of 1-benzyl-5-(4-methoxyphenyl)-1,2,3,6-tetrahydropyridine (1.5 g, 5.4 mmol) in 50 mL of methanol was added 10% Pd/C (1.14 g). Hydrogen gas was introduced via balloon and the reaction mixture was stirred overnight at rt. The reaction mixture was then filtered through Celite, and the filter pad was washed with additional methanol (100 mL). The filtrates were combined, and the methanol was evaporated under reduced pressure to give 3-(4-methoxyphenyl)piperidine (950 mg, 3.73 mmol, 69.4% yield). LCMS (Method 107): (ES-API), m/z 192.2 (M+H) RT=1.497 min; $^1$H NMR (300 MHz, DMSO-d6) δ 7.13 (dt, J=8.5, 2.0 Hz, 2H), 6.84 (dt, J=8.5, 2.2 Hz, 2H), 3.72 (s, 3H), 3.17 (s, 2H), 2.93 (d, J=10.6 Hz, 2H), 2.49-2.39 (m, 1H), 1.81 (d, J=1.9 Hz, 1H), 1.74-1.57 (m, 1H), 1.57-1.40 (m, 2H).

Intermediate 26 3-(4-Methoxyphenyl)azetidine

Step A. tert-Butyl 3-hydroxy-3-(4-methoxyphenyl)azetidine-1-carboxylate

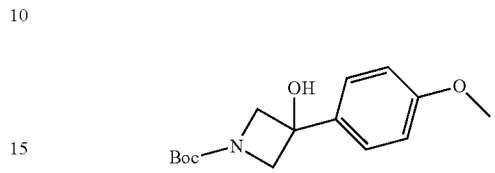

To a solution of tert-butyl 3-oxoazetidine-1-carboxylate (4 g, 23 mmol) in THF (100 mL) at 0° C. was added (4-methoxyphenyl)magnesium bromide (0.5 M in ether) (47 mL, 23 mmol). The reaction mixture was stirred for 3 h, and then a satd. ammonium chloride solution (200 mL) was added. The mixture was extracted with ethyl acetate (200 mL), and the organic layer was separated, dried over Na2SO4, and evaporated under reduced pressure to give a crude product. The product was purified by silica gel chromatography eluting with 25% ethyl acetate in hexane to give tert-butyl 3-hydroxy-3-(4-methoxyphenyl)azetidine-1-carboxylate (2.2 g, 7.64 mmol, 32.7% yield). LCMS (Method 107): m/z 280.7 (M+H) RT=1.929 min; $^1$H NMR (400 MHz, DMSO-$d_6$) δ 7.39 (d, J=8.8 Hz, 2H), 6.93 (d, J=8.8 Hz, 2H), 6.21 (s, 1H), 4.00 (s, 3H), 3.75 (s, 3H), 1.41 (s, 9H).

Step B tert-Butyl 3-(4-methoxyphenyl)azetidine-1-carboxylate

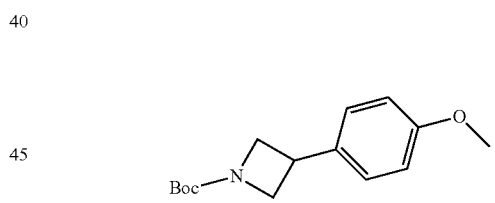

To a solution of tert-butyl 3-hydroxy-3-(4-methoxyphenyl)azetidine-1-carboxylate (1.1 g, 3.9 mmol) in DCM (15 mL) at 0° C. was added triethylsilane (5 mL, 31 mmol) followed by TFA (1 mL, 13.8 mmol). The reaction mixture was allowed to warm to rt and stirred overnight. The mixture was then diluted with a satd. sodium bicarbonate solution and extracted with DCM (100 mL). The organic layer was separated, dried over $Na_2SO_4$, filtered, and evaporated under reduced pressure to give a crude product which was purified by silica gel chromatography eluting with 10% ethyl aceate in hexane to give pure tert-butyl 3-(4-methoxyphenyl)azetidine-1-carboxylate (380 mg, 1.37 mmol, 34.8% yield). LCMS (Method 107): (ES-API), m/z 264.0 (M+H) RT=2.128 min; $^1$H NMR (400 MHz, DMSO-$d_6$) δ 7.31-7.20 (m, 2H), 6.96-6.87 (m, 2H), 4.27-4.17 (m, 2H), 3.82-3.69 (m, 6H), 1.41 (s, 9H).

Step C 3-(4-Methoxyphenyl)azetidine

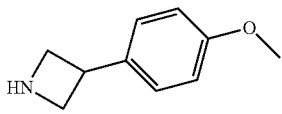

To a solution of tert-butyl 3-(4-methoxyphenyl)azetidine-1-carboxylate (380 mg, 1.4 mmol) in methanol (10 mL) was added conc HCl (0.44 mL, 5.2 mmol) and the reaction mixture was stirred at rt for 3 h. The solvents were removed by evaporation under reduced pressure and the solid residue was washed with diethyl ether three times (3×10 mL) and then dried under reduced pressure to give 3-(4-methoxyphenyl)azetidine, HCl (125 mg, 0.6 mmol, 41% yield). LCMS (Method 107): (ES-API), m/z 164.0 (M+H) RT=1.386 min; $^1$H NMR (400 MHz, DMSO-$d_6$) δ 9.39 (br. s., 1H), 9.12 (br. s., 1H), 7.37 (dt, J=8.5, 2.5 Hz, 2H), 6.96 (dt, J=8.5, 2.5 Hz, 2H), 4.31-4.13 (m, 2H), 4.12-3.89 (m, 3H), 3.76 (s, 3H).

Intermediate 27.
4-(4-Methoxy-2-methylphenyl)piperidine, HCl

Step A. tert-Butyl 4-hydroxy-4-(4-methoxy-2-methylphenyl)piperidine-1-carboxylate

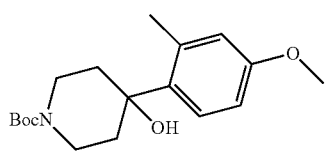 [SMILES: COc1ccc(C2(O)CCN(C(=O)OC(C)(C)C)CC2)c(C)c1]

A solution of tert-butyl 4-oxopiperidine-1-carboxylate (2 g, 10 mmol) in diethyl ether (100 mL) was chilled to 0° C., and a solution of (4-methoxy-3-methylphenyl)magnesium bromide (0.5 M in ether) (20 mL, 10 mmol) was added. The reaction mixture was allowed to warm to rt and stirred for 12 h. The reaction mixture was then quenched with a saturated NH$_4$Cl solution and the mixture was diluted with ethyl acetate. The organic layer was separated, washed with brine, dried over anhydrous Na$_2$SO$_4$, and then evaporated under reduced pressure to provide the desired product (2.3 g, 71%); $^1$H NMR (400 MHz, DMSO-$d_6$) δ 7.27 (d, J=8.0 Hz, 1H), 6.75-6.61 (m, 2H), 4.83 (s, 1H), 3.85-3.77 (m, 2H), 3.71 (s, 3H), 3.17 (d, J=5.0 Hz, 2H), 2.51 (s, 3H), 1.82-1.73 (m, 4H), 1.41 (s, 9H).

Step B. 4-(4-Methoxy-2-methylphenyl)-1,2,3,6-tetrahydropyridine hydrochloride

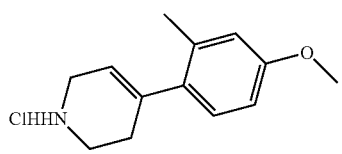

A solution of tert-butyl 4-hydroxy-4-(4-methoxy-2-methylphenyl)piperidine-1-carboxylate (2.3 g, 7.2 mmol) in 1,4-dioxane (20 mL) was chilled to 0° C. and treated with a solution of HCl in dioxane (4.0 M, 1.8 mL, 7.2 mmol). The reaction mixture was stirred at rt for 12 h, and then the solvents were evaporated to provide a crude compound which was triturated with diethyl ether to provide the desired product as a solid (1.2 g, 82%). LC/MS (Method P) RT=0.63 min. (M+H)$^+$=204.0; $^1$H NMR (300 MHz, DMSO-$d_6$) δ 9.51-9.09 (m, 2H), 7.00 (d, J=8.3 Hz, 1H), 6.79-6.71 (m, 2H), 5.52 (t, J=1.5 Hz, 1H), 3.73 (s, 3H), 3.67 (br. s., 2H), 3.26 (d, J=4.5 Hz, 2H), 2.45 (d, J=1.9 Hz, 2H), 2.25 (s, 3H)

Step C. 4-(4-Methoxy-2-methylphenyl)piperidine, HCl

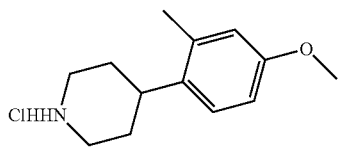

To a solution of 4-(4-methoxy-2-methylphenyl)-1,2,3,6-tetrahydropyridine (500 mg, 2.5 mmol) in MeOH (20 mL) was added 10% Pd/C (524 mg). Hydrogen gas was introduced under balloon pressure and the reaction mixture was stirred vigorously for 12 h. The reaction mixture was filtered through a glass fiber filter cartridge, and the filter pad was washed with ethyl acetate. The combined organic layers were evaporated under reduced pressure to give 4-(4-methoxy-2-methylphenyl)piperidine, hydrochloride (500 mg, 87% yield). LC/MS (Method P) RT=0.63 min. (M+H)$^+$=206.1; $^1$H NMR (400 MHz, DMSO-$d_6$) δ 9.21-8.25 (m, 2H), 7.05 (d, J=8.0 Hz, 1H), 6.78-6.71 (m, 2H), 3.71 (s, 3H), 3.30 (d, J=12.0 Hz, 2H), 3.02-2.86 (m, 3H), 2.29 (s, 3H), 1.87-1.65 (m, 4H).

Intermediate 28.
4-(3-Fluoro-4-methoxyphenyl)piperidine hydrochloride

Step A. tert-Butyl 4-(3-fluoro-4-methoxyphenyl)-4-hydroxypiperidine-1-carboxylate

To a solution of 4-bromo-2-fluoro-1-methoxybenzene (2 g, 9.7 mmol) in tetrahydrofuran (100 mL) at −78° C. was added a solution of n-butyllithium (1.6 M in hexanes, 7.9 mL, 12.7 mmol). The reaction mixture was stirred in the cold for 2 h, and then a solution of tert-butyl 4-oxopiperidine-1-carboxylate (1.94 g, 9.7 mmol) in THF (10 mL) was added dropwise. The mixture was then allowed to warm to rt and stir for 12 h. It was quenched with a saturated NH$_4$Cl solution and diluted with ethyl acetate. The organic layer was separated, washed with brine, dried over anhydrous Na$_2$SO$_4$, filtered, and evaporated under reduced pressure. The crude product was purified by silica gel chromatography to provide 2.0 g (63%) of the desired compound; $^1$H NMR (400 MHz, DMSO-$d_6$) δ 7.29 (dd, J=13.3, 2.3 Hz, 1H), 7.24-7.18 (m, 1H), 7.10 (t, J=8.0 Hz, 1H), 5.09 (s, 1H), 3.85 (br. s., 2H), 3.82 (s, 3H), 1.86-1.68 (m, 2H), 1.56 (d, J=12.0 Hz, 3H), 1.46-1.38 (m, 11H).

Step B. 4-(3-Fluoro-4-methoxyphenyl)-1,2,3,6-tetrahydropyridine hydrochloride

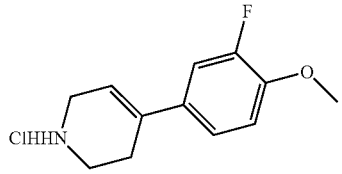

A solution of tert-butyl 4-(3-fluoro-4-methoxyphenyl)-4-hydroxypiperidine-1-carboxylate (0.5 g, 1.5 mmol) in 1,4-dioxane (20 mL) was chilled to 0° C. and treated with a solution of HCl in 1,4 dioxane (4.0 M, 10 mL, 40 mmol). The reaction mixture was stirred at rt for 12 h, and then the solvents were removed to provide a crude compound which was triturated with diethyl ether to provide the desired product as a solid (1.2 g, 82%). LC/MS (Method 109) RT=1.798 min. (M+H)$^+$=207.8; $^1$H NMR (300 MHz, DMSO-d$_6$) δ 9.51-9.09 (m, 2H), 7.00 (d, J=8.3 Hz, 1H), 6.79-6.71 (m, 2H), 5.52 (t, J=1.5 Hz, 1H), 3.73 (s, 3H), 3.67 (br. s., 2H), 3.26 (d, J=4.5 Hz, 2H), 2.45 (d, J=1.9 Hz, 2H), 2.25 (s, 3H)

Step C. 4-(3-Fluoro-4-methoxyphenyl)piperidine hydrochloride

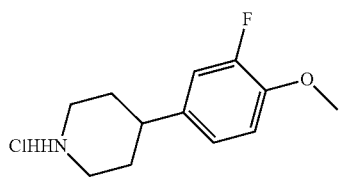

To a solution of 4-(3-fluoro-4-methoxyphenyl)-1,2,3,6-tetrahydropyridine (300 mg, 1.4 mmol) in MeOH (10 mL) was added Pd/C (154 mg). Hydrogen gas was introduced under balloon pressure and the reaction mixture was stirred vigorously for 12 h. The reaction mixture was filtered through a glass fiber filter cartridge, and the filter pad was washed with ethyl acetate. The combined organic layers were evaporated under reduced pressure to give 4-(4-methoxy-2-methylphenyl)piperidine (500 mg, 87% yield). LC/MS (Method P) RT=0.60 min. (M+H)$^+$=210.1.

Racemic 1-benzyl-3((4-methoxyphenyl)cycloalkylamino)pyrrolidin-2-ones

Racemic 1-benzyl-3((4-methoxyphenyl)cycloalkylamino)pyrrolidin-2-ones and -piperidones were synthesized by condensing the lactams from Table I with cyclic amines 21-28 in the presence of a hindered amine base. A representative procedure follows:

Intermediate A: 1-Benzyl-3-(4-(4-methoxyphenyl)piperidin-1-yl)pyrrolidin-2-one

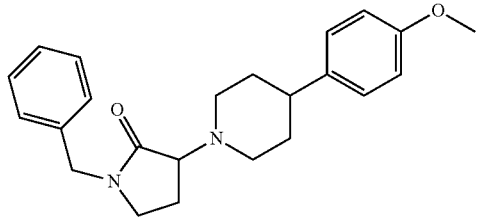 [SMILES: COc1ccc(C2CCN(C3CCN(Cc4ccccc4)C3=O)CC2)cc1]

A solution of 3-bromo-1-benzyl-pyrrolidin-2-one (1.4 g, 5.1 mmol)(intermediate 3), 4-(4-methoxyphenyl)-piperidine (0.98 g, 5.1 mmol) and DIPEA (3.6 mL, 20.6 mmol) in acetonitrile (15 mL) was heated at 90° C. for 18 h. The reaction mixture was concentrated and the residue was dissolved in ethyl acetate (150 mL), washed with water and brine, and dried over sodium sulfate. The organic layer was concentrated to yield 2.1 g of crude product, which was purified by flash chromatography on silica gel (24 g) using 100% EtOAc to yield 1-benzyl-3-(4-(4-methoxyphenyl)piperidin-1-yl)pyrrolidin-2-one (1.4 g, 71%). 1H NMR: 400 MHz, DMSO-d6: δ ppm 1.51-1.65 (m, 2H) 1.66-1.77 (m, 2H) 1.86-1.98 (m, 1H) 2.02-2.12 (m, 1H) 2.27-2.45 (m, 2H) 2.66-2.83 (m, 2H) 2.99-3.23 (m, 3H) 3.45-3.54 (m, 1H) 3.72 (s, 3H) 4.29-4.46 (m, 2H) 6.85 (d, J=9.04 Hz, 2H) 7.16 (d, J=9.04 Hz, 2H) 7.19-7.24 (m, 2H) 7.28 (s, 1H) 7.32-7.39 (m, 2H). LCMS: R.T. 1.76 min. LCMS (ES-API), 365.2 m/z (M+H).

Intermediate B: 1-Benzyl-3-(3-(4-methoxyphenyl)piperidin-1-yl)pyrrolidin-2-one

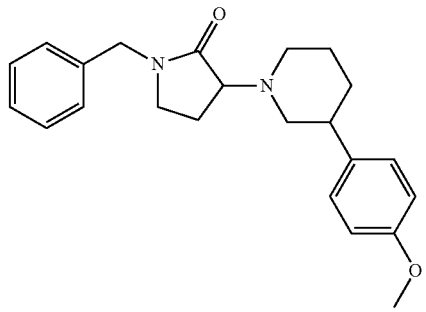 [SMILES: COc1ccc(C2CCCN(C3CCN(Cc4ccccc4)C3=O)C2)cc1]

By a procedure analogous to the synthesis of 1-benzyl-3-(4-(4-methoxyphenyl)piperidin-1-yl)pyrrolidin-2-one, 1-benzyl-3-(3-(4-methoxyphenyl)piperidin-1-yl)pyrrolidin-2-one was obtained from intermediate 3 and amine 25 (1.4 g, 71%). 1H NMR: 400 MHz, DMSO-d6: δ ppm 1.40 (br. s., 1H) 1.47-1.61 (m, 1H) 1.63-1.82 (m, 2H) 1.90-1.96 (m, 1H) 2.00-2.11 (m, 1H) 2.20 (s, 1H) 2.61 (br. s., 3H) 2.88-2.96 (m, 1H) 3.05-3.18 (m, 2H) 3.48 (d, J=2.01 Hz, 2H) 3.72 (d, J=1.00 Hz, 3H) 4.25-4.45 (m, 2H) 6.82-6.89 (m, 2H) 7.11-7.22 (m, 4H) 7.24-7.35 (m, 3H). LCMS: R.T. 1.75-1.76 min. LCMS (ES-API), 365.2 m/z (M+H).

The intermediates C-AJ in Table 2 were prepared by combining 1-benzyl-3-bromo-pyrrolidin-2-ones and -piperidin-2-ones from Table 1 with amines 21-28.

TABLE 2

Racemic 1-benzyl-3((4-methoxyphenyl)cycloalkylamino)pyrrolidin-2-ones

| Int. No. | Structure | LCMS R.T. (min) | LCMS Ion (M + H) |
|---|---|---|---|
| C | 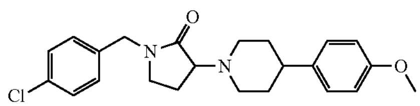 [SMILES: COc1ccc(C2CCN(C3CCN(Cc4ccc(Cl)cc4)C3=O)CC2)cc1] | 1.02 | 399.0 |
| D | 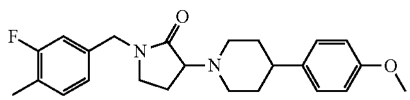 | 1.11 | 397.2 |
| E | 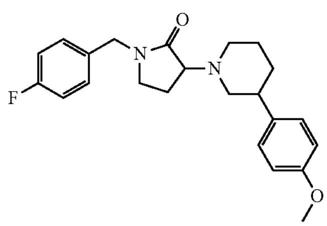 [SMILES: COc1ccc(C2CCCN(C3CCN(Cc4ccc(F)cc4)C3=O)C2)cc1] | 1.04 | 383.2 |
| F | 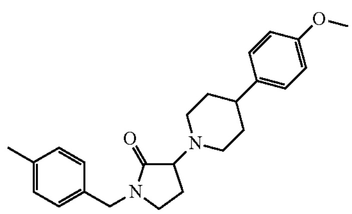 | 1.92 | 379.2 |
| G | 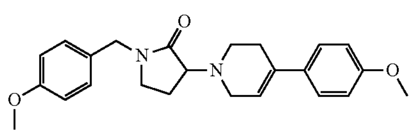 [SMILES: COc1ccc(CN2CCC(N3CC=C(c4ccc(OC)cc4)CC3)C2=O)cc1] | 2.03 | 393.2 |
| H | 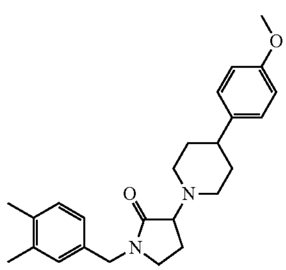 [SMILES: COc1ccc(C2CCN(C3CCN(Cc4ccc(C)c(C)c4)C3=O)CC2)cc1] | 2.53 | 393.2 |
| I | 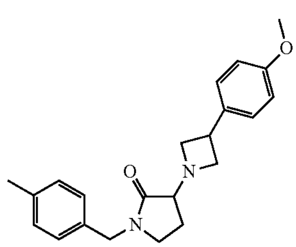 [SMILES: COc1ccc(C2CN(C3CCN(Cc4ccc(C)cc4)C3=O)C2)cc1] | 2.42 | 351.2 |
| J | 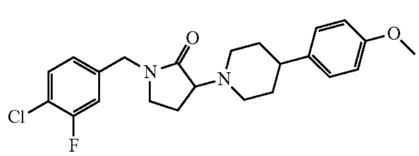 [SMILES: COc1ccc(C2CCN(C3CCN(Cc4ccc(Cl)c(F)c4)C3=O)CC2)cc1] | 0.82 | 417.0 |

TABLE 2-continued

Racemic 1-benzyl-3((4-methoxyphenyl)cycloalkylamino)pyrrolidin-2-ones

| Int. No. | Structure | LCMS R.T. (min) | LCMS Ion (M + H) |
|---|---|---|---|
| K | 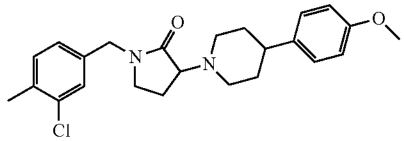 | 0.84 | 413.0 |
| L | 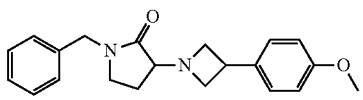 [SMILES: COc1ccc(C2CN(C3CCN(Cc4ccccc4)C3=O)C2)cc1] | 0.93 | 337.2 |
| M | 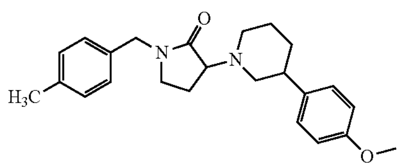 | 1.10 | 379.0 |
| N | 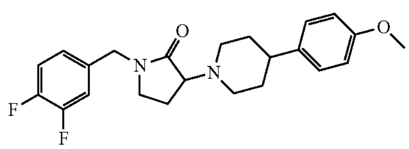 [SMILES: COc1ccc(C2CCN(C3CCN(Cc4ccc(F)c(F)c4)C3=O)CC2)cc1] | 1.99 | 401.0 |
| O | 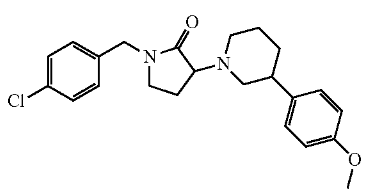 [SMILES: COc1ccc(C2CCCN(C3CCN(Cc4ccc(Cl)cc4)C3=O)C2)cc1] | 2.04 | 399.0 |
| P | 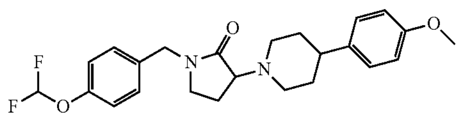 [SMILES: COc1ccc(C2CCN(C3CCN(Cc4ccc(OC(F)F)cc4)C3=O)CC2)cc1] | 2.04 | 431.0 |
| Q | 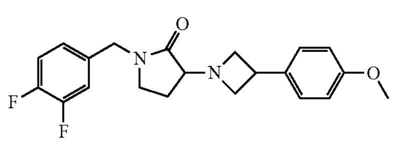 [SMILES: COc1ccc(C2CN(C3CCN(Cc4ccc(F)c(F)c4)C3=O)C2)cc1] | 2.01 | 373.0 |
| R | 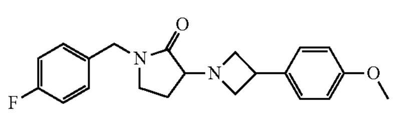 | 1.98 | 355.0 |
| S | 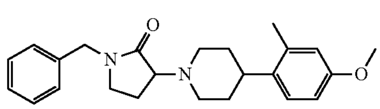 | 1.02 | 379.2 |
| T | 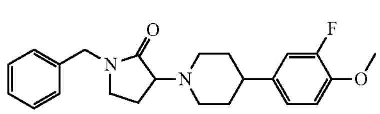 [SMILES: COc1ccc(C2CCN(C3CCN(Cc4ccccc4)C3=O)CC2)cc1F] | 1.0 | 383.2 |
| U | 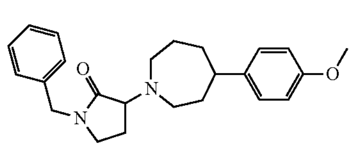 [SMILES: COc1ccc(C2CCCN(C3CCN(Cc4ccccc4)C3=O)CC2)cc1] | 0.77 | 379.2 |

TABLE 2-continued

Racemic 1-benzyl-3((4-methoxyphenyl)cycloalkylamino)pyrrolidin-2-ones

| Int. No. | Structure | LCMS R.T. (min) | LCMS Ion (M + H) |
|---|---|---|---|
| V | 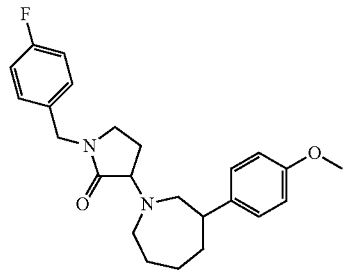 [SMILES: COc1ccc(C2CCCCN(C3CCN(Cc4ccc(F)cc4)C3=O)C2)cc1] | 1.09 | 397.2 |
| W | 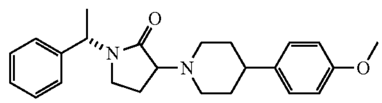 | 0.83 | 379.1 |
| X | 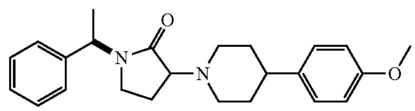 [SMILES: COc1ccc(C2CCN(C3CCN([C@H](C)c4ccccc4)C3=O)CC2)cc1] | 0.81 | 379.1 |
| Y | 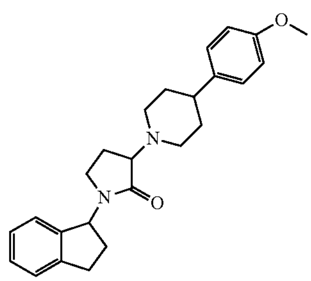 [SMILES: COc1ccc(C2CCN(C3CCN(C4CCc5ccccc54)C3=O)CC2)cc1] | 0.81 | 391.2 |
| Z | 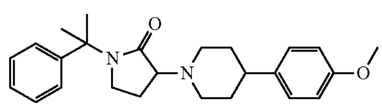 | 0.79 | 393.2 |
| AA | 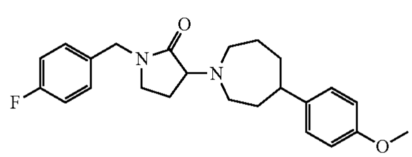 [SMILES: COc1ccc(C2CCCN(C3CCN(Cc4ccc(F)cc4)C3=O)CC2)cc1] | 0.78 | 397.2 |
| AB | 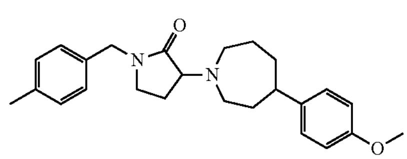 | 0.81 | 393.2 |
| AC | 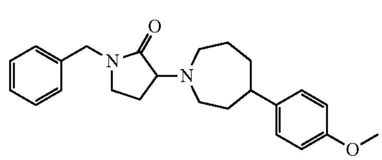 [SMILES: COc1ccc(C2CCCN(C3CCN(Cc4ccccc4)C3=O)CC2)cc1] | 0.77 | 379.2 |

TABLE 2-continued

Racemic 1-benzyl-3((4-methoxyphenyl)cycloalkylamino)pyrrolidin-2-ones

| Int. No. | Structure | LCMS R.T. (min) | LCMS Ion (M + H) |
|---|---|---|---|
| AD | 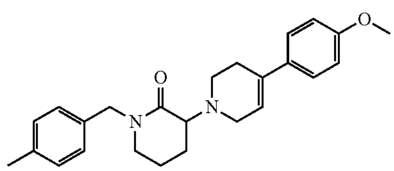 | 1.08 | 393.6 |
| AE | 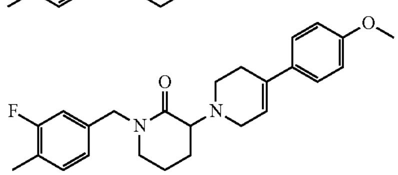 | 1.12 | 411.3 |
| AF | 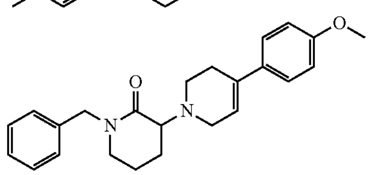 | 0.79 | 379.6 |
| AG | 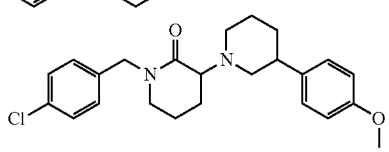 | 1.15 | 413.2 |
| AH | 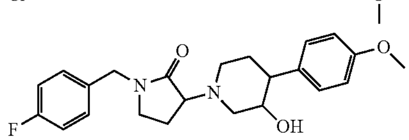 | 1.89 | 399.1 |
| AI | 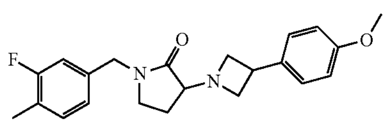 [SMILES: COc1ccc(C2CN(C3CCN(Cc4ccc(C)c(F)c4)C3=O)C2)cc1] | 1.03 | 369.2 |
| AJ | 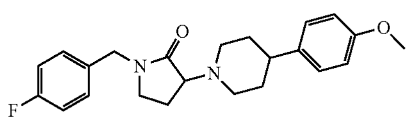 [SMILES: COc1ccc(C2CCN(C3CCN(Cc4ccc(F)cc4)C3=O)CC2)cc1] | 1.04 | 383.2 |

Final compounds were prepared via cleavage of the methoxy group of intermediates A-AJ using boron tribromide, followed in some cases by chiral chromatography to separate the individual enantiomers.

Example 1

1-(4-Fluorobenzyl)-3-(4-(4-hydroxyphenyl)piperidin-1-yl)pyrrolidin-2-one

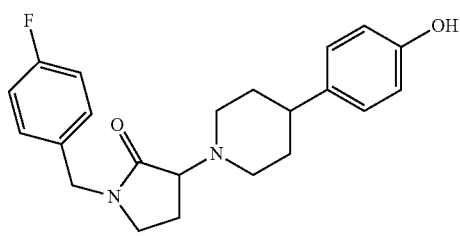 [SMILES: O=C1C(N2CCC(c3ccc(O)cc3)CC2)CCN1Cc1ccc(F)cc1]

To a solution of 1-(4-fluorobenzyl)-3-(4-(4-methoxyphenyl)piperidin-1-yl)pyrrolidin-2-one (AJ) (3 g, 7.9 mmol) in dry dichloromethane (100 mL) under a $N_2$ atmosphere at −78° C. was added 1 M boron tribromide in dichloromethane (39 mL, 39 mmol) and the resulting mixture was allowed to warm up to room temperature over 3 h, with stirring. The reaction was quenched with water (30 mL) and the organic layer was separated, washed with water and brine, and concentrated. The crude product was purified by flash chromatography on silica gel using 15% EtOAc in petroleum ether to yield racemic 1-(4-fluorobenzyl)-3-(4-(4-hydroxyphenyl)piperidin-1-yl)pyrrolidin-2-one (2.1 g, 73%); $^1$H NMR (400 MHz, DMSO-$d_6$) δ ppm 1.49-1.74 (m, 4H) 1.90-2.11 (m, 2H) 2.24-2.42 (m, 2H) 2.65-2.80 (m, 2H) 2.99-3.23 (m, 3H) 3.40-3.54 (m, 1H) 4.27-4.46 (m, 2H) 6.61-6.70 (m, 2H) 6.95-7.04 (m, 2H) 7.17-7.31 (m, 4H) 9.10-9.16 (m, 1H). LCMS: R.T. 0.880 min. LCMS (ES-API), 369.2 m/z (M+H). A portion of the racemate (40 mg) was separated via SFC on a Chiralpak-IA 250 mm×4.6 mm, 5 microm column eluting with 35% solvent B, where solvent A=$CO_2$ and solvent B=0.3% DEA in methanol at a total flow of 3 mL/min. Peak 1 showed a RT of 4.35 min and Peak 2 showed a RT of 6.29 min.

Example 2a (S)-1-(4-Fluorobenzyl)-3-(4-(4-hydroxyphenyl)-piperidin-1-yl)pyrrolidin-2-one

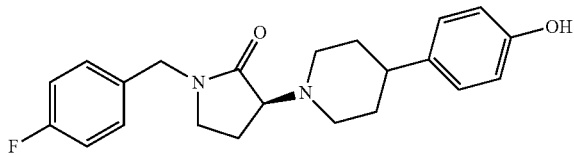 [SMILES: O=C1[C@@H](N2CCC(c3ccc(O)cc3)CC2)CCN1Cc1ccc(F)cc1]

First eluting enantiomer, Peak 1, from the chiral separation of Example 1. Yield 11 mg. LC/MS RT=1.275 min. (M+H)$^+$=369.2; $^1$H NMR (400 MHz, DMSO-d$_6$) δ ppm 1.47-1.59 (m, 1H) 1.65-1.75 (m, 1H) 1.84-1.96 (m, 1H) 2.03-2.12 (m, 1H) 2.24-2.43 (m, 1H) 2.63-2.72 (m, 2H) 2.72-2.85 (m, 2H) 2.96-3.05 (m, 2H) 3.09-3.23 (m, 2H) 3.41-3.54 (m, 1H) 4.23-4.50 (m, 2H) 6.58-6.71 (m, 2H) 6.96-7.10 (m, 2H) 7.15-7.21 (m, 2H) 7.26-7.34 (m, 2H) 9.06-9.19 (m, 1H).

Example 2b (R)-1-(4-Fluorobenzyl)-3-(4-(4-hydroxyphenyl)piperidin-1-yl)pyrrolidin-2-one

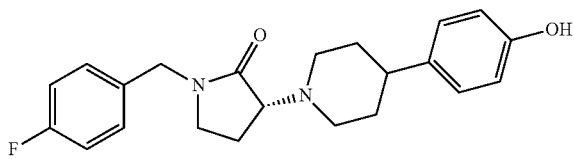 [SMILES: O=C1[C@H](N2CCC(c3ccc(O)cc3)CC2)CCN1Cc1ccc(F)cc1]

Second eluting enantiomer, Peak 2, from the chiral separation of Example 1. Yield 13 mg. LC/MS RT=1.277 min. (M+H)$^+$=369.2; $^1$H NMR (400 MHz, DMSO-d$_6$) δ ppm 1.47-1.59 (m, 1H) 1.65-1.75 (m, 1H) 1.84-1.96 (m, 1H) 2.03-2.12 (m, 1H) 2.24-2.43 (m, 1H) 2.63-2.72 (m, 2H) 2.72-2.85 (m, 2H) 2.96-3.05 (m, 2H) 3.09-3.23 (m, 2H) 3.41-3.54 (m, 1H) 4.23-4.50 (m, 2H) 6.58-6.71 (m, 2H) 6.96-7.10 (m, 2H) 7.15-7.21 (m, 2H) 7.26-7.34 (m, 2H) 9.06-9.19 (m, 1H).

Example 3

1-(4-Methylbenzyl)-3-(3-(4-hydroxyphenyl)piperidin-1-yl)pyrrolidin-2-one

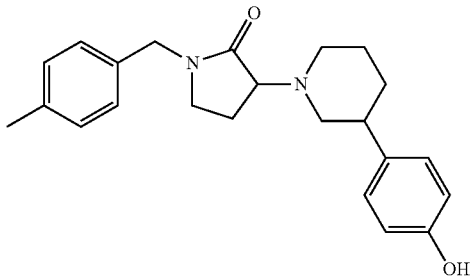 [SMILES: Cc1ccc(CN2CCC(N3CCCC(c4ccc(O)cc4)C3)C2=O)cc1]

Intermediate M (110 mg) was deprotected using the conditions in Example 1 to yield 103 mg product. LC/MS RT=1.48, 1.51 min. (M+H)$^+$=365; $^1$H NMR (400 MHz, DMSO-d$_6$) δ ppm 1.59-2.04 (m, 4H) 2.28 (d, J=5.52 Hz, 5H) 2.90-3.05 (m, 2H) 3.17 (s, 3H) 3.26 (d, J=6.53 Hz, 4H) 3.65-3.80 (m, 2H) 4.39 (d, J=3.01 Hz, 3H) 6.75 (d, J=8.53 Hz, 2H) 7.02-7.20 (m, 6H) 9.35-9.45 (m, 1H) 10.34-10.54 (m, 1H).

Example 4

1-(4-Fluorobenzyl)-3-(3-(4-hydroxyphenyl)piperidin-1-yl)pyrrolidin-2-one

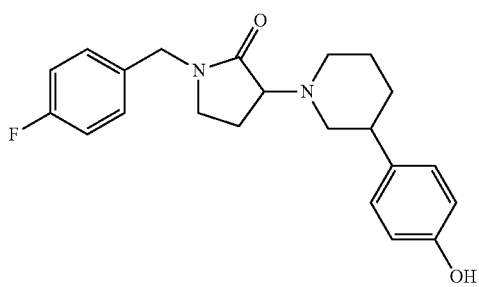 [SMILES: O=C1C(N2CCCC(c3ccc(O)cc3)C2)CCN1Cc1ccc(F)cc1]

Intermediate E (150 mg) was deprotected using the conditions in Example 1 to yield 80 mg product. LC/MS (Method N) RT=1.30, 1.41 min. (M+H)$^+$=369. $^1$H NMR (400 MHz, DMSO-d$_6$) δ ppm 1.27-1.39 (m, 1H) 1.47-1.56 (m, 1H) 1.68-1.82 (m, 1H) 1.86-1.96 (m, 1H) 2.00-2.08 (m, 1H) 2.10-2.22 (m, 1H) 2.30-2.37 (m, 1H) 2.53-2.60 (m, 1H) 2.61-2.74 (m, 1H) 2.85-2.94 (m, 1H) 3.07-3.15 (m, 1H) 3.40-3.50 (m, 1H) 4.21-4.46 (m, 2H) 6.66-6.73 (m, 2H) 6.97-7.04 (m, 1H) 7.06-7.18 (m, 2H) 7.20-7.27 (m, 2H) 9.08-9.16 (m, 1H).

Example 5

1-(3,4-Difluorobenzyl)-3-(4-(4-hydroxyphenyl)piperidin-1-yl)pyrrolidin-2-one

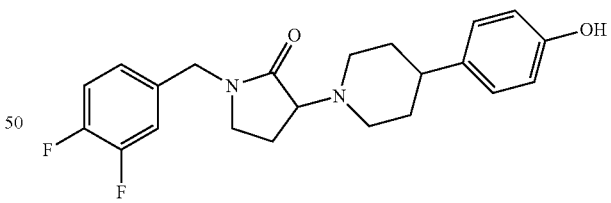

Intermediate N (150 mg) was deprotected using the conditions in Example 1 to yield 23 mg product. LC/MS RT=1.474 min. (M+H)$^+$=367; $^1$H NMR (400 MHz, DMSO-d$_6$) δ ppm 1.59-2.04 (m, 4H) 2.28 (d, J=5.52 Hz, 5H) 2.90-3.05 (m, 2H) 3.17 (s, 3H) 3.26 (d, J=6.53 Hz, 4H) 3.65-3.80 (m, 2H) 4.39 (d, J=3.01 Hz, 3H) 6.75 (d, J=8.53 Hz, 2H) 7.02-7.20 (m, 6H) 9.35-9.45 (m, 1H) 10.34-10.54 (m, 1H). A portion of the racemate (20 mg) was separated via SFC on a Chiralpak-AD H 250 mm×4.6 mm, 5 microm column eluting with 35% solvent B, where solvent A=CO$_2$ and solvent B=0.3% DEA in methanol at a total flow of 3 mL/min. Peak 1 showed a RT of 3.50 min and Peak 2 showed a RT of 7.17 min.

Example 6a (S)-1-(3,4-Difluorobenzyl)-3-(4-(4-hydroxyphenyl)piperidin-1-yl)pyrrolidin-2-one

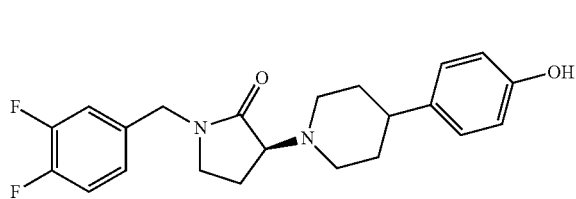 [SMILES: O=C1[C@@H](N2CCC(c3ccc(O)cc3)CC2)CCN1Cc1ccc(F)c(F)c1]

First eluting enantiomer, Peak 1, from the chiral separation of Example 5. Yield 1.5 mg. LC/MS RT=2.107 min. (M+H)$^+$=387; $^1$H NMR (400 MHz, CD$_3$OD) δ ppm 1.69-1.85 (m, 4H) 2.03-2.26 (m, 2H) 2.38-2.50 (m, 2H) 2.73-2.80 (m, 1H) 2.90 (d, J=11.04 Hz, 1H) 3.15-3.21 (m, 1H) 3.23-3.31 (m, 2H) 3.64 (t, J=8.78 Hz, 1H) 4.40-4.56 (m, 2H) 6.68-6.77 (m, 2H) 7.03-7.13 (m, 3H) 7.18-7.30 (m, 2H).

Example 6b (R)-1-(3,4-Difluorobenzyl)-3-(4-(4-hydroxyphenyl)piperidin-1-yl)pyrrolidin-2-one

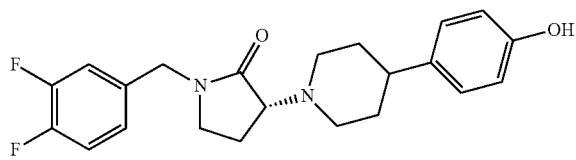 [SMILES: O=C1[C@H](N2CCC(c3ccc(O)cc3)CC2)CCN1Cc1ccc(F)c(F)c1]

Second eluting enantiomer, Peak 2, from the chiral separation of Example 5. Yield 1.8 mg. LC/MS RT=2.107 min. (M+H)$^+$=387; $^1$H NMR (400 MHz, CD$_3$OD) δ ppm 1.71-1.86 (m, 5H) 2.05-2.26 (m, 3H) 2.46 (td, J=10.67, 4.77 Hz, 3H) 2.75 (td, J=11.04, 3.51 Hz, 2H) 2.85-3.00 (m, 2H) 3.15-3.25 (m, 2H) 3.23-3.31 (m, 2H) 3.63-3.70 (m, 1H) 4.38-4.56 (m, 3H) 6.68-6.78 (m, 3H) 7.03-7.13 (m, 4H) 7.20-7.32 (m, 3H).

Example 7

1-(4-(Difluoromethoxy)benzyl)-3-(4-(4-hydroxyphenyl)pyrrolidin-1-yl)pyrrolidin-2-one

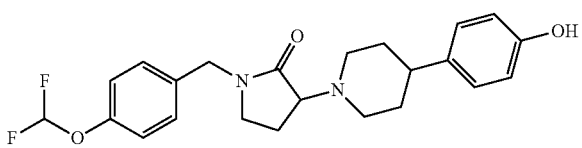 [SMILES: O=C1C(N2CCC(c3ccc(O)cc3)CC2)CCN1Cc1ccc(OC(F)F)cc1]

Intermediate P (209 mg) was deprotected using the conditions in Example 1 to yield 33 mg product. LC/MS RT=1.474 min. (M+H)$^+$=417; $^1$H NMR (400 MHz, DMSO-d$_6$) δ ppm 1.49-1.64 (m, 2H) 1.63-1.73 (m, 2H) 1.88-1.96 (m, 1H) 1.99-2.09 (m, 1H) 2.26-2.39 (m, 2H) 2.63-2.85 (m, 2H) 3.00-3.05 (m, 1H) 3.14 (d, J=8.03 Hz, 2H) 3.47 (s, 1H) 4.37 (d, J=18.07 Hz, 2H) 6.63-6.72 (m, 2H) 6.97-7.38 (m, 7H) 9.11 (s, 1H).

Example 8

1-(4-Fluorobenzyl)-3-(3-hydroxy-4-(4-hydroxyphenyl)piperidin-1-yl)pyrrolidin-2-one

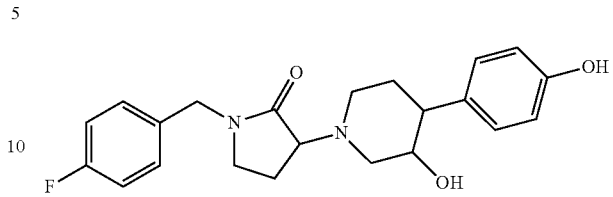

Intermediate AH (250 mg) was deprotected using the conditions in Example 1 to yield 36.8 mg product. LC/MS RT=0.815, 0.830 min. (M+H)$^+$=385; $^1$H NMR (400 MHz, DMSO-d6) δ ppm 1.51-1.68 (m, 2H) 1.86-1.96 (m, 1H) 2.01-2.11 (m, 1H) 2.13-2.24 (m, 1H) 2.34-2.43 (m, 0H) 2.54-2.73 (m, 1H) 2.83-2.95 (m, 1H) 3.17 (s, 5H) 3.40-3.55 (m, 3H) 4.35 (s, 3H) 6.66 (d, J=8.53 Hz, 2H) 7.01 (d, J=8.53 Hz, 2H) 7.17 (d, J=1.51 Hz, 2H) 7.26 (d, J=5.52 Hz, 2H). A portion of the product (31 mg) was separated into the individual diastereomers via SFC on a Chiralpak-AS H 250 mm×4.6 mm, 5 micron column eluting with 30% solvent B, where solvent A=CO$_2$ and solvent B=0.3% DEA in methanol at a total flow of 3 mL/min. Peak 1 showed a RT of 3.21 min, Peak 2 showed a RT of 3.76 min, Peak 3 showed a RT of 5.47 min, and Peak 4 showed a RT of 4.38 min.

Example 9a 1-(4-Fluorobenzyl)-3-(3-hydroxy-4-(4-hydroxyphenyl)piperidin-1-yl)pyrrolidin-2-one

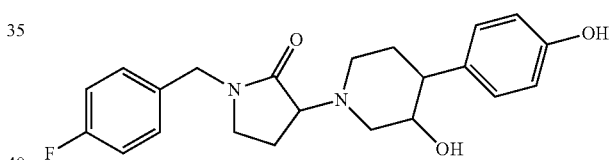

First eluting diastereomer, Peak 1, from the chiral separation of Example 8. Yield 4.5 mg. SFC (Method 108) RT=3.21 min. LC/MS RT=1.866 min. (M+H)$^+$=385; $^1$H NMR (400 MHz, CD$_3$OD) δ 7.29-7.33 (m, 2H), 7.07-7.12 (m, 4H), 6.75 (d, J=8.40 Hz, 2H), 4.41 (d, J=14.80 Hz, 1H), 4.53 (d, J=14.80 Hz, 1H), 3.77-3.78 (m, 1H), 3.65-3.70 (m, 1H), 3.25-3.31 (m, 3H), 2.78 (q, J=7.20 Hz, 2H), 2.23-2.30 (m, 3H), 2.09 (q, J=8.40 Hz, 1H), 1.75-1.78 (m, 2H).

Example 9b 1-(4-Fluorobenzyl)-3-(3-hydroxy-4-(4-hydroxyphenyl)-piperidin-1-yl)pyrrolidin-2-one

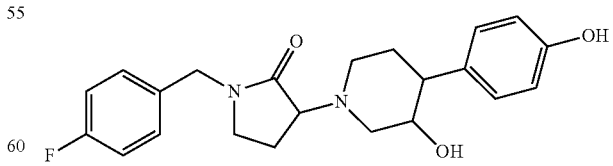

Second eluting diastereomer, Peak 2, from the chiral separation of Example 8. Yield 3.8 mg. SFC (Method 108) RT=3.76 min. LC/MS RT=1.872 min. (M+H)$^+$=385; $^1$H NMR 400 MHz (CD$_3$OD) δ 7.28-7.31 (m, 2H), 7.05-7.10 (m, 4H), 6.73 (d, J=8.40 Hz, 2H), 4.51 (d, J=14.80 Hz, 1H), 4.39 (d, J=14.40 Hz, 1H), 3.75-3.76 (m, 1H), 3.64-3.68 (m, 1H), 3.23-3.28 (m, 3H), 2.88 (q, J=7.20 Hz, 1H), 2.75 (s, 1H), 2.20-2.32 (m, 3H), 1.74-1.76 (m, 1H).

Example 9c 1-(4-Fluorobenzyl)-3-(3-hydroxy-4-(4-hydroxyphenyl)-piperidin-1-yl)pyrrolidin-2-one

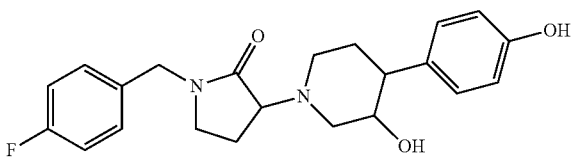 [SMILES: O=C1C(N2CCC(c3ccc(O)cc3)C(O)C2)CCN1Cc1ccc(F)cc1]

Third eluting diastereomer, Peak 3, from the chiral separation of Example 8. Yield 3.3 mg. SFC (Method 108) RT=5.47 min. LC/MS RT=1.866 min. (M+H)$^+$=385; $^1$H NMR (400 MHz, CD3OD) δ 7.30-7.33 (m, 2H), 7.07-7.12 (m, 4H), 6.75 (d, J=8.40 Hz, 2H), 4.54 (d, J=14.80 Hz, 1H), 4.42 (d, J=14.80 Hz, 1H), 3.77 (q, J=4.40 Hz, 1H), 3.67-3.72 (m, 1H), 3.25-3.34 (m, 2H), 2.99-3.01 (m, 2H), 2.30-2.49 (m, 3H), 2.07-2.10 (m, 1H), 1.77-1.80 (m, 2H).

Example 9d 1-(4-Fluorobenzyl)-3-(3-hydroxy-4-(4-hydroxyphenyl)piperidin-1-yl)pyrrolidin-2-one

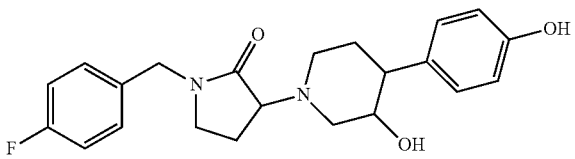 [SMILES: O=C1C(N2CCC(c3ccc(O)cc3)C(O)C2)CCN1Cc1ccc(F)cc1]

Fourth eluting diastereomer, Peak 4, from the chiral separation of Example 8. Yield 3.0 mg. SFC (Method 108) RT=4.38 min. LC/MS RT=1.869 min. (M+H)$^+$=385; $^1$H NMR (400 MHz, CD$_3$OD) δ 7.28-7.31 (m, 2H), 7.05-7.10 (m, 4H), 6.73 (d, J=8.40 Hz, 2H), 4.52 (d, J=14.80 Hz, 1H), 4.40 (d, J=14.80 Hz, 1H), 3.75 (q, J=4.40 Hz, 1H), 3.68 (t, J=18.00 Hz, 1H), 3.23-3.31 (m, 2H), 2.98 (t, J=14.00 Hz, 2H), 2.39-2.47 (m, 2H), 2.29 (q, J=6.40 Hz, 1H), 2.07 (q, J=8.40 Hz, 1H), 1.75-1.79 (m, 2H).

Example 10

1-(3,4-Difluorobenzyl)-3-(3-(4-hydroxyphenyl)azetidin-1-yl)pyrrolidin-2-one

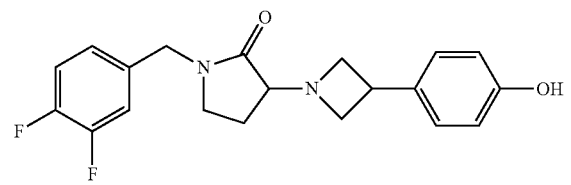 [SMILES: O=C1C(N2CC(c3ccc(O)cc3)C2)CCN1Cc1ccc(F)c(F)c1]

Intermediate Q (150 mg) was deprotected using the conditions in Example 1 to yield a crude product which was purified via preparative HPLC (Method B) to yield 95 mg product. LC/MS RT=1.245 min. (M+H)$^+$=359; $^1$H NMR (400 MHz, DMSO-d$_6$) δ ppm 1.59-1.71 (m, 1H) 1.99-2.16 (m, 1H) 3.08-3.26 (m, 9H) 3.48-3.55 (m, 2H) 3.63-3.73 (m, 2H) 4.36 (d, J=10.04 Hz, 2H) 6.70 (d, J=8.53 Hz, 2H) 7.05-7.12 (m, 1H) 7.15 (d, J=8.53 Hz, 2H) 7.22-7.33 (m, 1H) 7.37-7.47 (m, 1H) 8.90-9.52 (m, 1H).

Example 11

1-(4-Fluorobenzyl)-3-(3-(4-hydroxyphenyl)azetidin-1-yl)pyrrolidin-2-one

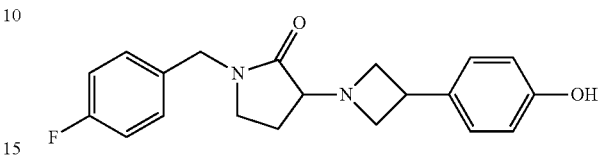

Intermediate R (160 mg) was deprotected using the conditions in Example 1 to yield a crude product which was purified via preparative HPLC (Method B) to yield 84 mg product. LC/MS RT=1.182 min. (M+H)$^+$=341; $^1$H NMR (400 MHz, DMSO-d$_6$) δ ppm 1.52-1.71 (m, 1H) 1.99-2.13 (m, 1H) 3.08-3.27 (m, 6H) 3.47-3.55 (m, 1H) 3.62-3.75 (m, 2H) 4.35 (d, J=11.55 Hz, 2H) 6.67-6.77 (m, 2H) 7.11-7.22 (m, 4H) 7.27 (dd, J=8.53, 5.52 Hz, 2H) 9.21 (s, 1H).

Example 12

1-Benzyl-3-(4-(4-hydroxyphenyl)piperidin-1-yl)pyrrolidin-2-one

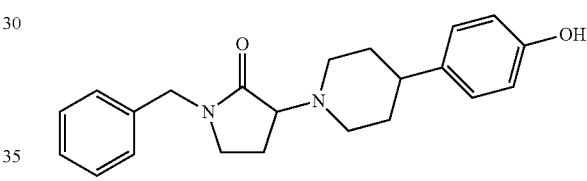

Intermediate A (1000 mg) was deprotected using the conditions in Example 1 to yield a crude product which was purified via preparative HPLC (Method B) to yield 290 mg product. LC/MS RT=1.394 min. (M+H)$^+$=351. 400 MHz, DMSO-d6: δ ppm 1.58-1.72 (m, 4H), 1.91-1.94 (m, 3H), 2.30-2.37 (m, 2H), 2.67-2.81 (m, 2H), 3.15-3.31 (m, 4H), 4.39 (q, J=50.00 Hz, 3H), 6.68 (d, J=8.40 Hz, 2H), 7.02 (d, J=8.40 Hz, 2H), 7.22-7.38 (m, 8H), 9.13 (s, 1H). Most of the product (250 mg) was separated into the individual enantiomers via SFC on a Chiralpak-IA 250 mm×4.6 mm, 5 microm column eluting with 30% solvent B, where solvent A=CO$_2$ and solvent B=0.3% DEA in methanol at a total flow of 3 mL/min. Peak 1 showed a RT of 5.84 min and Peak 2 showed a RT of 8.33 min.

Example 13a (S)-1-Benzyl-3-(4-(4-hydroxyphenyl)piperidin-1-yl)pyrrolidin-2-one

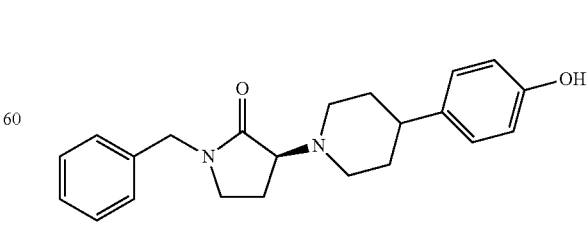

First eluting enantiomer, Peak 1, from the chiral separation of compound 12. Yield 88 mg. LC/MS RT=1.780 min.

(M+H)⁺=351.2; ¹H NMR (400 MHz, methanol-d₄) δ ppm 1.74-1.84 (m, 4H) 2.02-2.12 (m, 1H) 2.15-2.23 (m, 1H) 2.47 (td, J=10.79, 4.52 Hz, 2H) 2.76 (td, J=11.04, 3.51 Hz, 1H) 2.90 (d, J=11.04 Hz, 1H) 3.12-3.20 (m, 1H) 3.21-3.29 (m, 2H) 3.64 (t, J=9.04 Hz, 1H) 4.38-4.60 (m, 2H) 6.67-6.76 (m, 2H) 7.04-7.09 (m, 2H) 7.25-7.40 (m, 5H).

Example 13b (R)-1-Benzyl-3-(4-(4-hydroxyphenyl)piperidin-1-yl)pyrrolidin-2-one

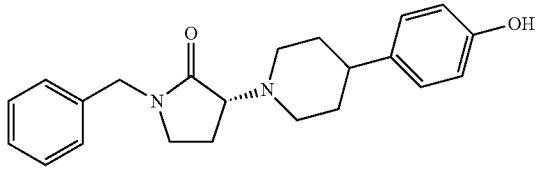 [SMILES: O=C1[C@H](N2CCC(c3ccc(O)cc3)CC2)CCN1Cc1ccccc1]

Second eluting enantiomer, Peak 2, from the chiral separation of compound 12. Yield 96 mg. LC/MS RT=1.783 min. (M+H)⁺=351.2; ¹H NMR (400 MHz, methanol-d₄) δ ppm 1.74-1.86 (m, 4H) 2.02-2.13 (m, 1H) 2.15-2.25 (m, 1H) 2.41-2.52 (m, 2H) 2.76 (td, J=11.04, 3.51 Hz, 1H) 2.90 (d, J=11.04 Hz, 1H) 3.14-3.30 (m, 2H) 3.64 (t, J=9.04 Hz, 1H) 4.38-4.58 (m, 2H) 6.69-6.75 (m, 2H) 7.03-7.09 (m, 2H) 7.25-7.39 (m, 5H).

Example 14

1-(3-Chloro-4-methylbenzyl)-3-(4-(4-hydroxyphenyl)piperidin-1-yl)pyrrolidin-2-one

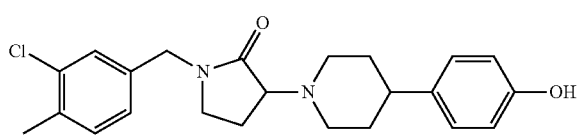

Intermediate K (200 mg) was deprotected using the conditions in Example 1 to yield a crude product which was purified via preparative HPLC (Method B) to yield 2 mg product. LC/MS RT=1.677 min. (M+H)⁺=399.0; ¹H NMR (400 MHz, DMSO-d₆) δ ppm 1.51-1.72 (m, 4H) 1.86-1.98 (m, 1H) 2.02-2.11 (m, 1H) 2.31 (s, 6H) 2.69-2.81 (m, 2H) 2.99-3.06 (m, 1H) 3.10-3.21 (m, 2H) 3.44-3.51 (m, 1H) 4.28-4.41 (m, 2H) 6.63-6.72 (m, 2H) 7.01 (s, 2H) 7.07-7.13 (m, 1H) 7.25-7.35 (m, 2H) 9.08-9.15 (m, 1H).

Example 15

1-(4-Chloro-3-fluorobenzyl)-3-(4-(4-hydroxyphenyl)piperidin-1-yl)pyrrolidin-2-one

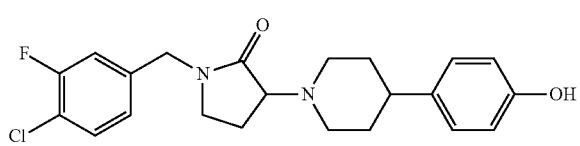 [SMILES: O=C1C(N2CCC(c3ccc(O)cc3)CC2)CCN1Cc1ccc(Cl)c(F)c1]

Intermediate J (200 mg) was deprotected using the conditions in Example 1 to yield a crude product which was purified via preparative HPLC (Method B) to yield 15 mg product. LC/MS RT=1.575 min. (M+H)⁺=403.0; ¹H NMR (400 MHz, DMSO-d₆) δ ppm 1.50-1.60 (m, 3H) 1.64-1.73 (m, 3H) 1.87-1.97 (m, 2H) 2.04-2.13 (m, 2H) 2.28-2.39 (m, 3H) 2.64-2.72 (m, 2H) 2.74-2.81 (m, 1H) 3.03 (d, J=11.55 Hz, 2H) 3.12-3.22 (m, 3H) 3.49 (t, J=8.53 Hz, 2H) 4.31-4.48 (m, 3H) 6.64-6.72 (m, 3H) 7.02 (d, J=8.53 Hz, 3H) 7.10 (dd, J=8.53, 1.51 Hz, 2H) 7.26 (dd, J=10.04, 2.01 Hz, 2H) 7.57 (t, J=8.03 Hz, 2H) 9.12 (br. s., 1H).

Example 16

1-Benzyl-3-(3-(4-hydroxyphenyl)azetidin-1-yl)pyrrolidin-2-one

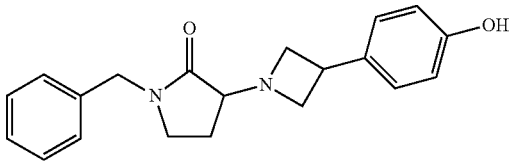 [SMILES: O=C1C(N2CC(c3ccc(O)cc3)C2)CCN1Cc1ccccc1]

Intermediate L (150 mg) was deprotected using the conditions in Example 1 to yield a crude product which was purified via preparative HPLC (Method B) to yield 40 mg product. LC/MS RT=1.154 min. (M+H)⁺=323.0; ¹H NMR (400 MHz, DMSO-d6) δ ppm 1.57-1.68 (m, 1H) 2.03-2.12 (m, 1H) 3.11-3.25 (m, 4H) 3.51 (t, J=7.37 Hz, 1H) 3.62-3.74 (m, 2H) 4.28-4.44 (m, 2H) 6.67-6.74 (m, 2H) 7.13-7.38 (m, 7H) 9.23 (br. s., 1H).

Example 17

1-(4-Chlorobenzyl)-3-(4-(4-hydroxyphenyl)piperidin-1-yl)pyrrolidin-2-one

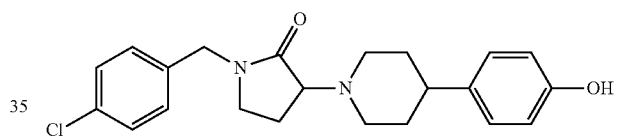

Intermediate C (150 mg) was deprotected using the conditions in Example 1 to yield a crude product which was purified via preparative HPLC (Method B) to yield 24 mg product. LC/MS RT=1.576 min. (M+H)⁺=385; ¹H NMR (400 MHz, DMSO-d₆) δ ppm 1.57-1.73 (m, 1H) 2.19-2.33 (m, 2H) 2.62 (d, J=7.93 Hz, 4H) 2.77 (d, J=18.51 Hz, 3H) 3.09-3.21 (m, 3H) 3.40-3.46 (m, 1H) 4.36 (s, 2H) 6.63-6.77 (m, 2H) 7.00 (d, J=8.69 Hz, 2H) 7.15-7.26 (m, 2H) 7.33-7.49 (m, 2H) 9.03-9.34 (m, 1H). The racemic product was separated into the individual enantiomers via SFC on a Chiralpak-IA 250 mm×4.6 mm, 5 microm column eluting with 30% solvent B, where solvent A=CO₂ and solvent B=0.3% DEA in methanol at a total flow of 3 mL/min. Peak 1 showed a RT of 5.94 min and Peak 2 showed a RT of 10.59 min.

Example 18a (S)-1-(4-Chlorobenzyl)-3-(4-(4-hydroxyphenyl)piperidin-1-yl)pyrrolidin-2-one

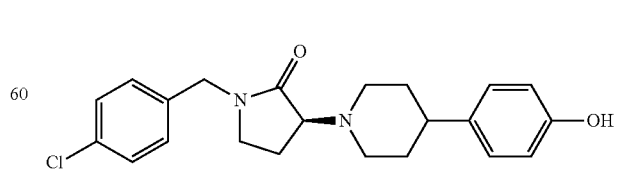

First eluting enantiomer, Peak 1, from the chiral separation of compound 17. Yield 3.9 mg. LC/MS RT=2.315 min. (M+H)⁺=385.0; ¹H NMR (400 MHz, methanol-d₄) δ ppm 1.68-1.85 (m, 4H) 1.99-2.09 (m, 1H) 2.16-2.24 (m, 1H) 2.37-2.50 (m, 2H) 2.70-2.79 (m, 1H) 2.86-2.95 (m, 1H) 3.23-3.32 (m, 3H) 3.56-3.66 (m, 1H) 4.37-4.45 (m, 1H) 4.48-4.58 (m, 1H) 6.71 (d, J=8.53 Hz, 2H) 7.01-7.13 (m, 2H) 7.20-7.30 (m, 2H) 7.36 (s, 2H).

Example 18b (R)-1-(4-Chlorobenzyl)-3-(4-(4-hydroxyphenyl)piperidin-1-yl)pyrrolidin-2-one

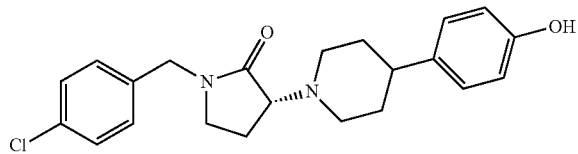 [SMILES: O=C1[C@H](N2CCC(c3ccc(O)cc3)CC2)CCN1Cc1ccc(Cl)cc1]

Second eluting enantiomer, Peak 2, from the chiral separation of compound 17. Yield 4.7 mg. LC/MS RT=2.350 min. (M+H)$^+$=385.2; $^1$H NMR (400 MHz, methanol-d4) δ ppm 1.68-1.85 (m, 4H) 1.99-2.09 (m, 1H) 2.16-2.24 (m, 1H) 2.37-2.50 (m, 2H) 2.70-2.79 (m, 1H) 2.86-2.95 (m, 1H) 3.23-3.32 (m, 3H) 3.56-3.66 (m, 1H) 4.37-4.45 (m, 1H) 4.48-4.58 (m, 1H) 6.71 (d, J=8.53 Hz, 2H) 7.01-7.13 (m, 2H) 7.20-7.30 (m, 2H) 7.36 (s, 2H).

Example 19

1-(3-Fluoro-4-methylbenzyl)-3-(4-(4-hydroxyphenyl)piperidin-1-yl)pyrrolidin-2-one

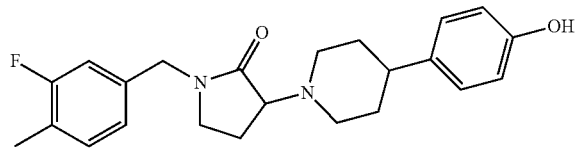 [SMILES: Cc1ccc(CN2CCC(N3CCC(c4ccc(O)cc4)CC3)C2=O)cc1F]

Intermediate D (120 mg) was deprotected using the conditions in Example 1 to yield a crude product which was purified via preparative HPLC (Method B) to yield 18 mg product. LC/MS RT=1.552 min. (M+H)$^+$=383.0; $^1$H NMR (300 MHz, DMSO-d$_6$) δ ppm 1.48-1.92 (m, 4H) 2.21 (d, J=1.13 Hz, 4H) 2.27-2.38 (m, 2H) 2.68-2.86 (m, 1H) 2.97-3.18 (m, 2H) 3.41-3.65 (m, 1H) 4.21-4.48 (m, 2H) 6.56-6.74 (m, 2H) 6.89-7.11 (m, 4H) 7.21-7.35 (m, 1H).

Example 20

1-(3-Fluoro-4-methylbenzyl)-3-(3-(4-hydroxyphenyl)azetidin-1-yl)pyrrolidin-2-one

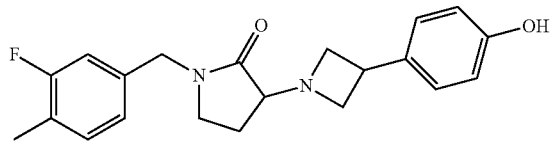 [SMILES: Cc1ccc(CN2CCC(N3CC(c4ccc(O)cc4)C3)C2=O)cc1F]

Intermediate AI (120 mg) was deprotected using the conditions in Example 1 to yield a crude product which was purified via preparative HPLC (Method B) to yield 35 mg product. LC/MS RT=1.400 min. (M+H)$^+$=355.0; $^1$H NMR (400 MHz, DMSO-d$_6$) δ ppm 1.59-1.68 (m, 1H) 2.02-2.12 (m, 1H) 2.21 (d, J=2.01 Hz, 3H) 3.06-3.15 (m, 2H) 3.22-3.33 (m, 2H) 3.51 (s, 2H) 3.62-3.76 (m, 3H) 4.33 (d, J=14.56 Hz, 2H) 6.61-6.77 (m, 2H) 6.87-7.02 (m, 2H) 7.09-7.21 (m, 2H) 7.25 (s, 1H). A portion of the product (25 mg) was separated into the individual enantiomers via SFC on a Chiralpak-IA 250 mm×4.6 mm, 5 microm column eluting with 40% solvent B, where solvent A=CO$_2$ and solvent B=0.3% DEA in methanol at a total flow of 4 mL/min. Peak 1 showed a RT of 1.81 min and Peak 2 showed a RT of 2.38 min.

Example 21a (R)-1-(3-Fluoro-4-methylbenzyl)-3-(3-(4-hydroxyphenyl)azetidin-1-yl)pyrrolidin-2-one

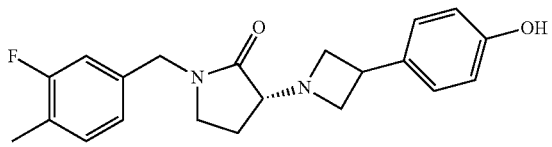 [SMILES: Cc1ccc(CN2CC[C@@H](N3CC(c4ccc(O)cc4)C3)C2=O)cc1F]

First eluting enantiomer, peak 1, from the chiral separation of Example 20. Yield 5.6 mg. LC/MS RT=2.056 min. (M+H)$^+$=355.0; $^1$H NMR (400 MHz, methanol-d$_4$) δ ppm 1.65-1.82 (m, 1H) 2.26 (d, J=2.01 Hz, 4H) 3.29 (d, J=16.56 Hz, 1H) 3.43-3.51 (m, 2H) 3.71 (s, 1H) 3.76-3.84 (m, 1H) 3.89-4.02 (m, 1H) 4.42 (d, J=17.07 Hz, 2H) 6.65-6.79 (m, 2H) 6.94-7.05 (m, 2H) 7.14-7.27 (m, 3H).

Example 21b (S)-1-(3-Fluoro-4-methylbenzyl)-3-(3-(4-hydroxyphenyl)azetidin-1-yl)pyrrolidin-2-one

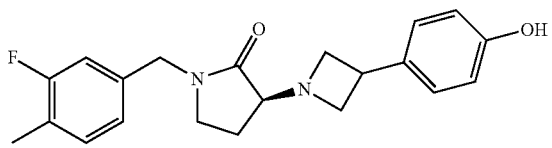 [SMILES: Cc1ccc(CN2CC[C@H](N3CC(c4ccc(O)cc4)C3)C2=O)cc1F]

Second eluting enantiomer, peak 2, from the chiral separation of Example 20. Yield 4.1 mg. LC/MS RT=2.043 min. (M+H)$^+$=355.0; $^1$H NMR (400 MHz, methanol-d$_4$) δ ppm 1.65-1.82 (m, 1H) 2.26 (d, J=2.01 Hz, 4H) 3.29 (d, J=16.56 Hz, 1H) 3.43-3.51 (m, 2H) 3.71 (s, 1H) 3.76-3.84 (m, 1H) 3.89-4.02 (m, 1H) 4.42 (d, J=17.07 Hz, 2H) 6.65-6.79 (m, 2H) 6.94-7.05 (m, 2H) 7.14-7.27 (m, 3H).

Example 22

3-(4-(4-Hydroxyphenyl)piperidin-1-yl)-1-(4-methylbenzyl)pyrrolidin-2-one

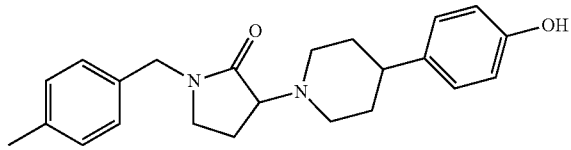 [SMILES: Cc1ccc(CN2CCC(N3CCC(c4ccc(O)cc4)CC3)C2=O)cc1]

Intermediate F (1000 mg) was deprotected using the conditions in Example 1 to yield a crude product which was purified via preparative HPLC (Method B) to yield 98 mg product. LC/MS RT=1.544 min. (M+H)$^+$=365; $^1$H NMR (400 MHz, DMSO-d$_6$) δ ppm 1.48-1.81 (m, 4H) 1.84-2.16 (m, 2H) 2.28 (s, 5H) 2.60-2.88 (m, 2H) 2.95-3.25 (m, 3H) 3.40-3.55 (m, 1H) 4.21-4.46 (m, 2H) 6.62-7.18 (m, 8H) 9.12 (br. s., 1H). The racemate was separated into the individual enantiomers via SFC on a Chiralpak-IA 250 mm×4.6 mm, 5 microm column eluting with 30% solvent B, where solvent A=CO$_2$ and solvent B=0.3% DEA in methanol at a total flow of 3 mL/min. Peak 1 showed a RT of 6.67 min and Peak 2 showed a RT of 9.74 min.

Example 23a (S)-3-(4-(4-Hydroxyphenyl)piperidin-1-yl)-1-(4-methylbenzyl)pyrrolidin-2-one

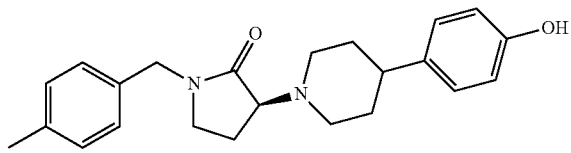 [SMILES: Cc1ccc(CN2CC[C@H](N3CCC(c4ccc(O)cc4)CC3)C2=O)cc1]

First eluting enantiomer, peak 1, from the chiral separation of Example 22. Yield 6 mg. LC/MS RT=1.849 min. (M+H)$^+$=365.2 1H NMR (400 MHz, methanol-d4) δ ppm 1.79 (ddd, J=9.91, 6.15, 4.02 Hz, 4H) 1.99-2.13 (m, 1H) 2.14-2.23 (m, 1H) 2.33 (s, 3H) 2.46 (d, J=4.02 Hz, 2H) 2.75 (d, J=3.51 Hz, 1H) 2.83-2.93 (m, 1H) 3.10-3.30 (m, 3H) 3.62 (t, J=8.78 Hz, 1H) 4.31-4.55 (m, 2H) 6.67-6.77 (m, 2H) 7.02-7.10 (m, 2H) 7.17 (br. s., 0H).

Example 23b (R)-3-(4-(4-Hydroxyphenyl)piperidin-1-yl)-1-(4-methylbenzyl)pyrrolidin-2-one

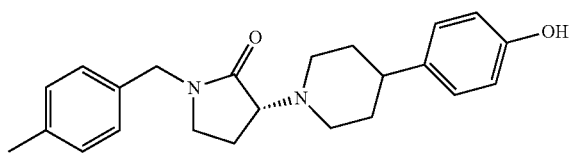 [SMILES: Cc1ccc(CN2CC[C@@H](N3CCC(c4ccc(O)cc4)CC3)C2=O)cc1]

Second eluting enantiomer, peak 2, from the chiral separation of Example 22. Yield 34 mg. LC/MS RT=1.841 min. (M+H)$^+$=365.2 1H NMR (400 MHz, methanol-d4) δ ppm 1.66-1.84 (m, 4H) 2.01-2.21 (m, 2H) 2.33 (s, 3H) 2.36-2.49 (m, 2H) 2.73 (br. s., 1H) 2.86 (br. s., 1H) 3.06-3.28 (m, 3H) 3.30-3.33 (m, 1H) 3.60 (s, 1H) 4.30-4.53 (m, 2H) 6.72 (d, J=8.53 Hz, 2H) 7.05 (d, J=8.03 Hz, 2H) 7.10-7.22 (m, 4H).

Example 24

1-(4-Hydroxybenzyl)-3-(4-(4-hydroxyphenyl)piperidin-1-yl)pyrrolidin-2-one

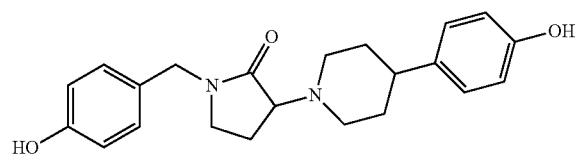 [SMILES: O=C1C(N2CCC(c3ccc(O)cc3)CC2)CCN1Cc1ccc(O)cc1]

Step A. 1-(4-Methoxybenzyl)-3-(4-(4-methoxyphenyl)piperidin-1-yl)pyrrolidin-2-one

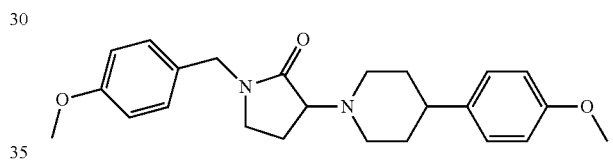

A mixture of 1-(4-methoxybenzyl)-3-(4-(4-methoxyphenyl)-5,6-dihydropyridin-1(2H)-yl)pyrrolidin-2-one (G) (400 mg, 1.02 mmol), MeOH (4 ml) and ethanol (8 ml) was flushed with nitrogen, followed by the addition of 10% Pd/C (108 mg). Then the mixture was stirred overnight at rt and 25 psi hydrogen pressure. The catalyst was removed by filtration through Celite and the filtrate was concentrated under vacuum. Yield: 400 mg. LCMS (method F) RT 2.36 min, m/z 395.2 (MH$^+$).

Step B. 1-(4-Hydroxybenzyl)-3-(4-(4-hydroxyphenyl)piperidin-1-yl)pyrrolidin-2-one The product from step A was deprotected using the conditions in Example 1 to yield a crude product which was purified via preparative HPLC (Method B) to yield 60 mg of the titled compound of Example 24. LC/MS RT=1.012 min. (M+H)$^+$=367.0 $^1$H NMR (400 MHz, DMSO-d$_6$) δ ppm 1.44-1.61 (m, 2H) 1.66-1.77 (m, 2H) 1.91 (s, 2H) 1.99-2.09 (m, 1H) 2.23-2.41 (m, 2H) 2.60-2.80 (m, 2H) 3.08 (s, 3H) 3.42-3.52 (m, 1H) 3.91 (s, 1H) 4.20-4.34 (m, 2H) 6.60-6.77 (m, 4H) 7.02 (d, J=8.03 Hz, 4H) 9.10 (s, 1H) 9.34 (s, 1H). A portion of the product (50 mg) was separated into the individual enantiomers via SFC on a Chiralpak-IA 250 mm×4.6 mm, 5 microm column eluting with 30% solvent B, where solvent A=CO$_2$ and solvent B=0.3% DEA in methanol at a total flow of 3 mL/min. Peak 1 showed a RT of 5.12 min and Peak 2 showed a RT of 6.47 min.

Example 25a (S)-1-(4-Hydroxybenzyl)-3-(4-(4-hydroxyphenyl)piperidin-1-yl)pyrrolidin-2-one

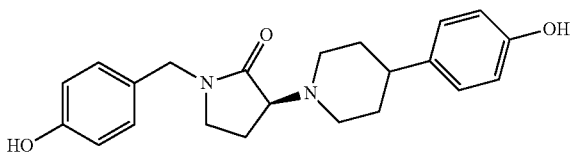 [SMILES: O=C1[C@@H](N2CCC(c3ccc(O)cc3)CC2)CCN1Cc1ccc(O)cc1]

First eluting enantiomer, peak 1, from the chiral separation of Example 24. Yield 18 mg. LC/MS RT=1.546 min. (M+H)$^+$=367.2 $^1$H NMR (400 MHz, methanol-d$_4$) δ ppm 1.66-1.83 (m, 4H) 1.96-2.21 (m, 2H) 2.38-2.51 (m, 2H) 2.73 (td, J=11.04, 3.51 Hz, 1H) 2.83-2.95 (m, 1H) 3.08-3.31 (m, 3H) 3.60 (t, J=8.78 Hz, 1H) 4.23-4.46 (m, 2H) 6.65-6.82 (m, 4H) 7.00-7.17 (m, 4H).

Example 25b (R)-1-(4-Hydroxybenzyl)-3-(4-(4-hydroxyphenyl)piperidin-1-yl)pyrrolidin-2-one

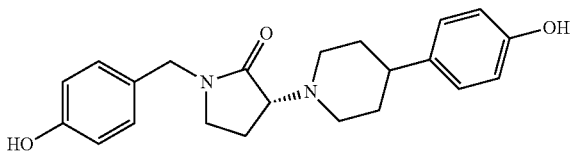 [SMILES: O=C1[C@H](N2CCC(c3ccc(O)cc3)CC2)CCN1Cc1ccc(O)cc1]

Second eluting enantiomer, peak 2, from the chiral separation of Example 24. Yield 20 mg. LC/MS RT=1.544 min. (M+H)$^+$=367.2 $^1$H NMR (400 MHz, methanol-d$_4$) δ ppm 1.66-1.84 (m, 4H) 1.98-2.08 (m, 1H) 2.11-2.21 (m, 1H) 2.38-2.49 (m, 2H) 2.74 (td, J=11.04, 3.51 Hz, 1H) 2.89 (d, J=2.01 Hz, 1H) 3.08-3.30 (m, 3H) 3.60 (t, J=8.53 Hz, 1H) 4.23-4.35 (m, 1H) 4.40-4.48 (m, 1H) 6.67-6.80 (m, 4H) 7.02-7.17 (m, 4H).

Example 26

1-(3,4-Dimethylbenzyl)-3-(4-(4-hydroxyphenyl)piperidin-1-yl)pyrrolidin-2-one

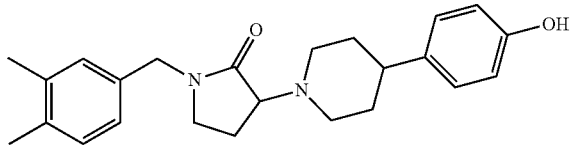 [SMILES: Cc1ccc(CN2CCC(N3CCC(c4ccc(O)cc4)CC3)C2=O)cc1C]

Intermediate H (200 mg) was deprotected using the conditions in Example 1 to yield a crude product which was purified via preparative HPLC (Method B) to yield 21 mg product. LC/MS RT=1.669 min. (M+H)$^+$=379.0 $^1$H NMR (400 MHz, DMSO-d$_6$) δ ppm 1.54-1.62 (m, 2H) 1.90 (d, J=13.05 Hz, 3H) 2.03-2.13 (m, 1H) 2.65-2.81 (m, 2H) 2.96-3.03 (m, 1H) 3.10 (s, 2H) 3.45 (s, 1H) 3.74 (s, 3H) 4.20-4.41 (m, 2H) 4.74 (s, 1H) 6.84-6.95 (m, 2H) 7.11-7.24 (m, 3H) 7.26-7.36 (m, 2H) 7.49 (dd, J=8.28, 1.25 Hz, 2H).

Example 27

3-(3-(4-Hydroxyphenyl)azetidin-1-yl)-1-(4-methylbenzyl)pyrrolidin-2-one

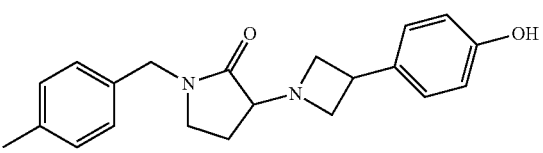 [SMILES: Cc1ccc(CN2CCC(N3CC(c4ccc(O)cc4)C3)C2=O)cc1]

Intermediate I (110 mg) was deprotected using the conditions in Example 1 to yield a crude product which was purified via preparative HPLC (Method B) to yield 44 mg product. LC/MS RT=1.341 min. (M+H)$^+$=337.0 $^1$H NMR (400 MHz, DMSO-d$_6$) δ ppm 1.56-1.66 (m, 1H) 2.08 (s, 1H) 2.29 (s, 3H) 3.11 (d, J=1.51 Hz, 3H) 3.23 (s, 2H) 3.46-3.53 (m, 1H) 3.61-3.75 (m, 2H) 4.31 (d, J=13.05 Hz, 2H) 6.65-6.75 (m, 2H) 7.05-7.20 (m, 6H) 9.19-9.27 (m, 1H). A portion of the product (34 mg) was separated into the individual enantiomers via SFC on a Lux Cellulose 2 250 mm×4.6 mm, 5 microm column eluting with 40% solvent B, where solvent A=

CO$_2$ and solvent B=0.3% DEA in methanol at a total flow of 3 mL/min. Peak 1 showed a RT of 4.65 min and Peak 2 showed a RT of 3.54 min.

Example 28a (S)-3-(3-(4-Hydroxyphenyl)azetidin-1-yl)-1-(4-methylbenzyl)pyrrolidin-2-one

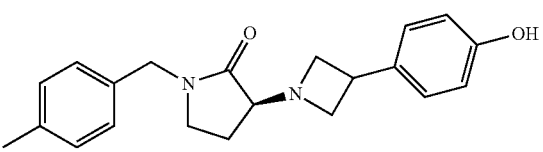 [SMILES: Cc1ccc(CN2CC[C@H](N3CC(c4ccc(O)cc4)C3)C2=O)cc1]

First eluting enantiomer, peak 1, from the chiral separation of Example 27. Yield 8 mg. LC/MS RT=1.683 min. (M+H)$^+$=337.2 $^1$H NMR (400 MHz, methanol-d$_4$) δ ppm 1.68-1.81 (m, 1H) 2.18-2.24 (m, 1H) 2.33 (s, 4H) 3.13-3.30 (m, 2H) 3.47 (s, 2H) 3.66-3.75 (m, 1H) 3.78-3.85 (m, 1H) 3.90-4.00 (m, 1H) 4.41 (d, J=7.03 Hz, 2H) 6.76 (d, J=8.53 Hz, 2H) 7.08-7.22 (m, 6H).

Example 28b (R)-3-(3-(4-Hydroxyphenyl)azetidin-1-yl)-1-(4-methylbenzyl)-pyrrolidin-2-one

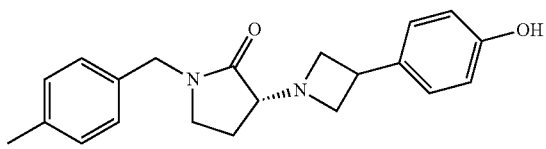

Second eluting enantiomer, peak 2, from the chiral separation of Example 27. Yield 6 mg. LC/MS RT=1.683 min. (M+H)$^+$=337.2 $^1$H NMR (400 MHz, methanol-d$_4$) δ ppm 1.71-1.81 (m, 1H) 2.19-2.26 (m, 1H) 2.33 (s, 3H) 3.04 (s, 1H) 3.15-3.26 (m, 1H) 3.24 (s, 2H) 3.45-3.58 (m, 2H) 3.68-3.73 (m, 1H) 3.78-3.85 (m, 1H) 3.91-4.00 (m, 1H) 4.41 (d, J=7.03 Hz, 2H) 6.67-6.80 (m, 2H) 7.10-7.22 (m, 6H).

Example 29

1-Benzyl-3-(4-(4-hydroxy-2-methylphenyl)piperidin-1-yl)pyrrolidin-2-one

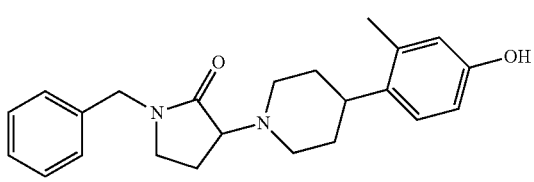 [SMILES: Cc1cc(O)ccc1C1CCN(C2CCN(Cc3ccccc3)C2=O)CC1]

Intermediate S (200 mg) was deprotected using the conditions in Example 1 to yield a crude product which was purified via preparative HPLC (Method B) to yield 30 mg product. LC/MS RT=1.47 min. (M+H)$^+$=365.2 $^1$H NMR (400 MHz, DMSO-d$_6$) δ ppm 1.47-1.67 (m, 4H) 1.84-1.98 (m, 1H) 2.01-2.13 (m, 1H) 2.20 (s, 3H) 2.27-2.39 (m, 1H) 2.67-2.82 (m, 1H) 2.99-3.07 (m, 2H) 3.08-3.22 (m, 1H) 3.43-3.54 (m, 2H) 4.29-4.47 (m, 2H) 6.53 (s, 2H) 6.95-7.01 (m, 1H) 7.17-7.27 (m, 2H) 7.25-7.32 (m, 1H) 7.35 (d, J=7.53 Hz, 2H) 8.98 (s, 1H).

Example 30

1-Benzyl-3-(4-(3-fluoro-4-hydroxyphenyl)piperidin-1-yl)pyrrolidin-2-one

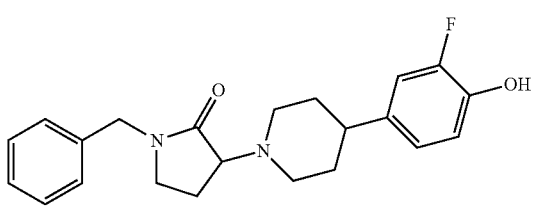 [SMILES: O=C1C(N2CCC(c3ccc(O)c(F)c3)CC2)CCN1Cc1ccccc1]

Intermediate T (200 mg) was deprotected using the conditions in Example 1 to yield a crude product which was purified via preparative HPLC (Method B) to yield 38 mg product. LC/MS RT=1.46 min. (M+H)$^+$=369 $^1$H NMR (400 MHz, DMSO-d$_6$) δ ppm 1.47-1.60 (m, 2H) 1.65-1.75 (m, 2H) 1.89-1.97 (m, 1H) 2.02-2.13 (m, 1H) 2.23-2.43 (m, 2H) 2.64-2.73 (m, 1H) 2.76-2.82 (m, 1H) 2.98-3.06 (m, 1H) 3.09-3.22 (m, 2H) 3.48 (s, 2H) 4.35 (s, 1H) 4.28-4.37 (s, 1H) 6.80-6.89 (m, 2H) 6.94-7.03 (m, 1H) 7.17-7.25 (m, 2H) 7.25-7.31 (m, 1H) 7.34 (d, J=7.53 Hz, 2H).

Example 31

1-(4-Fluorobenzyl)-3-(3-(4-hydroxyphenyl)azepan-1-yl)pyrrolidin-2-one

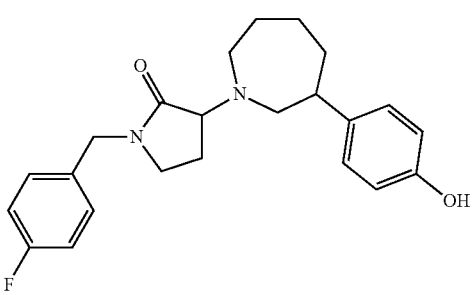 [SMILES: O=C1C(N2CCCCC(c3ccc(O)cc3)C2)CCN1Cc1ccc(F)cc1]

Intermediate V (120 mg) was deprotected using the conditions in Example 1 to yield a crude product which was purified via preparative HPLC (Method B) to yield 19 mg product. LC/MS RT=1.56 min. (M+H)$^+$=383; $^1$H NMR (400 MHz, DMSO-d$_6$) δ ppm 1.48-1.85 (m, 6H) 2.02-2.19 (m, 1H) 2.59-2.84 (m, 4H) 2.93-3.12 (m, 3H) 3.51-3.66 (m, 1H) 4.20-4.43 (m, 2H) 6.59-6.72 (m, 2H) 6.93-7.03 (m, 2H) 7.05-7.16 (m, 2H) 7.17-7.25 (m, 2H) 8.98-9.15 (m, 1H).

Example 32

3-(4-(4-Hydroxyphenyl)piperidin-1-yl)-1-((S)-1-phenylethyl)pyrrolidin-2-one

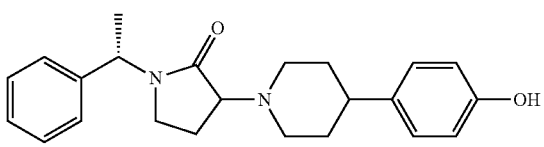

Intermediate W (220 mg) was deprotected using the conditions in Example 1 to yield a crude product which was purified via preparative HPLC (Method B) to yield 41 mg product. LC/MS RT=1.45 min. (M+H)$^+$=365.2; $^1$H NMR (400 MHz, DMSO-d$_6$) δ ppm 10.00 (q, J=7.20 Hz, 3H), 1.62 (t, J=46.00 Hz, 2H), 1.68 (d, J=1.20 Hz, 2H), 1.97-2.19 (m, 1H), 2.22-2.40 (m, 2H), 2.78 (t, J=7.60 Hz, 3H), 2.89-3.19 (m, 2H), 3.31 (d, J=3.60 Hz, 1H), 3.38-3.45 (m, 2H), 3.47-3.61 (m, 3H), 5.28 (d, J=6.80 Hz, 1H), 6.65-6.68 (m, 2H), 6.99-7.02 (m, 2H), 7.25-7.28 (m, 3H), 7.33-7.37 (m, 2H). A portion of the product (34 mg) was separated into the individual diastereomers via SFC on a Chiralpak-IA 250 mm×4.6 mm, 5 microm column eluting with 40% solvent B, where solvent A=CO$_2$ and solvent B=0.3% DEA in methanol at a total flow of 4 mL/min. Peak 1 showed a RT of 2.70 min and Peak 2 showed a RT of 4.03 min.

Example 33a (S)-3-(4-(4-Hydroxyphenyl)piperidin-1-yl)-1-((S)-1-phenylethyl)pyrrolidin-2-one

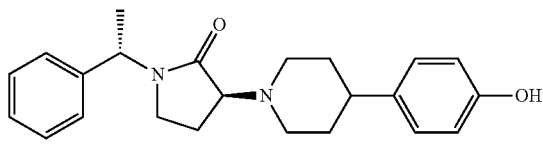

First eluting diastereomer, peak 1, from the chiral separation of Example 32. Yield 6 mg. LC/MS RT=2.28 min. (M+H)$^+$=365.0; $^1$H NMR (400 MHz, DMSO-d$_6$) δ 1.44 (d, J=7.2, 3H), 1.50-1.56 (m, 2H), 1.66 (m, 2H), 1.84 (m, 1H), 2.00-2.15 (m, 1H), 2.30-2.33 (m, 2H), 2.66 (m, 1H), 2.74 (m, 1H), 2.88-2.95 (m, 1H), 2.95-3.05 (m, 1H), 3.21 (m, 1H), 3.45 (t, J=8.8, 1H), 5.25 (d, J=7.2, 1H), 6.67 (dd, J=2, 6.8, 2H), 7.01 (d, J=8.4, 2H), 7.25-7.29 (m, 3H), 7.34-7.38 (m, 2H), 9.1 (s, 1H).

Example 33b (R)-3-(4-(4-Hydroxyphenyl)piperidin-1-yl)-1-((S)-1-phenylethyl)pyrrolidin-2-one

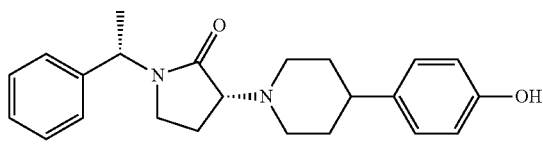 [SMILES: C[C@@H](c1ccccc1)N1CC[C@@H](N2CCC(c3ccc(O)cc3)CC2)C1=O]

Second eluting diastereomer, peak 2, from the chiral separation of Example 32. Yield 8 mg. LC/MS RT=2.29 min. (M+H)$^+$=365.2; $^1$H NMR (400 MHz, DMSO-d$_6$) δ ppm 1.47 (d, J=7.20 Hz, 3H), 1.51-1.58 (m, 2H), 1.66-1.69 (m, 2H), 1.89-2.02 (m, 1H), 2.02-2.19 (m, 1H), 2.29-2.35 (m, 2H), 2.62-2.73 (m, 1H), 2.75-2.83 (m, 2H), 2.97-3.15 (m, 1H), 3.60 (t, J=8.80 Hz, 1H), 5.28-5.30 (m, 1H), 6.67 (dd, J=2.00, 6.80 Hz, 2H), 7.02 (d, J=8.40 Hz, 2H), 7.25-7.29 (m, 3H), 7.34-7.38 (m, 2H), 9.10 (s, 1H).

Example 34

1-(2,3-Dihydro-1H-inden-1-yl)-3-(4-(4-hydroxyphenyl)piperidin-1-yl)pyrrolidin-2-one

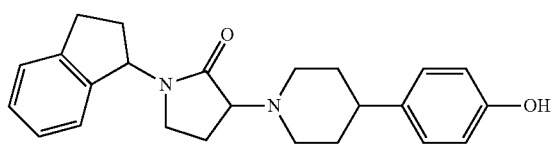 [SMILES: O=C1C(N2CCC(c3ccc(O)cc3)CC2)CCN1C1CCc2ccccc21]

Intermediate Y (280 mg) was deprotected using the conditions in Example 1 to yield a crude product which was purified via preparative HPLC (Method B) to yield 7 mg product. LC/MS RT=1.52 min. (M+H)$^+$=377; $^1$H NMR (400 MHz, DMSO-d$_6$) δ ppm 1.56-1.59 (m, 2H), 1.69-1.72 (m, 2H), 1.83-2.11 (m, 3H), 2.33-2.50 (m, 3H), 2.77-3.04 (m, 6H), 3.11-3.18 (m, 4H), 3.49 (t, J=8.40 Hz, 1H), 5.60 (t, J=8.00 Hz, 1H), 6.68 (dd, J=2.00, 6.60 Hz, 2H), 7.01-7.04 (m, 3H), 7.20-7.29 (m, 3H).

Example 35

1-(4-Fluorobenzyl)-3-(4-(4-hydroxyphenyl)azepan-1-yl)pyrrolidin-2-one

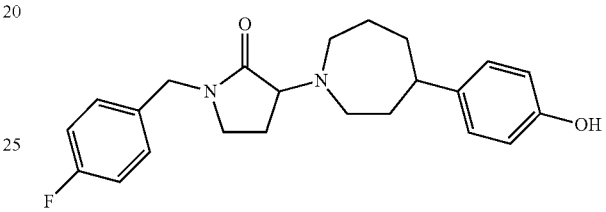

Intermediate AA (110 mg) was deprotected using the conditions in Example 1 to yield a crude product which was purified via preparative HPLC (Method B) to yield 25 mg product. LC/MS RT=1.50 min. (M+H)$^+$=383; $^1$H NMR (400 MHz, DMSO-d$_6$) δ ppm 1.67-1.81 (m, 7H), 2.15-2.20 (m, 1H), 2.65-2.70 (m, 3H), 2.79-2.92 (m, 2H), 3.09-3.02 (m, 1H), 3.13-3.18 (m, 2H), 3.58-3.61 (m, 2H), 4.35 (t, J=3.20 Hz, 2H), 6.65 (dd, J=3.60, 6.40 Hz, 2H), 6.97-6.99 (m, 2H), 7.15-7.19 (m, 2H), 7.24-7.28 (m, 2H)

Example 36

3-(4-(4-Hydroxyphenyl)azepan-1-yl)-1-(4-methylbenzyl)-pyrrolidin-2-one

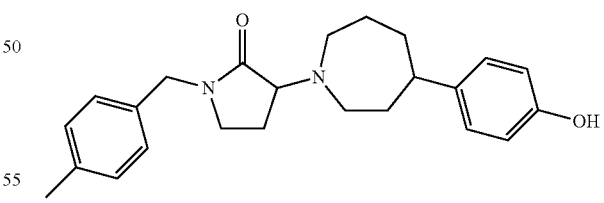

Intermediate AB (100 mg) was deprotected using the conditions in Example 1 to yield a crude product which was purified via preparative HPLC (Method B) to yield 14 mg product. LC/MS RT=1.60 min. (M+H)$^+$=379.2; $^1$H NMR (400 MHz, DMSO-d$_6$) δ ppm 1.50-89.00 (m, 7H), 2.13 (s, 1H), 2.28 (s, 3H), 2.71 (s, 1H), 2.84 (s, 2H), 3.12 (s, 3H), 3.62 (s, 1H), 4.35 (d, J=14.00 Hz, 2H), 6.66 (d, J=8.00 Hz, 2H), 6.99 (d, J=8.00 Hz, 2H), 7.14 (t, J=12.00 Hz, 5H), 9.06 (s, 1H).

Example 37

1-Benzyl-3-(4-(4-hydroxyphenyl)azepan-1-yl)pyrrolidin-2-one

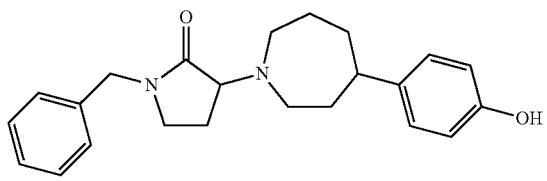 [SMILES: O=C1C(N2CCCC(c3ccc(O)cc3)CC2)CCN1Cc1ccccc1]

Intermediate AC (90 mg) was deprotected using the conditions in Example 1 to yield a crude product which was purified via preparative HPLC (Method B) to yield 15 mg product. LC/MS RT=1.44 min. (M+H)$^+$=365.2 $^1$H NMR (400 MHz, DMSO-d$_6$) δ ppm 1.70-1.85 (m, 8H), 2.19-2.25 (m, 1H), 2.66-2.71 (m, 3H), 2.79-2.93 (m, 2H), 2.96-3.15 (m, 1H), 3.14-3.20 (m, 3H), 3.61 (t, J=4.00 Hz, 3H), 4.37 (t, J=7.20 Hz, 4H), 6.65 (dd, J=2.00, 8.60 Hz, 2H), 6.98 (d, J=8.40 Hz, 2H), 7.20-7.33 (m, 3H), 7.35-7.37 (m, 2H).

Example 38

4-(4-Hydroxyphenyl)-1'-(4-methylbenzyl)-[1,3'-bipiperidin]-2'-one

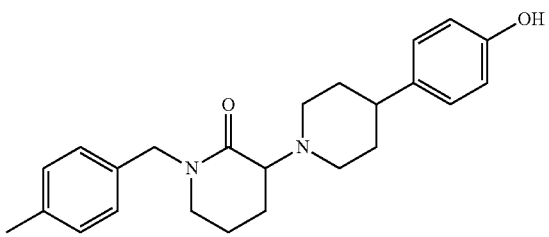 [SMILES: Cc1ccc(CN2CCCC(N3CCC(c4ccc(O)cc4)CC3)C2=O)cc1]

Step A. 4-(4-Methoxyphenyl)-1'-(4-methylbenzyl)-[1,3'-bipiperidin]-2'-one

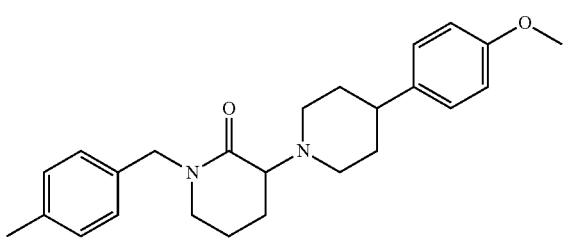

Intermediate AD (130 mg) was hydrogenated as in Example 24 to yield 130 mg 4-(4-methoxyphenyl)-1'-(4-methylbenzyl)-[1,3'-bipiperidin]-2'-one. LCMS (method)) RT 1.08 min, m/z 393.6 (MH$^+$).

Step B. 4-(4-Hydroxyphenyl)-1'-(4-methylbenzyl)-[1,3'-bipiperidin]-2'-one

The intermediate (4-(4-methoxyphenyl)-1'-(4-methylbenzyl)-[1,3'-bipiperidin]-2'-one) (130 mg) was deprotected using the conditions in Example 1 to yield a crude product which was purified via preparative HPLC (Method B) to yield 28 mg of the titled compound of Example 38. LC/MS RT=1.42 min. (M+H)$^+$=379.2 $^1$H NMR (400 MHz, DMSO-d$_6$) δ ppm 1.79-2.07 (m, 6H) 2.29 (s, 5H) 2.65-2.79 (m, 1H) 3.10-3.31 (m, 7H) 4.26-4.37 (m, 1H) 4.46 (s, 1H) 4.57-4.70 (m, 1H) 6.73 (d, J=8.53 Hz, 2H) 7.04 (d, J=8.53 Hz, 2H) 7.18 (s, 4H) 9.16-9.34 (s, 1H) 9.56-9.72, (s, 1H).

Example 39

1'-(3-Fluoro-4-methylbenzyl)-4-(4-hydroxyphenyl)-[1,3'-bipiperidin]-2'-one

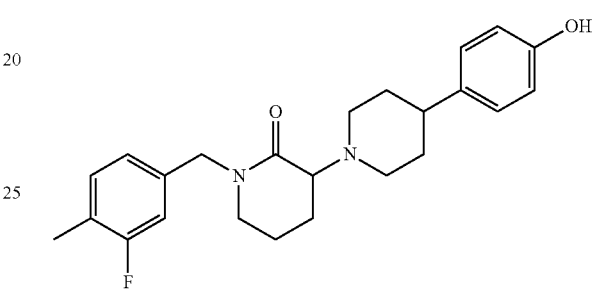

Step A. 1'-(3-Fluoro-4-methylbenzyl)-4-(4-methoxyphenyl)-[1,3'-bipiperidin]-2'-one

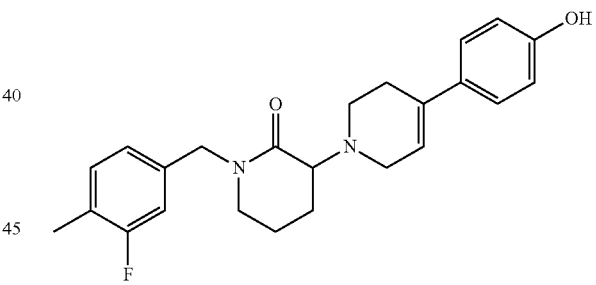

Intermediate AE (100 mg) was hydrogenated as in Example 24 to yield ~100 mg crude 1'-(3-fluoro-4-methylbenzyl)-4-(4-methoxyphenyl)-[1,3'-bipiperidin]-2'-one as a 2:1 mixture with unreacted starting material. LCMS (method)) RT 1.12 min, m/z 411.3 (MH$^+$), 1.16 min, m/z 409.2 (MH+-H$_2$).

Step B. 1'-(3-Fluoro-4-methylbenzyl)-4-(4-hydroxyphenyl)-[1,3'-bipiperidin]-2'-one The intermediate 1'-(3-fluoro-4-methylbenzyl)-4-(4-methoxyphenyl)-[1,3'-bipiperidin]-2'-one (100 mg) was deprotected using the conditions in Example 1 to yield a crude product which was purified via preparative HPLC (Method B) to yield 25 mg of the titled compound of Example 39. LC/MS RT=1.52 min. (M+H)$^+$=399 $^1$H NMR (400 MHz, DMSO-d$_6$) δ ppm 1.40-1.91 (m, 8H) 2.12-2.26 (m, 3H) 2.29-

2.49 (m, 2H) 2.75-2.93 (m, 2H) 2.98-3.27 (m, 4H) 4.36-4.59 (m, 2H) 6.59-6.75 (m, 2H) 6.92-7.07 (m, 4H) 7.19-7.31 (m, 1H) 9.00-9.20 (m, 1H).

Example 40

1'-Benzyl-4-(4-hydroxyphenyl)-[1,3'-bipiperidin]-2'-one

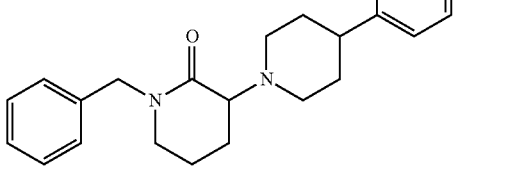

Step A. 1'-Benzyl-4-(4-methoxyphenyl)-[1,3'-bipiperidin]-2'-one

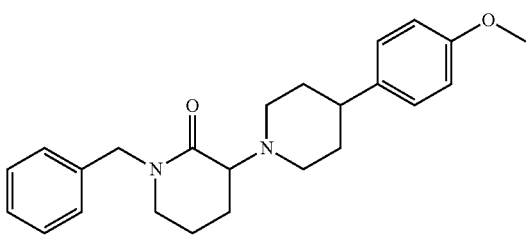 [SMILES: COc1ccc(C2CCN(C3CCCN(Cc4ccccc4)C3=O)CC2)cc1]

Intermediate AF (100 mg) was hydrogenated as in Example 24 to yield ~100 mg crude 1'-benzyl-4-(4-methoxyphenyl)-[1,3'-bipiperidin]-2'-one. LCMS (method)) RT 0.79 min, m/z 379.6 (MH+)

Step B. 1'-Benzyl-4-(4-hydroxyphenyl)-[1,3'-bipiperidin]-2'-one

The crude crude 1'-benzyl-4-(4-methoxyphenyl)-[1,3'-bipiperidin]-2'-one from step A was deprotected as in example 1 to yield a crude product which was purified via preparative HPLC (Method B) to yield 75 mg of the titled compound of Example 40. LC/MS RT=1.27 min. (M+H)+=365.2 $^1$H NMR (400 MHz, DMSO-$d_6$) δ ppm 1.46-1.60 (m, 2H) 1.63-1.90 (m, 5H) 2.31-2.48 (m, 2H) 2.80-2.91 (m, 2H) 3.18 (s, 6H) 4.43-4.61 (m, 2H) 6.68 (d, J=8.53 Hz, 2H) 7.02 (d, J=8.53 Hz, 2H) 7.21-7.29 (m, 3H) 7.34 (d, J=7.53 Hz, 2H). A portion (63 mg) was separated into the separate enantiomers via SFC on a Chiralpak-OD-H 250 mm×4.6 mm, 5 microm column eluting with 30% solvent B, where solvent A=CO$_2$ and solvent B=0.3% DEA in methanol at a total flow of 3 mL/min. Peak 1 showed a RT of 4.50 min and Peak 2 showed a RT of 5.86 min.

Example 41a

1'-Benzyl-4-(4-hydroxyphenyl)-[1,3'-bipiperidin]-2'-one

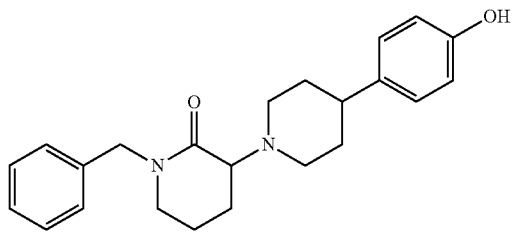 [SMILES: O=C1C(N2CCC(c3ccc(O)cc3)CC2)CCCN1Cc1ccccc1]

First eluting enantiomer, peak 1, from the chiral separation of Example 40. Yield 11 mg. LC/MS RT=1.94 min. (M+H)+=365.2 $^1$H NMR (400 MHz, DMSO-$d_6$) δ ppm 1.44-1.59 (m, 2H) 1.61-1.73 (m, 3H) 1.85 (s, 3H) 2.50 (br. s, 2H) 2.79-2.90 (m, 2H) 3.02-3.29 (m, 3H) 4.47 (s, 1H) 4.54 (s, 1H) 6.67 (d, J=8.53 Hz, 2H) 7.02 (d, J=8.53 Hz, 2H) 7.19-7.40 (m, 5H) 8.87-9.09 (m, 1H).

Example 41b

1'-Benzyl-4-(4-hydroxyphenyl)-[1,3'-bipiperidin]-2'-one

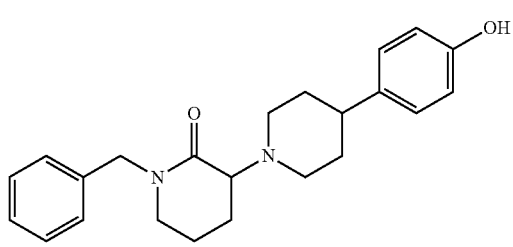 [SMILES: O=C1C(N2CCC(c3ccc(O)cc3)CC2)CCCN1Cc1ccccc1]

Second eluting enantiomer, peak 2, from the chiral separation of Example 40. Yield 7 mg. LC/MS RT=1.94 min. (M+H)+=365.2 1H NMR (300 MHz, DMSO-d6) δ ppm 1.54 (br. s., 2H) 1.65 (d, J=10.95 Hz, 3H) 1.82 (d, J=15.11 Hz, 3H) 2.44 (br. s., 2H) 2.85 (br. s., 2H) 3.02-3.20 (m, 3H) 3.25 (dd, J=9.82, 6.04 Hz, 2H) 4.35-4.50 (m, 1H) 4.52-4.67 (m, 1H) 6.57-6.72 (m, 2H) 6.94-7.08 (m, 2H) 7.18-7.31 (m, 3H) 7.34-7.36 (2, m), 8.89-9.24 (m, 1H).

Example 42

1'-(4-Chlorobenzyl)-3-(4-hydroxyphenyl)-[1,3'-bipiperidin]-2'-one

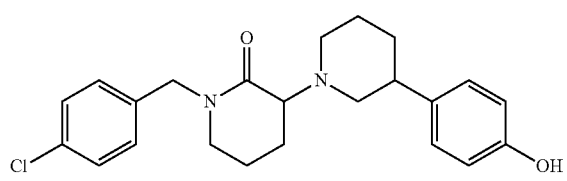 [SMILES: O=C1C(N2CCCC(c3ccc(O)cc3)C2)CCCN1Cc1ccc(Cl)cc1]

Intermediate AG (120 mg) was deprotected using the conditions in Example 1 to yield a crude product which was purified via preparative HPLC (Method B) to yield one pair of racemic diastereomers (out of two possible pairs). Yield 19 mg. LC/MS RT=1.56 min. (M+H)$^+$=399 $^1$H NMR (400 MHz, DMSO-d$_6$) δ ppm 1.60-1.72 (m, 1H) 1.78-1.89 (m, 3H) 1.93-2.08 (m, 3H) 2.22-2.36 (m, 1H) 3.05-3.20 (m, 3H) 3.22-3.38 (m, 5H) 4.17-4.31 (m, 1H) 4.44-4.54 (m, 1H) 4.58-4.71 (m, 1H) 6.67-6.78 (m, 2H) 7.01-7.14 (m, 2H) 7.24-7.38 (m, 2H) 7.34-7.49 (m, 2H) 9.23-9.41 (m, 1H) 9.60-9.76 (m, 1H).

Example 43

(R)-1-(3,4-Dihydroxybenzyl)-3-(4-(4-hydroxyphenyl)piperidin-1-yl)pyrrolidin-2-one

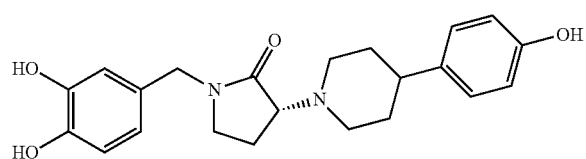

Step A. (R)-tert-Butyl(1-((3,4-dimethoxybenzyl)amino)-4-(methylthio)-1-oxobutan-2-yl)carbamate

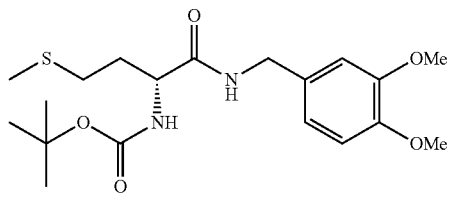 [SMILES: COc1ccc(CNC(=O)[C@@H](CCSC)NC(=O)OC(C)(C)C)cc1OC]

To a 0° C. solution of (3,4-dimethoxyphenyl)methanamine (2 g, 12 mmol) in DCM (20 mL) was added sequentially (R)-2-((tert-butoxycarbonyl)amino)-4-(methylthio)butanoic acid (3.28 g, 13.2 mmol), PyBOP (6.85 g, 13.2 mmol) and DIPEA (4.18 mL, 23.92 mmol). The reaction mixture was stirred and allowed to warm up to ambient temperature over 2 h. The reaction was then quenched by the addition of water and the mixture was extracted twice with 100 mL DCM. The organic fraction was washed with 50 mL water, 50 mL brine, and the layers were separated. The organic fraction was dried over sodium sulfate, filtered, and evaporated. The residue was purified via silica gel chromatography, eluting with 30% ethyl acetate/petroleum ether. Yield 3.5 gms (R)-tert-butyl(1-((3,4-dimethoxybenzyl)amino)-4-(methylthio)-1-oxobutan-2-yl)carbamate. LCMS (Method F) RT 2.3 min, m/z 399.2 (MH$^+$); $^1$H NMR (400 MHz, chloroform-d) δ 1.41 (s, 9H), 1.91-1.98 (m, 1H), 2.07 (s, 3H), 2.10-2.14 (m, 1H), 2.47-2.61 (m, 2H), 3.65 (s, 6H), 4.25-4.27 (br s, 1H), 4.33-4.42 (m, 2H), 5.16 (br s, 1H), 6.47 (br s, 1H), 6.80 (s, 3H).

Step B. (R)-(3-(tert-butoxycarbonylamino)-4-(3,4-dimethoxybenzylamino)-4-oxobutyl)dimethylsulfonium iodide

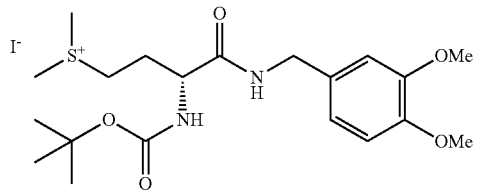 [SMILES: [I-] ; COc1ccc(CNC(=O)[C@@H](CC[S+](C)C)NC(=O)OC(C)(C)C)cc1OC]

A mixture of (R)-tert-butyl(1-((3,4-dimethoxybenzyl)amino)-4-(methylthio)-1-oxobutan-2-yl)carbamate (2 g, 5 mmol) and methyl iodide (24 ml, 381 mmol) was stirred at RT for 48 hrs. The solvent was then evaporated off and the residue was triturated with ether and dried under high vacuum. Yield 2 g. LCMS (Method J) RT 0.64 min, m/z 413.1 (M$^+$); $^1$H NMR (400 MHz, chloroform-d) δ 1.40 (s, 9H), 2.08-2.21 (br s, 1H), 2.55-2.70 (br s, 1H), 3.06 (s, 3H), 3.23 (s, 3H), 3.70-3.80 (br s, 1H), 3.85 (s, 3H), 3.89 (s, 3H), 4.34 (m, 2H), 4.45-4.55 (br s, 1H), 6.07 (d, J=6.8, 1H) 6.79 (d, J=8, 1H), 6.91 (m, 1H), 7.26 (s, 1H), 8.16 (s, 1H). The crude reaction product was used directly in the next step.

Step C. (R)-tert-Butyl(1-(3,4-dimethoxybenzyl)-2-oxopyrrolidin-3-yl)carbamate

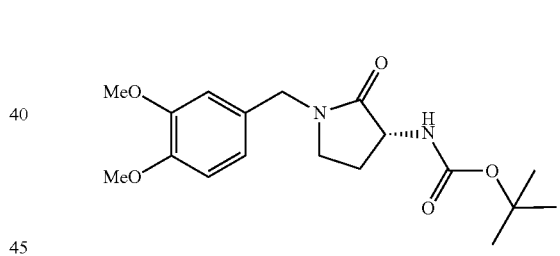

To a 0° C. solution of (R)-(3-((tert-butoxycarbonyl)amino)-4-((3,4-dimethoxybenzyl)amino)-4-oxobutyl)dimethylsulfonium, iodide salt (2 g, 3.7 mmol) in THF (50 mL) was added LHMDS (3.7 mL, 3.7 mmol) dropwise. The reaction was stirred at 0° C. for a further 2 hrs. Then was added saturated ammonium chloride solution and water. The mixture was extracted with 100 mL ethyl acetate. The layers were separated and the organic fraction was washed with water and brine. It was then dried over sodium sulfate, filtered, and evaporated. The residue was purified via silica gel chromatography using 50% ethyl acetate/petroleum ether. Yield 0.8 gms (R)-tert-butyl(1-(3,4-dimethoxybenzyl)-2-oxopyrrolidin-3-yl)carbamate. LCMS (method P) RT 0.82 min, m/z 351.2 (MH$^+$); $^1$H NMR (400 MHz, chloroform-d) δ 1.45 (s, 9H), 1.78-1.86 (m, 1H), 2.57-2.60 (br s, 1H), 3.15-3.23 (m, 2H), 3.68 (s, 6H), 4.12-4.25 (br s, 1H), 4.40 (m, 2H), 5.14 (br s, 1H), 6.75-6.82 (m, 3H).

Step D. (R)-3-Amino-1-(3,4-dimethoxybenzyl)pyrolidin-2-one

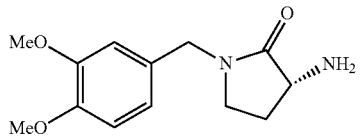 [SMILES: COc1ccc(CN2CC[C@@H](N)C2=O)cc1OC]

To a 0° C. solution of (R)-tert-butyl(1-(3,4-dimethoxybenzyl)-2-oxopyrrolidin-3-yl)carbamate (0.7 g, 2 mmol) in dioxane (2 mL) was added dropwise HCl (1 mL, 12 mmol). The solution was allowed to warm up to RT with stirring over 2 h. It was then concentrated under vacuum and the residue was triturated with diethyl ether. Yield 400 mg crude (R)-3-amino-1-(3,4-dimethoxybenzyl)-pyrrolidin-2-one. LCMS (Method J) RT 0.5 min, m/z 251.1 (MH+), $^1$H NMR (400 MHz, chloroform-d) δ 2.48 (br s, 4H), 3.35 (br s, 2H), 3.70 (s, 3H), 3.8-3.95 (m, 6H), 4.4 (br s, 3H), 6.76 (br s, 3H), 8.81 (br s, 3H).

Step E. (R)-1-(3,4-Dimethoxybenzyl)-3-(4-(4-methoxyphenyl)piperidin-1-yl)pyrrolidin-2-one

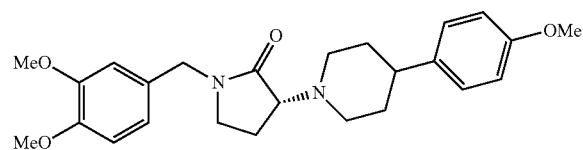 [SMILES: COc1ccc(C2CCN([C@@H]3CCN(Cc4ccc(OC)c(OC)c4)C3=O)CC2)cc1]

To a solution of (R)-3-amino-1-(3,4-dimethoxybenzyl)pyrrolidin-2-one (0.4 g, 1.6 mmol) in acetonitrile (10 mL) was added 2-(4-methoxyphenyl)propane-1,3-diyl dimethanesulfonate (0.8 g, 1.8 mmol) (prepared as in GAG Sulyok et al; *J Med Chem* 2001, 44, 1938-1950 and N Rios-Lombardia et al, *J Org Chem* 2011, 76, 5709-5718) and DIPEA (0.84 mL, 4.8 mmol). The reaction mixture was heated at 100° C. overnight. The mixture was then concentrated in vacuo, diluted with water, and extracted with 100 mL ethyl acetate. The organic layer was washed with water and brine, then dried over sodium sulfate. The drying agent was filtered off, the solvent was removed under vacuum and the residue was purified via silica gel chromatography using 20% ethyl acetate/pet ether to yield 200 mg (R)-1-(3,4-dimethoxybenzyl)-3-(4-(4-methoxyphenyl)piperidin-1-yl)pyrrolidin-2-one. LCMS (method J) RT 0.71 min, m/z 425.2 (MH+), $^1$H NMR (300 MHz, chloroform-d) δ 1.82-1.89 (m, 4H), 2.02-2.16 (m, 2H), 2.44-2.51 (m, 2H), 2.81 (m, 1H), 2.96 (m, 1H), 3.08-3.23 (m, 3H), 3.62 (m, 1H), 3.80 (s, 3H), 3.88 (s, 3H), 3.89 (s, 3H), 4.34 (d, J=14, 1H), 4.51 (d, J=14, 1H), 6.81 (s, 3H), 6.84-6.89 (m, 2H), 7.14-7.14 (m, 2H).

Step F. (R)-1-(3,4-Dihydroxybenzyl)-3-(4-(4-hydroxyphenyl)piperidin-1-yl)pyrrolidin-2-one To a 0° C. solution of (R)-1-(3,4-dimethoxybenzyl)-3-(4-(4-methoxyphenyl)piperidin-1-yl)pyrrolidin-2-one (0.03 g, 0.07 mmol) in DCM (5 mL) was added dropwise boron tribromide (0.07 mL, 0.07 mmol). The solution was allowed to warm up to RT with stirring over 3 h. The reaction was then quenched by the addition of saturated sodium bicarbonate solution (10 mL). The mixture was then extracted with DCM (100 mL) and washed with water (50 mL) and brine (50 mL). The organic fraction was dried over sodium sulfate, filtered, and concentrated under vacuum. The residue was subjected to preparative HPLC (method B) to yield 5.6 mg of the titled compound of Example 43, as a pale yellow solid. LCMS (method N) RT 0.93 min (99% AP) m/z 383.0 (MH+); $^1$H NMR (400 MHz, DMSO-d$_6$) ppm 1.45-1.65 (m, 4H), 1.66-1.75 (m, 1H), 1.88-1.92 (m, 1H), 2.32-2.36 (m, 2H), 2.67-2.68 (m, 2H), 3.04-3.31 (m, 3H), 4.06-4.25 (m, 2H), 6.46-6.49 (m, 1H), 6.60-6.68 (m, 4H), 7.00-7.03 (m, 2H), 8.79 (s, 1H), 8.89 (s, 1H), 9.11 (s, 1H).

Example 44

Enantiomer-1 and Enantiomer-2

1-(4-Fluorobenzyl)-3-(cis-3-hydroxy-4-(4-hydroxyphenyl)piperidin-1-yl)pyrrolidin-2-one

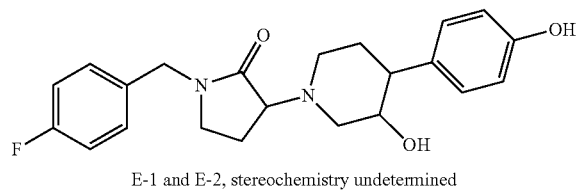 [SMILES: O=C1C(N2CCC(c3ccc(O)cc3)C(O)C2)CCN1Cc1ccc(F)cc1]

E-1 and E-2, stereochemistry undetermined

Step A. (±)-rel-(3S,4R)-tert-butyl 4-(4-(benzyloxy)phenyl)-3-(4-nitrobenzoyloxyl)piperidine-1-carboxylate

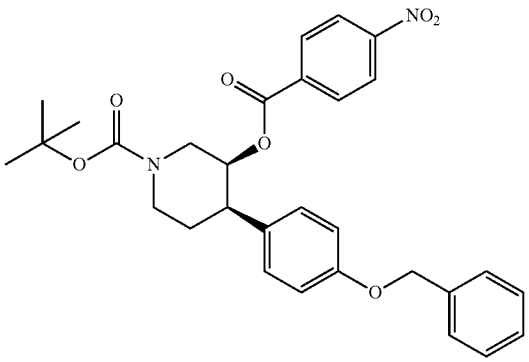 [SMILES: CC(C)(C)OC(=O)N1CC[C@H](c2ccc(OCc3ccccc3)cc2)[C@H](OC(=O)c2ccc([N+](=O)[O-])cc2)C1]

A mixture of diethylazodicarboxylate (12.9 mL, 81 mmol of 40% toluene solution), triphenyl phosphine (22 mL, 83 mmol), 4-nitrobenzoic acid (6.97 g, 42 mmol) and 200 mL tetrahydrofuran was stirred for 10 min under an Ar atmosphere. Then was added a solution of tert-butyl 4-(4-(benzyloxy)phenyl)-3-hydroxypiperidine-1-carboxylate (Example 56, step D, 8 g, 20.9 mmol) in tetrahydrofuran (100 mL) and the resulting mixture was stirred at rt overnight. It was then diluted with water and extracted twice with 50 mL ethyl acetate. The combined organic fractions were dried over Na$_2$SO$_4$, filtered, and evaporated to dryness. The residue was purified via silica gel chromatography (750 µm column, eluting with 0-50% ethyl acetate/hexane) to yield 6 gms (±)-rel-(3S,4R)-tert-butyl 4-(4-(benzyloxy)phenyl)-3-(4-nitrobenzoyloxyl)piperidine-1-carboxylate. LCMS (Method F) RT 2.68 min (87% AP), m/z 476.8 (MH⁺–t-butyl).

Step B. (±)-rel-(3S,4R)-tert-butyl 4-(4-(benzyloxy)phenyl)-3-hydroxypiperidine-1-carboxylate

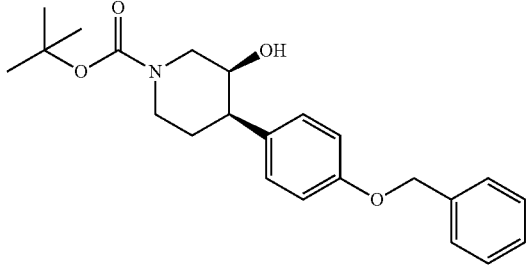 [SMILES: CC(C)(C)OC(=O)N1CC[C@H](c2ccc(OCc3ccccc3)cc2)[C@H](O)C1]

To a suspension of KOH (5.06 g, 90 mmol), water (60 ml) and tetrahydrofuran (200 ml) was added tert-butyl 4-(4-(benzyloxy)phenyl)-3-((4-nitrobenzoyl)oxy)piperidine-1-carboxylate (6 g, 11.3 mmol) and the reaction mixture was stirred at room temperature overnight. It was then diluted with 200 mL water and extracted twice with 200 mL ethyl acetate. The organic layer was washed with 1.5 N HCl solution and was then dried over Na$_2$SO$_4$, filtered, and evaporated to dryness. The crude product 4 g, (±)-rel-(3S,4R)-tert-butyl 4-(4-(benzyloxy)phenyl)-3-hydroxypiperidine-1-carboxylate), was used in the next step without further purification. LCMS (method F) RT 2.44 min (95% AP), m/z 382 (M–H) (negative mode); $^1$H NMR (300 MHz, DMSO-d$_6$) δ ppm 7.29-7.44 (m, 5H), 7.71 (d, J=8.4, 2H), 6.91 (d, J=8.4, 2H), 5.06 (s, 2H), 4.45 (br s, 1H), 3.80-4.20 (m, 2H), 3.70 (br s, 1H), 2.60-3.05 (m, 3H), 1.95-2.20 (m, 1H), 1.35 (s, 9H).

Step C. (±)-rel-(3S,4R)-4-(4-(benzyloxy)phenyl)piperidin-3-ol, hydrochloride

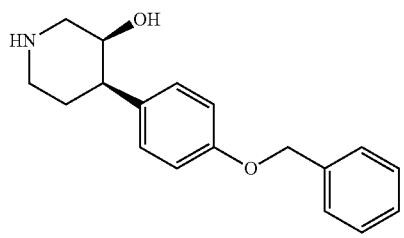 [SMILES: O[C@@H]1CNCC[C@@H]1c1ccc(OCc2ccccc2)cc1]

To a solution of tert-butyl 4-(4-(benzyloxy)phenyl)-3-hydroxypiperidine-1-carboxylate (100 mg, 0.26 mmol) in 10 mL diethyl ether was added 4 M HCl in dioxane (1.3 mL, 5.2 mmol) and the resulting mixture was stirred at rt overnight. The solvent was evaporated off and the residue triturated with ether. Yield 80 mg (88%), LCMS (Method J) RT 0.73 min (92% AP), m/z 284.2 (MH⁺), $^1$H NMR (300 MHz, DMSO-d$_6$) δ ppm 7.30-7.45 (m, 5H), 7.27 (d, J=8.4, 2H), 6.97 (d, J=8.7, 2H), 5.09 (s, 2H), 4.09 (s, 1H), 3.44 (d, J=12.6, 2H), 3.32-3.29 (m, 1H), 3.08-3.20 (m, 1H), 2.95 (d, J=12.6, 1H), 2.48-2.58 (m, 1H), 1.82 (d, J=13.2, 1H).

Step D. (±)-rel-3-((3S,4R)-4-(4-(benzyloxy)phenyl)-3-hydroxypiperidin-1-yl)-1-(4-fluorobenzyl)pyrrolidin-2-one

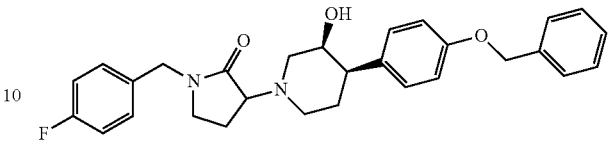

To a mixture of (±)-rel-(3S,4R)-4-(4-(benzyloxy)phenyl)piperidin-3-ol, HCl (260 mg, 0.81 mmol), 3-bromo-1-(4-fluorobenzyl)pyrrolidin-2-one (442 mg, 1.63 mmol, Intermediate 3) and DMF (3 mL) was added triethylamine (0.57 mL, 4 mmol) and the reaction mixture was heated in the microwave for 1 hour at 120° C. The reaction mixture was cooled, diluted with water, and twice extracted with 20 mL ethyl acetate. The combined organic fractions were dried over Na$_2$SO$_4$, filtered, and evaporated to dryness. The residue was subjected to preparative HPLC (method F), collecting two racemic diastereomers D1 (90 mg) and D2 (100 mg). The relative stereochemistry of D1 and D2 was not determined. Data for D1 (first eluting diastereomer): LCMS (method E) RT 2.90 min, m/z 475 (MH⁺), $^1$H NMR (400 MHz, DMSO-d$_6$) δ ppm 7.47-7.37 (m, 4H), 7.36-7.25 (m, 3H), 7.23-7.15 (m, 4H), 6.93-6.89 (m, 2H), 5.08 (s, 2H), 4.37 (d, J=14.1 Hz, 2H), 3.84 (d, J=7.5 Hz, 1H), 3.72-3.66 (m, 1H), 3.49 (s, 1H), 3.16 (d, J=19.6 Hz, 2H), 3.07-3.00 (m, 1H), 2.89 (s, 1H), 2.80-2.74 (m, 1H), 2.59-2.53 (m, 1H), 2.38-2.30 (m, 1H), 2.19-2.06 (m, 2H), 1.88 (s, 1H), 1.53-1.44 (m, 1H). Data for D2 (second eluting diastereomer): LCMS (method E) RT 2.37 min, m/z 475 (MH⁺), $^1$H NMR (400 MHz, DMSO-d$_6$) δ ppm 7.47-7.37 (m, 4H), 7.35-7.25 (m, 3H), 7.22-7.16 (m, 4H), 6.93-6.89 (m, 2H), 5.08 (s, 2H), 4.44-4.30 (m, 2H), 3.99 (d, J=7.5 Hz, 1H), 3.72 (d, J=7.5 Hz, 1H), 3.51 (t, J=8.5 Hz, 1H), 3.21-3.10 (m, 2H), 2.97-2.92 (m, 1H), 2.85-2.80 (m, 2H), 2.54 (br. s., 1H), 2.47 (s, 1H), 2.16-2.06 (m, 2H), 1.92 (s, 1H), 1.48-1.42 (m, 1H).

Step E. (±)-rel-1-(4-fluorobenzyl)-3-((3S,4R)-3-hydroxy-4-(4-hydroxyphenyl)piperidin-1-yl)pyrrolidin-2-one

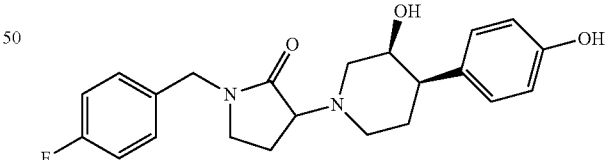

A mixture of 3-(4-(4-(benzyloxy)phenyl)-3-hydroxypiperidin-1-yl)-1-(4-fluorobenzyl)-pyrrolidin-2-one (D2 from step E, 85 mg, 0.18 mmol), methanol (5 mL), and 38 mg 10% Pd/C was stirred in a pressure vessel overnight under 125 psi hydrogen pressure. The catalyst was removed by filtration through Celite and the filtrate was evaporated to dryness to yield 70 mg of racemic 1-(4-fluorobenzyl)-3-(cis-3-hydroxy-4-(4-hydroxyphenyl)-piperidin-1-yl)pyrrolidin-2-one. LCMS (method J) RT=0.63 (52% AP), 0.66 (31% AP) min, m/z 385.4 (MH⁺); $^1$H NMR (400 MHz, DMSO-d$_6$) δ ppm 7.27-7.28 (m, 2H), 7.15-7.19 (m, 2H), 7.06 (d, J=8.4, 2H), 6.45 (d, J=8.4, 2H), 4.39 (d, J=15, 1H), 4.32 (d, J=15, 1H), 3.74-3.76 (m, 1H), 3.66 (m, 1H), 3.47 (m, 1H), 3.10-3.18 (m, 2H), 3.01 (m, 1H), 2.85-2.88 (m, 1H), 2.76 (m, 1H), 2.30-2.40 (m, 1H), 2.06-2.11 (m, 2H), 1.80-1.95 (m, 1H), 1.46 (d, J=12, 1H). The complete relative stereochemistry was not determined.

Step F. 1-(4-Fluorobenzyl)-3-(cis-3-hydroxy-4-(4-hydroxyphenyl)piperidin-1-yl)pyrrolidin-2-one The product from Step E, 1-(4-fluorobenzyl)-3-(3-hydroxy-4-(4-hydroxyphenyl)piperidin-1-yl)pyrrolidin-2-one (70 mg, 0.182 mmol), was separated via SFC (method C-3) into two enantiomers, Example 44 E-1 (12 mg) and E-2 (10 mg). E-1 was re-purified via preparative HPLC (method B). The absolute configurations were not determined. Data for E-1: LCMS (method N) RT 1.34 min (99% AP), m/z 385.0 (MH$^+$), Chiral SFC (method C-3) RT 3.2 min; $^1$H NMR (400 MHz, methanol-d$_4$) δ ppm 1.59-1.68 (m, 1H) 2.02-2.35 (m, 3H) 2.50-2.70 (m, 2H) 2.79-2.91 (m, 2H) 3.04-3.12 (m, 1H) 3.22-3.30 (m, 2H) 3.73 (s, 1H) 3.84 (br. s., 1H) 4.39-4.47 (m, 1H) 4.51-4.60 (m, 1H) 6.71-6.77 (m, 2H) 7.06-7.18 (m, 4H) 7.32 (dd, J=8.78, 5.27 Hz, 2H). Data for E-2: LCMS (method F) RT 1.97 min (95% AP), m/z 385.0 (MH$^+$), Chiral SFC (method C-3) RT 7.4 min; $^1$H NMR (400 MHz, methanol-d$_4$) δ ppm 1.59-1.68 (m, 1H) 2.02-2.35 (m, 3H) 2.50-2.70 (m, 2H) 2.79-2.91 (m, 2H) 3.04-3.12 (m, 1H) 3.22-3.30 (m, 2H) 3.73 (s, 1H) 3.84 (br. s., 1H) 4.39-4.47 (m, 1H) 4.51-4.60 (m, 1H) 6.71-6.77 (m, 2H) 7.06-7.18 (m, 4H) 7.32 (dd, J=8.78, 5.27 Hz, 2H).

Example 45

Peak-1, Peak-2, Peak-3, Peak-4

(S)-3-((3S,4S)-3-fluoro-4-(3-fluoro-4-hydroxyphenyl)piperidin-1-yl)-1-(3-fluoro-4-methylbenzyl)pyrrolidin-2-one and (R)-3-((3S,4S)-3-fluoro-4-(3-fluoro-4-hydroxyphenyl)piperidin-1-yl)-1-(3-fluoro-4-methylbenzyl)pyrrolidin-2-one

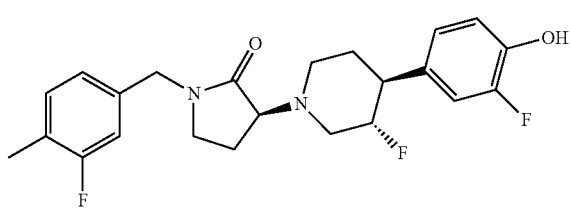

Example 45, P-1

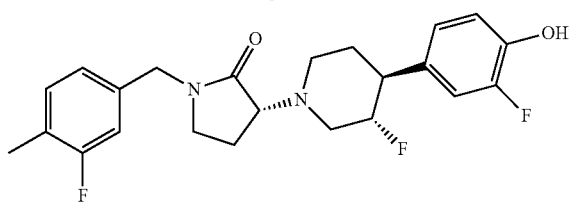

Example 45, P-2

(S)-3-((3R,4R)-3-Fluoro-4-(3-fluoro-4-hydroxyphenyl)piperidin-1-yl)-1-(3-fluoro-4-methylbenzyl)pyrrolidin-2-one and (R)-3-((3R,4R)-3-fluoro-4-(3-fluoro-4-hydroxyphenyl)piperidin-1-yl)-1-(3-fluoro-4-methylbenzyl)pyrrolidin-2-one

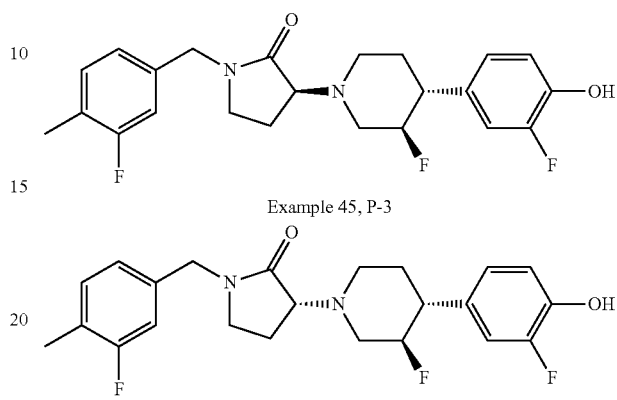

Example 45, P-3

Example 45, P-4

Step A. tert-butyl 4-(3-fluoro-4-methoxyphenyl)-4-hydroxypiperidine-1-carboxylate

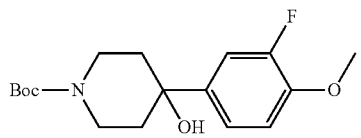 [SMILES: COc1ccc(C2(O)CCN(C(=O)OC(C)(C)C)CC2)cc1F]

A stirred solution of tert-butyl 4-oxopiperidine-1-carboxylate (4.5 g, 22.6 mmol) in diethyl ether (100 mL) at 0° C. was treated with a solution of (3-fluoro-4-methoxyphenyl)magnesium bromide (49.7 mL, 24.8 mmol, 0.5 M in tetrahydrofuran). The reaction mixture was allowed to warm to rt and was stirred at for 12 h. It was then diluted with 100 mL water and the layers were separated. The aqueous layer was extracted three times with 150 mL of ethyl acetate and the combined organic layers were dried over anhydrous sodium sulfate, filtered, and evaporated. The residue was purified by silica gel chromatography (120 g column) eluting with 30% ethyl acetate in petroleum ether to obtain 6.5 g of tert-butyl 4-(3-fluoro-4-methoxyphenyl)-4-hydroxypiperidine-1-carboxylate as a clear liquid; $^1$H NMR (400 MHz, DMSO-d$_6$) δ ppm 1.33-1.47 (m, 11H) 1.52-1.61 (m, 2H) 1.69-1.84 (m, 2H) 3.03-3.22 (m, 2H) 3.77-3.89 (m, 6H) 5.09 (s, 1H) 7.10 (s, 1H) 7.17-7.26 (m, 1H) 7.25-7.33 (m, 1H).

Step B. 4-(3-Fluoro-4-methoxyphenyl)-1,2,3,6-tetrahydropyridine hydrochloride

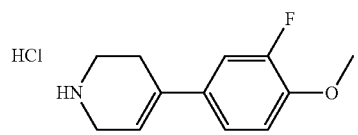

To a stirred solution of tert-butyl 4-(3-fluoro-4-methoxyphenyl)-4-hydroxypiperidine-1-carboxylate (6.5 g, 20 mmol) in 1,4-dioxane (100 mL) at 0° C. was added 50 mL of 1M HCl (dioxane solution) and the mixture was allowed to warm to rt and stirred for 12 h. The solvent was then removed under reduced pressure. The residue was triturated with ethyl acetate to obtain 4.5 g crude 4-(3-fluoro-4-methoxyphenyl)-1,2,3,6-tetrahydropyridine hydrochloride as a solid which was was isolated by filtration and used without further purification. LCMS (Method P) RT 0.57 min, m/z 208 (M+H$^+$); $^1$H NMR (400 MHz, DMSO-d$_6$) δ ppm 2.37-2.61 (m, 2H), 3.12-3.38 (m, 3H) 3.80-3.94 (m, 3H) 3.95-4.12 (m, 2H) 7.10-7.29 (m, 1H) 7.33-7.44 (m, 1H) 7.51 (dd, J=13.05, 2.51 Hz, 1H) 9.27-9.63 (m, 2H).

Step C. tert-Butyl 4-(3-fluoro-4-methoxyphenyl)-5,6-dihydropyridine-1(2H)-carboxylate

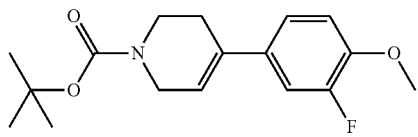

To a stirring solution of 4-(3-fluoro-4-methoxyphenyl)-1,2,3,6-tetrahydropyridine hydrochloride (4.5 g, 18.5 mmol) and triethylamine (7.7 mL, 55 mmol) in DCM (30 mL) at 0° C. was added 5.6 mL (24 mmol) of di-tert-butyl dicarbonate. The mixture was allowed to warm to rt and was stirred for 12 h. It was then diluted with DCM (100 mL) and water (100 mL) and the layers were separated. The aqueous layer was again extracted with DCM and the combined organic layers were washed with brine, dried over anhydrous Na$_2$SO$_4$, filtered and evaporated under reduced pressure to obtain crude tert-butyl 4-(3-fluoro-4-methoxyphenyl)-5,6-dihydro-pyridine-1(2H)-carboxylate (6 g) as a liquid which was purified using an 80 g silica gel column eluting with 17%-30% ethyl acetate/petroleum ether to obtain 4.5 g of the pure product as a liquid. LCMS (Method P) RT=1.21 min, m/z 252 (M+H$^+$–t-butyl); $^1$H NMR (400 MHz, DMSO-d$_6$) δ ppm 1.39-1.48 (m, 9H) 2.37-2.46 (m, 2H) 3.52 (s, 2H) 3.77-3.89 (m, 3H) 3.95-4.09 (m, 2H) 6.07-6.16 (m, 1H) 7.06-7.17 (m, 1H) 7.18-7.24 (m, 1H) 7.26-7.35 (m, 1H).

Step D. (±)-rel-(3S,4S)-tert-butyl 4-(3-fluoro-4-methoxyphenyl)-3-hydroxypiperidine-1-carboxylate

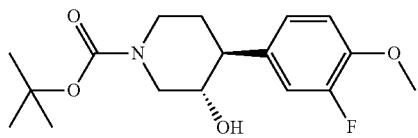 [SMILES: COc1ccc([C@@H]2CCN(C(=O)OC(C)(C)C)C[C@H]2O)cc1F]

To a suspension of NaBH$_4$ (0.37 g, 9.8 mmol) in tetrahydrofuran (50 mL) was added BF$_3$.OEt$_2$ (1.3 mL, 10 mmol) at 0° C. The reaction mixture was warmed to rt for 1 h and then re-cooled to 0° C. Tert-butyl 4-(3-fluoro-4-methoxyphenyl)-5,6-dihydropyridine-1(2H)-carboxylate (1 g, 3.3 mmol) in tetrahydrofuran (10 mL) was then added. The resulting mixture was allowed to warm to rt over 2 h. It was then re-cooled to 0° C. and water (4 mL), ethanol (4 mL), 30% H$_2$O$_2$ (3 mL, 29.4 mmol) and a NaOH solution (4 mL, 3.25 mmol) were added sequentially and the final mixture was heated to 65° C. for 12 h. It was cooled to room temperature, and 50 mL water and 200 mL ethyl acetate were added. The layers were separated and the aqueous layer was twice extracted with 150 mL of ethyl acetate. The combined organic layers were washed with 1N HCl followed by brine. The organic layer was dried over anhydrous Na$_2$SO$_4$, filtered, and evaporated under reduced pressure to obtain 2 g of crude (±)-rel-(3S,4S)-tert-butyl 4-(3-fluoro-4-methoxyphenyl)-3-hydroxypiperidine-1-carboxylate as a brown gum. The crude compound was purified on a 40 g silica gel column eluting with 30% ethyl acetate in petroleum ether to obtain 450 mg of the pure product as a liquid. LCMS (Method P) RT 0.98 min, m/z 252 (M+H$^+$–t-butyl), 270 (M+H$^+$–t-butyl, —H$_2$O); $^1$H NMR (400 MHz, DMSO-d$_6$) δ ppm 1.42 (s, 9H) 1.46-1.58 (m, 1H) 1.61-1.71 (m, 1H) 2.32-2.48 (m, 2H) 2.62-2.77 (m, 1H) 3.34-3.47 (m, 1H) 3.80 (s, 3H) 3.91-4.01 (m, 1H) 4.05-4.14 (m, 1H) 4.82 (s, 1H) 6.96-7.02 (m, 1H) 7.03-7.13 (m, 2H).

Step E. (±)-rel-(3S,4S)-tert-butyl 3-fluoro-4-(3-fluoro-4-methoxyphenyl)piperidine-1-carboxylate

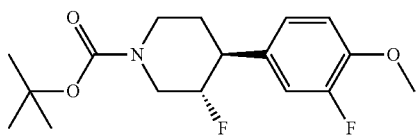

A stirred solution of trans-tert-butyl 4-(3-fluoro-4-methoxyphenyl)-3-hydroxypiperidine-1-carboxylate (100 mg, 0.31 mmol) in DCM (15 mL) at −78° C. was treated dropwise with DAST (0.08 mL, 0.6 mmol). The resulting mixture was stirred at −78° C. for 90 min. It was then quenched with ice water, warmed to rt, and extracted with DCM (50 mL). The organic layer was separated, washed with brine, dried over anhydrous Na$_2$SO$_4$, filtered, and evaporated under reduced pressure to obtain 70 mg of (±)-rel-(3S,4S)-tert-butyl 3-fluoro-4-(3-fluoro-4-methoxyphenyl)piperidine-1-carboxylate. LCMS (Method P) RT 1.11, 1.13 min, m/z 313 (M+H$^+$+CH$_3$CN–t-butyl). Three batches of product (~210 mg total) were combined and subjected to HPLC purification (Method A) to give 140 mg (±)-rel-(3S,4S)-tert-butyl 3-fluoro-4-(3-fluoro-4-methoxyphenyl)piperidine-1-carboxylate; $^1$H NMR (400 MHz, DMSO-d$_6$) δ ppm 1.43 (s, 9H) 1.55-1.67 (m, 1H) 1.74-1.82 (m, 1H) 2.72-2.90 (m, 3H) 3.82 (s, 3H) 3.89-4.03 (m, 1H) 4.24-4.34 (m, 1H) 4.50-4.71 (m, 1H) 7.09 (d, J=1.51 Hz, 2H) 7.18-7.28 (m, 1H).

Step F. (3R,4R)-tert-Butyl 3-fluoro-4-(3-fluoro-4-methoxyphenyl)piperidine-1-carboxylate and (3S,4S)-tert-butyl 3-fluoro-4-(3-fluoro-4-methoxyphenyl)piperidine-1-carboxylate

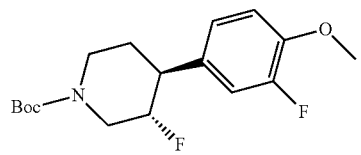

E-1

-continued

E-2

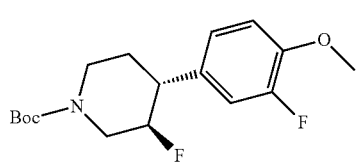

The purified product from step F was subjected to chiral SFC (method D) to afford the two separate enantiomers (E-1 and E-2). Data for E-1 (3S,4S)-tert-butyl 3-fluoro-4-(3-fluoro-4-methoxyphenyl)piperidine-1-carboxylate: chiral HPLC (method G) RT=2.45 min, 100% AP; LCMS (Method J) RT=1.04 min, m/z=252 (M+H+-HF, -t-butyl), 272 (M+H+-t-butyl); $^1$H NMR (400 MHz, methanol-$d_4$) δ ppm 7.02-7.11 (m, 3H) 4.36-4.59 (m, 2H) 4.07-4.16 (m, 1H) 3.87 (s, 3H) 2.76-2.95 (m, 3H) 1.82-1.93 (m, 1H) 1.64-1.76 (m, 1H) 1.51 (s, 9H). Data for E-2 (3R,4R)-tert-butyl 3-fluoro-4-(3-fluoro-4-methoxyphenyl)piperidine-1-carboxylate: chiral HPLC (method G) RT=2.82 min, 96.9% AP; LCMS (Method J) RT=1.04 min, m/z=252 (M+H+-HF, -t-butyl), 272 (M+H+-t-butyl); $^1$H NMR (400 MHz, methanol-$d_4$) δ ppm 7.05 (m, 3H) 4.39-4.60 (m, 2H) 4.07-4.16 (m, 1H) 3.87 (s, 3H) 2.76-2.94 (m, 3H) 1.84-1.91 (m, 1H) 1.63-1.76 (m, 1H) 1.51 (s, 9H).

Step G. (3S,4S)-3-Fluoro-4-(3-fluoro-4-methoxyphenyl)piperidine, hydrochloride

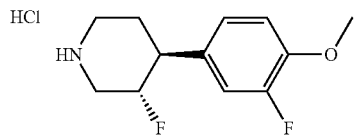 [SMILES: Cl ; COc1ccc([C@@H]2CCNC[C@H]2F)cc1F]

To a stirring solution of (3S,4S)-tert-butyl 3-fluoro-4-(3-fluoro-4-methoxyphenyl)piperidine-1-carboxylate (E-1, the first eluting enantiomer from step F, 44 mg, 0.134 mmol) in 1,4-dioxane (3 mL) at 0° C. was added 2 mL (8 mmol) of 4 M HCl in dioxane, and the resulting mixture was stirred at rt for 12 h. The solvent was removed under reduced pressure to afford (3S,4S)-3-fluoro-4-(3-fluoro-4-methoxyphenyl)piperidine hydrochloride (30 mg) as a white solid which was used without further purification. LCMS (Method J) RT=0.60 min, m/z 228.2 (M+H$^+$). $^1$H NMR (400 MHz, methanol-$d_4$) δ ppm 7.01-7.19 (m, 3H) 4.88-4.99 (m, 1H) 4.71-4.83 (m, 1H) 3.89 (s, 3H) 3.67-3.78 (m, 1H) 3.40-3.53 (m, 1H) 3.00-3.25 (m, 3H) 2.12-2.27 (m, 1H) 1.93-2.08 (m, 1H).

Step H. 3-((3S,4S)-3-Fluoro-4-(3-fluoro-4-methoxyphenyl)piperidin-1-yl)-1-(3-fluoro-4-methylbenzyl)pyrrolidin-2-one

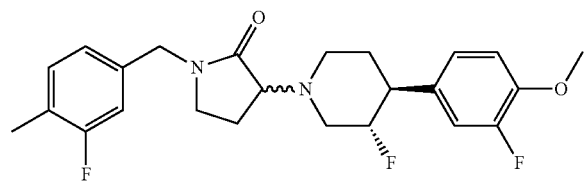

A mixture of (3S,4S)-3-fluoro-4-(3-fluoro-4-methoxyphenyl)piperidine hydrochloride (30 mg, 0.11 mmol, from step G), 3-bromo-1-(3-fluoro-4-methylbenzyl)pyrrolidin-2-one (54 mg, 0.19 mmol, intermediate 6,) and DIPEA (0.02 mL, 0.11 mmol) in DMF (3 mL) was heated to 120° C. for 90 min in a microwave reactor. The reaction mixture was cooled to rt and the solvent was removed under reduced pressure to obtain 60 mg of 3-((3S,4S)-3-fluoro-4-(3-fluoro-4-methoxyphenyl)piperidin-1-yl)-1-(3-fluoro-4-methylbenzyl)-pyrrolidin-2-one (diastereomeric pair), which was used in the next step without purification. LCMS (Method P) RT=1.12 min, m/z 433 (M+H$^+$).

Step I. 3-((3S,4S)-3-Fluoro-4-(3-fluoro-4-hydroxyphenyl)piperidin-1-yl)-1-(3-fluoro-4-methylbenzyl)pyrrolidin-2-one

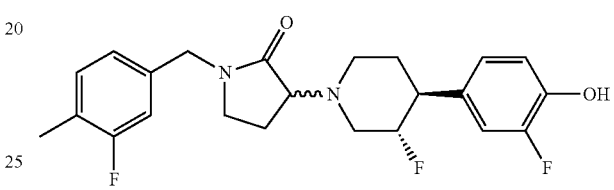

To a stirring solution of 3-((3S,4S)-3-fluoro-4-(3-fluoro-4-methoxyphenyl)piperidin-1-yl)-1-(3-fluoro-4-methylbenzyl)pyrrolidin-2-one (60 mg, 0.14 mmol, diastereomeric mixture from step H) in 10 mL of DCM at −78° C. was added 2.5 mL of boron tribromide (2.5 mmole) and the mixture allowed to warm to rt and stirred for 3 h. The reaction mixture was then cooled to 0° C. and quenched with saturated NaHCO$_3$ solution. The mixture was then diluted with DCM and the organic layer was separated and evaporated under reduced pressure. The crude compound was purified by preparative HPLC to give 3-((3S,4S)-3-fluoro-4-(3-fluoro-4-hydroxyphenyl)piperidin-1-yl)-1-(3-fluoro-4-methyl-benzyl) pyrrolidin-2-one (20 mg, 0.047 mmol, 34% yield) (diastereomeric pair). LCMS (Method Q) RT=1.17 min, m/z 419.0 (M+H$^+$).

Step J. (S)-3-((3S,4S)-3-fluoro-4-(3-fluoro-4-hydroxyphenyl)piperidin-1-yl)-1-(3-fluoro-4-methylbenzyl)pyrrolidin-2-one and (R)-3-((3S,4S)-3-fluoro-4-(3-fluoro-4-hydroxyphenyl)piperidin-1-yl)-1-(3-fluoro-4-methylbenzyl)pyrrolidin-2-one The product mixture from step I was subjected to chiral separation via SFC method C-6 to give two homochiral products: Example 45, P-1 (4.1 mg) and Example 45, P-2 (7.3 mg). Data for P-1 (S)-3-(3S,4S)-(3-fluoro-4-(3-fluoro-4-hydroxyphenyl)piperidin-1-yl)-1-(3-fluoro-4-methylbenzyl) pyrrolidin-2-one: HPLC (Method C) RT=7.09 min (Method D) RT=7.88 min; LCMS (Method F) RT=2.1 min, m/z 419 (M+H$^+$). Chiral HPLC (Method C-6) RT=2.87 min; $^1$H NMR (400 MHz, methanol-$d_4$) δ ppm 1.76-1.94 (m, 2H) 1.99-2.12 (m, 1H) 2.14-2.24 (m, 1H) 2.25-2.29 (m, 3H) 2.39-2.50 (m, 1H) 2.52-2.71 (m, 2H) 2.94-3.06 (m, 1H) 3.07-3.19 (m, 1H) 3.22-3.31 (m, 2H) 3.69-3.80 (m, 1H) 4.38-4.68 (m, 3H) 6.81-7.04 (m, 5H) 7.19-7.29 (m, 1H). Data for P-2 (R)-3-((3S,4S)-3-fluoro-4-(3-fluoro-4-hydroxyphenyl)piperidin-1-yl)-1-(3-fluoro-4-methylbenzyl)pyrrolidin-2-one: HPLC (Method C) RT=7.10 min (Method D) RT=7.88 min; LCMS (Method F) RT=2.098 min, m/z 419 (M+H$^+$). Chiral HPLC (Method C-6) RT=5.33 min; $^1$H NMR (400 MHz, methanol-$d_4$) δ ppm 1.72-1.90 (m, 2H) 2.02-2.14 (m, 1H) 2.15-2.23 (m, 1H) 2.23-2.29 (m, 3H) 2.38-2.49 (m, 1H) 2.53-2.72 (m, 2H) 2.73-2.82 (m, 1H) 3.22-3.32 (m, 2H) 3.38-3.47 (m, 1H) 3.59-3.64 (m, 1H) 3.69-3.76 (m, 1H) 4.38-4.54 (m, 2H) 4.60-4.71 (m, 1H) 6.85-7.04 (m, 5H) 7.20-7.28 (m, 1H).

Step K. (3R,4R)-3-Fluoro-4-(3-fluoro-4-methoxyphenyl)piperidine hydrochloride

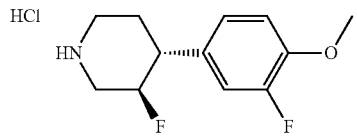 [SMILES: Cl ; COc1ccc([C@H]2CCNC[C@@H]2F)cc1F]

To a stirring solution of (3R,4R)-tert-butyl 3-fluoro-4-(3-fluoro-4-methoxyphenyl)piperidine-1-carboxylate (38 mg, 0.12 mmol, E-2, the second eluting enantiomer from step F) in 3 mL of 1,4-dioxane at 0° C. was added 2 mL of 4M HCl in 1,4-dioxane (8 mmol) and the mixture was allowed to warm up to rt over 12 h. The solvent was removed under reduced pressure to to obtain (3R,4R)-3-Fluoro-4-(3-fluoro-4-methoxyphenyl)piperidine hydrochloride (30 mg) as a semi-solid which was used without further purification. LCMS (Method K) RT=0.59 min, m/z 228, m/z 419 (M+H+); $^1$H NMR (400 MHz, methanol-$d_4$) δ ppm 6.99-7.22 (m, 3H) 4.73-4.84 (m, 1H) 3.89 (s, 3H) 3.67-3.78 (m, 2H) 3.41-3.52 (m, 1H) 3.00-3.25 (m, 3H) 2.09-2.26 (m, 1H) 1.88-2.08 (m, 1H).

Step L. 3-((3R,4R)-3-Fluoro-4-(3-fluoro-4-methoxyphenyl)piperidin-1-yl)-1-(3-fluoro-4-methylbenzyl)pyrrolidin-2-one

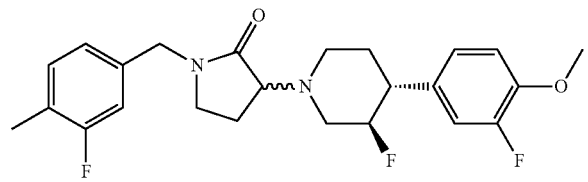

A mixture of (3R,4R)-3-fluoro-4-(3-fluoro-4-methoxyphenyl)piperidine hydrochloride (30 mg, 0.114 mmol, from step K), 3-bromo-1-(3-fluoro-4-methylbenzyl)pyrrolidin-2-one (54 mg, 0.189 mmol, intermediate 6) and DIPEA (0.020 mL, 0.114 mmol) in DMF (3 mL) was heated to 120° C. for 90 min in the a microwave reactor. The solvent was then removed under reduced pressure to obtain 60 mg of 3-((3R,4R)-3-Fluoro-4-(3-fluoro-4-methoxyphenyl)piperidin-1-yl)-1-(3-fluoro-4-methylbenzyl)pyrrolidin-2-one (diastereomeric pair) which was used in the next step without further purification. LCMS (Method P) RT=1.12 min, m/z 433 (M+H+).

Step M. 3-((3R,4R)-3-Fluoro-4-(3-fluoro-4-hydroxyphenyl)piperidin-1-yl)-1-(3-fluoro-4-methylbenzyl)pyrrolidin-2-one

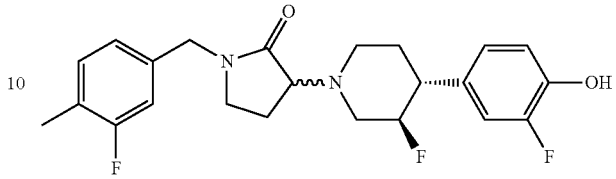

To a stirred solution of 3-((3R,4R)-3-fluoro-4-(3-fluoro-4-methoxyphenyl)piperidin-1-yl)-1-(3-fluoro-4-methylbenzyl)pyrrolidin-2-one (diastereomeric pair from step L, 50 mg, 0.12 mmol) in DCM (5 mL) at −78° C. was added boron tribromide (2 mL, 2 mmol, 1 M in DCM) and the resulting mixture was stirred at rt for 3 h. The solvent was evaporated and the residue subjected to preparative HPLC (method D) to yield 20 mg (0.04 mmol, 37%) of 3-((3R,4R)-3-Fluoro-4-(3-fluoro-4-hydroxyphenyl)piperidin-1-yl)-1-(3-fluoro-4-methylbenzyl)pyrrolidin-2-one (diastereomeric pair). LCMS (Method K) RT 1.16 min; m/z 419 (M+H+); $^1$H NMR (400 MHz, methanol-$d_4$) δ ppm 7.22-7.29 (m, 1H) 6.90-7.09 (m, 5H) 4.88-4.96 (m, 1H) 4.49-4.53 (m, 2H), 4.12-4.25 (m, 1H), 4.35-4.42 (m, 1H) 3.98-4.02 (m, 1H) 3.34-3.48 (m, 4H) 3.14-3.21 (m, 1H) 2.98-3.07 (m, 1H) 2.46-2.56 (m, 1H) 2.20-2.30 (m, 5H) 1.98-2.12 (m, 1H).

Step N. (S)-3-((3R,4R)-3-Fluoro-4-(3-fluoro-4-hydroxyphenyl)piperidin-1-yl)-1-(3-fluoro-4-methylbenzyl)pyrrolidin-2-one and (R)-3-((4R,4R)-3-fluoro-4-(3-fluoro-4-hydroxyphenyl)piperidin-1-yl)-1-(3-fluoro-4-methylbenzyl)pyrrolidin-2-one The product mixture from step M was subjected to chiral separation via SFC (method C-6) to give two homochiral products: Example 45, P-3 (3.6 mg) and Example 45, P-4 (2.2 mg). Data for P-3 (S)-3-(3R,4R)-3-fluoro-4-(3-fluoro-4-hydroxyphenyl)piperidin-1-yl)-1-(3-fluoro-4-methylbenzyl)pyrrolidin-2-one: HPLC (Method C) RT=7.03 min (Method D) RT=8.3 min, LCMS (Method F) RT=2.10 min, m/z 419.2 (M+H+), Chiral HPLC (Method C-6) RT=3.6 min; $^1$H NMR (400 MHz, methanol-$d_4$) δ ppm 1.73-1.90 (m, 2H) 2.02-2.24 (m, 2H) 2.25-2.31 (m, 3H) 2.39-2.48 (m, 1H) 2.52-2.71 (m, 2H) 2.74-2.82 (m, 1H) 3.13-3.30 (m, 2H) 3.38-3.47 (m, 1H) 3.67-3.76 (m, 1H) 4.37-4.70 (m, 4H) 6.82-7.04 (m, 5H) 7.18-7.28 (m, 1H). Data for P-4 (R)-3-((3R,4R)-3-fluoro-4-(3-fluoro-4-hydroxyphenyl)piperidin-1-yl)-1-(3-fluoro-4-methylbenzyl)pyrrolidin-2-one: HPLC (Method C) RT=7.05 min (Method D) RT=8.33 min, LCMS (Method F) RT=2.10 min, m/z 419.2 (M+H+), Chiral HPLC (Method C-6) RT=5.44 min; $^1$H NMR (400 MHz, methanol-$d_4$) δ ppm 1.67-1.93 (m, 2H) 2.01-2.13 (m, 1H) 2.14-2.23 (m, 1H) 2.25-2.28 (m, 3H) 2.39-2.51 (m, 1H) 2.52-2.72 (m, 2H) 2.97-3.07 (m, 1H) 3.09-3.18 (m, 1H) 3.22-3.32 (m, 2H) 3.68-3.78 (m, 1H) 4.38-4.55 (m, 2H) 4.58-4.70 (m, 1H) 6.84-7.05 (m, 5H) 7.19-7.28 (m, 1H).

Example 46

Peak-1, Peak-2, Peak-3, Peak-4

(S)-3-((3R,4R)-3-Fluoro-4-(4-hydroxyphenyl)piperidin-1-yl)-1-(4-methylbenzyl)pyrrolidin-2-one and (R)-3-((3R,4R)-3-fluoro-4-(4-hydroxyphenyl)piperidin-1-yl)-1-(4-methylbenzyl)pyrrolidin-2-one

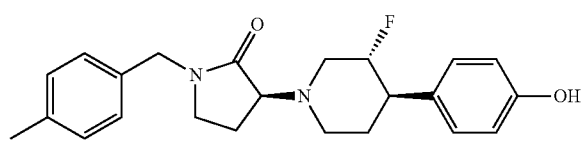

Example 46, P-1

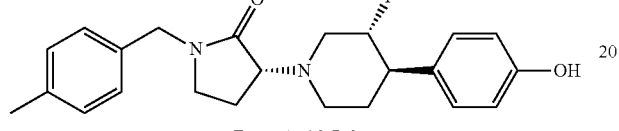

Example 46, P-2

(S)-3-((3S,4S)-3-Fluoro-4-(4-hydroxyphenyl)piperidin-1-yl)-1-(4-methylbenzyl)pyrrolidin-2-one and (R)-3-((3S,4S)-3-fluoro-4-(4-hydroxyphenyl)piperidin-1-yl)-1-(4-methylbenzyl)pyrrolidin-2-one

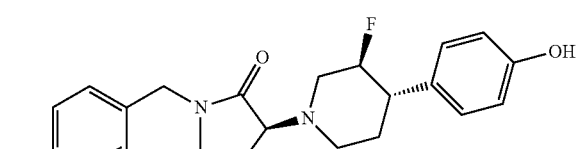

Example 46, P-3

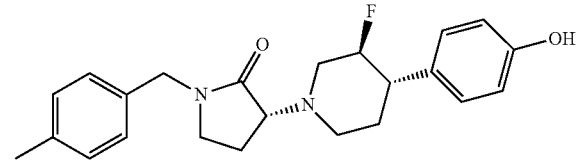

Example 46, P-4

Step A. (±)-rel-(3S,4S)-1-benzyl-4-(4-methoxyphenyl)piperidin-3-ol

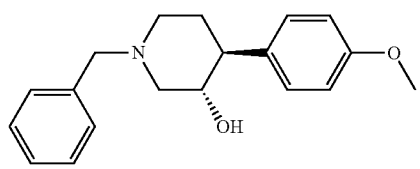

To a suspension of sodium tetrahydroborate (2.7 g, 72 mmol) in THF (200 mL) at 0° C. under a nitrogen atmosphere was added dropwise boron trifluoride etherate (8.8 mL, 70 mmol) and the resulting mixture was stirred for 30 minutes. Then 1-benzyl-4-(4-methoxyphenyl)-1,2,3,6-tetrahydropyridine (10 g, 36 mmol, from S. Halazy et al WO 97/28140 (8/7/97)) dissolved in 100 mL of tetrahydrofuran was added. The mixture was allowed to warm to rt and stirred for 2 h. The reaction was then quenched by the dropwise addition of 100 mL of water. Next were added sequentially 100 mL of ethanol, 100 mL of a 10% aqueous sodium hydroxide solution, and 30% hydrogen peroxide (18 mL, 180 mmol) and the mixture was stirred at reflux temperature overnight. The reaction mixture was then allowed to cool, diluted with saturated aqueous ammonium chloride (200 mL), and extracted with ethyl acetate (500 mL). The organic layer was dried over $Na_2SO_4$, filtered, and evaporated under reduced pressure to give (±)-rel-(3S,4S)-1-benzyl-4-(4-methoxyphenyl)piperidin-3-ol (8.5 g, 24.6 mmol, 69% yield) which was used without further purification. LCMS (Method K) RT 1.99 min; m/z 298.0 (M+H$^+$).

Step B. (±)-rel-(3S,4S)-4-(4-methoxyphenyl)piperidin-3-ol

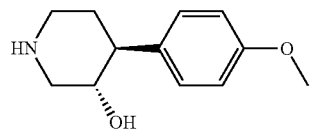

To a solution of (±)-rel-(3S,4S)-1-benzyl-4-(4-methoxyphenyl)piperidin-3-ol (9 g, 30 mmol) in methanol (150 mL) was added 10% Pd/C (4.8 g) and the reaction mixture was stirred overnight under a hydrogen atmosphere. The catalyst was then removed by filtration through Celite and the solvent was evaporated under reduced pressure to give (±)-rel-(3S,4S)-4-(4-methoxyphenyl)piperidin-3-ol (5.1 g, 24.6 mmol, 81% yield) which was used without further purification. $^1$H NMR (400 MHz, DMSO-d$_6$) δ ppm 7.10-7.15 (m, 2H) 6.80-6.86 (m, 2H) 4.30 (d, J=5.27 Hz, 1H) 3.37-3.43 (m, 1H) 3.04 (dd, J=11.58, 4.36 Hz, 1H) 2.86 (d, J=12.17 Hz, 1H) 2.43 (td, J=12.09, 2.67 Hz, 1H) 2.22-2.35 (m, 2H) 1.57-1.63 (m, 1H) 1.43-1.54 (m, 1H).

Step C. (±)-rel-(3S,4S)-tert-butyl 4-(4-(tert-butoxycarbonyloxy)phenyl)-3-hydroxypiperidine-1-carboxylate

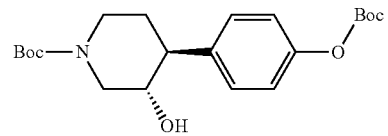 [SMILES: CC(C)(C)OC(=O)Oc1ccc([C@@H]2CCN(C(=O)OC(C)(C)C)C[C@H]2O)cc1]

To a solution of (±)-rel-(3S,4S)-4-(4-methoxyphenyl)piperidin-3-ol (4.5 g, 21.7 mmol) in DCM (150 mL) at −10° C. under nitrogen was added a 1 M solution of boron tribromide in DCM (109 mL, 109 mmol). The reaction mixture was allowed to warm to rt, stirred for 2 h, and then rechilled to 0° C. and quenched by the addition of a saturated aqueous sodium bicarbonate solution (300 mL). The aqueous layer was washed with 250 mL of DCM and then to it was added 200 mL 10% aqueous NaOH, followed by 9.5 g (43.5 mmol) of di-t-butyl dicarbonate and the resulting mixture was stirred for an additional 2 h. The mixture was then extracted with 200 mL ethyl acetate and the organic layer was separated, dried over $Na_2SO_4$, filtered, and evaporated under reduced pressure to (±)-rel-(3S,4S)-tert-butyl 4-(4-(tert-butoxycarbonyloxy)phenyl)-3-hydroxypiperidine-1-carboxylate (6.5 g, 12 mmol, 56% yield) which was used without further purification. LCMS (Method K) RT 2.33 min, m/z 282 (M+H$^+$-2 t-butyl), 370; $^1$H NMR (400 MHz, DMSO-d$_6$) δ ppm 7.27 (d, J=8.66 Hz, 2H) 7.08 (d, J=8.66 Hz, 2H) 4.85 (d, J=5.65 Hz, 1H) 4.13 (d, J=8.41 Hz, 1H) 3.97 (d, J=10.48 Hz, 1H) 3.45 (tt, J=10.27, 5.19 Hz, 1H) 1.67 (d, J=3.39 Hz, 1H) 1.50-1.59 (m, 1H) 1.49 (s, 11H).

Step D. (±)-rel-(3S,4S)-tert-butyl 3-hydroxy-4-(4-hydroxyphenyl)piperidine-1-carboxylate

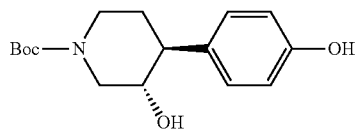

To a solution of (±)-rel-(3S,4S)-tert-butyl 4-(4-(tert-butoxycarbonyloxy)phenyl)-3-hydroxypiperidine-1-carboxylate (6.5 g, 16.5 mmol) in 100 mL of methanol was added 11.42 g of potassium carbonate (83 mmol) and the reaction mixture was stirred at rt for 5 h. The organic solvent was removed under reduced pressure and the residue was partitioned between 1N HCl (300 mL) and ethyl acetate (300 mL). The layers were separated and the organic layer was dried over Na$_2$SO$_4$ and evaporated under reduced pressure to give (±)-rel-(3S,4S)-tert-butyl 3-hydroxy-4-(4-hydroxyphenyl)piperidine-1-carboxylate (5 g, 15 mmol, 92% yield) which was used without further purification. LCMS (method F) RT 1.85 min, m/z 238 (M+H$^+$–t-butyl), 279 (M+H$^+$–t-butyl+CH$_3$CN), $^1$H NMR (400 MHz, DMSO-d$_6$) δ ppm 7.01 (d, J=8.53 Hz, 2H) 6.66 (d, J=8.53 Hz, 2H) 4.70 (d, J=5.02 Hz, 1H) 4.09 (br. s., 1H) 3.94 (d, J=11.55 Hz, 1H) 3.35-3.41 (m, 1H) 2.66-2.77 (m, 1H) 2.29-2.39 (m, 1H) 1.63 (dd, J=13.30, 3.26 Hz, 1H) 1.44-1.52 (m, 1H) 1.42 (s, 9H).

Step E. (3S,4S)-tert-Butyl 3-hydroxy-4-(4-hydroxyphenyl)piperidine-1-carboxylate and (3R,4R)-tert-butyl 3-hydroxy-4-(4-hydroxyphenyl)piperidine-1-carboxylate

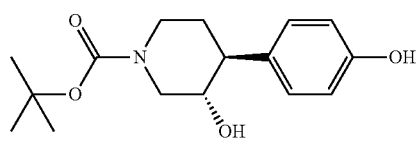
E-1

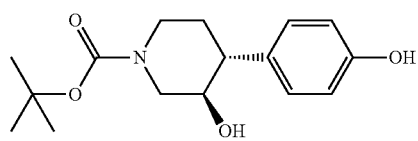
E-2

(±)-rel-(3S,4S)-tert-Butyl 3-hydroxy-4-(4-hydroxyphenyl)piperidine-1-carboxylate (5 g, 17 mmol, from step D) was subjected to chiral SFC separation (method C-5) to yield enantiomers E-1 (1.9 g, 6.48 mmol, 38.0% yield) and E-2 (2.4 g, 8.18 mmol, 48.0% yield). Data for E-1: chiral HPLC (method A5) retention time 3.42 min. Data for E-2: chiral HPLC (method A5) retention time 4.2 min.

Step F. (3R,4R)-tert-Butyl 4-(4-(benzyloxy)phenyl)-3-hydroxypiperidine-1-carboxylate

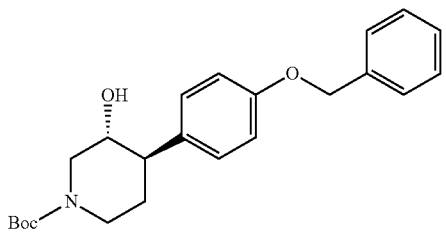 [SMILES: CC(C)(C)OC(=O)N1CC[C@H](c2ccc(OCc3ccccc3)cc2)[C@@H](O)C1]

A mixture of (3R,4R)-tert-butyl 3-hydroxy-4-(4-hydroxyphenyl)piperidine-1-carboxylate (620 mg, 2.1 mmol, E-2 from step E), potassium carbonate (584 mg, 4.2 mmol), and benzyl bromide (0.25 mL, 2.1 mmol) in DMF (5 mL) was stirred at rt for 16 h. The solvent was removed by evaporation and the residue was treated with 50 mL of water. The aqueous mixture was then extracted 4 times with 50 mL of chloroform. The combined organic phases were dried over anhydous Na$_2$SO$_4$, filtered, and evaporated to yield 750 mg of (3R,4R)-tert-butyl 4-(4-(benzyloxy)phenyl)-3-hydroxypiperidine-1-carboxylate which was used without further purification. LCMS (method F) RT 2.28 min, m/z=310 (M+H$^+$–t-butyl –water), 328 (M+H$^+$–t-butyl).

Step G. (3R,4R)-4-(4-(Benzyloxy)phenyl)piperidin-3-ol hydrochloride

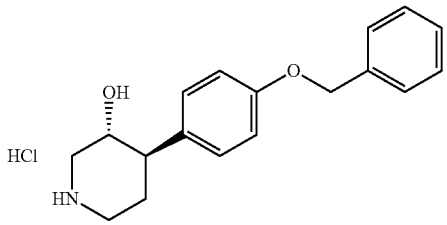 [SMILES: Cl ; O[C@H]1CNCC[C@@H]1c1ccc(OCc2ccccc2)cc1]

A mixture of (3R,4R)-tert-butyl 4-(4-(benzyloxy)phenyl)-3-hydroxypiperidine-1-carboxylate (750 mg, 2 mmol), dioxane (4 mL) and 4.9 mL of 4 M HCl in dioxane was stirred at rt for 2 h. The reaction was then evaporated to dryness to yield 550 mg of (3R,4R)-4-(4-(Benzyloxy)phenyl)piperidin-3-ol hydrochloride which was used without further purification. LCMS (method J) RT 0.70 min, m/z 284 (M+H$^+$).

Step H. 3-((3R,4R)-4-(4-(Benzyloxy)phenyl)-3-hydroxypiperidin-1-yl)-1-(4-methylbenzyl)pyrrolidin-2-one

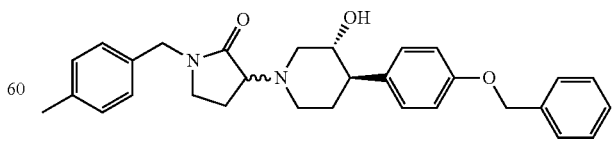

A mixture of 3-bromo-1-(4-methylbenzyl)pyrrolidin-2-one (Intermediate 2, 220 mg, 0.82 mmol), (3R,4R)-4-(4-(benzyloxy)phenyl)piperidin-3-ol hydrochloride (262 mg, 0.82 mmol, from step G) and triethylamine (11 mL, 8.2 mmol) was stirred at 60° C. for 1 h, 80° C. for 1 h, 100° C. for 1 h and 120° C. for 1 h. The reaction mixture was then allowed to cool, diluted with 40 mL of water and extracted four times with 50 mL of chloroform. The combined organic layers were washed with 60 mL brine, dried over anhydrous sodium sulfate, filtered, and evaporated to yield 382 mg of 3-((3R,4R)-4-(4-(benzyloxy)phenyl)-3-hydroxypiperidin-1-yl)-1-(4-methylbenzyl)pyrrolidin-2-one which was used without further purification. LCMS (method J) (main component of a mixture) RT 2.23 min, m/z 471 (M+H⁺).

Step I. 3-((3R,4R)-4-(4-(Benzyloxy)phenyl)-3-fluoropiperidin-1-yl)-1-(4-methylbenzyl)pyrrolidin-2-one

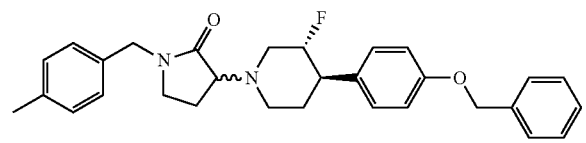 [SMILES: Cc1ccc(CN2CCC(N3CC[C@H](c4ccc(OCc5ccccc5)cc4)[C@@H](F)C3)C2=O)cc1]

A solution of 3-(-4-(4-(benzyloxy)phenyl)-3-hydroxypiperidin-1-yl)-1-(4-methylbenzyl)pyrrolidin-2-one (382 mg, 0.81 mmol) in DCM (5 mL) cooled to 0° C. was treated dropwise with DAST (0.32 mL, 2.4 mmol) over 3 min. The reaction mixture was then allowed to warm to rt and was stirred for 2 h. The reaction was then quenched with 50 mL of 10% aqueous sodium bicarbonate solution and extracted 4 times with 40 mL of DCM. The combined organic layers were washed with 50 mL of brine, dried over anhydrous sodium sulfate, filtered, and concentrated under vacuum to yield 382 mg of 3-((3R,4R)-4-(4-(benzyloxy)phenyl)-3-fluoropiperidin-1-yl)-1-(4-methylbenzyl)pyrrolidin-2-one as a mixture of two diastereomers and rearrangement products which was used without further purification. LCMS (method J) (main component of a mixture) RT 0.9 min, m/z 473 (M+H⁺).

Step J. 3-((3R,4R)-3-Fluoro-4-(4-hydroxyphenyl)piperidin-1-yl)-1-(4-methylbenzyl)pyrrolidin-2-one

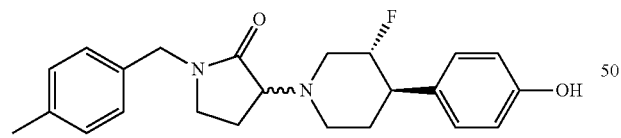

A mixture of 3-((3R,4R)-(4-(4-(benzyloxy)phenyl)-3-fluoropiperidin-1-yl)-1-(4-methylbenzyl)pyrrolidin-2-one (382 mg, 0.81 mmol) and methanol (4 mL) was flushed with nitrogen, followed by the addition of 172 mg of 10% Pd/C. Then the mixture was stirred at rt overnight under 25-99 psi hydrogen pressure. The reaction was then transferred to a 100 mL autoclave and stirred at 7 kg/cm² hydrogen pressure for 4 days. The catalyst was removed by filtration through Celite and the solvent was evaporated off. The crude product was subjected to HPLC purification (method B) to yield 77.3 mg 3-((3R,4R)-3-fluoro-4-(4-hydroxyphenyl)-piperidin-1-yl)-1-(4-methylbenzyl)pyrrolidin-2-one (diastereomeric pair) LCMS (method Q) RT 1.15 min, m/z 383.0 (M+H⁺).

Step K. (S)-3-((3R,4R)-3-Fluoro-4-(4-hydroxyphenyl)piperidin-1-yl)-1-(4-methylbenzyl)pyrrolidin-2-one and (R)-3-((3R,4R)-3-fluoro-4-(4-hydroxyphenyl)piperidin-1-yl)-1-(4-methylbenzyl)pyrrolidin-2-one The diastereomeric mixture from step J was separated by SFC method C-7 to yield homochiral Examples 46 P-1 (29.3 mg) and P-2 (32.8 mg). Data for P-1 (S)-3-((3R,4R)-3-fluoro-4-(4-hydroxyphenyl)piperidin-1-yl)-1-(4-methylbenzyl)pyrrolidin-2-one: LCMS (method F) RT 2.10 min, m/z 383.2 (M+H⁺), 405.2 (M+Na⁺); HPLC (method B) RT 8.24 min (98.8% AP); HPLC (method C) RT 6.52 min (99.1% AP); Chiral HPLC (method C-6) RT 4.1 min; ¹H NMR (400 MHz, methanol-d₄) δ ppm 1.76-1.86 (m, 2H) 2.07 (d, J=8.53 Hz, 1H) 2.13-2.21 (m, 1H) 2.34 (s, 3H) 2.43 (s, 0H) 2.55-2.60 (m, 1H) 2.65-2.70 (m, 1H) 2.75 (br. s., 1H) 3.20-3.30 (m, 2H) 3.38-3.45 (m, 1H) 3.70 (t, J=8.78 Hz, 1H) 4.44 (t, J=79.81 Hz, 3H) 4.63-4.71 (m, 1H) 6.70-6.80 (m, 2H) 7.07-7.15 (m, 2H) 7.07-7.12 (m, 1H) 7.13-7.22 (m, 4H); ¹⁹F NMR δ ppm-184.171. Data for P-2: (R)-3-((3R,4R)-3-fluoro-4-(4-hydroxyphenyl)piperidin-1-yl)-1-(4-methylbenzyl)pyrrolidin-2-one: LCMS (method F) RT 2.10 min, m/z 383.2 (M+H⁺), 405.2 (M+Na⁺); HPLC (method B) RT 8.29 min (99.7% AP); HPLC (method C) RT 6.52 min (99.8% AP); Chiral HPLC (method C-6) RT 6.92 min; ¹H NMR (400 MHz, methanol-d₄) δ ppm 1.80-1.90 (m, 2H) 2.07 (d, J=8.03 Hz, 1H) 2.19 (s, 1H) 2.34 (s, 3H) 2.41-2.48 (m, 1H) 2.66 (d, J=4.52 Hz, 2H) 2.95-3.03 (m, 1H) 3.10-3.18 (m, 1H) 3.20-3.30 (m, 2H) 3.68-3.78 (m, 1H) 4.38 (s, 1H) 4.51 (d, J=14.56 Hz, 2H) 6.70-6.80 (m, 2H) 7.05-7.13 (m, 2H) 7.13-7.22 (m, 4H); ¹⁹F NMR δ ppm-184.311.

Step L. (3S,4S)-tert-Butyl 3-fluoro-4-(4-hydroxyphenyl)piperidine-1-carboxylate

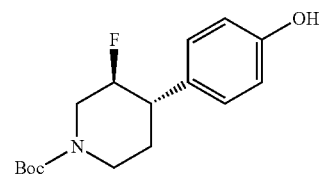 [SMILES: CC(C)(C)OC(=O)N1CC[C@@H](c2ccc(O)cc2)[C@H](F)C1]

To a solution of (3S,4S)-tert-butyl 3-hydroxy-4-(4-hydroxyphenyl)piperidine-1-carboxylate (400 mg, 1.36 mmol, the first eluting enantiomer E-1 from step E) in DCM (5 mL) cooled to 0° C. was added dropwise DAST (0.54 mL, 4.1 mmol) over 10 min. The mixture was allowed to warm up to rt and was stirred for 2 h. The reaction was slowly quenched with 50 mL of a 10% aqueous sodium bicarbonate solution and extracted four times with 50 mL of DCM. The combined organic layers were washed with 75 mL of brine, dried, and concentrated under vacuum to yield 390 mg of (3S,4S)-tert-butyl 3-fluoro-4-(4-hydroxyphenyl)piperidine-1-carboxylate which was used without further purification. LCMS (Method Q) RT 0.92 min, m/z 240.1 (M+H⁺).

Step M. 4-((3S,4S)-3-Fluoropiperidin-4-yl)phenol hydrochloride

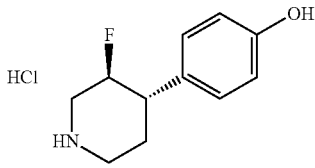 [SMILES: Cl ; Oc1ccc([C@@H]2CCNC[C@H]2F)cc1]

A mixture of (3S,4S)-tert-butyl 3-fluoro-4-(4-hydroxyphenyl)piperidine-1-carboxylate (390 mg, 1.3 mmol) and 4M HCl in dioxane (3.3 mL, 13.2 mmol) in dioxane (4 mL) was stirred at rt for 2 hr. It was then concentrated to dryness, washed with 10 mL of 5% DCM/diethyl ether mixture and the solid was isolated by filtration. Yield: 260 mg of 4-((3S,4S)-3-fluoropiperidin-4-yl)phenol hydrochloride; LCMS (method Q) RT 0.46 min, mz 196.1 (M+H$^+$) $^1$H NMR (400 MHz, DMSO-d$_6$) δ=9.57 (br. s., 4H), 8.92-8.68 (m, 1H), 7.14 (d, J=8.5 Hz, 1H), 7.06 (d, J=8.5 Hz, 2H), 6.82-6.73 (m, 2H), 5.07-4.85 (m, 1H), 3.77-3.36 (m, 9H), 3.32-3.22 (m, 2H), 3.13-2.85 (m, 5H), 2.06-1.88 (m, H).

Step N. 3-((3S,4S)-3-Fluoro-4-(4-hydroxyphenyl)piperidin-1-yl)-1-(4-methylbenzyl)pyrrolidin-2-one

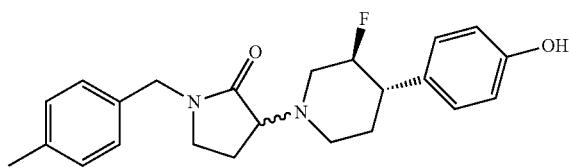 [SMILES: Cc1ccc(CN2CCC(N3CC[C@@H](c4ccc(O)cc4)[C@H](F)C3)C2=O)cc1]

A mixture of 3-bromo-1-(4-methylbenzyl)pyrrolidin-2-one (200 mg, 0.75 mmol), triethylamine (0.52 mL, 3.7 mmol) and 4-((3S,4S)-3-fluoropiperidin-4-yl)phenol hydrochloride (173 mg, 0.75 mmol) in DMF (3 mL) was heated to 120° C. in a microwave reactor for 1.5 h. The mixture was allowed to cool and was then mixed with 60 mL water and extracted 5 times with 40 mL of DCM. The combined organic extracts were washed with 80 mL of brine, dried over anhydrous sodium sulfate, filtered, and evaporated to give 265 mg of 3-((3S,4S)-3-fluoro-4-(4-hydroxy-phenyl)piperidin-1-yl)-1-(4-methylbenzyl)pyrrolidin-2-one as a mixture of 2 diastereoisomers. LCMS (method P) RT 0.92 min m/z 383.4 (M+H$^+$).

Step O. (S)-3-((3S,4S)-3-Fluoro-4-(4-hydroxyphenyl)piperidin-1-yl)-1-(4-methylbenzyl)pyrrolidin-2-one and (R)-3-((3S,4S)-3-fluoro-4-(4-hydroxyphenyl)piperidin-1-yl)-1-(4-methylbenzyl)pyrrolidin-2-one A portion of the diasteromer mixture from step N (130 mg) was subjected to chiral purification via SFC (method C-7) to give homochiral Examples 46 P-3 (37.7 mg) and P-4 (60.7 mg). Data for P-3 (S)-3-((3S,4S)-3-fluoro-4-(4-hydroxyphenyl)piperidin-1-yl)-1-(4-methylbenzyl)pyrrolidin-2-one: LCMS (Method F) RT=2.10 min, m/z 383.2 (M+H$^+$); HPLC (Method C) RT 6.54 min, (Method D) RT 8.20 min; chiral HPLC (method C-6) RT 3.42 min; $^1$H NMR (400 MHz, methanol-d$_4$) δ ppm 1.76-1.86 (m, 2H) 2.06 (d, J=8.53 Hz, 1H) 2.10-2.21 (m, 1H) 2.34 (s, 3H) 2.40-2.48 (m, 1H) 2.53-2.60 (m, 1H) 2.61-2.70 (m, 2H) 2.95-3.01 (m, 1H) 3.01 (s, 2H) 3.10-3.16 (m, 1H) 3.18-3.28 (m, 2H) 3.72 (s, 1H) 4.35-4.41 (m, 1H) 4.46-4.70 (m, 2H) 6.72-6.80 (m, 2H) 7.05-7.23 (m, 6H). Data for P-4 (R)-3-((3S,4S)-3-fluoro-4-(4-hydroxyphenyl)piperidin-1-yl)-1-(4-methylbenzyl)pyrrolidin-2-one: LCMS (Method F) RT 2.11 min, m/z 383.2 (M+H$^+$); HPLC (Method C) RT 6.50 min, (Method D) RT 8.21 min; chiral HPLC (method C-6) RT 6.31 min; $^1$H NMR (400 MHz, methanol-d$_4$) δ ppm 1.81 (dd, J=7.28, 2.76 Hz, 2H) 2.06 (d, J=9.04 Hz, 2H) 2.33 (s, 3H) 2.43 (s, 1H) 2.55 (br s, 1H) 2.66 (d, J=40.16 Hz, 2H) 2.75-2.80 (m, 1H) 2.96-3.10 (m, 2H) 3.20-3.28 (m, 2H) 3.41 (d, J=5.52 Hz, 1H) 3.66-3.75 (m, 1H) 4.31-4.41 (m, 1H) 4.46-4.71 (m, 2H) 6.76 (d, J=8.53 Hz, 2H) 7.05-7.23 (m, 6H).

Example 47

(S)-3-((3S,4S)-3-Fluoro-4-(4-hydroxyphenyl)piperidin-1-yl)-1-(3-fluoro-4-methylbenzyl)pyrrolidin-2-one, (S)-3-((3R,4R)-3-fluoro-4-(4-hydroxyphenyl)piperidin-1-yl)-1-(3-fluoro-4-methylbenzyl)pyrrolidin-2-one, (R)-3-((3S,4S)-3-fluoro-4-(4-hydroxyphenyl)piperidin-1-yl)-1-(3-fluoro-4-methylbenzyl)pyrrolidin-2-one, and (R)-3-((3R,4R)-3-fluoro-4-(4-hydroxyphenyl)piperidin-1-yl)-1-(3-fluoro-4-methylbenzyl)pyrrolidin-2-one

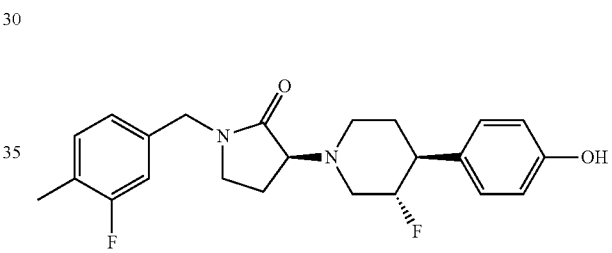

Example 47, P-1

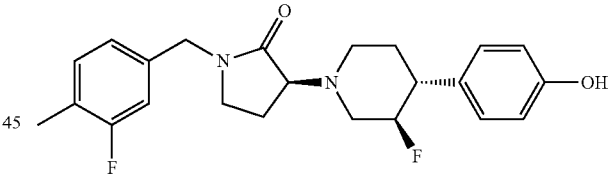

Example 47, P-2

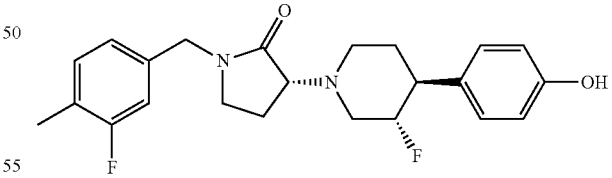

Example 47, P-3

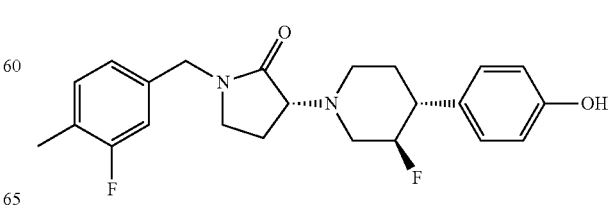

Example 47, P-4

Step A. (±)-rel-1-(3-Fluoro-4-methylbenzyl)-3-((3S,4S)-3-hydroxy-4-(4-methoxyphenyl)piperidin-1-yl)pyrrolidin-2-one

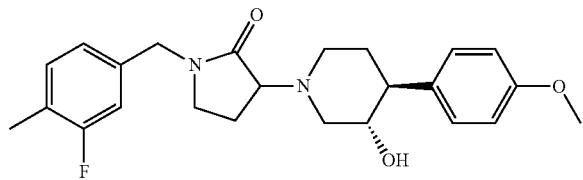

To a solution of 3-bromo-1-(3-fluoro-4-methylbenzyl)pyrrolidin-2-one (Intermediate 6, 200 mg, 0.7 mmol) and (±)-rel-(3S,4S)-4-(4-methoxyphenyl)piperidin-3-ol (145 mg, 0.7 mmol, from Example 46, step B) in acetonitrile (15 mL) was added triethylamine (0.1 mL, 0.7 mmol) and the resulting mixture was heated in the microwave at 100° C. for 1 h. The cooled reaction mixture was diluted with a saturated ammonium chloride solution and extracted with ethyl acetate (100 mL). The organic layer was separated, dried over $Na_2SO_4$, filtered, and evaporated under reduced pressure to give (±)-rel-1-(3-fluoro-4-methylbenzyl)-3-((3S,4S)-3-hydroxy-4-(4-methoxyphenyl)piperidin-1-yl)pyrrolidin-2-one (280 mg, 0.51 mmol, 73% yield, mixture of 4 diasteroisomers), which was used directly in the next step. LCMS (Method F) RT 1.99 min m/z 413.2 (M+H+).

Step B. (±)-rel-1-(3-fluoro-4-methylbenzyl)-3-((3S,4S)-3-hydroxy-4-(4-hydroxyphenyl)piperidin-1-yl)pyrrolidin-2-one

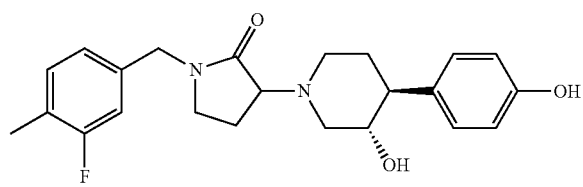 [SMILES: Cc1ccc(CN2CCC(N3CC[C@@H](c4ccc(O)cc4)[C@H](O)C3)C2=O)cc1F]

To a solution of (±)-rel-1-(3-fluoro-4-methylbenzyl)-3-((3S,4S)-3-hydroxy-4-(4-methoxyphenyl)piperidin-1-yl)pyrrolidin-2-one (300 mg, 0.73 mmol) in DCM (20 mL) under nitrogen at −10° C. was added boron tribromide (0.17 mL, 1.8 mmol) and the reaction mixture was stirred at rt for 1 h. The reaction was then quenched with saturated sodium bicarbonate solution and extracted with 200 mL of ethyl acetate. The organic layer was separated, dried over $Na_2SO_4$, filtered, and evaporated under reduced pressure to give (±)-rel-1-(3-fluoro-4-methylbenzyl)-3-((3S,4S)-3-hydroxy-4-(4-hydroxyphenyl)piperidin-1-yl)pyrrolidin-2-one (290 mg, 0.36 mmol, 50% yield, mixture of 4 diastereoisomers); LCMS (Method F) RT 1.854 min m/z 399.2 (M+H+).

Step C. (±)-rel-3-((3S,4S)-3-Fluoro-4-(4-hydroxyphenyl)piperidin-1-yl)-1-(3-fluoro-4-methylbenzyl)pyrrolidin-2-one

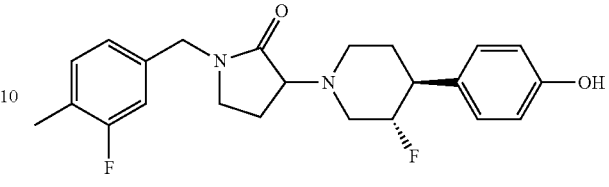

To a solution of (±)-rel-1-(3-fluoro-4-methylbenzyl)-3-((3S,4S)-3-hydroxy-4-(4-hydroxyphenyl)piperidin-1-yl)pyrrolidin-2-one (280 mg, 0.7 mmol) in DCM (20 mL) was added DAST (0.5 mL, 3.5 mmol) and the reaction mixture was stirred under nitrogen for 1 h. The reaction was then quenched by the addition of 100 mL of a saturated sodium bicarbonate solution and the mixture was diluted with 100 mL of ethyl acetate. The organic layer was separated, dried over $Na_2SO_4$, filtered, and evaporated under reduced pressure. The residue was subjected to preparative HPLC (method B) to yield 22 mg of (±)-rel-3-((3S,4S)-3-fluoro-4-(4-hydroxyphenyl)piperidin-1-yl)-1-(3-fluoro-4-methylbenzyl)pyrrolidin-2-one as a mixture of 4 diastereomers. LCMS (method P) RT 1.64 min; m/z=401.0 (M+H+).

Step D. (S)-3-((3S,4S)-3-Fluoro-4-(4-hydroxyphenyl)piperidin-1-yl)-1-(3-fluoro-4-methylbenzyl)pyrrolidin-2-one, (S)-3-((3R,4R)-3-fluoro-4-(4-hydroxyphenyl)piperidin-1-yl)-1-(3-fluoro-4-methylbenzyl)pyrrolidin-2-one, (R)-3-((3S,4S)-3-fluoro-4-(4-hydroxyphenyl)piperidin-1-yl)-1-(3-fluoro-4-methylbenzyl)pyrrolidin-2-one, and (R)-3-((3R,4R)-3-fluoro-4-(4-hydroxyphenyl)piperidin-1-yl)-1-(3-fluoro-4-methylbenzyl)pyrrolidin-2-one The compound (±)-rel-3-((3S,4S)-3-fluoro-4-(4-hydroxyphenyl)piperidin-1-yl)-1-(3-fluoro-4-methylbenzyl)pyrrolidin-2-one (85 mg, 0.212 mmol) isolated from Step C was separated into the homochiral Examples 47 P-1, P-2, P-3, and P-4 via chiral SFC (method I): Data for P-1 (S)-3-((3S,4S)-3-fluoro-4-(4-hydroxyphenyl)piperidin-1-yl)-1-(3-fluoro-4-methylbenzyl)-pyrrolidin-2-one: LCMS (Method F) RT 2.03 min, m/z 401 (M+H+); HPLC (Method A) RT=6.73 min (96.8% AP), (method B) RT=7.719 min (97% AP); Chiral SFC (Method E) RT 5.17 min (100% AP); $^1$H NMR (400 MHz, methanol-$d_4$) δ ppm 1.84 (dd, J=7.28, 3.26 Hz, 2H) 2.01-2.27 (m, 5H) 2.39-2.68 (m, 3H) 2.97-3.06 (m, 1H) 3.15 (s, 1H) 3.22-3.30 (m, 1H) 3.73 (t, J=8.78 Hz, 1H) 4.38-4.71 (m, 3H) 6.73-6.79 (m, 2H) 6.93-7.03 (m, 2H) 7.08-7.16 (m, 1H) 7.23 (t, J=7.53 Hz, 1H). Data for P-2 (S)-3-((3R,4R)-3-fluoro-4-(4-hydroxyphenyl)piperidin-1-yl)-1-(3-fluoro-4-methylbenzyl)-pyrrolidin-2-one: LCMS (Method F) RT 2.30 min, m/z 401 (M+H+); HPLC (Method A) RT=6.71 min (99% AP), Method B RT=7.73 min (98.1% AP); Chiral SFC (Method E) RT 6.21 min (96.5% AP); $^1$H NMR (400 MHz, methanol-$d_4$) δ ppm 1.74-1.86 (m, 2H) 2.03-2.13 (m, 1H) 2.15-2.27 (m, 4H) 2.43 (td, J=10.04, 4.52 Hz, 1H) 2.50-2.71 (m, 2H) 2.76 (d, J=1.51 Hz, 1H) 3.20-3.30 (m, 2H) 3.38-3.46 (m, 1H) 3.71 (t, J=9.04 Hz, 1H) 4.37-4.70 (m, 3H) 6.72-6.78 (m, 2H) 6.92-7.02 (m, 2H) 7.09-7.13 (m, 1H) 7.23 (t, J=7.78 Hz, 1H). Data for P-3 (R)-3-((3S,4S)-3-fluoro-4-(4-hydroxyphenyl)piperidin-1-yl)-1-(3-fluoro-4-methylbenzyl)-pyrrolidin-2-one: LCMS (Method F) RT 2.04 min, m/z 401

(M+H⁺); HPLC (Method A) RT=6.68 min (98% AP), (Method B) RT=7.70 min (99.2% AP); Chiral SFC (Method E) RT 7.22 min (98.5% AP); ¹H NMR (400 MHz, methanol-d₄) δ ppm 1.74-1.86 (m, 2H) 2.02-2.27 (m, 5H) 2.43 (td, J=10.04, 5.02 Hz, 1H) 2.50-2.72 (m, 3H) 2.73-2.82 (m, 3H) 3.23-3.30 (m, 2H) 3.38-3.46 (m, 1H) 3.71 (t, J=8.78 Hz, 1H) 4.36-4.72 (m, 4H) 6.73-6.79 (m, 2H) 6.94-7.02 (m, 2H) 7.08-7.14 (m, 2H) 7.23 (t, J=7.78 Hz, 1H). Data for P-4 (R)-3-((3R,4R)-3-fluoro-4-(4-hydroxyphenyl)piperidin-1-yl)-1-(3-fluoro-4-methylbenzyl)pyrrolidin-2-one: LCMS (Method F) RT: 2.03 min, m/z 401 (M+H⁺). HPLC (Method A) RT=6.71 min (90% AP); (Method B) RT=7.68 min (91.5% AP); Chiral SFC (Method E) RT 7.89 min (97% AP); ¹H NMR (400 MHz, methanol-d₄) δ ppm 1.78-1.88 (m, 2H) 2.09 (d, J=8.53 Hz, 1H) 2.26 (d, J=2.01 Hz, 4H) 2.40-2.47 (m, 1H) 2.66 (d, J=4.52 Hz, 2H) 2.96-3.06 (m, 1H) 3.15 (s, 1H) 3.21-3.30 (m, 2H) 3.73 (s, 1H) 4.37-4.69 (m, 3H) 6.72-6.79 (m, 2H) 6.94-7.03 (m, 2H) 7.07-7.13 (m, 1H) 7.23 (t, J=7.53 Hz, 1H).

Step E. (3R,4R)-4-(4-Hydroxyphenyl)piperidin-3-ol hydrochloride

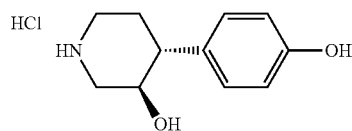

E-2a

To a solution of (3R,4R)-tert-butyl 3-hydroxy-4-(4-hydroxyphenyl)piperidine-1-carboxylate (1.5 g, 5.1 mmol, E-2 from example 46 step E) in methanol (50 mL) under nitrogen was added 12.8 mL of 4 M HCl in dioxane and the reaction was stirred for 1 h at rt. The mixture was then evaporated under reduced pressure to dryness and the residue was washed twice with 20 mL of diethyl ether. The solid residue was dried under vacuum to give (3R,4R)-4-(4-hydroxyphenyl)-piperidin-3-ol hydrochloride E-2a (950 mg, 4.1 mmol). LCMS (method F) RT: 0.17 min, m/z 194 (M+H⁺). ¹H NMR (400 MHz, DMSO-d₆) δ ppm 1.74-1.93 (m, 2H) 2.61-2.68 (m, 1H) 2.81-2.93 (m, 1H) 3.21-3.33 (m, 2H) 3.78-3.90 (m, 1H) 6.72 (d, J=8.53 Hz, 2H) 7.00 (d, J=8.53 Hz, 2H) 9.14-9.25 (m, 1H) 9.27-9.44 (m, 1H).

Step F. 1-(3-Fluoro-4-methylbenzyl)-3-((3R,4R)-3-hydroxy-4-(4-hydroxyphenyl)piperidin-1-yl)pyrrolidin-2-one

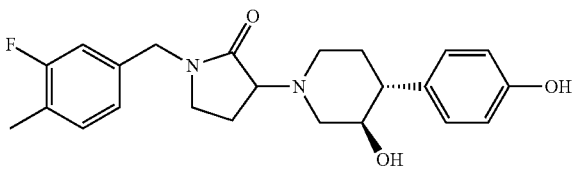 [SMILES: Cc1ccc(CN2CCC(N3CC[C@H](c4ccc(O)cc4)[C@@H](O)C3)C2=O)cc1F]

To a solution of racemic 3-bromo-1-(3-fluoro-4-methylbenzyl)pyrrolidin-2-one (1.5 g, 5.2 mmol, Intermediate 6) and (3R,4R)-4-(4-hydroxyphenyl)piperidin-3-ol, HCl (1.2 g, 5.2 mmol) in acetonitrile (20 mL) was added triethylamine (2.2 mL, 15.7 mmol) and the resulting mixture was heated for 5 h at 60° C. The reaction mixture was then evaporated and the residue was diluted with saturated ammonium chloride solution and extracted with 200 mL of ethyl acetate. The layers were separated and the organic layer was washed with brine, dried over Na₂SO₄, filtered, and evaporated to yield 1-(3-fluoro-4-methylbenzyl)-3-((3R,4R)-3-hydroxy-4-(4-hydroxyphenyl)-piperidin-1-yl)pyrrolidin-2-one (1.9 g, 4 mmol) as a mixture of two diastereomers. LCMS (method F) RT 1.93 min, m/z 399 (M+H⁺).

Step G. 3-((3R,4R)-3-fluoro-4-(4-hydroxyphenyl)piperidin-1-yl)-1-(3-fluoro-4-methylbenzyl)pyrrolidin-2-one

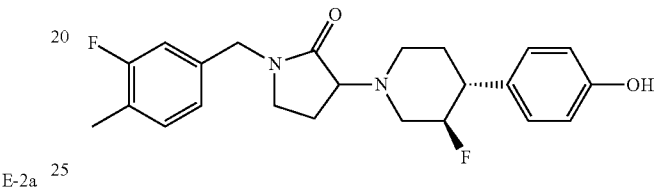

To a solution of 1-(3-fluoro-4-methylbenzyl)-3-((3R,4R)-3-hydroxy-4-(4-hydroxyphenyl)-piperidin-1-yl)pyrrolidin-2-one (from step F, 1.9 g, 4.8 mmol) in DCM (35 mL) at 0° C. was added DAST (3.2 mL, 23.8 mmol) under nitrogen. The reaction mixture was allowed to warm to rt and stirred for 2 h, and then diluted with saturated bicarbonate solution and extracted with 200 mL of DCM. The organic layer was dried over Na₂SO₄, filtered, and evaporated under reduced pressure to give a crude product which was purified via preparative HPLC (method J) to yield 3-((3R,4R)-3-fluoro-4-(4-hydroxyphenyl)piperidin-1-yl)-1-(3-fluoro-4-methylbenzyl)pyrrolidin-2-one (1.1 g, 2.6 mmol) as a pair of diastereomers. LCMS (Method F) RT: 2.13 min, m/z 401. (M+H)⁺.

Step H, (R)-3-((3R,4R)-3-Fluoro-4-(4-hydroxyphenyl)piperidin-1-yl)-1-(3-fluoro-4-methylbenzyl)pyrrolidin-2-one The mixture of diastereomers of 3-((3R,4R)-3-fluoro-4-(4-hydroxyphenyl)piperidin-1-yl)-1-(3-fluoro-4-methylbenzyl)pyrrolidin-2-one (1.1 g) from step G was separated by chiral SFC chromatography (method J). The second-eluting isomer, (R)-3-((3R,4R)-3-fluoro-4-(4-hydroxyphenyl)piperidin-1-yl)-1-(3-fluoro-4-methylbenzyl)pyrrolidin-2-one, was isolated (355 mg) and its data was consistent with those of Example 47, P-4. LCMS (Method F) RT 2.14 min, m/z 401 (M+H⁺); HPLC (Method A) RT 6.70 min (99.6% AP), (Method B) RT 8.16 min (99.7% AP); Chiral SFC (Method E) RT 7.62 (100% AP); ¹H NMR (400 MHz, methanol-d₄) δ ppm 1.85 (dd, J=7.28, 2.76 Hz, 2H) 2.09 (d, J=8.03 Hz, 1H) 2.13-2.27 (m, 4H) 2.45 (s, 1H) 2.51-2.60 (m, 1H) 2.61-2.71 (m, 1H) 2.98-3.06 (m, 1H) 3.15 (s, 1H) 3.23-3.30 (m, 1H) 3.62 (s, 1H) 3.69-3.77 (m, 1H) 4.39-4.70 (m, 4H) 6.72-6.80 (m, 2H) 6.95-7.03 (m, 2H) 7.09-7.15 (m, 2H) 7.24 (t, J=7.78 Hz, 1H).

Example 48

Peak 1, Peak 2, Peak 3, Peak 4

(S)-1-(4-fluorobenzyl)-3-((3S,4S)-3-hydroxy-4-(4-methoxyphenyl)piperidin-1-yl)pyrrolidin-2-one, (S)-1-(4-fluorobenzyl)-3-((3R,4R)-3-hydroxy-4-(4-methoxyphenyl)piperidin-1-yl)pyrrolidin-2-one, (R)-1-(4-fluorobenzyl)-3-((3S,4S)-3-hydroxy-4-(4-methoxyphenyl)piperidin-1-yl)pyrrolidin-2-one, and (R)-1-(4-fluorobenzyl)-3-((3R,4R)-3-hydroxy-4-(4-methoxyphenyl)piperidin-1-yl)pyrrolidin-2-one

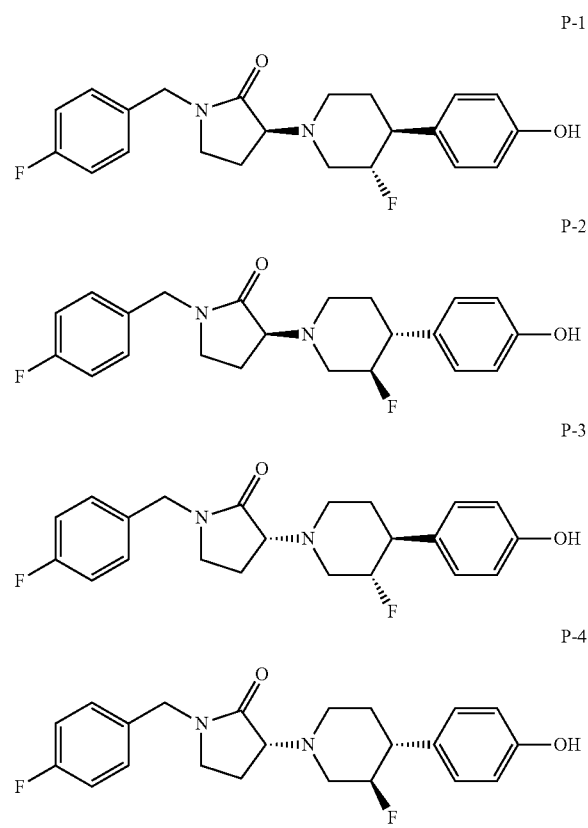

Step A. (±)-rel-1-(4-Fluorobenzyl)-3-((3S,4S)-3-hydroxy-4-(4-methoxyphenyl)piperidin-1-yl)pyrrolidin-2-one

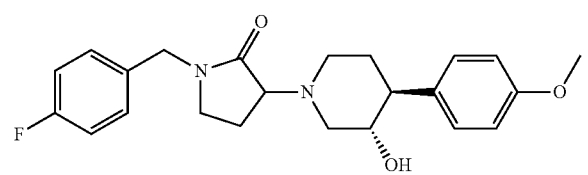 [SMILES: COc1ccc([C@@H]2CCN(C3CCN(Cc4ccc(F)cc4)C3=O)C[C@H]2O)cc1]

To a solution of 3-bromo-1-(4-fluorobenzyl)pyrrolidin-2-one (Intermediate 1, 300 mg, 1.1 mmol) and trans-4-(4-methoxyphenyl)piperidin-3-ol (from Example 46, step B, 240 mg, 1.16 mmol) in acetonitrile (10 mL) was added triethylamine (560 mg, 5.5 mmol) and the mixture was heated at 120° C. in a microwave reactor for 1 h. The reaction mixture was then diluted with water and extracted with 100 mL of ethyl acetate. The organic layer was dried over $Na_2SO_4$, filtered, and evaporated under reduced pressure to give (±)-rel-1-(4-fluorobenzyl)-3-((3S,4S)-3-hydroxy-4-(4-methoxyphenyl)piperidin-1-yl)pyrrolidin-2-one (450 mg, 0.7 mmol) as a mixture of four diastereomers which was used without further purification. LCMS (Method S) RT 1.89 min, m/z 399.1 (M+H$^+$).

Step B. (±)-rel-3-((3S,4S)-3-Fluoro-4-(4-methoxyphenyl)piperidin-1-yl)-1-(4-fluorobenzyl)pyrrolidin-2-one

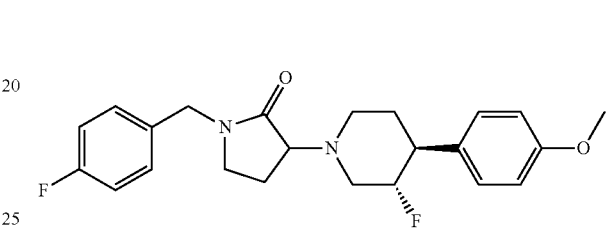

To a solution of 1-(4-fluorobenzyl)-3-(trans-3-hydroxy-4-(4-methoxyphenyl)piperidin-1-yl)pyrrolidin-2-one from step B (2.5 g, 6.3 mmol) in 50 mL DCM was added DAST (4.1 mL, 31 mmol) and the reaction was stirred at ambient temperature for 1 h. The reaction was then quenched with a sat.bicarbonate solution (200 mL) and the mixture was extracted with 200 mL of DCM. The organic layer was dried over $Na_2SO_4$, filtered, and evaporated under reduced pressure. The residue was purified via silica gel chromatography eluting with 28% ethyl acetate in hexane to give (±)-rel-3-((3S,4S)-3-fluoro-4-(4-methoxyphenyl)piperidin-1-yl)-1-(4-fluorobenzyl)pyrrolidin-2-one (900 mg, 1.6 mmol) as a mixture of four diastereomers. LCMS (method P) RT 0.89 min, m/z 401.2 (M+H$^+$).

Step C. 3-((3S,4S)-3-Fluoro-4-(4-hydroxyphenyl)piperidin-1-yl)-1-(4-fluorobenzyl)pyrrolidin-2-one

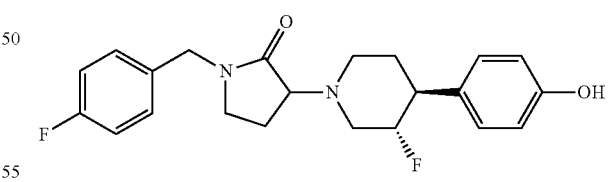

To a solution of (trans-3-fluoro-4-(4-methoxyphenyl)piperidin-1-yl)-1-(4-fluorobenzyl)pyrrolidin-2-one (700 mg, 1.75 mmol) in 50 mL of DCM at 0° C. was added BBr$_3$ (0.3 mL, 3.5 mmol). The reaction mixture was allowed to warm up to room temperature over 1 h. The mixture was then diluted with a sat. bicarbonate solution and extracted with 200 mL of DCM. The organic layer was dried over $Na_2SO_4$, filtered, and evaporated under reduced pressure.

The residue was purified by preparative HPLC (method A) to yield 120 mg of 3-((3S,4S)-3-fluoro-4-(4-hydroxyphenyl)

piperidin-1-yl)-1-(4-fluorobenzyl)pyrrolidin-2-one as a mixture of four diastereomers. LCMS (method N) RT 1.45 min, m/z 387.0 (M+H⁺).

Step D. (S)-1-(4-fluorobenzyl)-3-((3S,4S)-3-hydroxy-4-(4-methoxyphenyl)piperidin-1-yl)pyrrolidin-2-one, (S)-1-(4-fluorobenzyl)-3-((3R,4R)-3-hydroxy-4-(4-methoxyphenyl)piperidin-1-yl)pyrrolidin-2-one, (R)-1-(4-fluorobenzyl)-3-((3S,4S)-3-hydroxy-4-(4-methoxyphenyl)piperidin-1-yl)pyrrolidin-2-one, and (R)-1-(4-fluorobenzyl)-3-((3R,4R)-3-hydroxy-4-(4-methoxyphenyl)piperidin-1-yl)pyrrolidin-2-one The diastereomeric mixture from step C was separated via chiral SFC (method F) into the 4 homochiral diastereomers, Example 48 P-1, P-2, P-3, and P-4. Data for P-1 (S)-1-(4-fluorobenzyl)-3-((3S,4S)-3-hydroxy-4-(4-methoxyphenyl)piperidin-1-yl)pyrrolidin-2-one: Chiral SFC (Method F) RT 3.32 min, 100% AP; HPLC (Method A) RT 6.53 min, 96.0% AP, (Method B) RT 6.7 min, 96.3% AP; LCMS (Method F) RT 2.02 min, m/z 387.0 (M+H⁺); ¹H NMR (400 MHz, methanol-$d_4$) δ ppm 7.32 (dd, J=8.78, 5.27 Hz, 2H) 7.07-7.14 (m, 4H) 6.76 (d, J=8.53 Hz, 2H) 4.41-4.56 (m, 2H) 3.74 (t, J=8.78 Hz, 1H) 3.23-3.31 (m, 2H) 3.10-3.17 (m, 1H) 3.01 (d, J=11.04 Hz, 1H) 2.88 (d, J=7.03 Hz, 1H) 2.66 (td, J=10.04, 4.52 Hz, 1H) 2.57 (dd, J=10.54, 6.53 Hz, 1H) 2.40-2.49 (m, 1H) 2.16-2.25 (m, 1H) 2.03-2.13 (m, 1H) 1.80-1.88 (m, 2H). Data for P-2 (S)-1-(4-fluorobenzyl)-3-((3R,4R)-3-hydroxy-4-(4-methoxyphenyl)piperidin-1-yl)pyrrolidin-2-one: Chiral SFC (Method F) RT 4.15 min, 99.7% AP; HPLC (Method A) RT 6.52 min, 98.1% AP, (Method B) RT 6.92 min, 98.6% AP; LCMS (Method F) RT 2.03 min, m/z 387.0 (M+H⁺); ¹H NMR (400 MHz, methanol-$d_4$) δ ppm 7.29-7.34 (m, 2H) 7.07-7.14 (m, 4H) 6.76 (d, J=9.04 Hz, 2H) 3.71 (t, J=8.78 Hz, 1H) 3.39-3.45 (m, 1H) 3.24-3.31 (m, 2H) 2.74-2.80 (m, 1H) 2.64-2.72 (m, 1H) 2.57 (dd, J=10.54, 6.02 Hz, 1H) 2.43 (td, J=10.04, 5.02 Hz, 1H) 2.15-2.25 (m, 1H) 2.05-2.14 (m, 1H) 1.77-1.85 (m, 2H). Data for P-3 (R)-1-(4-fluorobenzyl)-3-((3S,4S)-3-hydroxy-4-(4-methoxyphenyl)piperidin-1-yl)pyrrolidin-2-one: Chiral SFC (Method F) RT 4.56 min, 97.4% AP; HPLC (Method A) RT 6.53 min, 96.0% AP, (Method B) RT 6.94 min, 96.4% AP; LCMS (Method F) RT 2.02 min, m/z 387.0 (M+H⁺); ¹H NMR (400 MHz, methanol-$d_4$) δ ppm 7.29-7.34 (m, 2H) 7.07-7.13 (m, 4H) 6.74-6.78 (m, 2H) 4.40-4.55 (m, 2H) 3.71 (t, J=9.04 Hz, 1H) 3.38-3.45 (m, 1H) 3.23-3.31 (m, 2H) 2.76 (br. s., 1H) 2.64-2.72 (m, 1H) 2.57 (dd, J=10.54, 6.02 Hz, 1H) 2.43 (td, J=10.04, 5.02 Hz, 1H) 2.16-2.25 (m, 1H) 2.05-2.14 (m, 1H) 1.77-1.87 (m, 2H). Data for P-4 (R)-1-(4-fluorobenzyl)-3-((3R,4R)-3-hydroxy-4-(4-methoxyphenyl)piperidin-1-yl)pyrrolidin-2-one: Chiral SFC (Method F) RT 5.57 min, 99.9% AP; HPLC (Method A) RT 6.55 min, 99.9% AP, (Method B) RT 6.90 min, 99.9% AP; LCMS (Method F) RT 2.03 min, m/z 387.0 (M+H⁺); ¹H NMR (400 MHz, methanol-$d_4$) δ ppm 7.32 (dd, J=8.78, 5.27 Hz, 2H) 7.07-7.14 (m, 4H) 6.76 (d, J=8.53 Hz, 2H) 4.41-4.56 (m, 3H) 3.74 (t, J=8.53 Hz, 1H) 3.24-3.32 (m, 2H) 3.10-3.17 (m, 1H) 2.66 (td, J=9.91, 4.77 Hz, 1H) 2.57 (dd, J=10.54, 6.53 Hz, 1H) 2.41-2.49 (m, 1H) 2.16-2.24 (m, 1H) 2.04-2.12 (m, 1H) 1.80-1.88 (m, 2H).

Example 49

Peak-1 and Peak-2

(S)-3-((3R,4R)-3-fluoro-4-(4-hydroxyphenyl)piperidin-1-yl)-1-(3-fluoro-4-methylphenyl)pyrrolidin-2-one and (R)-3-((3R,4R)-3-fluoro-4-(4-hydroxyphenyl)piperidin-1-yl)-1-(3-fluoro-4-methylphenyl)pyrrolidin-2-one

P-1

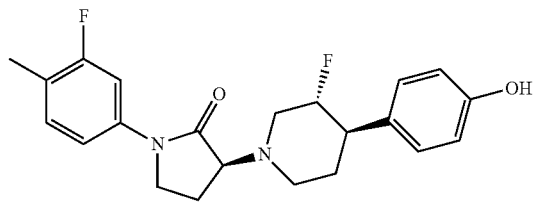

P-2

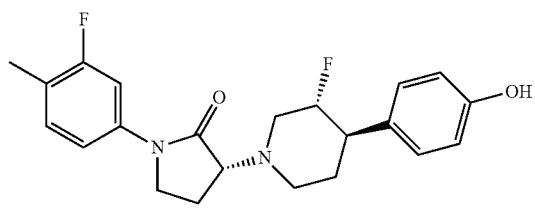

Step A. (3R,4R)-tert-Butyl 3-fluoro-4-(4-hydroxyphenyl)piperidine-1-carboxylate

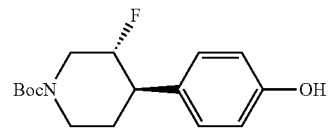

To a solution of (3R,4R)-tert-butyl 3-hydroxy-4-(4-hydroxyphenyl)piperidine-1-carboxylate (MG Bursavich et al; Organic Letters 2001, 3, 2317, 150 mg, 0.51 mmol) in 5 mL of DCM at −78° C. under nitrogen was added DAST (0.2 mL, 1.5 mmol). The mixture was allowed to warm up to rt with stirring over 3 h. To the mixture was added 100 mL of ethyl acetate and the organic layer was separated, washed with a saturated NaHCO₃ solution, and then evaporated under vacuum. The residue was purified via silica gel chromatography eluting with 0-100% ethyl acetate/hexanes to give (3R,4R)-tert-butyl 3-fluoro-4-(4-hydroxyphenyl)piperidine-1-carboxylate (120 mg, 0.41 mmol); LCMS (Method T) RT 3.09 min, m/z 294.3. (M−H)⁻; ¹H NMR (500 MHz, chloroform-d) δ 7.11 (d, J=8.5 Hz, 2H), 6.93 (br. s., 1H), 6.89-6.82 (m, 2H), 4.56-4.47 (m, 1H), 4.45-4.38 (m, 1H), 4.16 (d, J=7.2 Hz, 1H), 2.89-2.69 (m, 3H), 1.89-1.83 (m, 1H), 1.76-1.65 (m, 1H), 1.53 (s, 9H).

Step B. 4-((3R,4R)-3-Fluoropiperidin-4-yl)phenol trifluoroacetate

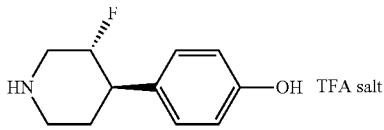

To a solution of (3R,4R)-tert-butyl 3-fluoro-4-(4-hydroxyphenyl)piperidine-1-carboxylate (120 mg, 0.41 mmol) in 1.5 mL DCM at rt was added TFA (0.5 mL, 6.5 mmol), and the mixture was stirred for 3 h. The mixture was then concentrated in vacuo to dryness to yield 4-((3R,4R)-3-fluoropiperidin-4-yl)phenol trifluoroacetate (126 mg, 0.41 mmol), which was used directly in step D.

Step C. 3-Bromo-1-(3-fluoro-4-methylphenyl)pyrrolidin-2-one

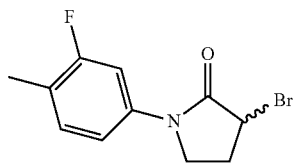

To a solution of 2,4-dibromobutanoyl chloride (10 g, 38 mmol) in 100 mL of DCM at 0° C. under nitrogen was added 3-fluoro-4-methylaniline (5.21 g, 42 mmol) followed by $Et_3N$ (6.3 mL, 45 mmol). The mixture was stirred at rt for 2 h, then concentrated in vacuo. The residue was dissolved in diethyl ether, then hexanes was added and a solid precipitated. The solid was removed by filtration and discarded. The filtrate was then concentrated in vacuo to give a dry residue. To a solution of this residue in 100 mL DMF at 0° C. under nitrogen was slowly added 60% NaH (1.82 g, 45 mmol). The mixture was stirred and allowed to warm up to rt over 30 min. The reaction mixture was slowly poured into 400 mL of icewater and allowed to stand overnight. A solid formed, and was filtered off and dried, then purified via silica gel chromatography eluting with 0-50% ethyl acetate/hexanes to give racemic 3-bromo-1-(3-fluoro-4-methylphenyl)pyrrolidin-2-one (5.6 g, 20.6 mmol). LCMS (method U) RT 3.41 min, m/z 273.97 (M+H$^+$). $^1$H NMR (500 MHz, chloroform-d) δ 7.50 (dd, J=11.7, 2.2 Hz, 1H), 7.31-7.27 (m, 1H), 7.23-7.17 (m, 1H), 4.60 (dd, J=7.0, 2.9 Hz, 1H), 4.03 (ddd, J=9.8, 7.9, 6.8 Hz, 1H), 3.82 (ddd, J=10.0, 7.7, 2.7 Hz, 1H), 2.75 (dq, J=14.6, 7.5 Hz, 1H), 2.48 (ddt, J=14.3, 6.7, 2.7 Hz, 1H), 2.28 (d, J=1.7 Hz, 3H).

Step D. (S)-3-((3R,4R)-3-fluoro-4-(4-hydroxyphenyl)piperidin-1-yl)-1-(3-fluoro-4-methylphenyl)pyrrolidin-2-one and (R)-3-((3R,4R)-3-fluoro-4-(4-hydroxyphenyl)piperidin-1-yl)-1-(3-fluoro-4-methylphenyl)pyrrolidin-2-one To a solution of 4-((3R,4R)-3-fluoropiperidin-4-yl)phenol trifluoroacetate, from step B (120 mg, 0.39 mmol) in DMF (2.0 mL) was added $K_2CO_3$ (134 mg, 0.97 mmol) and racemic 3-bromo-1-(3-fluoro-4-methyl-phenyl)pyrrolidin-2-one (106 mg, 0.39 mmol, from step C). The mixture was heated to 60° C. and stirred for 30 min. It was then allowed to cool to rt and stirred overnight, followed by the addition of 50 mL of EtOAc, which induced precipitation of a solid. The solid was removed by filtration and discarded, and the filtrate was concentrated in vacuo. The residue was purified via silica gel chromatography eluting with a gradient of 0-100% ethyl acetate/hexanes to give 110 mg of (R and S) 3-((3R,4R)-3-fluoro-4-(4-hydroxyphenyl)piperidin-1-yl)-1-(3-fluoro-4-methylphenyl)pyrrolidin-2-one) as a mixture of two diastereomers. A portion (35 mg) of the diastereomer mixture was separated (chiral HPLC method H) into homochiral example 49 P-1 (14 mg) and P-2 (14 mg). Data for P-1 (S)-3-((3R,4R)-3-fluoro-4-(4-hydroxyphenyl)piperidin-1-yl)-1-(3-fluoro-4-methylphenyl)-pyrrolidin-2-one: Chiral HPLC (method H-2) RT 6.97 min, 98% AP; $^1$H NMR (500 MHz, methanol-d$_4$) δ 7.60-7.52 (m, 1H), 7.32-7.22 (m, 2H), 7.12 (d, J=8.5 Hz, 2H), 6.76 (d, J=8.5 Hz, 2H), 4.72-4.65 (m, 1H), 4.63-4.55 (m, 1H), 3.84 (d, J=9.2 Hz, 4H), 3.51-3.44 (m, 1H), 2.87-2.80 (m, 1H), 2.76-2.68 (m, 1H), 2.64-2.54 (m, 1H), 2.53-2.46 (m, 1H), 2.37-2.30 (m, 1H), 2.26 (d, J=1.4 Hz, 3H), 2.24-2.18 (m, 1H), 1.84 (br s, 3H). Data for P-2 (R)-3-((3R,4R)-3-fluoro-4-(4-hydroxyphenyl)-piperidin-1-yl)-1-(3-fluoro-4-methylphenyl)-pyrrolidin-2-one: Chiral HPLC (method H-2) RT 8.84 min, 99.3% AP; $^1$H NMR (500 MHz, methanol-d$_4$) δ 7.56 (dd, J=12.0, 1.9 Hz, 1H), 7.32-7.23 (m, 2H), 7.12 (d, J=8.4 Hz, 2H), 6.80-6.73 (m, 2H), 4.70-4.63 (m, 1H), 4.60-4.54 (m, 1H), 3.88-3.77 (m, 5H), 3.23-3.17 (m, 2H), 3.07 (d, J=10.7 Hz, 2H), 2.75-2.68 (m, 2H), 2.64-2.48 (m, 4H), 2.33 (dd, J=6.6, 2.4 Hz, 2H), 2.26 (d, J=1.5 Hz, 5H), 2.21 (dd, J=12.7, 9.6 Hz, 2H), 1.90-1.83 (m, 4H).

Example 50

Peak-1, Peak-2, Peak-3, and Peak 4

(S)-3-((3R,4R)-3-Fluoro-4-(4-hydroxyphenyl)piperidin-1-yl)-1-((S)-1-(4-fluorophenyl)-ethyl)pyrrolidin-2-one and (R)-3-((3R,4R)-3-fluoro-4-(4-hydroxyphenyl)piperidin-1-yl)-1-((S)-1-(4-fluorophenyl)ethyl)pyrrolidin-2-one

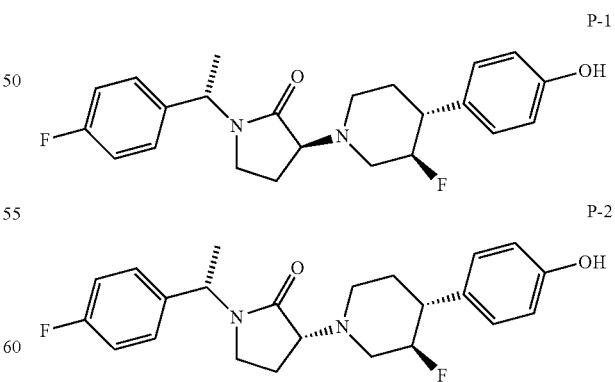

(S)-3-((3S,4S)-3-Fluoro-4-(4-hydroxyphenyl)piperidin-1-yl)-1-((S)-1-(4-fluorophenyl)ethyl)pyrrolidin-2-one and (R)-3-((3S,4S)-3-fluoro-4-(4-hydroxyphenyl)piperidin-1-yl)-1-((S)-1-(4-fluorophenyl)-ethyl)pyrrolidin-2-one

P-3

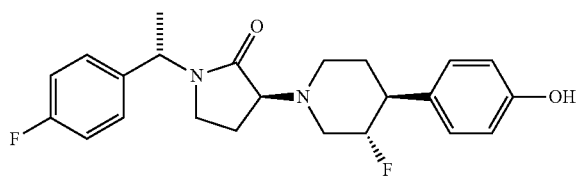

P-4

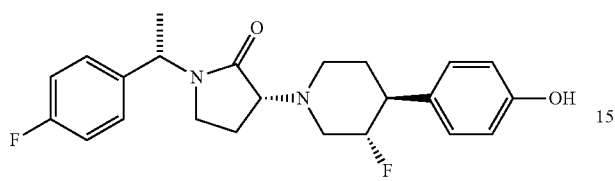

Step A. 2,4-Dibromo-N—((S)-1-(4-fluorophenyl)ethyl)butanamide

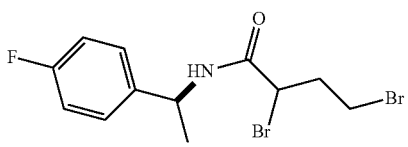 [SMILES: C[C@H](NC(=O)C(Br)CCBr)c1ccc(F)cc1]

To a stirred solution of (S)-1-(4-fluorophenyl)ethanamine (3.2 g, 23 mmol) in diethyl ether (50 mL) and triethylamine (9.6 mL, 69 mmol) at 0° C. was added 2,4-dibromobutanoyl chloride (7.3 g, 27.6 mmole) and the mixture was allowed to warm to rt and stirred for 12 h. A solid formed which was removed by filtration, washed with ethyl acetate, and then discarded. The combined filtrates were evaporated under reduced pressure and the residue was subjected to silica gel chromatography eluting with 20-30% ethyl acetate/petroleum ether yielding 4.5 g of 2,4-dibromo-N—((S)-1-(4-fluorophenyl)ethyl)butanamide as a brown solid. LCMS (method O) RT=0.99 min, m/z 366, 368, 370 (M+H$^+$, M+H$^+$+2, M+H$^+$+4); $^1$H NMR (400 MHz, DMSO-d$_6$) δ ppm 1.25-1.44 (m, 3H) 2.27-2.46 (m, 2H) 3.46-3.58 (m, 2H) 4.55-4.66 (m, 1H) 4.81-5.00 (m, 1H) 7.03-7.24 (m, 2H) 7.30-7.45 (m, 2H) 8.89 (d, J=8.03 Hz, 1H).

Step B. 3-Bromo-1-((S)-1-(4-fluorophenyl)ethyl)pyrrolidin-2-one

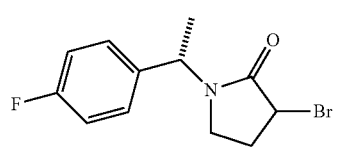 [SMILES: C[C@@H](c1ccc(F)cc1)N1CCC(Br)C1=O]

To a stirred solution of 2,4-dibromo-N—((S)-1-(4-fluorophenyl)ethyl)butanamide (3 g, 8.2 mmol) in tetrahydrofuran (50 mL) at 0° C. was added NaH (1.29 g, 32 mmol) and the mixture was allowed to warm to rt and stirred for 3 h. The mixture was then poured into ice-cold water and diluted with ethyl acetate. The organic phase was separated, washed with brine solution, dried over anhydrous Na$_2$SO$_4$, filtered and evaporated under reduced pressure yielding 1.6 g of liquid. The residue was purified by silica gel chromatography eluting with 30% ethyl acetate/petroleum ether to obtain 1 g of 3-bromo-1-((S)-1-(4-fluorophenyl)ethyl)pyrrolidin-2-one as a brown solid (mixture of two diastereomers). LCMS (method O) RT 0.83/0.86 min, mz $^{286}/_{288}$ (M+H$^+$), 308 (M+Na$^+$); $^1$H NMR (400 MHz, DMSO-d$_6$) δ ppm 1.50 (d, J=7.03 Hz, 3H) 2.08-2.25 (m, 1H) 2.57-2.69 (m, 1H) 2.99 (d, J=10.04 Hz, 1H) 3.35-3.44 (m, 1H) 4.71 (dd, J=7.03, 3.01 Hz, 1H) 5.13-5.30 (m, 1H) 7.21 (t, J=9.04 Hz, 2H) 7.30-7.42 (m, 2H).

Step C. tert-Butyl 4-(4-(benzyloxy)phenyl)-5,6-dihydropyridine-1(2H)-carboxylate

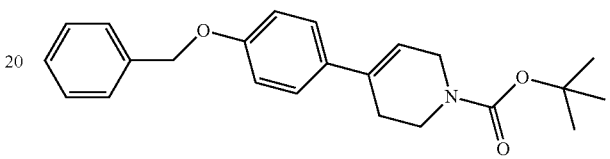

To a stirring mixture of tert-butyl 4-(4,4,5,5-tetramethyl-1,3,2-dioxaborolan-2-yl)-5,6-dihydropyridine-1(2H)-carboxylate (16.45 g, 53 mmol), dimethoxyethane (200 mL) and water (50 mL) was added 1-(benzyloxy)-4-bromobenzene (14 g, 53 mmol), sodium carbonate (16.9 g, 160 mmol) and bis-(triphenylphosphine)palladium(II) chloride (1.867 g, 2.66 mmol) at rt. The reaction mixture was purged with nitrogen for 15 min, then heated at 80° C. for 4 h. The mixture was allowed to cool to rt and then was filtered through Celite and diluted with 200 mL of water. The mixture was then extracted three times with 200 mL of ethyl acetate and the combined organic layers were dried over anhydrous Na$_2$SO$_4$, filtered and concentrated. The residue was subjected to silica gel chromatography eluting with 20% ethyl acetate/petroleum ether to obtain 16 g of tert-butyl 4-(4-(benzyloxy)phenyl)-5,6-dihydropyridine-1(2H)-carboxylate (16 g, 82% yield) as an off-white solid. LCMS (method O) RT 1.32 min, m/z 366 (M+H$^+$); $^1$H NMR (300 MHz, DMSO-d$_6$) δ 1.47 (s, 9H), 2.42 (d, J=1.50 Hz, 2H), 3.52 (t, J=11.40 Hz, 2H), 3.97 (s, 2H), 5.11 (s, 2H), 6.04 (s, 1H), 6.98 (d, J=9.00 Hz, 2H), 7.30-7.46 (m, 7H).

Step D. (±)-rel-(3S,4S)-tert-butyl 4-(4-(benzyloxy)phenyl)-3-hydroxypiperidine-1-carboxylate

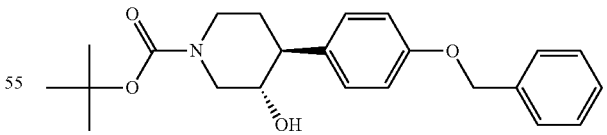

To a stirring mixture of NaBH$_4$ (0.93 g, 24.6 mmol) in THF (25 mL) cooled to 0° C. was added boron trifluoride etherate (3.2 mL, 25 mmol) and the mixture was allowed to warm up to rt over 1 h. It was then re-cooled to 0° C. and to it was added a solution of tert-butyl 4-(4-(benzyloxy)-phenyl)-5,6-dihydropyridine-1(2H)-carboxylate (3 g, 8.2 mmol) in THF (10 mL). The resulting mixture was allowed to warm up to rt over 2 h. The reaction mixture was cooled again to 0° C. and H$_2$O (10 mL), ethanol (10 mL), 10 M NaOH (10 mL) and H$_2$O$_2$ (8 mL, 26 mmol) were sequentially added. The final mixture was heated to 65° C. overnight. After cooling, the reaction was quenched with water and the mixture was extracted with ethyl acetate (2×100 mL). The combined organic layers were dried over Na$_2$SO$_4$ and concentrated in vacuo yielding 2.7 g of (±)-rel-(3S,4S)-tert-butyl 4-(4-(benzyloxy)phenyl)-3-hydroxypiperidine-1-carboxylate (82% yield) as off-white solid. LCMS (method O) RT 2.41 min, m/z 382 (M–H). $^1$H NMR (400 MHz, DMSO-d$_6$) δ 1.41 (s, 9H), 1.63 (m, 1H), 1.67 (m, 1H), 2.67 (m, 1H), 3.37-3.41 (m, 1H), 3.92 (m, 1H), 4.10 (m, 1H), 4.73 (d, J=2.4, 1H), 5.07 (s, 2H), 6.91 (d, J=9, 2H), 7.14 (d, J=9, 2H), 7.31-7.44 (m, 4H).

Step E. (3S,4S)-tert-Butyl 4-(4-(benzyloxy)phenyl)-3-fluoropiperidine-1-carboxylate and (3R,4R)-tert-butyl 4-(4-(benzyloxy)phenyl)-3-fluoropiperidine-1-carboxylate

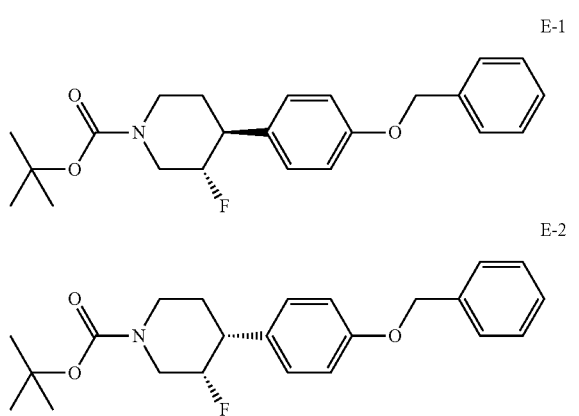

To a solution of racemic trans-tert-butyl 4-(4-(benzyloxy)phenyl)-3-hydroxypiperidine-1-carboxylate (1 g, 2.6 mmol, from step D) in DCM (15 mL) cooled to 0° C. was added DAST (1.7 mL, 13 mmol) and the mixture was stirred at 0° C. for 15 min. The reaction was then quenched by the addition of ice water and the mixture was extracted twice with 20 mL of DCM. The combined organic layers were dried over anhydrous Na$_2$SO$_4$, filtered and concentrated to a pale yellow solid (1 g). The two desired products were separated from a complex mixture via chiral SFC (method D) to afford E-1 (0.13 g) and E-2 (0.14 g). Data for E-1 (3S,4S)-tert-butyl 4-(4-(benzyloxy)phenyl)-3-fluoropiperidine-1-carboxylate: LCMS (method P) RT 1.35 min, m/z 330.4 (M-C4H8); chiral HPLC (method G-2) RT 5.8 min; $^1$H NMR (300 MHz, DMSO-d$_6$) δ 1.42 (s, 9H), 1.56-1.61 (m, 1H), 1.74-1.78 (m, 1H), 2.73-2.84 (m, 3H), 3.94 (d, J=12.30 Hz, 1H), 4.25 (d, J=18.00 Hz, 1H), 4.43-4.64 (m, 1H), 5.08 (s, 2H), 6.95 (d, J=8.70 Hz, 2H), 7.23 (d, J=8.70 Hz, 2H), 7.32-7.46 (m, 5H). Data for E-2 (3R,4R)-tert-butyl 4-(4-(benzyloxy)phenyl)-3-fluoropiperidine-1-carboxylate: LCMS (method P) RT 1.35 min, m/z 330.4 (M-C$_4$H$_8$); chiral HPLC (method G-2) RT 6.51 min; $^1$H NMR (300 MHz, DMSO-d$_6$) δ 1.42 (s, 9H), 1.56-1.61 (m, 1H), 1.74-1.78 (m, 1H), 2.73-2.84 (m, 3H), 3.94 (d, J=12.30 Hz, 1H), 4.25 (d, J=18.00 Hz, 1H), 4.43-4.64 (m, 1H), 5.08 (s, 2H), 6.95 (d, J=8.70 Hz, 2H), 7.23 (d, J=8.70 Hz, 2H), 7.32-7.46 (m, 5H).

Step F. (3R,4R)-4-(4-(Benzyloxy)phenyl)-3-fluoropiperidine hydrochloride

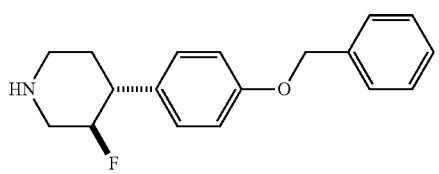

To a solution of (3R,4R)-tert-butyl 4-(4-(benzyloxy)phenyl)-3-fluoropiperidine-1-carboxylate (0.12 g, 0.31 mmol, E-2 from step E) in 1,4-dioxane (3 mL) was added a 4 M HCl in dioxane solution (2 mL, 8 mmol) and the reaction mixture was stirred at rt overnight. The solvent was then evaporated and the solid was triturated with ethyl acetate and dried to afford E-2a (3R,4R)-4-(4-(benzyloxy)phenyl)-3-fluoropiperidine hydrochloride (0.09 g, 83% yield) as an off-white solid. LCMS (method O) RT: 0.95 min m/z 286 (M+H$^+$); $^1$H NMR (400 MHz, DMSO-d$_6$) δ 1.92-1.92 (m, 1H), 2.29-2.33 (m, 1H), 3.04-3.14 (m, 3H), 3.45-3.60 (m, 2H), 4.83-4.95 (m, 1H), 5.10 (s, 2H), 7.01-7.04 (m, 2H), 7.25-7.31 (m, 2H), 7.32-7.46 (m, 5H), 9.09 (s, 1H).

Step G. 4-((3R,4R)-3-Fluoropiperidin-4-yl)phenol hydrochloride

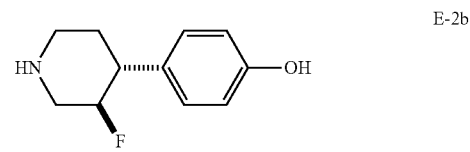

To a solution of (3R,4R)-4-(4-(benzyloxy)phenyl)-3-fluoropiperidine hydrochloride (0.09 g, 0.28 mmol, E-2a from step F) in methanol (3 mL) was added 10% Pd/C (0.09 g) and the mixture was stirred at rt under hydrogen balloon pressure for 12 h. The mixture was then filtered through Celite and concentrated to afford E-2b 4-((3R,4R)-3-fluoropiperidin-4-yl)phenol hydrochloride (0.06 g, 77% yield) as brown solid. LCMS (method P) RT 0.5 min; m/z 196 (M+H$^+$); $^1$H NMR (400 MHz, DMSO-d6) δ 1.90-1.94 (m, 2H), 2.90-3.03 (m, 3H), 3.27-3.35 (m, 1H), 3.57-3.61 (m, 1H), 4.79-4.97 (m, 1H), 6.75 (d, J=8.40 Hz, 2H), 7.05 (d, J=8.80 Hz, 2H), 9.28 (s, 1H), 9.35 (s, 1H).

Step H. (S)-3-((3R,4R)-3-Fluoro-4-(4-hydroxyphenyl)piperidin-1-yl)-1-((S)-1-(4-fluorophenyl)-ethyl)pyrrolidin-2-one and (R)-3-((3R,4R)-3-fluoro-4-(4-hydroxyphenyl)piperidin-1-yl)-1-((S)-1-(4-fluorophenyl)ethyl)pyrrolidin-2-one A mixture of 3-bromo-1-((S)-1-(4-fluorophenyl)ethyl) pyrrolidin-2-one (mixture of diastereomers from step B) (60 mg, 0.21 mmol), 4-((3R,4R)-3-fluoropiperidin-4-yl)phenol hydrochloride (20.5 mg, 0.1 mmol, E-2b from step G) and DIPEA (0.1 mL, 0.6 mmol) in DMF (1 mL) was heated in a microwave reactor at 120° C. for 90 min. The mixture was allowed to cool and the solvent was then removed under reduced pressure. The diastereomeric products were then separated via preparative HPLC (method B), yielding homochiral examples 50 P-1 (2.4 mg) and P-2 (9.5 mg). Data for P-1 (S)-3-((3R,4R)-3-fluoro-4-(4-hydroxyphenyl)-piperidin-1-yl)-1-((S)-1-(4-fluorophenyl)ethyl)pyrrolidin-2-one: LCMS (method N) RT 1.60 min, m/z 401 (M+H$^+$), (method O) RT 1.02 min, m/z 401 (M+H$^+$); $^1$H NMR (400 MHz, methanol-d$_4$) δ ppm 7.30-7.43 (m, 2H) 7.05-7.15 (m, 4H) 6.75 (d, J=8.53 Hz, 2H) 5.36-5.46 (m, 1H) 4.46-4.69 (m, 1H) 3.64-3.75 (m, 1H) 3.34-3.42 (m, 2H) 3.01-3.10 (m, 1H) 2.48-2.78 (m, 3H) 2.33-2.43 (m, 1H) 2.10-2.24 (m, 1H) 1.90-2.04 (m, 1H) 1.71-1.84 (m, 2H) 1.55 (d, J=7.53 Hz, 3H). Data for P-2 (R)-3-((3R,4R)-3-fluoro-4-(4-hydroxyphenyl)piperidin-1-yl)-1-((S)-1-(4-fluorophenyl)ethyl)-pyrrolidin-2-one: LCMS (method N) RT 1.63 min, m/z 401 (M+H$^+$), (method O) RT 1.05 min, m/z 401 (M+H$^+$); $^1$H NMR (400 MHz, methanol-d$_4$) δ ppm 7.30-7.42 (m, 2H) 7.06-7.16 (m, 4H) 6.67-6.80 (m, 2H) 5.36-5.50 (m, 1H) 4.60-4.72 (m, 1H) 4.50-4.59 (m, 1H) 3.59-3.70 (m, 1H) 3.40-3.54 (m, 2H) 3.08-3.18 (m, 1H) 2.87-3.05 (m, 2H) 2.51-2.72 (m, 2H) 2.39-2.49 (m, 1H) 2.00-2.20 (m, 2H) 1.75-1.90 (m, 2H) 1.50-1.64 (m, 3H).

Step I. (3S,4S)-4-(4-(Benzyloxy)phenyl)-3-fluoropiperidine hydrochloride

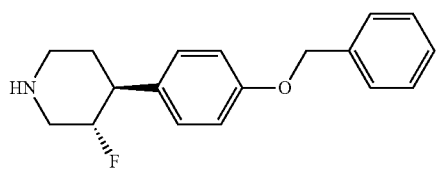

E-1a

To a solution of (3S,4S)-t-butyl 4-(4-(benzyloxy)phenyl)-3-fluoropiperidine-1-carboxylate (0.12 g, 0.31 mmol, E-1 from step E) in 1,4-dioxane (3 mL) was added a 4 M HCl in dioxane solution (2 mL, 8 mmol) and the reaction mixture was stirred at rt overnight. The mixture was concentrated in vacuo and the solid was triturated with ethyl acetate and dried to afford E-1a (3S,4S)-4-(4-(benzyloxy)phenyl)-3-fluoropiperidine hydrochloride (0.09 g, 88% yield) as an off-white solid. LCMS (method P) RT 0.95 min, m/z 286 (M+H$^+$; 400 MHz, DMSO-d6: δ 1.94-1.96 (m, 2H), 2.97-3.04 (m, 3H), 3.38-3.62 (m, 2H), 4.84-4.95 (m, 1H), 5.10 (s, 2H), 7.00-7.03 (m, 2H), 7.17-7.20 (m, 2H), 7.31-7.46 (m, 5H), 9.30 (s, 1H).

Step J. ((3S,4S)-3-Fluoropiperidin-4-yl)phenol

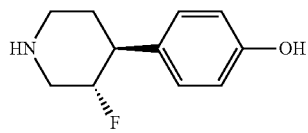

E-1b

A mixture of (3S,4S)-4-(4-(benzyloxy)phenyl)-3-fluoropiperidine hydrochloride (0.09 g, 0.28 mmol, E-1a from step I) in methanol (3 mL) was added 10% Pd/C (0.09 g) and the reaction mixture was stirred at rt under hydrogen balloon pressure for 12 h. The mixture was filtered through Celite and concentrated in vacuo to afford E-1b ((3S,4S)-3-fluoropiperidin-4-yl)phenol (0.05 g, 68.7% yield) as an off-white solid. LCMS (method P) RT 0.50 min, m/z 196 (M+H$^+$); $^1$H NMR (400 MHz DMSO-d$_6$) δ 1.90-1.94 (m, 2H), 2.91-3.05 (m, 3H), 3.24-3.27 (m, 1H), 3.59-3.62 (m, 1H), 4.78-4.97 (m, 1H), 6.71-6.76 (m, 2H), 6.99-7.06 (m, 2H), 9.27 (s, 1H), 9.36 (s, 1H).

Step K. (S)-3-((3S,4S)-3-Fluoro-4-(4-hydroxyphenyl)piperidin-1-yl)-1-((S)-1-(4-fluorophenyl)ethyl)pyrrolidin-2-one and (R)-3-((3S,4S)-3-fluoro-4-(4-hydroxyphenyl)piperidin-1-yl)-1-((S)-1-(4-fluorophenyl)-ethyl)pyrrolidin-2-one To a solution of ((3S,4S)-3-fluoropiperidin-4-yl)phenol (0.02 g, 0.1 mmol, E-1b from step J) in DMF (2 mL) was added DIPEA (0.05 mL, 0.31 mmol) followed by 3-bromo-1-((S)-1-(4-fluorophenyl)ethyl)pyrrolidin-2-one (0.059 g, 0.21 mmol, mixture of diastereomers from step B), and the mixture was then heated to 120° C. in a microwave reactor for 90 min. The mixture was allowed to cool and then the diastereomeric products were subjected to preparative HPLC (method B) to afford homochiral examples 50 P-3 (2.7 mg, 6% yield) and P-4 (8.2 mg, 19.8% yield). Data for P-3 (S)-3-((3S,4S)-3-Fluoro-4-(4-hydroxyphenyl)piperidin-1-yl)-1-((S)-1-(4-fluorophenyl)ethyl)pyrrolidin-2-one: pale yellow solid; LCMS (method N) RT 1.60 min, m/z 401 (M+H$^+$); $^1$H NMR (400 MHz, methanol-d$_4$) δ 1.56 (d, J=7.20 Hz, 3H), 1.81-1.85 (m, 2H), 2.16-2.22 (m, 1H), 2.42-2.44 (m, 1H), 2.51-2.67 (m, 2H), 3.06-3.09 (m, 3H), 3.35-3.40 (m, 2H), 3.70-3.75 (m, 1H), 4.35-4.70 (m, 1H), 5.42 (q, J=7.20 Hz, 1H), 6.74-6.76 (m, 2H), 7.09-7.14 (m, 4H), 7.37-7.41 (m, 2H). Data for P-4 (R)-3-((3S,4S)-3-fluoro-4-(4-hydroxyphenyl)piperidin-1-yl)-1-((S)-1-(4-fluorophenyl)ethyl)-pyrrolidin-2-one: pale yellow solid; LCMS (method N) RT 1.63 min, m/z 401 (M+H$^+$); $^1$H NMR (400 MHz, methanol-d$_4$) δ 1.59 (d, J=7.20 Hz, 3H), 1.81-1.84 (m, 2H), 2.08-2.16 (m, 2H), 2.42-2.43 (m, 1H), 2.51-2.59 (m, 1H), 2.65-2.72 (m, 1H), 2.73-2.81 (m, 1H), 2.92-2.95 (m, 1H), 3.34-3.37 (m, 2H), 3.61-3.66 (m, 1H), 4.50-4.71 (m, 1H), 5.43 (q, J=6.80 Hz, 1H), 6.75-6.77 (m, 2H), 7.09-7.13 (m, 4H), 7.35-7.38 (m, 2H).

Example 51

Peak-1, Peak-2, Peak-3, and Peak-4

(S)-3-((R)-3,3-Difluoro-4-(4-hydroxyphenyl)piperidin-1-yl)-1-(4-methylbenzyl)pyrrolidin-2-one, (S)-3-((S)-3,3-difluoro-4-(4-hydroxyphenyl)piperidin-1-yl)-1-(4-methylbenzyl)pyrrolidin-2-one, (R)-3-((R)-3,3-difluoro-4-(4-hydroxyphenyl)piperidin-1-yl)-1-(4-methylbenzyl)pyrrolidin-2-one, and (R)-3-((S)-3,3-difluoro-4-(4-hydroxyphenyl)piperidin-1-yl)-1-(4-methylbenzyl)pyrrolidin-2-one

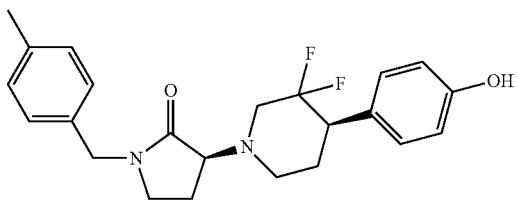

-continued

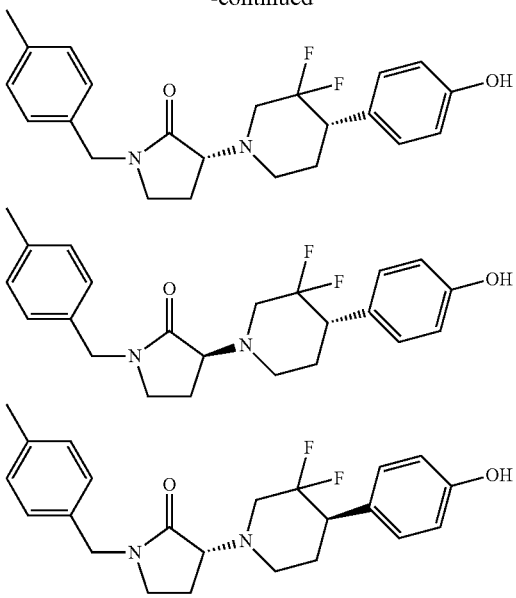

Step A. 1-Benzyl-4-(4-methoxyphenyl)piperidin-4-ol

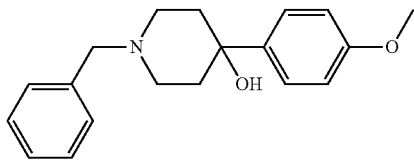 [SMILES: COc1ccc(C2(O)CCN(Cc3ccccc3)CC2)cc1]

To a solution of 1-bromo-4-methoxybenzene (5 g, 27 mmol) in THF (100 mL) at −78° C. was added a solution of 1.6 M N-butyl lithium/hexanes (18.4 mL, 29.4 mmol), and the reaction mixture was stirred for 1 hr. Then a solution of 1-benzylpiperidin-4-one (4.81 g, 25.4 mmol) in 50 mL of THF was added. After the addition, the mixture was allowed to warm up to rt and was stirred for 1 h. The reaction was then quenched by the addition of 100 mL of 1.5 M aqueous HCl and the mixture was extracted with 200 mL of ethyl acetate. The organic layer was dried over $Na_2SO_4$, filtered, and concentrated under vacuum to yield 7.1 g (72% yield) of 1-benzyl-4-(4-methoxyphenyl)piperidin-4-ol. LCMS (method F) RT 2.19 min, 81% AP, m/z 298.4 (M+H$^+$), $^1$H NMR (300 MHz, DMSO-d$_6$) δ 7.23-7.39 (m 8.5H), 6.94 (m, 0.5H), 6.84-6.94 (m, 2H), 4.66 (s, 1H), 3.74 (s, 0.8H), 3.72 (s, 3H), 3.32 (s, 2H), 2.50-2.67 (m, 2H), 2.34-2.45 (m, 3H), 1.83-1.90 (m, 2H), 1.55 (d, J=11, 2H).

Step B. 1-Benzyl-4-(4-methoxyphenyl)-1,2,3,6-tetrahydropyridine

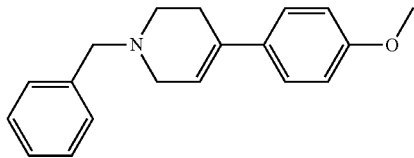 [SMILES: COc1ccc(C2=CCN(Cc3ccccc3)CC2)cc1]

To a solution of 1-benzyl-4-(4-methoxyphenyl)piperidin-4-ol (7 g, 23.5 mmol) in DCM (150 mL) was added trifluoroacetic acid (2.68 g, 23.5 mmol) and the reaction mixture was stirred at rt overnight. The mixture was then evaporated under reduced pressure and partitioned between 500 mL saturated aqueous sodium bicarbonate and 500 mL of ethyl acetate. The organic layer was separated, dried over $Na_2SO_4$, filtered, and evaporated under reduced pressure to yield 1-benzyl-4-(4-methoxyphenyl)-1,2,3,6-tetrahydropyridine (5.9 g, 88% yield). LCMS (method F) RT 2.84 min, 100% AP, m/z 280.4 (M+H$^+$).

Step C. (±)-rel-(3S,4S)-1-Benzyl-4-(4-methoxyphenyl)piperidin-3-ol

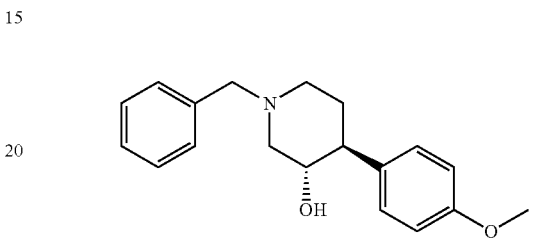

To a suspension of NaBH$_4$ (2.7 g, 72 mmol) in THF (150 mL) at −10° C. was added boron trifluoride etherate (9.1 mL, 72 mmol) and the solution was stirred for 15 minutes. Then a solution of 1-benzyl-4-(4-methoxyphenyl)-1,2,3,6-tetrahydropyridine (10 g, 36 mmol) in 100 mL tetrahydrofuran was added and the mixture was stirred for an additional hour. Next were sequentially added 25 mL of water, 25 mL of 10% aqueous sodium hydroxide, 50 mL of ethanol, and 12.8 mL of 30% aqueous hydrogen peroxide (125 mmol) and the final mixture was heated to reflux overnight. The mixture was allowed to cool and was then diluted with 200 mL of water and extracted with 300 mL of ethyl acetate. The organic layer was separated, dried over $Na_2SO_4$, filtered, and evaporated under reduced pressure. The residue was triturated with diethyl ether to yield 7.5 g (57%) (±)-rel-(3S,4S)-1-benzyl-4-(4-methoxyphenyl)piperidin-3-ol. LCMS (method A) RT 2.03 min, 81.5% AP, m/z 298.4 (M+H$^+$), $^1$H NMR (300 MHz, DMSO-d$_6$) δ ppm 7.28-7.35 (m, 5H) 7.14 (d, J=8.69 Hz, 2H) 6.83 (d, J=8.69 Hz, 2H) 4.43 (d, J=6.04 Hz, 1H) 3.51 (d, J=19.26 Hz, 4H) 3.33 (s, 3H) 2.97 (dd, J=10.01, 3.59 Hz, 1H) 2.81 (d, J=10.95 Hz, 1H) 2.19-2.29 (m, 1H) 1.96-1.98 (m, 1H) 1.78 (t, J=10.20 Hz, 1H) 1.58-1.68 (m, 2H).

Step D. (±)-rel-(3 S,4S)-4-(4-Methoxyphenyl)piperidin-3-ol

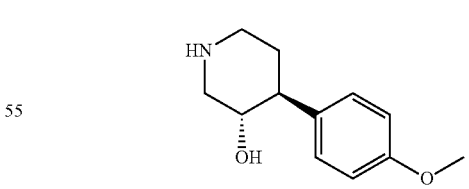

To a solution of (±)-rel-(3S,4S)-1-benzyl-4-(4-methoxyphenyl)piperidin-3-ol (7 g, 23.5 mmol) in methanol (100 mL) was added 10% Pd/C (3.76 g) and the reaction mixture was stirred overnight under a hydrogen atmosphere (balloon pressure). The catalyst was removed by filtrathou through Celite and the solvent was evaporated under reduced pressure to give (±)-rel-(3S,4S)-4-(4-methoxyphenyl)piperidin-3-ol (4.8 g, 89% yield). LCMS (method F) RT 1.485 (61.5% AP)

m/z 207.8 (M+H⁺), 1.536 (29.7% AP), m/z 207.8 (M+H⁺); ¹H NMR (DMSO-d6) δ 7.133 (d, J=7, 2H), 6.83 (d, J=7, 2H), 4.31 (br s, 1H), 3.7 (s, 3H), 3.02 (m, 1H), 2.86 (d, J=12, 1H), 2.45 (m, 1H), 2.22-2.39 (m, 2H), 1.62-1.61 (m, 1H), 1.610-1.46 (m, 1H).

Step E. (±)-rel-3-((3R,4R)-3-Hydroxy-4-(4-methoxyphenyl)piperidin-1-yl)-1-(4-methylbenzyl)pyrrolidin-2-one

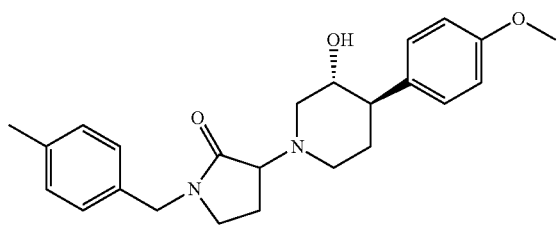

A mixture of 3-bromo-1-(4-methylbenzyl)pyrrolidin-2-one (Intermediate 2, 450 mg, 1.68 mmol), (±)-rel-(3S,4S)-4-(4-methoxyphenyl)piperidin-3-ol (313 mg, 1.5 mmol) and triethylamine (23 mL, 16.8 mmol) was stirred at 60° C. for 1 h, followed by heating at 85° C. for 1 h, 120° C. for 1 h and at 140° C. for 1 h. The mixture was cooled and then quenched with 40 mL of water and extracted with 3×50 mL of chloroform. The combined organic layers were dried over $Na_2SO_4$, filtered, and concentrated under vacuum. The residue was purified via silica gel chromatography (24 g column, gradient of 0-80% ethyl acetate/petroleum ether) to yield 375 mg of (±)-rel-3-((3R,4R)-3-hydroxy-4-(4-methoxyphenyl)piperidin-1-yl)-1-(4-methylbenzyl)pyrrolidin-2-one as a mixture of four diastereomers. LCMS (method F) RT 1.84 min (74% AP), m/z 395.2 (M+H⁺); ¹H NMR (300 MHz, DMSO-d₆) δ ppm 7.31-7.41 (m, 8H) 6.86 (d, J=9.07 Hz, 2H) 4.66 (s, 1H) 3.73 (s, 3H) 3.49 (s, 2H) 2.59 (d, J=10.58 Hz, 2H) 2.32-2.47 (m, 3H) 1.89 (td, J=12.65, 4.53 Hz, 2H) 1.56 (d, J=11.71 Hz, 2H).

Step F. 4-(4-Methoxyphenyl)-1-(1-(4-methylbenzyl)-2-oxopyrrolidin-3-yl)piperidin-3-one

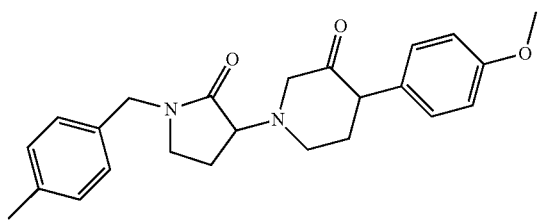

A mixture of DMSO (0.17 mL, 2.46 mmol) and DCM (4 mL) was cooled to −78° C., and oxalyl chloride (0.2 mL, 2.3 mmol) was added dropwise over 2 min. Following the addition, the mixture was stirred at the same temperature for 10 min. To the reaction was then added dropwise (±)-rel-3-((3R,4R)-3-hydroxy-4-(4-methoxyphenyl)piperidin-1-yl)-1-(4-methylbenzyl)pyrrolidin-2-one (375 mg, 0.95 mmol, mixture of four diastereomers from step E) in DCM over 5 min. The mixture was stirred for 1 h, and then triethylamine (1 mL, 7.6 mmol) was added and the mixture was stirred for 15 min, slowly warmed to rt, and then extracted with 3×40 mL of DCM. The combined organic layers were washed with 50 mL of brine, dried over $Na_2SO_4$, filtered, and concentrated under vacuum to yield 345 mg of 4-(4-methoxyphenyl)-1-(1-(4-methylbenzyl)-2-oxopyrrolidin-3-yl)piperidin-3-one (as a mixture of 4 diastereomers), which was used directly in the next step. LCMS (method)) RT 1.12 min, m/z 393 (M+H⁺), 411 (M+H⁺+18), 1.18 min, m/z 393 (M+H⁺).

Step G. 3-(3,3-Difluoro-4-(4-methoxyphenyl)piperidin-1-yl)-1-(4-methylbenzyl)pyrrolidin-2-one

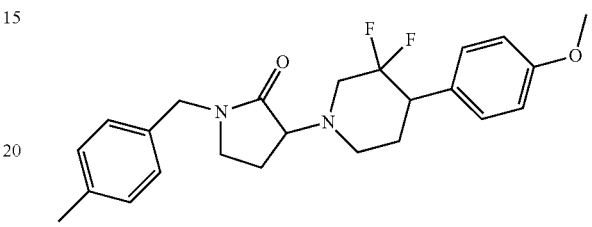

A mixture of 4-(4-methoxyphenyl)-1-(1-(4-methylbenzyl)-2-oxopyrrolidin-3-yl)piperidin-3-one (370 mg, 0.94 mmol) and DCM (5 mL) was cooled to 0° C., followed by the drop-wise addition of DAST (0.62 mL, 4.7 mmol) over 2 minutes. The mixture was warmed to rt and stirred overnight. The reaction was then quenched with 50 mL of aqueous sodium bicarbonate and extracted with 3×50 mL of DCM. The combined organic layers were washed with 50 mL of brine, separated, dried over $Na_2SO_4$, filtered, and concentrated under vacuum to yield 380 mg of 3-(3,3-difluoro-4-(4-methoxyphenyl)piperidin-1-yl)-1-(4-methylbenzyl)pyrrolidin-2-one (as a mixture of 4 diastereomers), which was used directly in the next step. LCMS (method J) RT 1.32 min (29% AP), m/z 397, 478, 1.36 min (45% AP), m/z 415.2 (M+H⁺).

Step H. 3-(3,3-Difluoro-4-(4-hydroxyphenyl)piperidin-1-yl)-1-(4-methylbenzyl)pyrrolidin-2-one

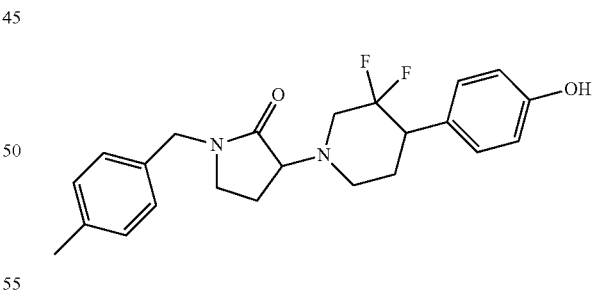

A mixture of 3-(3,3-difluoro-4-(4-methoxyphenyl)piperidin-1-yl)-1-(4-methylbenzyl)pyrrolidin-2-one (230 mg, 0.55 mmol) and 4 mL DCM was cooled to −78° C., followed by the dropwise addition of boron tribromide (0.05 mL, 0.55 mmol). The mixture was then allowed to warm up to rt over 4 h. The reaction was then quenched with 50 mL of 10% aqueous sodium bicarbonate and extracted with 4×50 mL DCM. The combined organic fractions were dried over $Na_2SO_4$, filtered, and concentrated. The residue was subjected to preparative HPLC (method B) to afford 28.1 mg 3-(3,3-difluoro-4-(4-hydroxyphenyl)piperidin-1-yl)-1-(4-methylbenzyl)pyrroli din-2-one as a mixture of 4 diastereomers. LCMS (method N) RT 1.59 min, m/z 401 (M+H⁺).

Step I. (S)-3-((R)-3,3-Difluoro-4-(4-hydroxyphenyl) piperidin-1-yl)-1-(4-methylbenzyl)pyrrolidin-2-one, (S)-3-((S)-3,3-difluoro-4-(4-hydroxyphenyl)piperidin-1-yl)-1-(4-methylbenzyl)pyrrolidin-2-one, (R)-3-((R)-3,3-difluoro-4-(4-hydroxyphenyl)piperidin-1-yl)-1-(4-methylbenzyl)pyrrolidin-2-one, and (R)-3-((S)-3,3-difluoro-4-(4-hydroxyphenyl)piperidin-1-yl)-1-(4-methylbenzyl)pyrrolidin-2-one A mixture of 4 diastereomers of 3-(3,3-difluoro-4-(4-hydroxyphenyl)piperidin-1-yl)-1-(4-methylbenzyl)pyrrolidin-2-one from step H (34 mg) was separated via chiral SFC (method K) to yield homochiral Examples 51 P-1 (6.8 mg), P-2 (3.7 mg), P-3 (3.7 mg), and P-4 (4.5 mg) which include (S)-3-((R)-3,3-difluoro-4-(4-hydroxyphenyl)piperidin-1-yl)-1-(4-methylbenzyl)pyrrolidin-2-one, (S)-3-((S)-3,3-difluoro-4-(4-hydroxyphenyl)piperidin-1-yl)-1-(4-methylbenzyl)pyrrolidin-2-one, (R)-3-((R)-3,3-difluoro-4-(4-hydroxyphenyl)piperidin-1-yl)-1-(4-methylbenzyl)pyrrolidin-2-one, and (R)-3-((S)-3,3-difluoro-4-(4-hydroxyphenyl)piperidin-1-yl)-1-(4-methylbenzyl)pyrrolidin-2-one. The absolute and relative stereochemical configurations were not determined. The compounds were arbitrarily designated as P-1, P-2, P-3, and P-4 based on their order of elution during the chiral separation. Data for P-1: ¹H NMR (400 MHz, methanol-d₄) δ=7.19-7.11 (m, 6H), 6.76-6.72 (m, 2H), 4.51-4.36 (m, 2H), 3.70 (t, J=8.8 Hz, 1H), 3.30-3.20 (m, 2H), 3.16-3.07 (m, 3H), 2.98-2.84 (m, 1H), 2.53 (t, J=1.0 Hz, 1H), 2.34 (s, 3H), 2.28-2.13 (m, 2H), 2.03 (s, 1H), 1.88-1.80 (m, 1H); ¹⁹F NMR (methanol-d₄) δ s-102.58, s-103.22, s-115.114, s-115.753; HPLC (method D) RT 8.21 min, 97.5% AP, (method C) RT 8.0 min, 97.6% AP; LCMS (method P) RT 2.37 min, m/z 401 (M+H⁺); chiral SFC (method C-5) RT 5.56 min, 100% AP. Data for P-2: ¹H NMR (400 MHz, methanol-d₄) δ=7.18-7.12 (m, 6H), 6.77-6.73 (m, 2H), 4.44 (q, J=1.0 Hz, 2H), 3.68 (t, J=8.8 Hz, 1H), 3.41-3.35 (m, 1H), 3.31-3.20 (m, 2H), 3.01-2.83 (m, 3H), 2.72-2.60 (m, 1H), 2.34 (s, 3H), 2.27-2.11 (m, 2H), 2.08-1.96 (m, 1H), 1.82 (tdd, J=2.5, 5.0, 13.1 Hz, 1H); ¹⁹F NMR (methanol-d₄) δ s-102.461, s-103.102, s-114.549, s-115.189; HPLC (method D) RT 8.33 min, 98.3% AP, (method C) RT 8.21 min, 98.2% AP; LCMS (method P) RT 2.37 min, m/z 401 (M+H⁺); chiral SFC (method C-5) RT 7.39 min, 99.7% AP. Data for P-3: ¹H NMR (400 MHz, methanol-d₄) δ ppm 1.78-1.87 (m, 1H) 1.98-2.08 (m, 1H) 2.14-2.27 (m, 2H) 2.34 (s, 3H) 2.60-2.72 (m, 1H) 2.83-3.01 (m, 3H) 3.21-3.31 (m, 2H) 3.35-3.41 (m, 1H) 3.68 (t, J=8.78 Hz, 1H) 4.44 (q, J=1.00 Hz, 2H) 6.72-6.76 (m, 2H) 7.11-7.18 (m, 6H); ¹⁹F NMR (377 MHz, methanol-d₄) δ s-102.457, s-103.097, s-114.554, s-115.194; HPLC (method D) RT 8.34 min, 98.6% AP, (method C) RT 8.21 min, 99% AP; LCMS (method P) RT 2.29 min, m/z 401 (M+H⁺); chiral SFC (method C-5) RT 10.1 min, 97.8% AP. Data for P-4: ¹H NMR (400 MHz, methanol-d₄) δ ppm 1.80-1.90 (m, 1H) 2.03 (s, 1H) 2.13-2.29 (m, 2H) 2.34 (s, 3H) 2.53 (t, J=1.00 Hz, 1H) 2.85-3.00 (m, 1H) 3.07-3.18 (m, 3H) 3.20-3.31 (m, 2H) 3.71 (t, J=8.78 Hz, 1H) 4.44 (q, J=1.00 Hz, 2H) 6.73-6.78 (m, 2H) 7.12-7.19 (m, 6H); ¹⁹F NMR (methanol-d₄) δ s-102.579, s-103.217, s-115.087, s-115.726; HPLC (method D) RT 8.2 min, 96.4% AP, (method C) RT 8.0 min, 96.5% AP; LCMS (method P) RT 2.21 min, m/z 401 (M+H⁺); chiral SFC (method C-5) RT 13.6 min, 100% AP.

Example 52

Peak-1, Peak-2, Peak-3, and Peak-4

(R)-3-((S)-3,3-difluoro-4-(4-hydroxyphenyl)piperidin-1-yl)-1-(3-fluoro-4-methylbenzyl)pyrrolidin-2-one, (R)-3-((R)-3,3-difluoro-4-(4-hydroxyphenyl)piperidin-1-yl)-1-(3-fluoro-4-methylbenzyl)pyrrolidin-2-one, (S)-3-((S)-3,3-difluoro-4-(4-hydroxyphenyl)piperidin-1-yl)-1-(3-fluoro-4-methylbenzyl)pyrrolidin-2-one, and (S)-3-((R)-3,3-difluoro-4-(4-hydroxyphenyl)piperidin-1-yl)-1-(3-fluoro-4-methylbenzyl)pyrrolidin-2-one

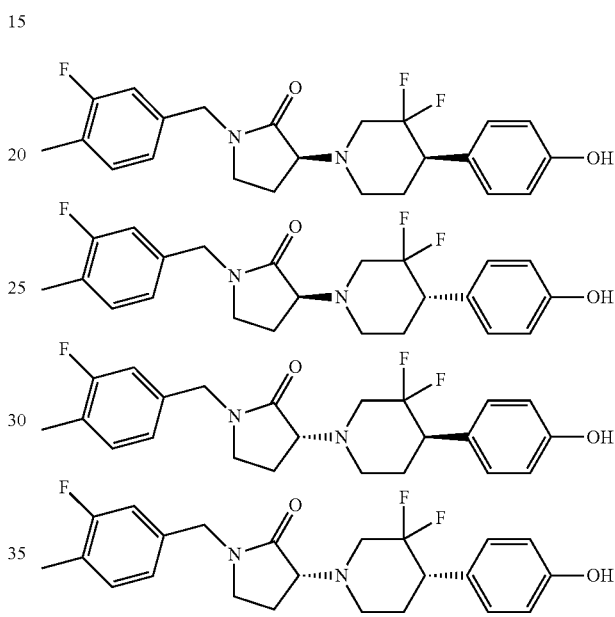

Step A. tert-Butyl 4-(4-(benzyloxy)phenyl)-3-oxopiperidine-1-carboxylate

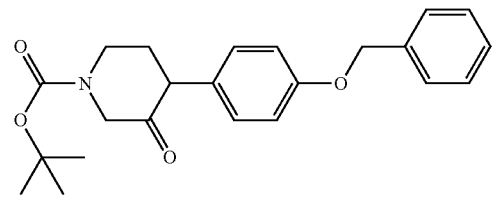 [SMILES: CC(C)(C)OC(=O)N1CCC(c2ccc(OCc3ccccc3)cc2)C(=O)C1]

To a solution of DMSO (3.7 mL, 52 mmol) in 50 mL of DCM under nitrogen at −78° C. was added oxalyl chloride (4.45 mL, 51 mmol). The mixture was stirred for 10 minutes after the completion of the addition. Then a solution of (±)-rel-(3S,4S)-tert-butyl 4-(4-(benzyloxy)phenyl)-3-hydroxypiperidine-1-carboxylate (from Example 50, step D, 6.5 g, 17 mmol) in 50 mL of DCM was added and the mixture was stirred in the cold for a further 90 minutes. The reaction was then quenched by the addition of 11.8 mL of triethylamine (85 mmol) and allowed to warm up to rt. The mixture was then partitioned between 200 mL brine and 200 mL DCM. The layers were separated, and the organic layer was dried over Na₂SO₄, filtered, and concentrated. The residue was subjected to column chromatography on 48 g of basic alumina eluting with 8% ethyl acetate/hexanes to afford 4.7 g (67%) of racemic tert-butyl 4-(4-(benzyloxy)phenyl)-3-oxopiperidine-1-carboxylate. LCMS (method F) RT 2.376 min, m/z 381.2 (M+); chiral SFC (method G) RT 4.54 min (46.9% AP, 4.93 min (49.7% AP). $^1$H NMR (400 MHz, DMSO-$d_6$) δ 7.30-7.40 (m, 5H), 7.07 (d, J=7 Hz, 2H) 6.94 (d, J=7), 2H; 5.08 (s, 2H), 4.10 (d, J=17.6, 1H), 3.97 (d, J=17.6, 1H), 3.77 (m, 2H), 3.43 (br s, 1H), 2.16 (m, 2H), 1.42 (s, 9H).

Step B. tert-Butyl 4-(4-(benzyloxy)phenyl)-3,3-difluoropiperidine-1-carboxylate

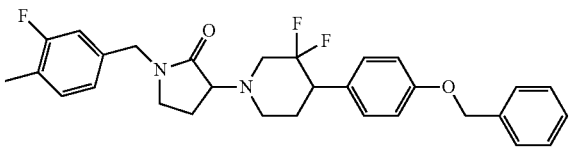

To a solution of tert-butyl 4-(4-(benzyloxy)phenyl)-3-oxopiperidine-1-carboxylate (4.7 g, 12.3 mmol) in 100 mL DCM at 0° C. was added DAST (8.1 mL, 62 mmol) and the reaction mixture was stirred for 1 h. It was then allowed to warm to rt and partitioned between saturated sodium bicarbonate and 200 mL of DCM. The layers were separated and the organic phase was dried over Na$_2$SO$_4$, filtered, and concentrated to afford 4.2 g (68%) of racemic tert-butyl 4-(4-(benzyloxy)phenyl)-3,3-difluoropiperidine-1-carboxylate. LCMS (method P) RT 1.16 min, m/z 348.1 (M−t-butyl+H)+.

Step C. 4-(4-(Benzyloxy)phenyl)-3,3-difluoropiperidine

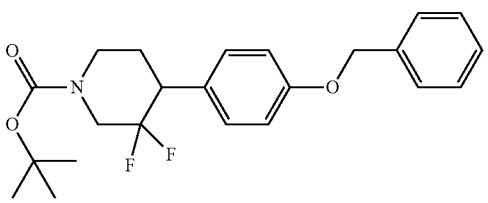 [SMILES: CC(C)(C)OC(=O)N1CCC(c2ccc(OCc3ccccc3)cc2)C(F)(F)C1]

To a solution of t-butyl 4-(4-(benzyloxy)phenyl)-3,3-difluoropiperidine-1-carboxylate (5.2 g, 12.9 mmol) in MeOH (100 mL) was added 4 M HCl/dioxane (32.2 mL, 130 mmol) and the reaction mixture was stirred at rt for 5 h. The mixture was then evaporated under reduced pressure, and the residue was diluted with a saturated sodium bicarbonate solution and extracted with 200 mL of ethyl acetate. The layers were separated and the organic phase was dried over Na$_2$SO$_4$, filtered, and concentrated under vacuum. The residue was subjected to preparative HPLC (method C) to afford 2.5 grams (63%) of racemic 4-(4-(benzyloxy)phenyl)-3,3-difluoropiperidine. LCMS (method F) RT 2.044 min, m/z 304 (M+H+); $^1$H NMR (400 MHz, DMSO-$d_6$) δ ppm 7.31-7.48 (m, 5H) 7.21 (d, J=8.53 Hz, 2H) 6.98 (d, J=9.04 Hz, 2H) 5.10 (s, 2H) 3.05-3.20 (m, 2H) 2.98 (d, J=13.05 Hz, 1H) 2.74-2.87 (m, 1H) 2.60 (t, J=11.55 Hz, 1H) 1.88-2.00 (m, 4H) 1.72 (d, J=13.05 Hz, 1H), $^{19}$F NMR (377 MHz, DMSO-$d_6$) δ-102.276, -102.900, -115.135, -115.759.

Step D. 3-(4-(4-(Benzyloxy)phenyl)-3,3-difluoropiperidin-1-yl)-1-(3-fluoro-4-methylbenzyl)pyrrolidin-2-one

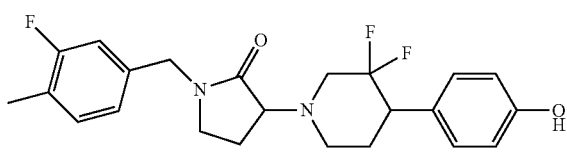

To a mixture of 3-bromo-1-(3-fluoro-4-methylbenzyl)pyrrolidin-2-one (0.51 g, 1.8 mmol, Intermediate 6) and 4-(4-(benzyloxy)phenyl)-3,3-difluoropiperidine (0.3 g, 1 mmol, from step C) was added triethylamine (0.69 mL, 4.9 mmol) and the resulting mixture was heated in a sealed tube at 120° C. for 1 h. The reaction mixture was allowed to cool and then diluted with water and the mixture was extracted with ethyl acetate. The organic layer was separated, washed with brine, dried over Na$_2$SO$_4$, filtered, and concentrated. The residue (0.45 grams, 64%, mixture of 4 diastereoisomers) was used directly in the next step without further purification, LCMS (method P) RT 1.19 min, m/z 509 (M+H+).

Step E. 3-(3,3-Difluoro-4-(4-hydroxyphenyl)piperidin-1-yl)-1-(3-fluoro-4-methylbenzyl)pyrrolidin-2-one

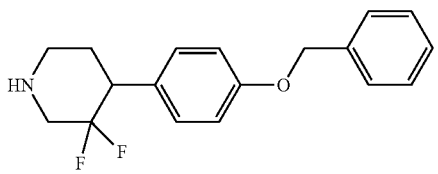 [SMILES: FC1(F)CNCCC1c1ccc(OCc2ccccc2)cc1]

To a stirred solution of 3-(4-(4-(benzyloxy)phenyl)-3,3-difluoropiperidin-1-yl)-1-(3-fluoro-4-methylbenzyl)pyrrolidin-2-one (0.45 g, 0.89 mmol, mixture of diastereomers from step D) in MeOH (8 mL) at rt was added 0.56 g of 10% Pd/C and the reaction mixture was stirred at rt under a hydrogen atmosphere overnight. The catalyst was removed by filtration through Celite and the solvent was removed in vacuo. The residue was subjected to HPLC purification (method E) to yield 200 mg of 3-(3,3-difluoro-4-(4-hydroxyphenyl)piperidin-1-yl)-1-(3-fluoro-4-methylbenzyl)pyrrolidin-2-one as a mixture of four diastereoisomers.

Step F. (R)-3-((S)-3,3-difluoro-4-(4-hydroxyphenyl) piperidin-1-yl)-1-(3-fluoro-4-methylbenzyl)pyrrolidin-2-one, (R)-3-((R)-3,3-difluoro-4-(4-hydroxyphenyl)piperidin-1-yl)-1-(3-fluoro-4-methylbenzyl)-pyrrolidin-2-one, (S)-3-((S)-3,3-difluoro-4-(4-hydroxyphenyl)piperidin-1-yl)-1-(3-fluoro-4-methylbenzyl)pyrrolidin-2-one, and (S)-3-((R)-3,3-difluoro-4-(4-hydroxyphenyl)piperidin-1-yl)-1-(3-fluoro-4-methylbenzyl)pyrrolidin-2-one The mixture of diastereomers of 3-(3,3-difluoro-4-(4-hydroxyphenyl)piperidin-1-yl)-1-(3-fluoro-4-methylbenzyl) pyrrolidin-2-one (0.1 g, 0.239 mmol) from step E was subjected to chiral SFC purification to afford homochiral Examples 52 P-1 (12.8 mg), P-2 (13.7 mg), P-3 (6.7 mg), and P-4 (13.1 mg) which include (R)-3-((S)-3,3-difluoro-4-(4-hydroxyphenyl)piperidin-1-yl)-1-(3-fluoro-4-methylbenzyl) pyrrolidin-2-one, (R)-3-((R)-3,3-difluoro-4-(4-hydroxyphenyl)piperidin-1-yl)-1-(3-fluoro-4-methylbenzyl)-pyrrolidin-2-one, (S)-3-((S)-3,3-difluoro-4-(4-hydroxyphenyl)piperidin-1-yl)-1-(3-fluoro-4-methylbenzyl)pyrrolidin-2-one, and (S)-3-((R)-3,3-difluoro-4-(4-hydroxyphenyl)piperidin-1-yl)-1-(3-fluoro-4-methylbenzyl)pyrrolidin-2-one. The absolute and relative stereochemical configurations were not determined. The compounds were arbitrarily designated as P-1, P-2, P-3, and P-4 based on their order of elution during the chiral separation. Data for P-1: yellow solid; LCMS (method F) RT 2.05 min, 100% AP, m/z 419.2 (M+H+); HPLC (method A) RT 8.45 min 98.2% AP, (method B) RT 8.56 min, 97.8% AP; chiral SFC (method C-5) RT 4.52 min, 100% AP; $^1$H NMR (400 MHz, methanol-d$_4$) δ 7.23 (t, J=7.8 Hz, 1H), 7.15 (d, J=8.0 Hz, 2H), 7.03-6.93 (m, 2H), 6.75 (d, J=8.5 Hz, 2H), 4.52-4.36 (m, 2H), 3.71 (t, J=8.8 Hz, 1H), 3.31-3.23 (m, 3H), 3.19-3.12 (m, 2H), 3.11-3.07 (m, 1H), 3.00-2.83 (m, J=13.2, 4.7, 4.7 Hz, 1H), 2.53 (t, J=11.0 Hz, 1H), 2.26 (d, J=1.5 Hz, 3H), 2.25-2.21 (m, 1H), 2.20-2.13 (m, 1H), 2.11-1.99 (m, 1H), 1.89-1.78 (m, 1H); $^{19}$F NMR (377 MHz, chloroform-d) δ-133.04 (s, 1F), -133.68 (s, 1F), -145.26 (s, 1F), -145.90 (s, 1F), -147.99 (s, 1F). Data for P-2: yellow solid; LCMS (method F) RT 2.05 min, 95.8% AP, m/z 419.2 (M+H+); HPLC (method A) RT 8.64 min 97.8% AP, (method B) RT 8.71 min, 97.6% AP; chiral SFC (method C-5) RT 6.35 min, 95.4% AP; $^1$H NMR (400 MHz, methanol-d$_4$) δ 7.23 (t, J=7.8 Hz, 1H), 7.15 (d, J=8.5 Hz, 2H), 7.04-6.92 (m, 2H), 6.81-6.70 (m, 2H), 4.53-4.35 (m, 2H), 3.69 (t, J=8.8 Hz, 1H), 3.46-3.35 (m, 2H), 3.31-3.22 (m, 2H), 3.04-2.94 (m, 2H), 2.93-2.83 (m, 2H), 2.74-2.58 (m, 1H), 2.28-2.25 (m, 3H), 2.25-2.15 (m, 2H), 1.87-1.78 (m, 1H); $^{19}$F NMR (377 MHz, chloroform-d) δ-132.68 (s, 1F), -133.32 (s, 1F), -144.55 (s, 1F), -145.19 (s, 1F), -147.96 (s, 1F). Data for P-3: yellow solid; LCMS (method F) RT 2.05 min, 92.1% AP, m/z 419.2 (M+H+; HPLC (method A) RT 8.70 min 97.3% AP, (method B) RT 8.64 min, 97.1% AP; chiral SFC (method C-5) RT 8.81 min, 98.2% AP; $^1$H NMR (400 MHz, methanol-d$_4$) δ 7.24 (t, J=7.5 Hz, 1H), 7.15 (d, J=8.5 Hz, 2H), 7.05-6.91 (m, 2H), 6.81-6.68 (m, 2H), 4.45 (dd, J=30.5, 14.5 Hz, 2H), 3.69 (t, J=8.8 Hz, 1H), 3.46-3.36 (m, 2H), 3.31-3.22 (m, 2H), 3.05-2.94 (m, 2H), 2.93-2.81 (m, 2H), 2.75-2.56 (m, J=8.0, 8.0 Hz, 1H), 2.27 (d, J=1.5 Hz, 3H), 2.25-2.11 (m, 1H), 2.05 (dd, J=13.3, 8.3 Hz, 1H), 1.90-1.76 (m, 1H); $^{19}$F NMR (377 MHz, chloroform-d) δ-132.68 (s, 1F), -133.32 (s, 1F), -144.53 (s, 1F), -145.17 (s, 1F), -147.94 (s, 1F). Data for P-4: yellow solid; LCMS (method F) RT 2.05 min, 94.5% AP, m/z 419.2 (M+H+); HPLC (method A) RT 8.45 min 96.9% AP, (method B) RT 8.56 min, 97.0% AP; chiral SFC (method C-5) RT 12.13 min, 99.4% AP; $^1$H NMR (400 MHz, methanol-d$_4$) δ 7.23 (t, J=7.8 Hz, 1H), 7.19-7.11 (m, J=8.5 Hz, 2H), 7.04-6.92 (m, 2H), 6.81-6.71 (m, J=8.5 Hz, 2H), 4.53-4.35 (m, 2H), 3.72 (t, J=8.8 Hz, 1H), 3.32-3.22 (m, 2H), 3.20-3.07 (m, 3H), 3.04-2.82 (m, 1H), 2.53 (t, J=11.3 Hz, 1H), 2.26 (d, J=1.5 Hz, 3H), 2.25-2.12 (m, 2H), 2.12-2.01 (m, 2H), 1.92-1.78 (m, 1H); $^{19}$F NMR (377 MHz, chloroform-d) δ-133.04 (s, 1F), -133.68 (s, 1F), -145.25 (s, 1F), -145.89 (s, 1F), -147.99 (s, 1F).

Example 53

Peak-1 and Peak-2

3-(3,3-Difluoro-4-(4-hydroxyphenyl)piperidin-1-yl)-1-(4-(trifluoromethyl)-benzyl)pyrrolidin-2-one

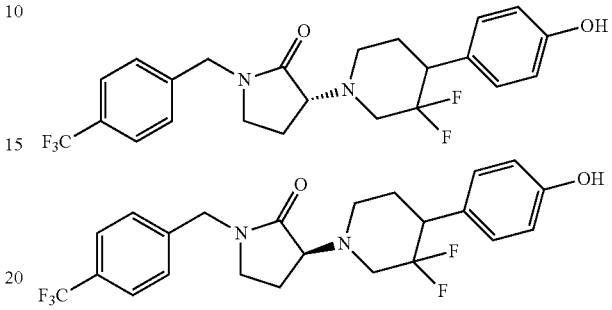

Step A. 2,4-Dibromo-N-(4-(trifluoromethyl)benzyl) butanamide

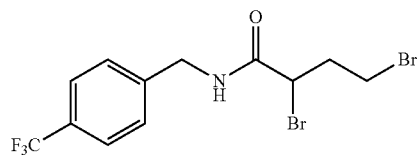 [SMILES: O=C(NCc1ccc(C(F)(F)F)cc1)C(Br)CCBr]

To a solution of (4-(trifluoromethyl)phenyl)methanamine (3 g, 17 mmol) in diethyl ether (60 mL) under nitrogen at 0° C. was added 2,4-dibromobutanoyl chloride (2.3 mL, 17 mmol) and the reaction mixture was stirred for 1 h at rt. The mixture was then diluted with water and extracted with 200 mL of ethyl acetate. The organic layer was dried over Na$_2$SO$_4$, filtered, and evaporated under reduced pressure to afford 2,4-dibromo-N-(4-(trifluoromethyl)benzyl)-butanamide (6.5 g, 87%). LCMS (method F) RT 2.01 min, m/z 434.8, 483.8; $^1$H NMR (400 MHz, DMSO-d$_6$) δ ppm 2.39-2.47 (m, 2H) 3.50-3.67 (m, 2H) 4.41 (dd, J=13.05, 6.02 Hz, 2H) 4.59-4.64 (m, 1H) 7.49 (d, J=7.53 Hz, 2H) 7.71 (d, J=8.03 Hz, 2H) 9.06 (s, 1H).

Step B. 3-Bromo-1-(4-(trifluoromethyl)benzyl)pyrrolidin-2-one

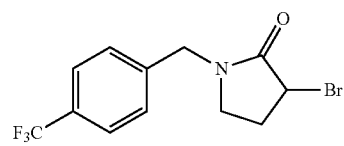

To a suspension of 2,4-dibromo-N-(4-(trifluoromethyl) benzyl)butanamide (6.8 g, 16.9 mmol) in tetrahydrofuran (200 mL) was added NaH (1.35 g, 34 mmol) and the reaction was stirred at rt for 4 h. The reaction mixture was then diluted with water and twice extracted with 30 mL of ethyl acetate. The combined organic layers were dried over Na$_2$SO$_4$, filtered, and evaporated to dryness. The residue was purified by silica gel chromatography eluting with 0-40% ethyl acetate/hexanes to afford 2.8 g of 3-bromo-1-(4-(trifluoromethyl) benzyl)pyrrolidin-2-one (48%). LCMS (method Q) RT 0.90 min, m/z 322.1 (M+H+); $^1$H NMR (400 MHz, chloroform-d) δ 12.39 (d, J=8.0 Hz, 2H), 12.16 (d, J=8.0 Hz, 2H), 9.46-9.38 (m, 1H), 9.25 (d, J=1.8 Hz, 2H), 8.27-8.17 (m, 1H), 7.99 (s, 1H), 7.43-7.31 (m, 1H), 7.14-7.05 (m, 1H).

Step C. (R)-4-(4-(benzyloxy)phenyl)-3,3-difluoropiperidine and (S)-4-(4-(benzyloxy)phenyl)-3,3-difluoropiperidine

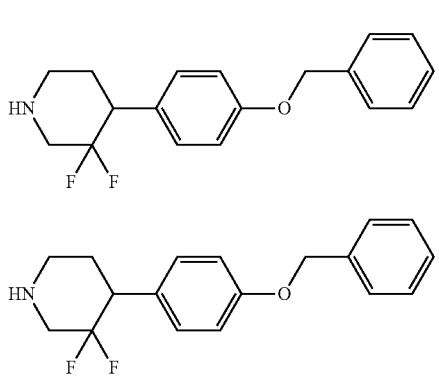

Racemic 4-(4-(benzyloxy)phenyl)-3,3-difluoropiperidine (2.2 g, 7.3 mmol, from Example 52, step C) was submitted to chiral separation (method H-4) and the chirally pure fractions were collected and evaporated under under reduced pressure to give E1 (850 mg, 2.77 mmol, 38.3% yield) and E2 (780 mg, 2.55 mmol, 35.1% yield) (R)-4-(4-(benzyloxy)phenyl)-3,3-difluoropiperidine and (S)-4-(4-(benzyloxy)phenyl)-3,3-difluoropiperidine (absolute configuration not assigned). Data for E-1: LCMS (method F) RT 2.16 min, m/z 304 (M+H+); Chiral HPLC (method H-3) RT 11.1 min, 100% AP; $^1$H NMR (400 MHz, DMSO-d$_6$) δ ppm 1.72 (d, J=13.55 Hz, 1H) 1.94 (dd, J=12.55, 4.02 Hz, 1H) 2.60 (t, J=12.05 Hz, 1H) 2.74-2.88 (m, 1H) 2.98 (d, J=12.55 Hz, 1H) 3.04-3.20 (m, 2H) 5.10 (s, 2H) 6.95-7.02 (m, 2H) 7.21 (d, J=8.53 Hz, 2H) 7.30-7.50 (m, 5H); $^{19}$F NMR (400 MHz, DMSO-d$_6$) δ ppm-102.275, -102, 900, -115.135, -115.759. Data for E-2:; LCMS (method F) RT 2.16 min, m/z 304 (M+H+); Chiral HPLC (method H-3) RT 18.28 min, 99.7% AP; $^1$H NMR (400 MHz, DMSO-d$_6$) δ ppm 1.72 (d, J=12.55 Hz, 1H) 1.94 (dd, J=13.05, 4.02 Hz, 1H) 2.55-2.64 (m, 1H) 2.74-2.88 (m, 1H) 2.98 (d, J=13.05 Hz, 1H) 3.05-3.20 (m, 2H) 5.10 (s, 2H) 6.95-7.00 (m, 2H) 7.21 (d, J=8.53 Hz, 2H) 7.30-7.49 (m, 5H): $^{19}$F NMR (400 MHz, DMSO-d$_6$) δ ppm-102.276, -102, -900, -115.134, -115.748.

Step D. 4-(3,3-Difluoropiperidin-4-yl)phenol

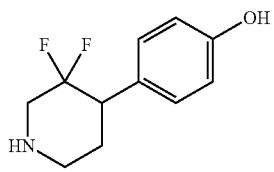

A mixture of 4-(4-(benzyloxy)phenyl)-3,3-difluoropiperidine (E-2 from Step C, above, 1 g, 3.3 mmol) and methanol (15 mL) was flushed with nitrogen, followed by the addition of 10% Pd/C (0.7 g). The reaction mass then stirred overnight at rt under 160 psi of hydrogen pressure in a 100 mL autoclave. The catalyst was then removed by filtration through Celite and the filtrate was concentrated under vacuum. A yield of 0.65 g (78%) of E-2a 4-(3,3-difluoropiperidin-4-yl)phenol was obtained. LCMS (method Q) RT 0.47 min, m/z 214.1 (M+H+).

Step E. 3-(3,3-Difluoro-4-(4-hydroxyphenyl)piperidin-1-yl)-1-(4-(trifluoromethyl)benzyl)pyrrolidin-2-one

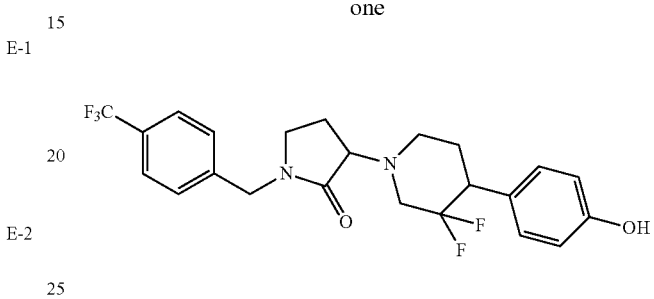

A mixture of 4-(3,3-difluoropiperidin-4-yl)phenol (200 mg, 0.94 mmol, E-2a from step D), 3-bromo-1-(4-(trifluoromethyl)benzyl)pyrrolidin-2-one (604 mg, 1.9 mmol), triethylamine (0.65 mL, 4.7 mmol), and 2 mL of DMF was heated in a microwave reactor at 120° C. for 1 h. The cooled reaction mixture was partitioned between water and 30 mL of ethyl acetate, and the aqueous phase was again extracted with 30 mL of ethyl acetate. The combined organic layers were dried over Na$_2$SO$_4$, filtered, and concentrated to afford 150 mg of 3-(3,3-difluoro-4-(4-hydroxyphenyl)piperidin-1-yl)-1-(4-(trifluoromethyl)-benzyl)pyrrolidin-2-one (0.33 mmol, 35%, 2 diastereoisomers) which was purified and separated in step F. LCMS (method J) RT 0.8 min (60% AP), m/z 455.4 (M+H+).

Step F. 3-(3,3-Difluoro-4-(4-hydroxyphenyl)piperidin-1-yl)-1-(4-(trifluoromethyl)-benzyl)pyrrolidin-2-one The product 3-(3,3-difluoro-4-(4-hydroxyphenyl)piperidin-1-yl)-1-(4-(trifluoromethyl)-benzyl)pyrrolidin-2-one (150 mg, 0.33 mmol), from step E was separated via SFC (method C-7) to give the separated diastereomers, which were individually purified via preparative HPLC (method B) to give homochiral Examples 53 P-1 (40.8 mg) and P-2 (39.3 mg). The products differ at the lactam 3-position stereocenter; however, the relative stereochemical configurations were not determined. Data for P-1: pale yellow solid. LCMS (method N) RT 1.70 min (99.7% AP), m/z 455.0 (M+H+); $^1$H NMR (400 MHz, methanol-d$_4$) δ=7.69 (d, J=8.5 Hz, 2H), 7.49 (d, J=8.0 Hz, 2H), 7.15 (d, J=8.0 Hz, 2H), 6.80-6.71 (m, 2H), 4.58 (d, J=16.6 Hz, 2H), 3.75 (s, 1H), 3.30-3.25 (m, 2H), 3.23-3.09 (m, 3H), 3.02-2.85 (m, 1H), 2.59-2.50 (m, 1H), 2.33-2.03 (m, 3H), 1.91-1.80 (m, 1H). $^{19}$F NMR (400 MHz, methanol-d$_4$) δ-64.073, -102.629, -103.268, -115.125, -115.764. Data for P-2: pale yellow solid. LCMS (method N) RT 1.71 min (99.7% AP), m/z 455.0 (M+H+); $^1$H NMR (400 MHz, methanol-d$_4$) δ=7.69 (d, J=8.0 Hz, 2H), 7.49 (d, J=8.0 Hz, 2H), 7.15 (d, J=8.0 Hz, 2H), 6.79-6.72 (m, 2H), 4.65-4.52 (m, 2H), 3.72 (t, J=9.0 Hz, 1H), 3.47-3.38 (m, 1H), 3.31-3.26 (m, 1H), 3.03-2.84 (m, 3H), 2.74-2.61 (m, 1H), 2.31-2.01 (m, 3H), 1.88-1.80 (m, 1H). $^{19}$F NMR (400 MHz, methanol-d$_4$) δ -64.074, -102.511, -103.151, -114.583, -115.225.

Example 54

Peak-1, Peak-2, Peak-3, and Peak-4

(R)-3-((R)-3,3-difluoro-4-(4-hydroxyphenyl)piperidin-1-yl)-1-(4-fluorobenzyl)pyrrolidin-2-one, (R)-3-((S)-3,3-difluoro-4-(4-hydroxyphenyl)piperidin-1-yl)-1-(4-fluorobenzyl)pyrrolidin-2-one, (S)-3-((R)-3,3-difluoro-4-(4-hydroxyphenyl)piperidin-1-yl)-1-(4-fluorobenzyl)pyrrolidin-2-one, and (S)-3-(S)-3,3-difluoro-4-(4-hydroxyphenyl)piperidin-1-yl)-1-(4-fluorobenzyl)pyrrolidin-2-one

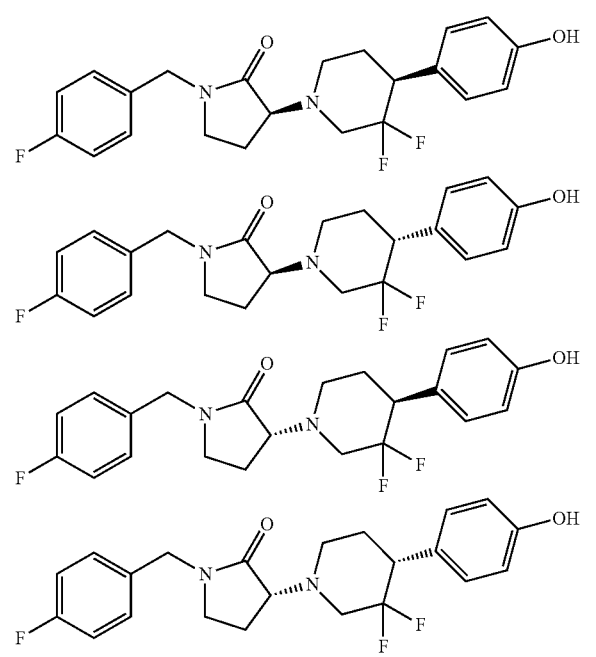

Step A. (3S,4S)-4-(4-Methoxyphenyl)piperidin-3-ol and (3R,4R)-4-(4-methoxyphenyl)piperidin-3-ol

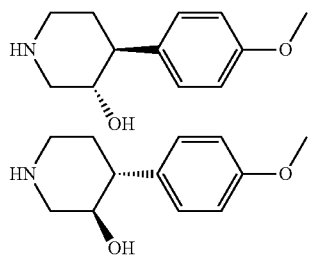

Racemic (±)-rel-(3S,4S)-4-(4-methoxyphenyl)piperidin-3-ol (2.6 g, 12.54 mmol, from Example 51, step D) was subjected to SFC chiral purification (Method H-1), which gave enantiomers E-1 (680 mg) and E-2 (720 mg), (3S,4S)-4-(4-methoxyphenyl)piperidin-3-ol and (3R,4R)-4-(4-methoxyphenyl)piperidin-3-ol (absolute configurations not assigned). Data for E-1, 1st eluting isomer: Chiral SFC (method H) RT 2.57 min; 98% AP; $^1$H NMR (400 MHz, DMSO-d$_6$) δ ppm 7.13 (d, J=9 Hz, 2H) 6.84 (d, J=9 Hz, 2H) 4.43 (br. s., 1H) 3.72 (s, 3H) 3.43 (d, J=10.54 Hz, 2H) 3.08 (dd, J=11.80, 4.77 Hz, 1H) 2.92 (d, J=12.05 Hz, 1H) 2.28-2.39 (m, 2H) 1.47-1.68 (m, 2H). Data for E-2, 2nd eluting isomer: Chiral SFC (method H) RT 3.18 min; 94.3% AP; $^1$H NMR (400 MHz, DMSO-d$_6$) δ ppm 7.13 (d, J=9 Hz, 2H) 6.85 (d, J=8 Hz, 2H) 4.58 (br. s., 1H) 3.72 (s, 3H) 3.43 (br d, 3H) 3.11 (m, 2H) 2.61 (m, 1H) 2.28-2.39 (m, 2H) 1.47-1.68 (m, 2H).

Step B. 1-(4-Fluorobenzyl)-3-(trans-3-hydroxy-4-(4-methoxyphenyl)piperidin-1-yl)pyrrolidin-2-one

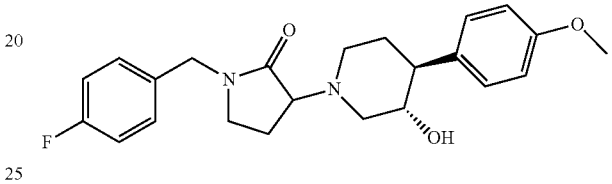

To a mixture of 3-bromo-1-(4-fluorobenzyl)pyrrolidin-2-one (Intermediate 1, 200 mg, 0.74 mmol), trans-4-(4-methoxyphenyl)piperidin-3-ol (152 mg, 0.74 mmol, E-2 from step A) and acetonitrile (15 mL) was added triethylamine (0.5 mL, 3.7 mmol) and the resulting mixture was heated at 100° C. for 1 h. The reaction was then diluted with water and extrated with ethyl acetate (100 mL). The layers were separated, and the organic layer was dried over Na$_2$SO$_4$, filtered, and evaporated under reduced pressure to afford 1-(4-fluorobenzyl)-3-(trans-3-hydroxy-4-(4-methoxyphenyl)piperidin-1-yl)pyrrolidin-2-one (mixture of 2 diastereomers, 320 mg, 73.% yield). LCMS (method F) RT 1.706 min (67% AP) m/z 399.4 (M+H$^+$).

Step C. 1-(1-(4-Fluorobenzyl)-2-oxopyrrolidin-3-yl)-4-(4-methoxyphenyl)piperidin-3-one

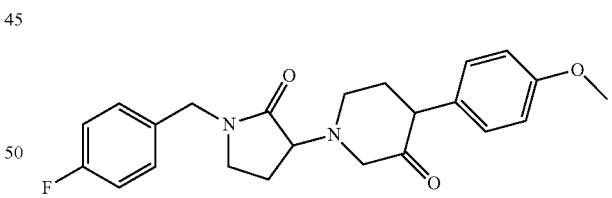

To a mixture of DMSO (0.14 mL, 2 mmol) and DCM (20 mL) at −78° C. under nitrogen was added oxalyl chloride (0.18 mL, 2 mmol) and the reaction mixture was stirred for 10 min. Then 1-(4-fluorobenzyl)-3-(trans-3-hydroxy-4-(4-methoxyphenyl)-piperidin-1-yl)pyrrolidin-2-one (320 mg, 0.8 mmol) was added and the reaction was stirred for one hour at same temperature. Triethylamine (0.56 mL, 4 mmol) was then added, and the reaction mixture was allowed to warm to rt. The mixture was then partitioned between water (100 mL) and DCM (200 mL). The organic layer was separated, dried over Na$_2$SO$_4$, filtered, and evaporated under reduced pressure to give afford the crude product, which was taken on to step D without further purification. LCMS (method Q) RT 0.68 min (47% AP), m/z 397.1 (M+H$^+$).

Step D. 3-(3,3-Difluoro-4-(4-methoxyphenyl)piperidin-1-yl)-1-(4-fluorobenzyl)pyrrolidin-2-one

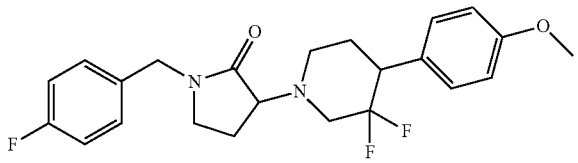 [SMILES: COc1ccc(C2CCN(C3CCN(Cc4ccc(F)cc4)C3=O)CC2(F)F)cc1]

To a solution of 1-(1-(4-fluorobenzyl)-2-oxopyrrolidin-3-yl)-4-(4-methoxyphenyl)piperidin-3-one (350 mg, 0.88 mmol) in 15 mL of DCM at −10° C. was added DAST (0.58 mL, 4.4 mmol) and the reaction was stirred under nitrogen for 1 h. The mixture was then diluted with a saturated sodium bicarbonate solution (100 mL) and extracted with 250 mL of DCM. The organic layer was separated, dried over $Na_2SO_4$, filtered, and evaporated under reduced pressure to yield 3-(3,3-difluoro-4-(4-methoxyphenyl)piperidin-1-yl)-1-(4-fluorobenzyl)pyrrolidin-2-one (mixture of diastereomers), which was used in step E without further purification. LCMS (method F) RT 1.939 min, 55.8% AP, m/z 381.2, 471.2.

Step E. 3-(3,3-Difluoro-4-(4-hydroxyphenyl)piperidin-1-yl)-1-(4-fluorobenzyl)pyrrolidin-2-one

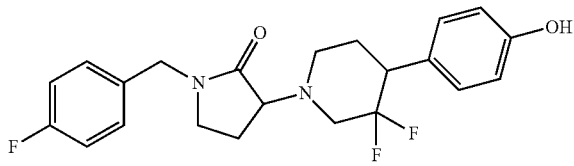 [SMILES: O=C1C(N2CCC(c3ccc(O)cc3)C(F)(F)C2)CCN1Cc1ccc(F)cc1]

To a solution of 3-(3,3-difluoro-4-(4-methoxyphenyl)piperidin-1-yl)-1-(4-fluorobenzyl)pyrrolidin-2-one (200 mg, 0.48 mmol, mixture of diastereomers from step D) in DCM (15 mL) at −10° C. was added boron tribromide (0.05 mL, 0.48 mmol) and the reaction mixture was stirred under nitrogen for one hour. The mixture was then diluted with a satd. sodium bicarbonate solution and extracted with 100 mL of DCM. The organic layer was separated, dried over $Na_2SO_4$, filtered, and evaporated under reduced pressure. The residue was purified via preparative HPLC (method D) to yield 3-(3,3-difluoro-4-(4-hydroxyphenyl)-piperidin-1-yl)-1-(4-fluorobenzyl)pyrrolidin-2-one (mixture of 4 diastereomers, 34 mg, 17% yield). LCMS (method N) RT 1.497 min, m/z 405.0 $(M+H^+)$.

Step F. (R)-3-((R)-3,3-difluoro-4-(4-hydroxyphenyl)piperidin-1-yl)-1-(4-fluorobenzyl)pyrrolidin-2-one, (R)-3-((S)-3,3-difluoro-4-(4-hydroxyphenyl)piperidin-1-yl)pyrrolidin-2-one, (S)-3-((R)-3,3-difluoro-4-(4-hydroxyphenyl)piperidin-1-yl)-1-(4-fluorobenzyl)pyrrolidin-2-one, and (S)-3-((S)-3,3-difluoro-4-(4-hydroxyphenyl)piperidin-1-yl)-1-(4-fluorobenzyl)pyrrolidin-2-one The diasteromeric mixture of 3-(3,3-difluoro-4-(4-hydroxyphenyl)piperidin-1-yl)-1-(4-fluorobenzyl)pyrrolidin-2-one (32 mg, 0.08 mmol, from step E) was purified by SFC (method C-8) to obtain homochiral Examples 54 P-1 (5.2 mg), P-2 (5.2 mg), P-3 (5.4 mg), and P-4 (5.4 mg), (R)-3-((R)-3,3-difluoro-4-(4-hydroxyphenyl)piperidin-1-yl)-1-(4-fluorobenzyl)pyrrolidin-2-one, (R)-3-((S)-3,3-difluoro-4-(4-hydroxyphenyl)piperidin-1-yl)-1-(4-fluorobenzyl)pyrrolidin-2-one, (S)-3-((R)-3,3-difluoro-4-(4-hydroxyphenyl)piperidin-1-yl)-1-(4-fluorobenzyl)pyrrolidin-2-one, and (S)-3-((S)-3,3-difluoro-4-(4-hydroxyphenyl)piperidin-1-yl)-1-(4-fluorobenzyl)pyrrolidin-2-one. The absolute and relative stereochemical configurations were not determined. The compounds were arbitrarily designated as P-1, P-2, P-3, and P-4 based on their order of elution during the chiral separation. The presence of 4 instead of 2 diastereoisomers implies racemization of the starting homochiral piperidine during the course of the synthesis. Data for P-1: HPLC (method D) RT 7.87 min, 95.8% AP, (method A) RT 7.58 min, 97.5% AP; LCMS (method F) RT 2.05 min, 100% AP, m/z 405.0 $(M+H^+)$; chiral SFC (method C-5) RT 4.77 min; $^1H$ NMR (400 MHz, methanol-$d_4$) δ ppm 7.32 (dd, J=8.78, 5.27 Hz, 2H) 7.06-7.17 (m, 4H) 6.72-6.77 (m, 2H) 4.40-4.53 (m, 2H) 3.71 (t, J=8.78 Hz, 1H) 3.22-3.31 (m, 2H) 3.07-3.18 (m, 3H) 2.85-2.99 (m, 1H) 2.52 (t, J=11.29 Hz, 1H) 1.99-2.31 (m, 3H) 1.84 (ddt, J=13.30, 4.77, 2.26, 2.26 Hz, 1H). Data for P-2: HPLC (method D) RT 7.89 min, 100% AP, (method A) RT 7.77 min, 95.1% AP; LCMS (method F) RT 2.04 min, 100% AP, m/z 405.0 $(M+H^+)$; chiral SFC (method C-5) RT 6.6 min; $^1H$ NMR (400 MHz, methanol-$d_4$) δ ppm 7.31 (dd, J=8.78, 5.27 Hz, 2H) 7.06-7.17 (m, 4H) 6.75 (d, J=8.53 Hz, 2H) 4.47 (q, J=15.06 Hz, 2H) 3.68 (t, J=9.04 Hz, 1H) 3.35-3.42 (m, 1H) 3.22-3.30 (m, 1H) 2.82-3.02 (m, 3H) 2.59-2.74 (m, 1H) 1.98-2.28 (m, 3H) 1.82 (ddt, J=13.18, 4.64, 2.38, 2.38 Hz, 1H). Data for P-3: HPLC (method D) RT 7.99 min, 100% AP, (method A) RT 7.77 min, 96.3% AP; LCMS (method F) RT 2.04 min, 100% AP, m/z 405.0 $(M+H^+)$; chiral SFC (method C-5) RT 7.25 min; $^1H$ NMR (400 MHz, methanol-$d_4$) δ ppm 7.31 (dd, J=8.78, 5.27 Hz, 2H) 7.06-7.17 (m, 4H) 6.72-6.78 (m, 2H) 4.40-4.53 (m, 2H) 3.68 (t, J=9.04 Hz, 1H) 3.34-3.43 (m, 1H) 3.21-3.30 (m, 1H) 2.77-3.01 (m, 3H) 2.60-2.72 (m, 1H) 1.98-2.29 (m, 3H) 1.82 (ddt, J=13.30, 4.77, 2.26, 2.26 Hz, 1H). Data for P-4: HPLC (method A) RT 7.58 min, 96.9% AP; LCMS (method F) RT 2.04 min, 100% AP, m/z 405.0 $(M+H^+)$; chiral SFC (method C-5) RT 10.3 min; $^1H$ NMR (400 MHz, methanol-$d_4$) δ ppm 7.32 (dd, J=8.78, 5.27 Hz, 2H) 7.06-7.17 (m, 4H) 6.75 (d, J=8.53 Hz, 2H) 4.39-4.54 (m, 2H) 3.71 (t, J=8.78 Hz, 1H) 3.24-3.30 (m, 1H) 3.07-3.18 (m, 3H) 2.85-2.99 (m, 1H) 2.52 (t, J=11.29 Hz, 1H) 1.98-2.30 (m, 3H) 1.84 (ddt, J=13.36, 4.83, 2.45, 2.45 Hz, 1H).

Example 55

Peak-1, Peak-2, Peak-3, and Peak-4

(R)-3-((S)-3,3-difluoro-4-(4-hydroxyphenyl)piperidin-1-yl)-1-(3-fluoro-4-methylphenyl)pyrrolidin-2-one, (R)-3-((R)-3,3-difluoro-4-(4-hydroxyphenyl)piperidin-1-yl)-1-(3-fluoro-4-methylphenyl)pyrrolidin-2-one, (S)-3-((S)-3,3-difluoro-4-(4-hydroxyphenyl)piperidin-1-yl)-1-(3-fluoro-4-methylphenyl)pyrrolidin-2-one, and (S)-3-((R)-3,3-difluoro-4-(4-hydroxyphenyl)piperidin-1-yl)-1-(3-fluoro-4-methylphenyl)pyrrolidin-2-one

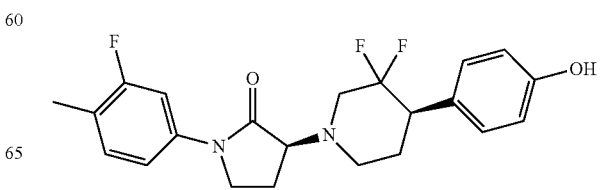

-continued

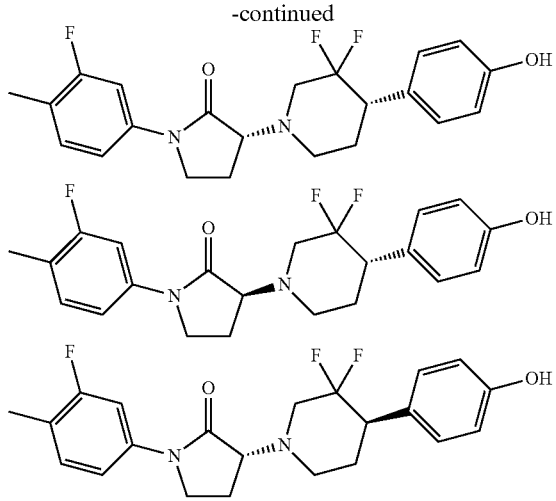

Step A. (3R,4R)-tert-Butyl 3-hydroxy-4-(4-methoxyphenyl)piperidine-1-carboxylate

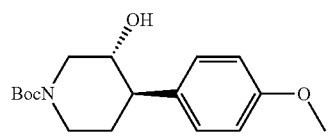 [SMILES: COc1ccc([C@H]2CCN(C(=O)OC(C)(C)C)C[C@@H]2O)cc1]

To a solution of (3R,4R)-tert-butyl 3-hydroxy-4-(4-hydroxyphenyl)piperidine-1-carboxylate (490 mg, 1.67 mmol, procedure from WO 2000/63173) in DMF (6 mL) was added $K_2CO_3$ (577 mg, 4.2 mmol) followed by methyl iodide (0.52 mL, 8.4 mmol) at rt. The mixture was stirred at rt for 18 h. It was then diluted with 50 mL ethyl acetate and the solids were removed by filtration. The solvent was then evaporated under vacuum and the residue was purified via silica gel chromatography (hexanes-100% EtOAc) to yield (3R,4R)-tert-butyl 3-hydroxy-4-(4-methoxyphenyl)piperidine-1-carboxylate (450 mg, 88% yield). LCMS (method T) RT 3.068 min, m/z 306.3 (M−H)−; $^1$H NMR (500 MHz, chloroform-d) δ 7.15 (d, J=8.7 Hz, 2H), 6.87 (d, J=8.7 Hz, 2H), 4.40-4.30 (m, 1H), 4.25-4.05 (m, 1H), 3.78 (s, 3H), 3.64-3.52 (m, 1H), 2.77-2.66 (m, 1H), 2.65-2.51 (m, 1H), 2.45 (br. s., 1H), 2.26-2.10 (m, 1H), 1.76 (d, J=2.7 Hz, 1H), 1.71-1.60 (m, 1H), 1.48 (s, 9H).

Step B. tert-Butyl 4-(4-methoxyphenyl)-3-oxopiperidine-1-carboxylate

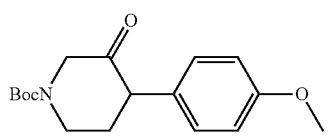 [SMILES: COc1ccc(C2CCN(C(=O)OC(C)(C)C)CC2=O)cc1]

To a solution of (3R,4R)-tert-butyl 3-hydroxy-4-(4-methoxyphenyl)piperidine-1-carboxylate (180 mg, 0.59 mmol) in DCM (3 mL) at 0° C. under $N_2$ was added Dess-Martin Periodinane (373 mg, 0.88 mmol). The mixture was allowed to warm to rt and stirred for 3 h. The reaction mixture was directly purified via silica gel chromatography eluting with 30% EtOAc in hexanes to afford tert-butyl 4-(4-methoxyphenyl)-3-oxopiperidine-1-carboxylate (155 mg, 87% yield). Subsequent results revealed that the 4R stereochemistry is lost in this reaction and the racemic product was obtained. $^1$H NMR (500 MHz, chloroform-d) δ 7.09-7.03 (m, 2H), 6.93-6.87 (m, 2H), 4.24 (d, J=18.0 Hz, 1H), 4.11-4.02 (m, 1H), 3.80 (s, 3H), 3.61 (dd, J=11.9, 5.6 Hz, 1H), 3.56-3.46 (m, 1H), 2.34-2.16 (m, 2H), 1.50 (s, 9H).

Step C. tert-butyl 3,3-difluoro-4-(4-methoxyphenyl)piperidine-1-carboxylate

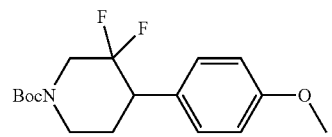

To a solution of tert-butyl 4-(4-methoxyphenyl)-3-oxopiperidine-1-carboxylate (90 mg, 0.3 mmol, from step B) in DCM (5 mL) at −78° C. under $N_2$ was added DAST (0.16 mL, 1.18 mmol). The mixture was stirred from −78° C. to rt over 1 h, then allowed to stand in the refrigerator overnight. It was then concentrated and tert-butyl 3,3-difluoro-4-(4-methoxyphenyl)piperidine-1-carboxylate (65 mg, 67.4% yield) was isolated which was used without further purification. LCMS (method U) m/z 350.2 (M+Na); $^1$H NMR (500 MHz, chloroform-d) δ 7.39 (d, J=8.7 Hz, 2H), 6.95-6.86 (m, 3H), 4.10 (br. s., 2H), 3.83 (s, 3H), 3.82 (s, 1H), 3.64-3.58 (m, 2H), 3.06-2.93 (m, 1H), 2.57-2.45 (m, 2H), 1.50 (s, 9H).

Step D. 3,3-Difluoro-4-(4-methoxyphenyl)piperidine trifluoroacetate

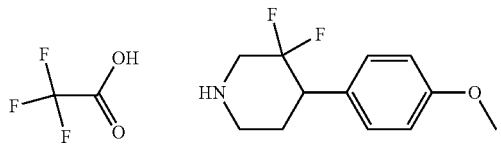 [SMILES: O=C(O)C(F)(F)F ; COc1ccc(C2CCNCC2(F)F)cc1]

To a solution of (R)-t-butyl 3,3-difluoro-4-(4-methoxyphenyl)piperidine-1-carboxylate (65 mg, 0.2 mmol) in DCM (0.8 mL) was added TFA (0.4 mL, 5.2 mmol) at rt. The mixture was stirred for 2 h, then concentrated to dryness in vacuo to afford crude 3,3-difluoro-4-(4-methoxyphenyl)piperidine trifluoroacetate (67.8 mg, 0.2 mmol, 100% yield), which was used in step G without further purification.

Step E. 3-(3,3-difluoro-4-(4-methoxyphenyl)piperidin-1-yl)-1-(3-fluoro-4-methylphenyl)pyrrolidin-2-one

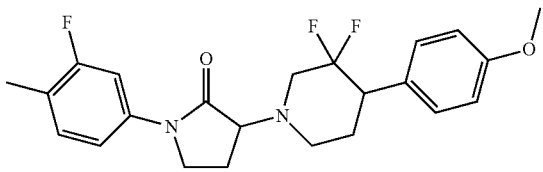

To a solution of 3,3-difluoro-4-(4-methoxyphenyl)piperidine trifluoroacetate (67 mg, 0.2 mmol) in DMF (0.8 mL) was added 3-bromo-1-(3-fluoro-4-methylphenyl)pyrrolidin-2-one (from Example 49, step C, 96 mg, 0.35 mmol) and DIPEA (0.1 mL, 0.6 mmol). The mixture was stirred at rt for 18 h, then raised to 80° C. for 2 h. The mixture was cooled, the solvent was removed under vacuum and the residue was purified via silica gel chromatography, eluting with a gradient from 0 to 100% ethyl acetate in hexanes to yield 62 mg of 3-(3,3-difluoro-4-(4-methoxyphenyl)piperidin-1-yl)-1-(3-fluoro-4-methylphenyl)pyrrolidin-2-one (along with 20 mg of the sideproduct, 1-(3-fluoro-4-methylphenyl)-3-hydroxy-pyrrolidin-2-one). LCMS (method U) RT 3.755 min, m/z 419.3 (M+H$^+$); $^1$H NMR (500 MHz, chloroform-d) δ 7.51 (d, J=11.9, 2H), m 7.26-7.26 (3H), m 7.20 (1H), 6.90 (d, J=8.7) 3.82 (s, 3H), 3.65-3.78 (m, 3H), 3.2-3.45 (m, 3H), 2.87-3.00 (m, 1H), 2.72-2.85 (m, 0.4H), 2.65 (t, 0.5H), 2.37-2.48 (m, 1H), 2.27 (s, 3H), 2.1-2.25 (m, 2H), 1.87-1.95 (m, 1H). Chiral HPLC (method A-2) revealed that the chirality present in the starting material for step A had been lost.

Step F. (R)-3-((S)-3,3-difluoro-4-(4-hydroxyphenyl)piperidin-1-yl)-1-(3-fluoro-4-methylphenyl)pyrrolidin-2-one, (R)-3-((R)-3,3-difluoro-4-(4-hydroxyphenyl)piperidin-1-yl)-1-(3-fluoro-4-methylphenyl)pyrrolidin-2-one, (S)-3-((S)-3,3-difluoro-4-(4-hydroxyphenyl)piperidin-1-yl)-1-(3-fluoro-4-methylphenyl)pyrrolidin-2-one, and (S)-3-((R)-3,3-difluoro-4-(4-hydroxyphenyl)piperidin-1-yl)-1-(3-fluoro-4-methylphenyl)pyrrolidin-2-one To a solution of 3-(3,3-difluoro-4-(4-methoxyphenyl)piperidin-1-yl)-1-(3-fluoro-4-methylphenyl)pyrrolidin-2-one (62 mg, 0.15 mmol) in DCM (0.8 mL) at −78° C. under N$_2$ was added boron tribromide (0.04 mL, 0.44 mmol). The reaction was warmed to rt and stirred for a further 2 h. It was then quenched with several drops of EtOH, and 50 mL of EtOAc was added. After stirring at rt for 1 h, the solid was removed by filtration and washed with MeOH. The filtrates were combined and concentrated. The residue was purified via silica gel chromatography eluting with a gradient of 0 to 10% MeOH in EtOAc to give a mixture containing all four diastereomers, which were separated via chiral HPLC (method A-2) to give homochiral Examples 55 P-1, P-2, P-3, and P-4, (R)-3-((S)-3,3-difluoro-4-(4-hydroxyphenyl)piperidin-1-yl)-1-(3-fluoro-4-methylphenyl)pyrrolidin-2-one, (R)-3-((R)-3,3-difluoro-4-(4-hydroxyphenyl)piperidin-1-yl)-1-(3-fluoro-4-methylphenyl)pyrrolidin-2-one, (S)-3-((S)-3,3-difluoro-4-(4-hydroxyphenyl)piperidin-1-yl)-1-(3-fluoro-4-methylphenyl)pyrrolidin-2-one, and (S)-3-((R)-3,3-difluoro-4-(4-hydroxyphenyl)piperidin-1-yl)-1-(3-fluoro-4-methylphenyl)pyrrolidin-2-one. The absolute and relative stereochemical configurations were not determined. The compounds were arbitrarily designated as P-1, P-2, P-3, and P-4 based on their order of elution during the chiral separation. Data for P-1: 7.3 mg; LCMS (method U) RT 2.19 min (82% AP), m/z 405.1, 427.3 (M+H$^+$, M+Na$^+$); chiral HPLC (method A-3) RT 6.28 min, 98.1% AP; $^1$H NMR (500 MHz, chloroform-d) δ 7.49 (dd, J=11.8, 1.8 Hz, 1H), 7.26 (d, J=1.7 Hz, 1H), 7.24-7.16 (m, 3H), 6.83 (d, J=8.4 Hz, 2H), 3.84-3.71 (m, 3H), 3.37 (t, J=9.2 Hz, 1H), 3.31-3.22 (m, 1H), 3.14 (d, J=10.8 Hz, 1H), 3.00-2.88 (m, 1H), 2.87-2.77 (m, 1H), 2.50-2.40 (m, 1H), 2.28 (s, 3H), 2.25-2.11 (m, 3H), 1.94-1.86 (m, 1H). Data for P-2: 4.4 mg; LCMS (method U) RT 2.19 min (86% AP), m/z 405.2, 427.2 (M+H$^+$, M+Na$^+$); chiral HPLC (method A-3) RT 8.77 min, 78.4% AP; $^1$H NMR (500 MHz, chloroform-d) δ 7.50 (dd, J=11.9, 2.1 Hz, 1H), 7.28-7.24 (m, 1H), 7.24-7.15 (m, 3H), 6.85 (d, J=8.4 Hz, 2H), 3.83-3.68 (m, 3H), 3.43-3.19 (m, 2H), 2.99-2.87 (m, 1H), 2.87-2.76 (m, 1H), 2.62 (t, J=11.5 Hz, 1H), 2.49-2.39 (m, 1H), 2.27 (s, 3H), 2.25-2.12 (m, 2H), 1.96-1.85 (m, 2H). Data for P-3: 2.0 mg; LCMS (method U) RT 2.20 min (76% AP), m/z 405.2, 427.2 (M+H$^+$, M+Na$^+$); chiral HPLC (method A-3) RT 11.46 min, 76.3% AP; $^1$H NMR (500 MHz, chloroform-d) δ 7.50 (dd, J=11.7, 2.1 Hz, 1H), 7.26 (dd, J=8.5, 2.4 Hz, 1H), 7.24-7.16 (m, 3H), 6.83 (d, J=8.5 Hz, 2H), 3.83-3.71 (m, 3H), 3.36 (br. s., 1H), 3.31-3.22 (m, 1H), 3.15 (br. s., 1H), 3.00-2.88 (m, 1H), 2.82 (dd, 1H), 2.50-2.42 (m, 1H), 2.28 (s, 3H), 2.25-2.12 (m, 3H), 1.95-1.86 (m, 1H). Data for P-4: 7.1 mg; LCMS (method U) RT 2.19 min (84% AP), m/z 405.2, 427.2 (M+H$^+$, M+Na$^+$); chiral HPLC (method A-3) RT 12.58 min, 89.5% AP; $^1$H NMR (500 MHz, chloroform-d) δ 7.49 (dd, J=11.9, 1.8 Hz, 1H), 7.26 (d, J=2.0 Hz, 1H), 7.24-7.14 (m, 3H), 6.83 (d, J=8.4 Hz, 2H), 3.83-3.70 (m, 3H), 3.43-3.19 (m, 3H), 2.99-2.87 (m, 1H), 2.63 (t, J=11.4 Hz, 1H), 2.49-2.39 (m, 1H), 2.27 (s, 3H), 2.25-2.12 (m, 3H), 1.95-1.86 (m, 1H).

Example 56

Example 56 (Peak-1, Peak-2, Peak-3, and Peak-4

(S)-3-((R)-3,3-difluoro-4-(4-hydroxyphenyl)piperidin-1-yl)-1-((S)-1-(4-fluorophenyl)ethyl)pyrrolidin-2-one, (S)-3-((S)-3,3-difluoro-4-(4-hydroxyphenyl)piperidin-1-yl)-1-((S)-1-(4-fluorophenyl)ethyl)pyrrolidin-2-one, (R)-3-((S)-3,3-difluoro-4-(4-hydroxyphenyl)piperidin-1-yl)-1-((S)-1-(4-fluorophenyl)ethyl)pyrrolidin-2-one, and (R)-3-((R)-3,3-difluoro-4-(4-hydroxyphenyl)piperidin-1-yl)-1-((S)-1-(4-fluorophenyl)ethyl)pyrrolidin-2-one

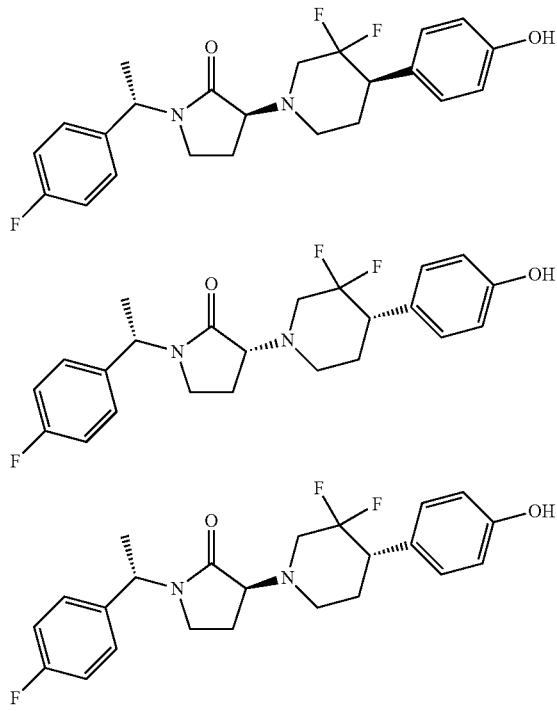

-continued

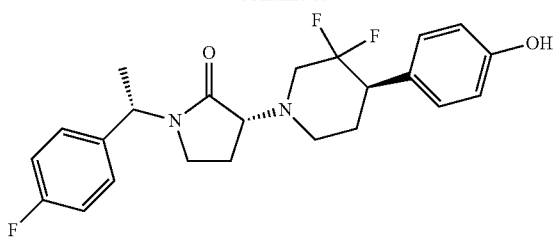

Step B. 4-(3,3-Difluoropiperidin-4-yl)phenol

E-2a

To a stirred solution of 4-(4-(benzyloxy)phenyl)-3,3-difluoropiperidine (0.6 g, 2 mmol) (E-2 from step A) in 20 mL methanol at rt was added 10% Pd/C (0.21 g) and the reaction mixture was allowed to stir under 8 kPa of hydrogen pressure for 4 h. The catalyst was removed by filtration and the mixture was concentrated under vacuum. The residue was triturated with ether and the solid was isolated by filteration to yield 0.4 g of E-2a 4-(3,3-difluoropiperidin-4-yl)phenol (homochiral), which was used directly in the next step. LCMS (method P) RT 0.53 min, m/z 214.4 (M+H$^+$).

Step C. 3-(3,3-Difluoro-4-(4-hydroxyphenyl)piperidin-1-yl)-1-((S)-1-(4-fluorophenyl)ethyl)pyrrolidin-2-one A mixture of 3-bromo-1-((S)-1-(4-fluorophenyl)ethyl)pyrrolidin-2-one (from Example 50, step B) (0.145 g, 0.51 mmol), 4-(3,3-difluoropiperidin-4-yl)phenol (0.06 g, 0.28 mmol, E-2a from Example 56 step B) and 0.2 mL of triethylamine (1.4 mmol) was heated at 120° C. for 1 h. The cooled reaction mixture was partitioned between water and ethyl acetate. The organic phase was washed with water and brine, and then it was dried over Na$_2$SO$_4$, filtered, and concentrated to afford 3-(3,3-difluoro-4-(4-hydroxyphenyl)piperidin-1-yl)-1-((S)-1-(4-fluorophenyl)ethyl)pyrrolidin-2-one as a pair of diastereomers. These diastereomers were separated via preparative HPLC (method B) to yield 3-(3,3-difluoro-4-(4-hydroxyphenyl)piperidin-1-yl)-1-((S)-1-(4-fluorophenyl)ethyl)pyrrolidin-2-one homochiral Examples 56 P-1 (10.7 mg) and P-2 (5.5 mg). The relative and absolute configurations of Examples 56 P-1 and P-2 were not determined and are arbitrarily named P-1 and P-2 based on the order of elution during the HPLC purification. Data for P-1: pale yellow solid; LCMS (method O) RT 1.21 min (95.8% AP) m/z 419.0 (M+H$^+$); $^1$H NMR (400 MHz, methanol-d$_4$) δ ppm 1.55 (m, 3H) 1.78-1.90 (m, 1H), 1.90-2.01 (M, 1H), 2.1-2.2 (m, 1H), 2.21-2.35 (m, 1H), 2.49 (m, 1H), 2.80-2.99 (m, 1H), 3.01-3.10 (m, 4H), 3.33-3.38 (m, 3H), 3.63 (t, 1H), 5.40 (m, 1H), 6.75 (m, 2H), 7.09-7.15 (m, 4H), 7.38-7.41 (m, 2H); $^{19}$F NMR δ ppm-76.948, -102.623, -103.262, -115.103, -115.743, -117.043. Data for P-2: solid; LCMS (methods N, O) 99% AP; $^1$H NMR (400 MHz, methanol-d$_4$) δ ppm 1.59 (d, J=7.03 Hz, 3H) 1.79-1.90 (m, 1H) 2.01-2.23 (m, 3H) 2.62-2.72 (m, 1H) 2.86-3.19 (m, 5H) 3.40-3.74 (m, 2H) 4.36-4.56 (m, 1H) 5.28-5.48 (m, 1H) 6.76 (d, J=9.04 Hz, 2H) 7.08-7.19 (m, 4H) 7.30-7.42 (m, 2H); $^{19}$F NMR δ ppm-76.938, -102.480, -012.630, -103.120, -103.146, -103.269, -114.559, -115.124, -115.199, -115.763, -116.990, -117.049.

Step A. (R)-4-(4-(Benzyloxy)phenyl)-3,3-difluoropiperidine and (S)-4-(4-(benzyloxy)phenyl)-3,3-difluoropiperidine

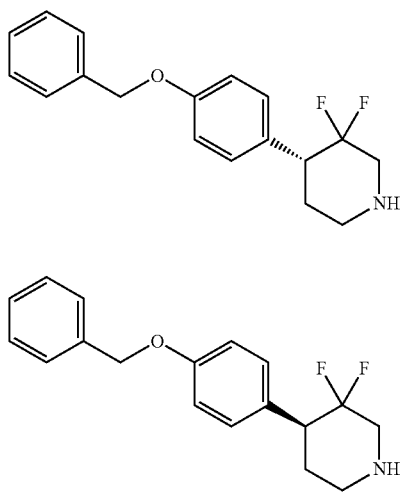

Racemic 4-(4-(benzyloxy)phenyl)-3,3-difluoropiperidine (Example 52, step C, 5 g) was separated using chiral HPLC (method H-3) to yield both pure enantiomers E-1 (1.5 g, 4.94 mmol, 39.5% yield) and E-2 (1.4 g, 4.62 mmol, 36.8% yield). The absolute configurations were not assigned. Data for E-1: Chiral SFC (method C-6) RT 3.58 min, 100% AP; LCMS (method F) RT 2.32 min, 100% AP, m/z 304.0 (M+H$^+$); HPLC (method H) RT 6.746 min, 91.2% AP; $^1$H NMR (400 MHz, DMSO-d$_6$) d ppm 1.72 (d, J=13.55 Hz, 1H) 1.94 (dd, J=12.55, 4.02 Hz, 1H) 2.60 (t, J=12.05 Hz, 1H) 2.74-2.88 (m, 1H) 2.98 (d, J=12.55 Hz, 1H) 3.04-3.20 (m, 2H) 5.10 (s, 2H) 6.95-7.02 (m, 2H) 7.21 (d, J=8.53 Hz, 2H) 7.30-7.50 (m, 5H). Data for E-2: Chiral SFC (method C-6) RT 6.56 min, 99.3% AP; LCMS (method F) RT 2.32 min, 97.5% AP, m/z 304.0 (M+H$^+$); HPLC (method H) RT 6.767 min, 91.7% AP. $^1$H NMR (400 MHz, DMSO-d$_6$) δ ppm 1.72 (d, J=13.55 Hz, 1H) 1.94 (dd, J=12.55, 4.02 Hz, 1H) 2.60 (t, J=12.05 Hz, 1H) 2.74-2.88 (m, 1H) 2.98 (d, J=12.55 Hz, 1H) 3.04-3.20 (m, 2H) 5.10 (s, 2H) 6.95-7.02 (m, 2H) 7.21 (d, J=8.53 Hz, 2H) 7.30-7.50 (m, 5H).

Step D. 4-(3,3-Difluoropiperidin-4-yl)phenol

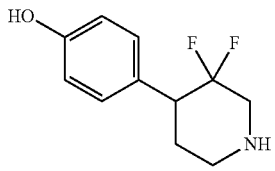

E-1a

To a stirred solution of 4-(4-(benzyloxy)phenyl)-3,3-difluoropiperidine (0.6 g, 2 mmol, E-1 from step A) in MeOH (20 mL) at rt was added 10% Pd/C (0.21 g) and the reaction mixture was allowed to stir under 8 kPa of hydrogen pressure for 4 h. The catalyst was removed by filtration through Celite and the filtrate was concentrated under vacuum to afford 0.4 g of homochiral E-1a 4-(3,3-difluoropiperidin-4-yl)phenol. LCMS (method P) RT 0.55 min (74% AP), m/z 214.4 (M+H$^+$).

Step E. 3-(3,3-Difluoro-4-(4-hydroxyphenyl)piperidin-1-yl)-1-((S)-1-(4-fluorophenyl)ethyl)pyrrolidin-2-one To a mixture of 3-bromo-1-((S)-1-(4-fluorophenyl)ethyl)pyrrolidin-2-one (0.134 g, 0.47 mmol, from Example 50, step B) and 4-(3,3-difluoropiperidin-4-yl)phenol (0.05 g, 0.23 mmol, E-1a from Example 56, step D) was added triethylamine (0.16 mL, 1.2 mmol) and the resulting mixture was heated at 120° C. for 1 h. After cooling, the reaction was partitioned between ethyl acetate and water. The layers were separated and the organic phase was washed with water and brine, then dried over Na$_2$SO$_4$, filtered, and concentrated under vacuum. The residue was purified via preparative HPLC (method B) to yield the homochiral Examples 56 P-3 and P-4 3-(3,3-difluoro-4-(4-hydroxyphenyl)piperidin-1-yl)-1-((S)-1-(4-fluorophenyl)ethyl)pyrrolidin-2-one diastereomers. The relative and absolute configurations of Examples 56 P-3 and P-4 were not determined and are arbitrarily named P-3 and P-4 based on the order of elution during the HPLC purification. Data for P-3: 11.5 mg pale yellow solid, LCMS (method O) RT 1.23 min (99.8% AP), m/z 419.0 (M+H$^+$); $^1$H NMR (400 MHz, methanol-d$_4$) δ ppm 1.55 (d, J=7.2, 3H), 1.83 (m, 1H), 1.91-1.99 (m, 1H), 2.10-2.30 (m, 2H), 2.57-2.64 (q, 1H), 2.82-3.95 (m, 3H), 3.07-3.20, (m, 1H), 3.33-3.42 (m, 2H), 3.67 (t, J=9, 1H), 5.40 (d, J=7.2, 1H), 6.75 (m, 2H), 7.09-7.15 (m, 4H), 7.37-7.41 (m, 2H); $^{19}$F NMR δ ppm-102.515, -103.158, -114.576, -115.216, -117.070. Data for P-4: 13.7 mg pale yellow solid; LCMS (method O) RT 1.215 min (100% AP), m/z 419.0 (M+H$^+$); $^1$H NMR (400 MHz, methanol-d$_4$) δ ppm 1.59 (d, J=6.4, 3H), 1.80-1.90 (m, 1H), 2.01-2.29 (m, 3H), 2.53 (t, 1H), 2.81-2.97 (m, 3H), 3.01-3.25 (m, 3H), 3.34-3.43 (m, 1H), 3.64 (t, J=8.8, 1H), 5.42 (d, J=7.2, 1H), 6.74-6.77 (m, 2H), 7.09-7.16 (m, 4H), 7.35-7.38 (m, 2H); $^{19}$F NMR δ ppm-102.632, -103.271, -115.162, -115.801, -116.989.

General Procedure A

Used for preparation of Examples 57-73

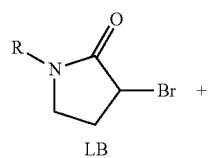

LB

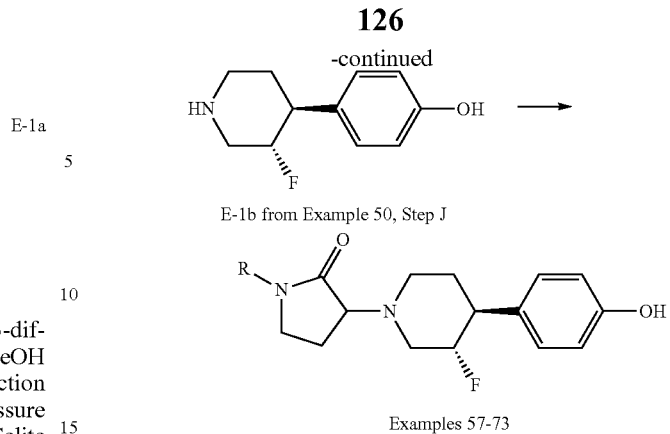

E-1b from Example 50, Step J

Examples 57-73

To a microwave vial containing 4-((3S,4S)-3-fluoropiperidin-4-yl)phenol (25 mg, 0.128 mmol, E-1b from Example 50, step J) and the corresponding lactam bromide (0.256 mmol, compound LB) was added DMF (1 mL) and triethylamine (0.09 mL, 0.64 mmol). The vial was capped and the reaction mixture was heated to 110° C. using microwave irradiation for 1 h. LC/MS data were collected using method 100. The samples were directly purified by preparative HPLC under conditions B. Products were a mixture of diastereoisomers. In some cases, the diastereomers were further separated into the individual homochiral components under the conditions reported in the specific examples.

Example 57

(S)-1-Benzyl-3-((3S,4S)-3-fluoro-4-(4-hydroxyphenyl)piperidin-1-yl)pyrrolidin-2-one

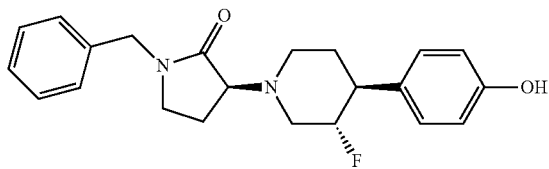 [SMILES: O=C1[C@@H](N2CC[C@@H](c3ccc(O)cc3)[C@H](F)C2)CCN1Cc1ccccc1]

and

Example 58

(R)-1-Benzyl-3-((3S,4S)-3-fluoro-4-(4-hydroxyphenyl)piperidin-1-yl)pyrrolidin-2-one

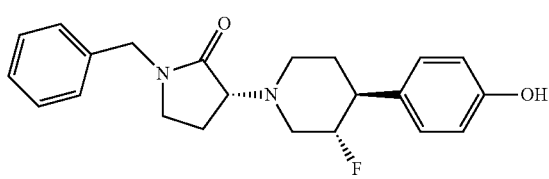 [SMILES: O=C1[C@H](N2CC[C@@H](c3ccc(O)cc3)[C@H](F)C2)CCN1Cc1ccccc1]

A diastereomeric mixture of 1-benzyl-3-((3S,4S)-3-fluoro-4-(4-hydroxyphenyl)piperidin-1-yl)pyrrolidin-2-one (prepared using general procedure A) was separated by SFC (method C-6) to afford the titled compounds of Examples 57 and 58. Data for Example 57: SFC (Method 105) RT=3.06 min. LC/MS RT=2.01 min, (M+H)+=369.2; $^1$H NMR (400

MHz, methanol-d4) δ ppm 1.78-1.88 (m, 2H) 2.04-2.12 (m, 1H) 2.20 (ddd, J=16.56, 12.80, 3.26 Hz, 1H) 2.41-2.51 (m, 1H) 2.55-2.62 (m, 1H) 2.67 (dt, J=9.79, 5.15 Hz, 2H) 3.01 (d, J=7.03 Hz, 1H) 3.12-3.18 (m, 1H) 3.22-3.29 (m, 1H) 3.75 (t, J=8.53 Hz, 1H) 4.51-4.61 (m, 2H) 4.67 (dt, J=10.04, 5.02 Hz, 1H) 6.70-6.83 (m, 2H) 7.07-7.14 (m, 2H) 7.27-7.33 (m, 3H) 7.34-7.41 (m, 2H). Data for Example 58: SFC (Method 105) RT=5.76 min. LC/MS RT=2.01 min, (M+H)+=369.2; $^1$H NMR (400 MHz, methanol-$d_4$) δ ppm 1.78-1.89 (m, 2H) 2.08 (dd, J=13.30, 8.78 Hz, 2H) 2.15-2.21 (m, 1H) 2.43 (dt, J=10.29, 4.89 Hz, 2H) 2.51-2.60 (m, 2H) 2.63-2.71 (m, 2H) 2.77 (br. s., 2H) 3.23-3.29 (m, 2H) 3.36-3.47 (m, 2H) 3.72 (t, J=8.78 Hz, 1H) 4.40-4.48 (m, 2H) 4.54 (s, 1H) 6.71-6.80 (m, 2H) 7.07-7.14 (m, 2H) 7.20-7.33 (m, 3H) 7.34-7.41 (m, 2H).

Example 59

3-((3S,4S)-3-Fluoro-4-(4-hydroxyphenyl)piperidin-1-yl)-1-(2-methylbenzyl)pyrrolidin-2-one

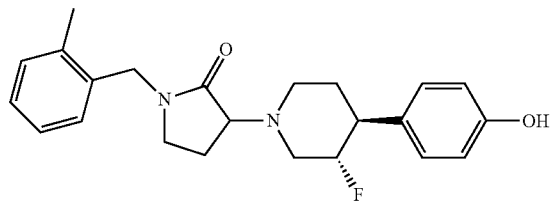 [SMILES: Cc1ccccc1CN1CCC(N2CC[C@@H](c3ccc(O)cc3)[C@H](F)C2)C1=O]

A diastereomeric mixture of 3-((3S,4S)-3-fluoro-4-(4-hydroxyphenyl)piperidin-1-yl)-1-(2-methylbenzyl)pyrrolidin-2-one (Example 59) was prepared using general procedure A. Data for Example 59: LC/MS RT=1.612 min, (M+H)+=383.0 $^1$H NMR (400 MHz, DMSO-$d_6$) δ=9.20 (s, 1H), 7.23-7.06 (m, 6H), 6.73-6.67 (m, 2H), 4.66-4.42 (m, 2H), 4.33-4.26 (m, 1H), 3.64-3.55 (m, 1H), 3.43-3.36 (m, 1H), 3.19-3.04 (m, 3H), 2.77-2.65 (m, 2H), 2.57-2.53 (m, 1H), 2.36-2.23 (m, 4H), 2.15-2.05 (m, 1H), 1.98-1.86 (m, 1H), 1.77-1.56 (m, 1H).

Example 60

3-((3S,4S)-3-Fluoro-4-(4-hydroxyphenyl)piperidin-1-yl)-1-(3-methylbenzyl)pyrrolidin-2-one

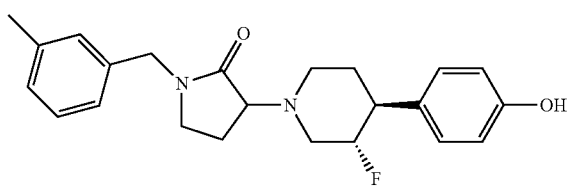 [SMILES: Cc1cccc(CN2CCC(N3CC[C@@H](c4ccc(O)cc4)[C@H](F)C3)C2=O)c1]

A diastereomeric mixture of 3-((3S,4S)-3-fluoro-4-(4-hydroxyphenyl)piperidin-1-yl)-1-(3-methylbenzyl)pyrrolidin-2-one was prepared using general procedure A. Data for Example 60: LC/MS RT=1.628 min, (M+H)+=383.0 $^1$H NMR (400 MHz, DMSO-$d_6$) δ=9.20 (s, 1H), 7.27-7.20 (m, 1H), 7.09 (d, J=8.5 Hz, 3H), 7.05-6.98 (m, 2H), 6.73-6.67 (m, 2H), 4.66-4.42 (m, 1H), 4.41-4.26 (m, 2H), 3.61-3.53 (m, 1H), 3.44-3.34 (m, 1H), 3.21-3.08 (m, 3H), 2.95 (d, J=11.1 Hz, 1H), 2.76-2.65 (m, 2H), 2.57-2.53 (m, 1H), 2.35-2.24 (m, 5H), 2.16-2.05 (m, 1H), 1.98-1.86 (m, 1H), 1.78-1.55 (m, 2H).

Example 61

1-(4-(Difluoromethoxy)benzyl)-3-((3S,4S)-3-fluoro-4-(4-hydroxyphenyl)piperidin-1-yl)pyrrolidin-2-one

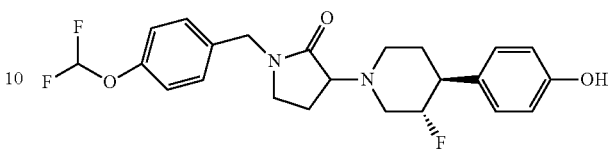

A diastereomeric mixture of 1-(4-(difluoromethoxy)benzyl)-3-((3S,4S)-3-fluoro-4-(4-hydroxyphenyl)piperidin-1-yl)pyrrolidin-2-one was prepared using general procedure A. Data for Example 61: LC/MS RT=1.594 min, (M+H)+=435.0 $^1$H NMR (400 MHz, DMSO-$d_6$) δ=9.20 (s, 1H), 7.41-7.01 (m, 7H), 6.73-6.67 (m, 2H), 4.66-4.44 (m, 1H), 4.44-4.30 (m, 2H), 3.61-3.53 (m, 1H), 3.43-3.35 (m, 1H), 3.23-3.09 (m, 3H), 2.95 (d, J=10.0 Hz, 0H), 2.76-2.63 (m, 2H), 2.56 (d, J=4.6 Hz, 0H), 2.35-2.24 (m, 1H), 2.15-2.05 (m, 1H), 1.98-1.86 (m, 1H), 1.78-1.56 (m, 2H).

Example 62

(S)-1-(3-Chloro-4-(difluoromethoxy)phenyl)-3-((3S,4S)-3-fluoro-4-(4-hydroxyphenyl)-piperidin-1-yl)pyrrolidin-2-one

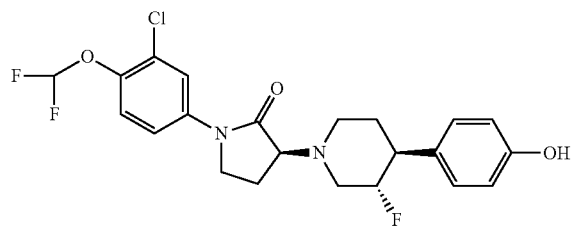 [SMILES: O=C1[C@@H](N2CC[C@@H](c3ccc(O)cc3)[C@H](F)C2)CCN1c1ccc(OC(F)F)c(Cl)c1]

and

Example 63

(R)-1-(3-Chloro-4-(difluoromethoxy)phenyl)-3-((3S,4S)-3-fluoro-4-(4-hydroxyphenyl)-piperidin-1-yl)pyrrolidin-2-one

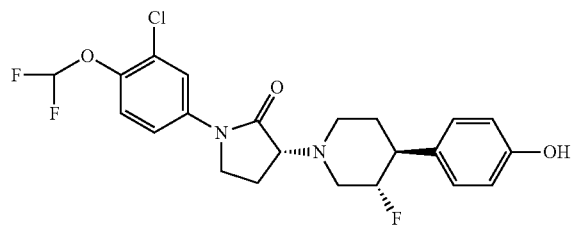 [SMILES: O=C1[C@H](N2CC[C@@H](c3ccc(O)cc3)[C@H](F)C2)CCN1c1ccc(OC(F)F)c(Cl)c1]

A diastereomeric mixture of 1-(3-chloro-4-(difluoromethoxy)phenyl)-3-((3S,4S)-3-fluoro-4-(4-hydroxyphenyl)piperidin-1-yl)pyrrolidin-2-one (prepared using general procedure A) was separated by SFC (method 101) to afford the titled compounds of Examples 62 and 63. Data for Example 62: SFC (Method 106) RT=3.78 min. LC/MS (Method O): RT=2.177 min, (M+H)+=455.0; ¹H NMR (400 MHz, methanol-d₄) δ ppm 1.28-1.35 (m, 3H) 1.83-1.91 (m, 2H) 2.19-2.28 (m, 1H) 2.32-2.43 (m, 2H) 2.49-2.63 (m, 2H) 2.73 (td, J=10.04, 4.52 Hz, 1H) 2.98-3.12 (m, 2H) 3.20-3.29 (m, 1H) 3.76-3.91 (m, 3H) 4.69 (dt, J=10.04, 5.02 Hz, 1H) 6.64-6.90 (m, 3H) 7.10-7.19 (m, 2H) 7.35 (d, J=9.04 Hz, 1H) 7.62 (dd, J=9.04, 3.01 Hz, 1H) 8.01 (d, J=2.51 Hz, 1H). Data for Example 63: SFC (Method 106) RT=5.03 min. LC/MS (Method O): RT=2.189 min, (M+H)+=455.0; ¹H NMR (400 MHz, methanol-d4) δ ppm 1.25 (t, J=7.28 Hz, 3H) 1.80-1.90 (m, 2H) 2.22-2.39 (m, 3H) 2.45-2.63 (m, 3H) 2.81-2.95 (m, 4H) 3.44-3.54 (m, 2H) 3.78-3.92 (m, 3H) 4.69-4.77 (m, 2H) 6.76 (d, J=9.04 Hz, 3H) 7.13 (d, J=8.53 Hz, 2H) 7.30-7.38 (m, 1H) 7.56-7.65 (m, 1H) 8.01 (d, J=2.51 Hz, 1H).

Example 64

(S)-1-(4-Chlorobenzyl)-3-((3S,4S)-3-fluoro-4-(4-hydroxyphenyl)piperidin-1-yl)pyrrolidin-2-one

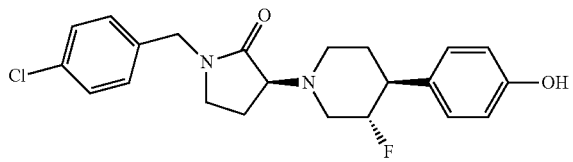 [SMILES: O=C1[C@@H](N2CC[C@@H](c3ccc(O)cc3)[C@H](F)C2)CCN1Cc1ccc(Cl)cc1]

and

Example 65

(R)-1-(4-Chlorobenzyl)-3-((3S,4S)-3-fluoro-4-(4-hydroxyphenyl)piperidin-1-yl)pyrrolidin-2-one

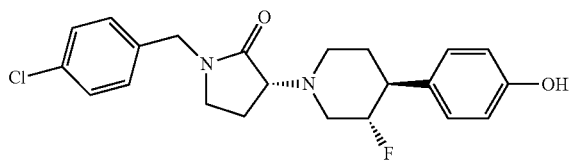

A diastereomeric mixture of 1-(4-Chlorobenzyl)-3-((3S,4S)-3-fluoro-4-(4-hydroxyphenyl)piperidin-1-yl)pyrrolidin-2-one (prepared using general procedure A) was separated by SFC (method 104) to afford the titled compounds of Example 64 and 65. Data for Example 64: SFC (Method 106) RT=4.24 min. LC/MS (Method O): RT=2.10 min, (M+H)+=403.2; ¹H NMR (400 MHz, methanol-d₄) δ=7.42-7.35 (m, 2H), 7.32-7.25 (m, 2H), 7.15-7.08 (m, 2H), 6.79-6.72 (m, 2H), 4.59-4.38 (m, 3H), 3.74 (t, J=8.8 Hz, 1H), 3.30-3.23 (m, 2H), 3.18-3.10 (m, 1H), 3.02 (d, J=11.0 Hz, 1H), 2.67 (dt, J=4.8, 9.9 Hz, 1H), 2.57 (dd, J=6.5, 10.5 Hz, 1H), 2.49-2.41 (m, 1H), 2.26-2.03 (m, 2H), 1.88-1.80 (m, 2H). Data for Example 65: SFC (Method 106) RT=7.88 min. LC/MS (Method O): RT=2.10 min, (M+H)+=403.2; ¹H NMR (400 MHz, methanol-d4) δ=7.41-7.35 (m, 2H), 7.32-7.25 (m, 2H), 7.14-7.08 (m, 2H), 6.79-6.73 (m, 2H), 4.58-4.40 (m, 3H), 3.72 (t, J=8.8 Hz, 1H), 3.46-3.40 (m, 1H), 3.30-3.24 (m, 2H), 2.80-2.75 (m, 1H), 2.74-2.52 (m, 2H), 2.44 (dt, J=4.5, 10.0 Hz, 1H), 2.27-2.05 (m, 2H), 1.88-1.77 (m, 2H).

Example 66

(S)-1-(4-Chloro-3-fluorobenzyl)-3-((3S,4S)-3-fluoro-4-(4-hydroxyphenyl)piperidin-1-yl)pyrrolidin-2-one

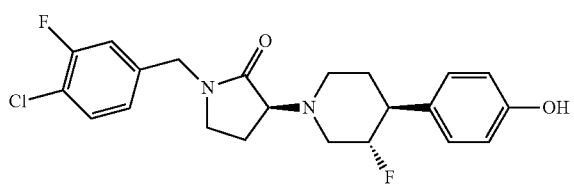 [SMILES: O=C1[C@@H](N2CC[C@@H](c3ccc(O)cc3)[C@H](F)C2)CCN1Cc1ccc(Cl)c(F)c1]

and

Example 67

(R)-1-(4-Chloro-3-fluorobenzyl)-3-((3S,4S)-3-fluoro-4-(4-hydroxyphenyl)piperidin-1-yl)pyrrolidin-2-one

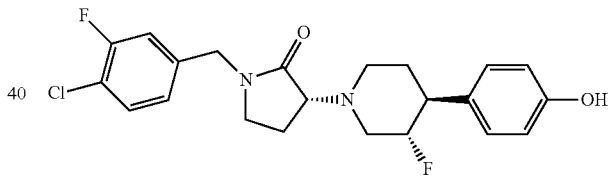

A diastereomeric mixture of 1-(4-chloro-3-fluorobenzyl)-3-((3S,4S)-3-fluoro-4-(4-hydroxyphenyl)piperidin-1-yl) pyrrolidin-2-one (prepared using general procedure A) was separated by SFC (method 105) to afford the titled compounds of Example 66 and 67. Data for Example 66: SFC (Method 105) RT=6.59 min. LC/MS (Method O): RT=2.122 min, (M+H)+=421.2; ¹H NMR (400 MHz, methanol-d₄) δ ppm 1.77-1.88 (m, 2H) 2.04-2.16 (m, 1H) 2.18-2.26 (m, 1H) 2.49-2.61 (m, 2H) 2.67-2.79 (m, 2H) 3.43-3.52 (m, 2H) 3.60-3.64 (m, 1H) 3.70-3.75 (m, 1H) 4.43-4.53 (m, 2H) 4.57-4.60 (m, 2H) 6.74-6.80 (m, 2H) 7.03-7.15 (m, 3H) 7.17-7.24 (m, 1H) 7.45-7.52 (m, 1H). Data for Example 67: SFC (Method 105) RT=3.51 min. LC/MS (Method O): RT=2.124 min, (M+H)+=421.2; ¹H NMR (400 MHz, methanol-d₄) δ ppm 1.84 (d, J=4.02 Hz, 2H) 2.10 (dd, J=13.05, 8.53 Hz, 1H) 2.22 (dd, J=12.55, 3.51 Hz, 1H) 2.42-2.50 (m, 1H) 2.68 (td, J=9.79, 4.52 Hz, 1H) 3.04 (d, J=13.05 Hz, 1H) 3.13-3.19 (m, 1H) 3.38 (br. s., 1H) 3.75 (t, J=8.53 Hz, 1H) 4.45-4.53 (m, 2H) 4.58 (s, 1H) 6.74-6.81 (m, 2H) 7.12 (d, J=8.53 Hz, 3H) 7.20 (dd, J=10.04, 2.01 Hz, 1H) 7.44-7.53 (m, 1H).

Example 68

3-((3S,4S)-3-Fluoro-4-(4-hydroxyphenyl)piperidin-1-yl)-1-(1-phenylethyl)pyrrolidin-2-one

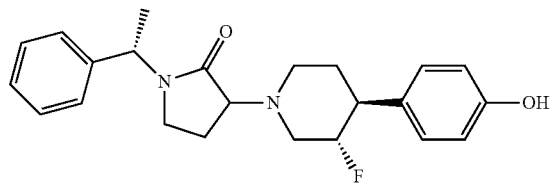 [SMILES: C[C@@H](c1ccccc1)N1CCC(N2CC[C@@H](c3ccc(O)cc3)[C@H](F)C2)C1=O]

The titled compound of Example 68 was prepared using the general procedure A. Only one diastereomer was isolated after purification. Data for Example 68: LC/MS RT=1.60 min, (M+H)+=383.0; $^1$H NMR (400 MHz, DMSO-$d_6$) δ=9.20 (s, 1H), 7.39-7.33 (m, 2H), 7.31-7.25 (m, 3H), 7.09 (d, J=8.5 Hz, 2H), 6.72-6.68 (m, 2H), 5.29 (q, J=7.4 Hz, 1H), 4.66-4.46 (m, 1H), 3.50 (t, J=8.5 Hz, 1H), 3.44-3.35 (m, 2H), 2.84-2.62 (m, 3H), 2.35-2.23 (m, 1H), 2.06 (dd, J=4.3, 8.3 Hz, 1H), 1.91 (dd, J=8.3, 12.3 Hz, 1H), 1.76-1.68 (m, 1H), 1.59 (dd, J=4.3, 12.8 Hz, 1H), 1.48 (d, J=7.0 Hz, 2H).

Example 69

1-(3,4-Difluorobenzyl)-3-((3S,4S)-3-fluoro-4-(4-hydroxyphenyl)piperidin-1-yl)pyrrolidin-2-one

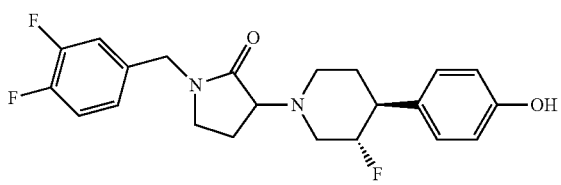 [SMILES: O=C1C(N2CC[C@@H](c3ccc(O)cc3)[C@H](F)C2)CCN1Cc1ccc(F)c(F)c1]

The titled compound of example 69 was prepared as a mixture of diastereomers using general procedure A. Data for Example 69: LC/MS RT=1.568 min, (M+H)+=405.0; $^1$H NMR (400 MHz, DMSO-$d_6$) δ=9.20 (s, 1H), 7.47-7.38 (m, 1H), 7.32-7.25 (m, 1H), 7.09 (d, J=8.0 Hz, 3H), 6.73-6.68 (m, 2H), 4.66-4.41 (m, 1H), 4.37 (d, J=4.0 Hz, 2H), 3.63-3.54 (m, 1H), 3.44-3.35 (m, 1H), 3.16 (s, 3H), 2.99-2.92 (m, 1H), 2.76-2.65 (m, 2H), 2.57-2.54 (m, 1H), 2.35-2.23 (m, 1H), 2.08 (s, 1H), 2.00-1.88 (m, 1H), 1.80-1.54 (m, 2H).

Example 70

1-(3,4-Dichlorobenzyl)-3-((3S,4S)-3-fluoro-4-(4-hydroxyphenyl)piperidin-1-yl)pyrrolidin-2-one

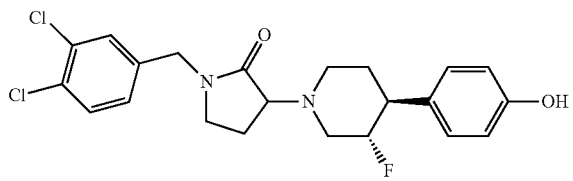

The titled compound of example 70 was prepared as a mixture of diastereomers using the general procedure A. Data for Example 70: $^1$H NMR (400 MHz, DMSO-$d_6$) δ=9.20 (s, 1H), 7.63 (dd, J=0.8, 8.4, 1H), 7.50 (s, 1H), 7.22 (dd, J=1.2, 8, 1H), 7.08 (d, J=8.4, 2H), 6.90 (dd, J=2, 6.4, 2H), 4.60 (m, 1H), 4.45 (m, 1H), 4.39 (m, 1H), 3.58 (m, 1H), 3.40 (m, 1H), 3.30-3.10 (m, 3H), 2.69 (m, 2H), 2.35-2.21 (m, 1H), 2.10 (m, 1H), 1.95 (m, 1H), 1.70 (m, 1H), 1.60 (m, 1H).

Example 71

(S)-3-((3S,4S)-3-Fluoro-4-(4-hydroxyphenyl)piperidin-1-yl)-1-(4-(trifluoromethyl)-benzyl)pyrrolidin-2-one

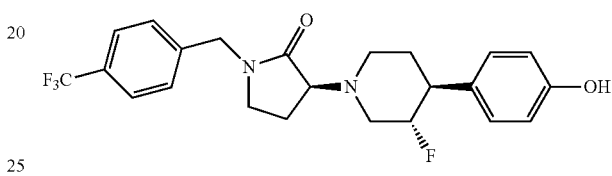

and

Example 72

(R)-3-((3S,4S)-3-Fluoro-4-(4-hydroxyphenyl)piperidin-1-yl)-1-(4-(trifluoromethyl)benzyl)-pyrrolidin-2-one

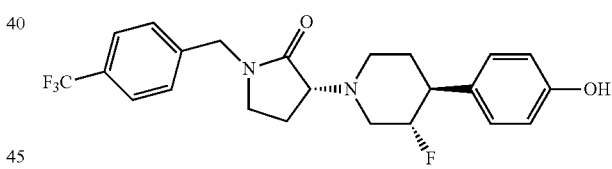

A diastereomeric mixture of 3-((3S,4S)-3-fluoro-4-(4-hydroxyphenyl)piperidin-1-yl)-1-(4-(trifluoromethyl)benzyl)-pyrrolidin-2-one (prepared using general procedure A) was separated by SFC (method 105) to afford the titled compounds of Example 71 and 72. Data for Example 71: SFC (Method 105) RT=2.31 min. LC/MS (Method O): RT=2.233 min, (M+H)+=437.2; $^1$H NMR (400 MHz, methanol-$d_4$) δ ppm 7.68 (d, J=8.16 Hz, 2H) 7.48 (d, J=8.03 Hz, 2H) 7.08-7.15 (m, 2H) 6.70-6.78 (m, 2H) 4.50-4.70 (m, 3H) 3.76 (t, J=8.88 Hz, 1H) 3.12-3.18 (m, 1H) 2.99-3.07 (m, 1H) 2.68 (td, J=9.91, 4.77 Hz, 1H) 2.53-2.62 (m, 1H) 2.42-2.50 (m, 1H) 2.17-2.27 (m, 1H) 2.04-2.16 (m, 1H) 1.80-1.88 (m, 1H). Data for Example 72: SFC (Method 105) RT=3.31 min. LC/MS (Method O): RT=2.208 min, (M+H)+=437.2; $^1$H NMR (400 MHz, methanol-d4) δ ppm 7.68 (d, J=8.09 Hz, 3H) 7.48 (d, J=8.03 Hz, 3H) 7.09-7.14 (m, 4H) 6.71-6.79 (m, 2H) 4.51-4.71 (m, 3H) 3.74 (t, J=8.97 Hz, 1H) 3.41-3.47 (m, 1H) 2.74-2.83 (m, 0H) 2.65-2.73 (m, 1H) 2.51-2.62 (m, 1H) 2.44 (td, J=9.99, 4.80 Hz, 1H) 2.17-2.27 (m, 1H) 2.05-2.16 (m, 1H) 1.76-1.87 (m, 2H).

Example 73

1-(3-Chloro-4-fluorobenzyl)-3-((3S,4S)-3-fluoro-4-(4-hydroxyphenyl)piperidin-1-yl)pyrrolidin-2-one

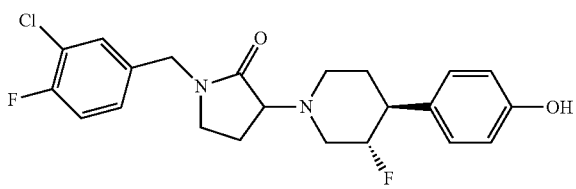

The titled compound of example 73 was prepared as a mixture of diastereomers using general procedure A. Data for Example 73: LC/MS RT=1.674 min, (M+H)+=421.0; $^1$H NMR (400 MHz, DMSO-d$_6$) δ=9.20 (s, 1H), 7.48-7.36 (m, 2H), 7.29-7.21 (m, 1H), 7.09 (d, J=8.5 Hz, 2H), 6.73-6.67 (m, 2H), 4.38 (d, J=4.0 Hz, 3H), 3.64-3.53 (m, 1H), 3.44-3.35 (m, 1H), 3.16 (s, 3H), 2.99-2.91 (m, 1H), 2.76-2.63 (m, 2H), 2.36-2.22 (m, 1H), 2.08 (s, 1H), 2.00-1.85 (m, 1H), 1.79-1.52 (m, 2H).

General Procedure B

Used for preparation of Examples 74-89.

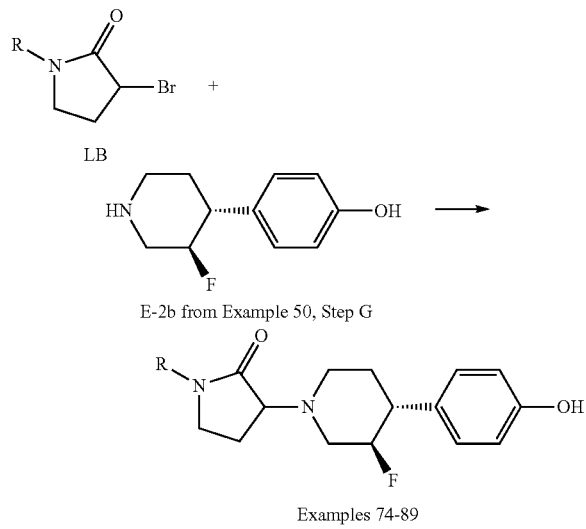

To a microwave vial containing 4-(3S,4S)-3-fluoropiperidin-4-yl)phenol (23 mg, 0.12 mmol, E-2b from Example 50, Step G) and the corresponding lactam bromide (0.21 mmol, compound LB) was added DMF (1 mL) and triethylamine (0.08 mL, 0.59 mmol). The vial was capped and the reaction mixture was heated to 110° C. using microwave irradiation for 1 h. LC/MS data were collected using method 100. The samples were directly purified by preparative HPLC under conditions B. Products are a mixture of diastereoisomers. In some cases, the diastereo-isomers were further separated into the individual homochiral components under the conditions reported in the specific examples.

Example 74

(S)-1-Benzyl-3-((3R,4R)-3-fluoro-4-(4-hydroxyphenyl)piperidin-1-yl)pyrrolidin-2-one

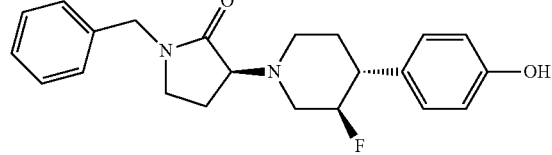

and

Example 75

(R)-1-Benzyl-3-((3R,4R)-3-fluoro-4-(4-hydroxyphenyl)-piperidin-1-yl)pyrrolidin-2-one

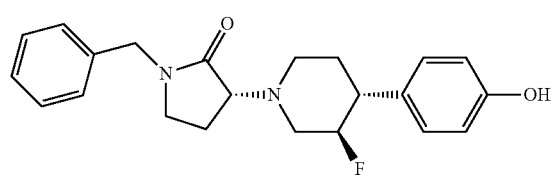 [SMILES: O=C1[C@H](N2CC[C@H](c3ccc(O)cc3)[C@@H](F)C2)CCN1Cc1ccccc1]

A diastereomeric mixture of 1-benzyl-3-((3R,4R)-3-fluoro-4-(4-hydroxyphenyl)piperidin-1-yl)pyrrolidin-2-one (prepared using general procedure B) was separated by SFC (method 105) to afford the titled compounds of Example 74 and 75. Data for Example 74: SFC (Method 105) RT=3.59 min. LC/MS (Method O): RT=2.099 min, (M+H)+=369.2; $^1$H NMR (400 MHz, methanol-d4) δ ppm 7.26-7.40 (m, 5H) 7.08-7.13 (m, 2H) 6.71-6.79 (m, 2H) 4.40-4.71 (m, 3H) 3.68-3.75 (m, 1H) 3.38-3.45 (m, 1H) 3.22-3.31 (m, 2H) 2.74-2.81 (m, 1H) 2.64-2.72 (m, 1H) 2.51-2.63 (m, 1H) 2.43 (td, J=10.01, 4.83 Hz, 1H) 2.14-2.24 (m, 1H) 2.02-2.13 (m, 1H) 1.75-1.87 (m, 2H). Data for Example 75: SFC (Method 105) RT=6.2 min. LC/MS (Method O): RT=2.091 min, (M+H)+ =369.2; $^1$H NMR (400 MHz, methanol-d4) δ ppm 7.25-7.39 (m, 5H) 7.03-7.14 (m, 2H) 6.70-6.84 (m, 2H) 4.38-4.72 (m, 3H) 3.74 (t, J=8.82 Hz, 1H) 3.22-3.30 (m, 2H) 3.10-3.18 (m, 1H) 2.94-3.05 (m, 2H) 2.66 (td, J=9.91, 4.77 Hz, 1H) 2.51-2.60 (m, 1H) 2.40-2.49 (m, 1H) 2.14-2.25 (m, 1H) 1.99-2.12 (m, 1H) 1.79-1.89 (m, 2H).

Example 76

3-((3R,4R)-3-Fluoro-4-(4-hydroxyphenyl)piperidin-1-yl)-1-(2-methylbenzyl)pyrrolidin-2-one

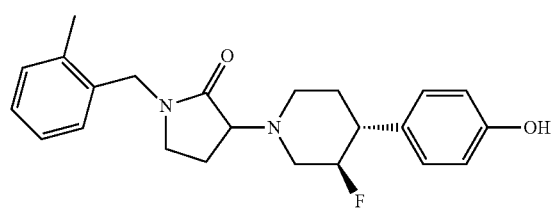 [SMILES: Cc1ccccc1CN1CCC(N2CC[C@H](c3ccc(O)cc3)[C@@H](F)C2)C1=O]

The titled compound of example 76 was prepared as a mixture of diastereomers using the general procedure B. Data for Example 76: LC/MS RT=1.588 min, (M+H)+=383.0; $^1$H NMR (400 MHz, DMSO-$d_6$) δ ppm 1.56-1.78 (m, 2H) 1.87-1.97 (m, 1H) 2.08 (s, 1H) 2.23-2.35 (m, 5H) 2.64-2.79 (m, 2H) 3.04-3.18 (m, 3H) 3.36-3.44 (m, 1H) 3.60 (d, J=7.03 Hz, 1H) 4.27-4.34 (m, 1H) 4.43-4.65 (m, 2H) 6.66-6.73 (m, 2H) 7.06-7.22 (m, 6H) 9.20 (s, 1H).

Example 77

3-((3R,4R)-3-Fluoro-4-(4-hydroxyphenyl)piperidin-1-yl)-1-(3-methylbenzyl)pyrrolidin-2-one

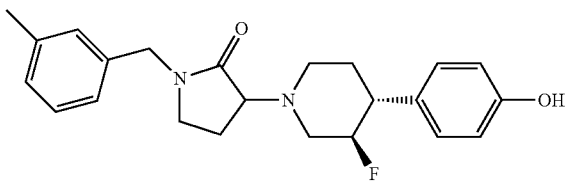 [SMILES: Cc1cccc(CN2CCC(N3CC[C@H](c4ccc(O)cc4)[C@@H](F)C3)C2=O)c1]

The titled compound of example 77 was prepared as a mixture of diastereomers using the general procedure B. Data for Example 77: LC/MS RT=1.600 min, (M+H)+=383.0; $^1$H NMR (400 MHz, DMSO-$d_6$) δ ppm 1.57-1.76 (m, 2H) 1.86-1.98 (m, 1H) 2.08 (s, 1H) 2.29 (s, 2H) 2.65-2.76 (m, 1H) 3.09-3.21 (m, 2H) 3.57 (d, J=7.53 Hz, 1H) 4.25-4.41 (m, 2H) 4.44-4.69 (m, 1H) 6.66-6.74 (m, 2H) 6.98-7.04 (m, 2H) 7.09 (d, J=8.53 Hz, 3H) 7.20-7.28 (m, 1H) 9.21 (s, 1H).

Example 78

1-(4-(Difluoromethoxy)benzyl)-3-((3R,4R)-3-fluoro-4-(4-hydroxyphenyl)piperidin-1-yl)pyrrolidin-2-one

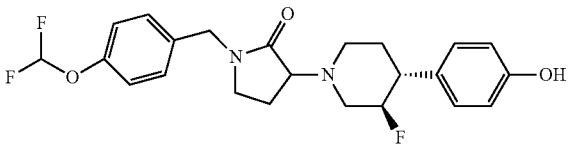 [SMILES: O=C1C(N2CC[C@H](c3ccc(O)cc3)[C@@H](F)C2)CCN1Cc1ccc(OC(F)F)cc1]

The titled compound of example 78 was prepared as a mixture of diastereomers using the general procedure B. Data for Example 78: LC/MS RT=1.565 min, (M+H)+=435.0; $^1$H NMR (400 MHz, DMSO-$d_6$) δ ppm 1.53-1.75 (m, 2H) 1.86-1.97 (m, 1H) 2.04-2.14 (m, 1H) 2.20-2.35 (m, 1H) 2.63-2.78 (m, 1H) 3.06-3.24 (m, 2H) 3.51-3.61 (m, 1H) 4.37 (d, J=12.55 Hz, 2H) 4.46-4.66 (m, 1H) 6.70 (d, J=8.53 Hz, 1H) 6.99-7.11 (m, 1H) 7.13-7.23 (m, 1H) 7.26-7.32 (m, 1H) 7.40 (s, 1H) 9.21 (s, 1H).

Example 79

1-(3-Chloro-4-(difluoromethoxy)phenyl)-3-((3R,4R)-3-fluoro-4-(4-hydroxyphenyl)-piperidin-1-yl)pyrrolidin-2-one

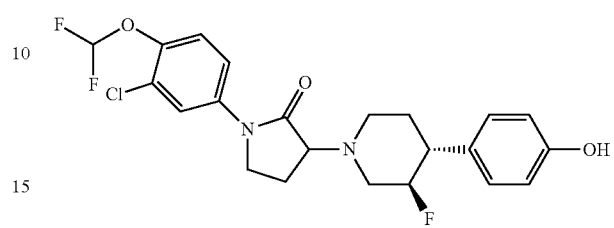

The titled compound of example 79 was prepared as a mixture of diastereomers using the general procedure B. Data for Example 79: LC/MS RT=1.762 min, (M+H)+=455.0; $^1$H NMR (400 MHz, DMSO-$d_6$) δ ppm 1.59-1.80 (m, 2H) 2.01-2.14 (m, 1H) 2.20-2.27 (m, 1H) 2.30-2.41 (m, 1H) 2.72-2.80 (m, 1H) 3.17 (s, 1H) 3.69-3.84 (m, 3H) 4.41-4.69 (m, 1H) 6.62-6.75 (m, 2H) 6.98-7.27 (m, 4H) 7.35-7.45 (m, 2H) 7.64 (d, J=3.51 Hz, 1H) 8.03 (t, J=2.51 Hz, 1H) 9.13-9.30 (m, 1H).

Example 80

(S)-1-(4-Chlorobenzyl)-3-((3R,4R)-3-fluoro-4-(4-hydroxyphenyl)piperidin-1-yl)pyrrolidin-2-one

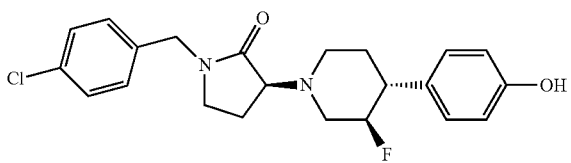 [SMILES: O=C1[C@@H](N2CC[C@H](c3ccc(O)cc3)[C@@H](F)C2)CCN1Cc1ccc(Cl)cc1]

and

Example 81

(R)-1-(4-Chlorobenzyl)-3-((3R,4R)-3-fluoro-4-(4-hydroxyphenyl)piperidin-1-yl)pyrrolidin-2-one

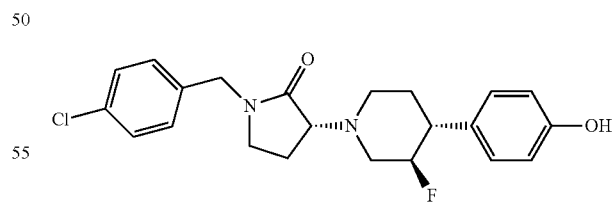

A diastereomeric mixture of 1-(4-chlorobenzyl)-3-((3R,4R)-3-fluoro-4-(4-hydroxyphenyl)piperidin-1-yl)pyrrolidin-2-one (prepared using general procedure B) was separated by SFC (method 105) to afford the titled compounds of Example 80 and 81. Data for Example 80: SFC (Method 105) RT=4.58 min. LC/MS (Method O): RT=2.216 min, (M+H)+ =403.2; $^1$H NMR (400 MHz, methanol-d4) δ ppm 1.76-1.89 (m, 2H) 2.06-2.27 (m, 3H) 2.40-2.55 (m, 2H) 2.65-2.70 (m, 1H) 2.77 (d, J=10.54 Hz, 1H) 3.39-3.46 (m, 2H) 3.62 (s, 1H)

3.72 (t, J=8.78 Hz, 2H) 4.36-4.60 (m, 4H) 6.74-6.78 (m, 2H) 7.11 (d, J=8.53 Hz, 2H) 7.24-7.30 (m, 2H) 7.35-7.41 (m, 2H). Data for Example 81: SFC (Method 105) RT=9.5 min. LC/MS (Method O): RT=2.233 min, (M+H)+=403.2; $^1$H NMR (400 MHz, methanol-$d_4$) δ ppm 1.84 (d, J=3.51 Hz, 2H) 2.45 (dd, J=14.81, 11.29 Hz, 1H) 2.68 (dd, J=10.04, 4.52 Hz, 1H) 2.97-3.06 (m, 2H) 3.10-3.16 (m, 2H) 3.25-3.31 (m, 2H) 3.62 (s, 1H) 4.49 (d, J=19.58 Hz, 3H) 4.66 (dd, J=10.04, 5.02 Hz, 2H) 6.72-6.79 (m, 2H) 7.12 (d, J=8.53 Hz, 2H) 7.26-7.32 (m, 2H) 7.35-7.40 (m, 2H).

Example 82

(S)-1-(4-Chloro-3-fluorobenzyl)-3-((3R,4R)-3-fluoro-4-(4-hydroxyphenyl)piperidin-1-yl)pyrrolidin-2-one

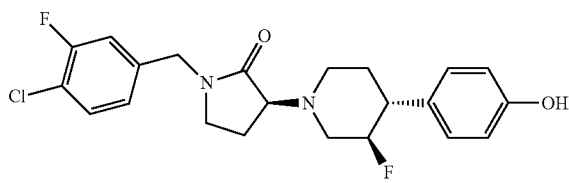 [SMILES: O=C1[C@@H](N2CC[C@H](c3ccc(O)cc3)[C@@H](F)C2)CCN1Cc1ccc(Cl)c(F)c1]

and

Example 83

(R)-1-(4-Chloro-3-fluorobenzyl)-3-((3R,4R)-3-fluoro-4-(4-hydroxyphenyl)piperidin-1-yl)pyrrolidin-2-one

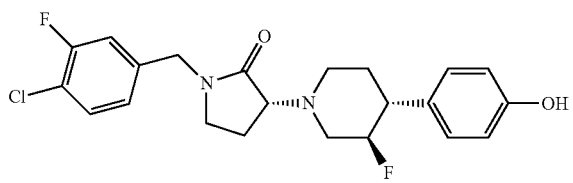 [SMILES: O=C1[C@H](N2CC[C@H](c3ccc(O)cc3)[C@@H](F)C2)CCN1Cc1ccc(Cl)c(F)c1]

A diastereomeric mixture of 1-(4-chloro-3-fluorobenzyl)-3-((3R,4R)-3-fluoro-4-(4-hydroxyphenyl)piperidin-1-yl)pyrrolidin-2-one (prepared using general procedure B) was separated by SFC (method 106) to afford the titled compounds of Example 82 and 83. Data for Example 82: SFC (Method 106) RT=3.9 min. LC/MS (Method O): RT=2.081 min, (M+H)+=421.2; $^1$H NMR (400 MHz, methanol-d4) δ ppm 7.44-7.50 (m, 1H) 7.16-7.21 (m, 1H) 7.08-7.14 (m, 1H) 6.72-6.81 (m, 2H) 4.42-4.71 (m, 4H) 3.69-3.75 (m, 1H) 3.40-3.47 (m, 1H) 3.25-3.31 (m, 1H) 2.74-2.80 (m, 1H) 2.64-2.72 (m, 1H) 2.53-2.62 (m, 1H) 2.39-2.48 (m, 1H) 2.17-2.27 (m, 1H) 2.04-2.16 (m, 1H) 1.77-1.87 (m, 2H). Data for Example 83: SFC (Method 106) RT=7.05 min. LC/MS (Method O): RT=2.210 min, (M+H)+=421.2; $^1$H NMR (400 MHz, methanol-d4) δ ppm 7.45-7.50 (m, 1H) 7.17-7.22 (m, 1H) 7.08-7.14 (m, 2H) 6.73-6.78 (m, 2H) 4.43-4.70 (m, 3H) 3.71-3.78 (m, 1H) 3.25-3.31 (m, 1H) 3.10-3.18 (m, 1H) 2.98-3.08 (m, 1H) 2.62-2.71 (m, 1H) 2.52-2.61 (m, 1H) 2.39-2.49 (m, 1H) 2.17-2.27 (m, 1H) 2.03-2.15 (m, 1H) 1.79-1.90 (m, 2H).

Example 84

3-((3R,4R)-3-Fluoro-4-(4-hydroxyphenyl)piperidin-1-yl)-1-((S)-1-phenylethyl)pyrrolidin-2-one

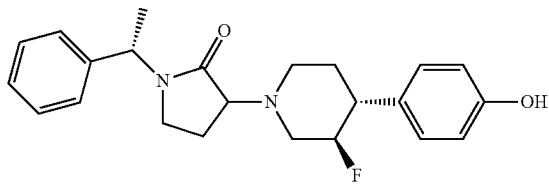 [SMILES: C[C@@H](c1ccccc1)N1CCC(N2CC[C@H](c3ccc(O)cc3)[C@@H](F)C2)C1=O]

The titled compound of example 84 was prepared as a mixture of diastereomers using the general procedure B. Data for Example 84: LC/MS RT=1.574 min, (M+H)+=383.0; $^1$H NMR (400 MHz, DMSO-$d_6$) δ ppm 1.48 (d, J=7.53 Hz, 3H) 1.84-1.94 (m, 1H) 2.00-2.13 (m, 1H) 2.23-2.31 (m, 1H) 2.66-2.75 (m, 1H) 2.81 (dt, J=9.66, 7.72 Hz, 1H) 2.95 (d, J=9.04 Hz, 1H) 3.12-3.19 (m, 1H) 3.51 (t, J=8.53 Hz, 1H) 4.42-4.62 (m, 1H) 5.26-5.32 (m, 1H) 6.67-6.74 (m, 2H) 7.07-7.11 (m, 2H) 7.25-7.31 (m, 3H) 7.33-7.39 (m, 2H) 9.20 (s, 1H).

Example 85

1-(3,4-Difluorobenzyl)-3-((3R,4R)-3-fluoro-4-(4-hydroxyphenyl)-piperidin-1-yl)pyrrolidin-2-one

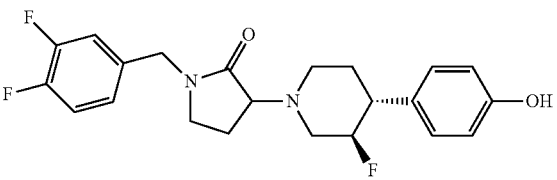 [SMILES: O=C1C(N2CC[C@H](c3ccc(O)cc3)[C@@H](F)C2)CCN1Cc1ccc(F)c(F)c1]

The titled compound of example 85 was prepared as a mixture of diastereomers using the general procedure B. Data for Example 85: LC/MS RT=1.540 min, (M+H)+=405.0 $^1$H NMR (400 MHz, DMSO-$d_6$) δ ppm 1.51-1.78 (m, 2H) 1.86-2.01 (m, 1H) 2.08 (s, 1H) 2.22-2.35 (m, 1H) 2.71 (br. s., 2H) 3.09-3.24 (m, 3H) 3.54-3.64 (m, 1H) 4.37 (d, J=4.02 Hz, 2H) 4.43-4.69 (m, 1H) 6.70 (d, J=8.53 Hz, 2H) 7.09 (d, J=8.53 Hz, 3H) 7.24-7.32 (m, 1H) 7.43 (s, 1H) 9.20 (s, 1H).

Example 86

1-(3,4-Dichlorobenzyl)-3-((3R,4R)-3-fluoro-4-(4-hydroxyphenyl)-piperidin-1-yl)pyrrolidin-2-one

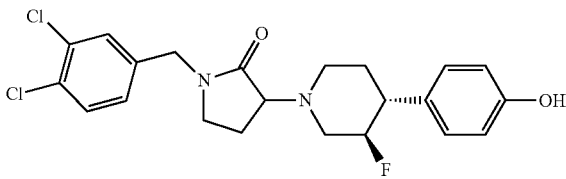

The titled compound of example 86 was prepared as a mixture of diastereomers using the general procedure B. Data for Example 86: LC/MS RT=1.768 min, (M+H)+=437.0 $^1$H NMR (400 MHz, DMSO-d$_6$) δ ppm 1.51-1.76 (m, 2H) 1.85-2.00 (m, 1H) 2.05-2.15 (m, 1H) 2.21-2.34 (m, 1H) 2.66-2.75 (m, 2H) 3.07-3.25 (m, 3H) 3.37 (s, 1H) 3.59 (d, J=6.53 Hz, 1H) 4.39 (d, J=5.52 Hz, 2H) 4.43 (s, 1H) 6.67-6.74 (m, 2H) 7.09 (d, J=8.53 Hz, 2H) 7.20-7.28 (m, 1H) 7.50 (t, J=2.01 Hz, 1H) 7.62 (dd, J=8.03, 1.00 Hz, 1H) 9.21 (s, 1H).

Example 87

(S)-3-((3R,4R)-3-Fluoro-4-(4-hydroxyphenyl)piperidin-1-yl)-1-(4-(trifluoromethyl)benzyl)-pyrrolidin-2-one

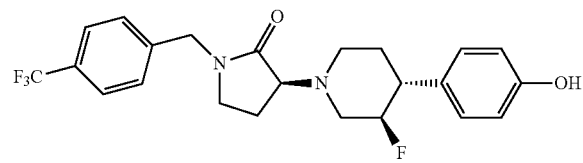 [SMILES: O=C1[C@@H](N2CC[C@H](c3ccc(O)cc3)[C@@H](F)C2)CCN1Cc1ccc(C(F)(F)F)cc1]

and

Example 88

(R)-3-((3R,4R)-3-Fluoro-4-(4-hydroxyphenyl)piperidin-1-yl)-1-(4-(trifluoromethyl)benzyl)-pyrrolidin-2-one

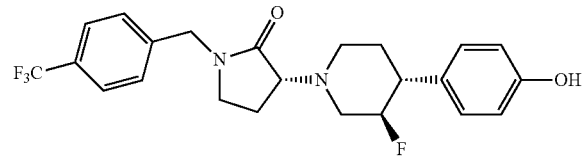 [SMILES: O=C1[C@H](N2CC[C@H](c3ccc(O)cc3)[C@@H](F)C2)CCN1Cc1ccc(C(F)(F)F)cc1]

A diastereomeric mixture of 3-((3R,4R)-3-fluoro-4-(4-hydroxyphenyl)piperidin-1-yl)-1-(4-(trifluoromethyl)benzyl)-pyrrolidin-2-one (prepared using general procedure B) was separated by SFC (method 106) to afford the titled compounds of Example 87 and 88. Data for Example 87: SFC (Method 106) RT=2.09 min. LC/MS (Method O): RT=2.14 min, (M+H)+=437.2; $^1$H NMR (400 MHz, methanol-d$_4$) δ=7.69 (d, J=8.0 Hz, 2H), 7.49 (d, J=8.0 Hz, 2H), 7.15-7.09 (m, 2H), 6.80-6.72 (m, 2H), 4.71-4.51 (m, 3H), 3.74 (t, J=9.0 Hz, 1H), 3.48-3.41 (m, 1H), 3.30-3.25 (m, 2H), 2.83-2.75 (m, 1H), 2.73-2.65 (m, 1H), 2.62-2.52 (m, 1H), 2.45 (dt, J=4.5, 10.0 Hz, 1H), 2.28-2.07 (m, 2H), 1.88-1.77 (m, 2H). Data for Example 88: SFC (Method 106) RT=3.19 min. LC/MS (Method O): RT=2.13 min, (M+H)+=437.2; $^1$H NMR (400 MHz, methanol-d4) δ=7.72-7.66 (m, 2H), 7.53-7.45 (m, 2H), 7.16-7.08 (m, 2H), 6.80-6.72 (m, 2H), 4.69-4.49 (m, 3H), 3.81-3.72 (m, 1H), 3.32-3.26 (m, 2H), 3.19-3.11 (m, 1H), 3.09-3.00 (m, 1H), 2.74-2.65 (m, 1H), 2.62-2.53 (m, 1H), 2.51-2.42 (m, 1H), 2.28-2.18 (m, 1H), 2.16-2.04 (m, 1H), 1.90-1.79 (m, 2H).

Example 89

1-(3-Chloro-4-fluorobenzyl)-3-((3R,4R)-3-fluoro-4-(4-hydroxyphenyl)piperidin-1-yl)pyrrolidin-2-one

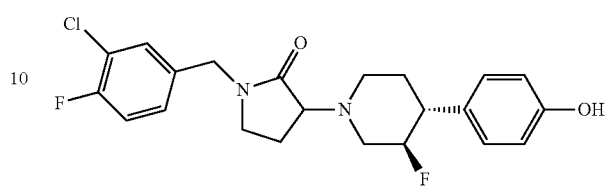

The titled compound of example 89 was prepared as a mixture of diastereomers using the general procedure B. Data for Example 89: LC/MS RT=1.645 min, (M+H)+=421.0 $^1$H NMR (400 MHz, DMSO-d$_6$) δ ppm 1.49-1.79 (m, 2H) 1.86-1.99 (m, 2H) 2.08 (s, 2H) 2.21-2.35 (m, 2H) 2.65-2.76 (m, 2H) 3.16 (s, 4H) 3.36-3.44 (m, 1H) 3.54-3.64 (m, 1H) 4.38 (d, J=4.02 Hz, 2H) 4.44-4.68 (m, 1H) 6.70 (d, J=8.53 Hz, 2H) 7.09 (d, J=8.53 Hz, 2H) 7.21-7.27 (m, 1H) 7.40 (s, 2H) 9.20 (s, 1H).

General Procedure C

Used for preparation of Examples 90-117.

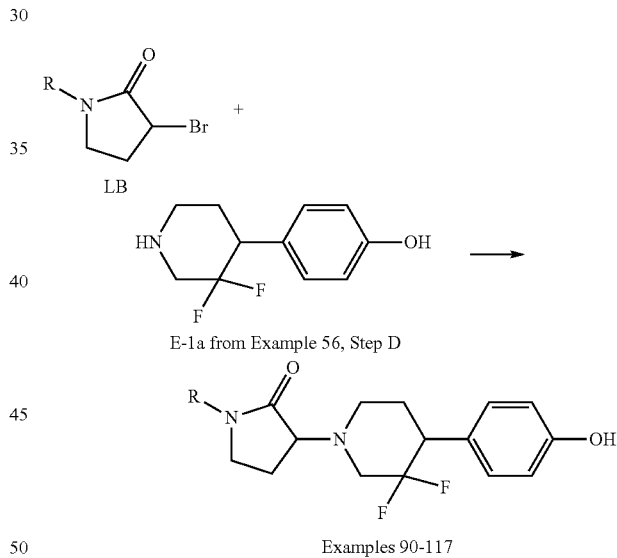

Examples 90-117

To a microwave vial containing 4-(3,3-difluoropiperidin-4-yl)phenol HCl (30 mg, 0.14 mmol, E-1a from Example 56, Step D) and the appropriate lactam bromide (0.28 mmol, compound LB) was added DMF (1 mL) and triethylamine (0.1 mL, 0.7 mmol). The vial was capped and the reaction mixture was heated to 120° C. using microwave irradiation for 1 h. LC/MS data were collected using method 100. The samples were directly purified by preparative HPLC under conditions B. Products are a mixture of diastereoisomers. In some cases, the diastereo-isomers were further separated into the individual homochiral components under the conditions reported in the specific examples. Assignment of lactam stereochemistry followed biological activity but was not rigorously determined chemically, therefore individual compounds are identified by the retention time in SFC. The absolute configuration of the homochiral 4-(3,3-difluoropiperidin-4-yl)phenol used has not been determined.

Example 90

1-(3-Chloro-4-(difluoromethoxy)phenyl)-3-(3,3-difluoro-4-(4-hydroxyphenyl)piperidin-1-yl)pyrrolidin-2-one

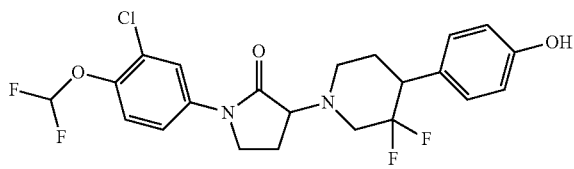 [SMILES: O=C1C(N2CCC(c3ccc(O)cc3)C(F)(F)C2)CCN1c1ccc(OC(F)F)c(Cl)c1]

The titled compound of example 90 was prepared as a mixture of diastereomers using the general procedure C. Data for Example 90: LC/MS RT=1.769 min, (M+H)+=473.0 $^1$H NMR (400 MHz, DMSO-d$_6$) δ=9.31 (s, 1H), 8.03 (t, J=3.0 Hz, 1H), 7.68-7.62 (m, 1H), 7.44-7.07 (m, 4H), 6.72 (d, J=8.0 Hz, 2H), 3.80 (d, J=10.0 Hz, 3H), 3.17 (d, J=5.0 Hz, 2H), 3.06-2.85 (m, 2H), 2.73-2.60 (m, 1H), 2.48-2.43 (m, 1H), 2.35-2.22 (m, 1H), 2.13-1.93 (m, 4H), 1.81-1.70 (m, 1H).

Example 91

Peak-1

1-Benzyl-3-(3,3-difluoro-4-(4-hydroxyphenyl)piperidin-1-yl)pyrrolidin-2-one

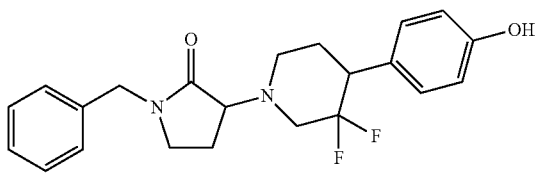

and

Example 91

Peak-2

1-Benzyl-3-(3,3-difluoro-4-(4-hydroxyphenyl)piperidin-1-yl)pyrrolidin-2-one

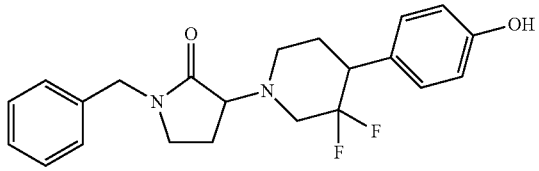 [SMILES: O=C1C(N2CCC(c3ccc(O)cc3)C(F)(F)C2)CCN1Cc1ccccc1]

1-Benzyl-3-(3,3-difluoro-4-(4-hydroxyphenyl)piperidin-1-yl)pyrrolidin-2-one was prepared as a mixture of diastereomers using the general procedure C. The mixture of diastereomers was separated into the individual homochiral compounds of example 91 P-1 and P-2 by SFC using method 105. The relative and absolute configurations of were not determined and are arbitrarily named P-1 and P-2 based on the order of elution during the SFC purification. Data for Example 91, P-1: SFC (Method 105) RT=5.29 min. LC/MS (Method O): RT=2.103 min, (M+H)+=387.2; $^1$H NMR (400 MHz, methanol-d4) δ ppm 7.26-7.39 (m, 5H) 7.15 (d, J=8.35 Hz, 2H) 6.73-6.77 (m, 2H) 4.41-4.59 (m, 3H) 3.69 (t, J=8.85 Hz, 1H) 3.36-3.42 (m, 1H) 3.22-3.30 (m, 2H) 3.06 (d, J=7.28 Hz, 1H) 2.84-3.01 (m, 3H) 2.60-2.73 (m, 1H) 1.98-2.28 (m, 3H) 1.82 (ddt, J=13.18, 4.76, 2.38, 2.38 Hz, 1H). Data for Example 91, P-2: SFC (Method 105) RT=5.18 min. LC/MS (Method O): RT=2.117 min, (M+H)+=387.2; $^1$H NMR (400 MHz, methanol-d4) δ ppm 7.26-7.39 (m, 5H) 7.15 (d, J=8.41 Hz, 2H) 6.73-6.77 (m, 2H) 4.41-4.57 (m, 2H) 3.72 (t, J=8.82 Hz, 1H) 3.22-3.30 (m, 1H) 3.03-3.18 (m, 4H) 2.86-3.00 (m, 1H) 2.53 (t, J=11.39 Hz, 1H) 1.99-2.30 (m, 3H) 1.80-1.88 (m, 1H).

Example 92

3-(3,3-Difluoro-4-(4-hydroxyphenyl)piperidin-1-yl)-1-(2-methylbenzyl)pyrrolidin-2-one

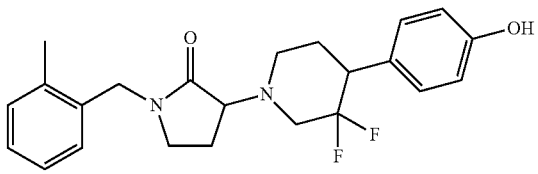 [SMILES: Cc1ccccc1CN1CCC(N2CCC(c3ccc(O)cc3)C(F)(F)C2)C1=O]

The titled compound of example 92 was prepared as a mixture of diastereomers using the general procedure C. Data for Example 92: LC/MS RT=1.609 min, (M+H)+=401.0 $^1$H NMR (400 MHz, DMSO-d$_6$) δ=9.30 (d, J=1.5 Hz, 1H), 7.22-7.07 (m, 6H), 6.71 (d, J=8.0 Hz, 2H), 4.48-4.42 (m, 1H), 4.35-4.28 (m, 1H), 3.62 (d, J=9.0 Hz, 1H), 3.19-3.04 (m, 4H), 3.02-2.78 (m, 2H), 2.69-2.54 (m, 1H), 2.45-2.32 (m, 1H), 2.25 (d, J=1.0 Hz, 3H), 2.18-2.07 (m, 1H), 1.94 (d, J=17.1 Hz, 2H), 1.80-1.69 (m, 1H).

Example 93

3-(3,3-Difluoro-4-(4-hydroxyphenyl)piperidin-1-yl)-1-(3-methylbenzyl)pyrrolidin-2-one

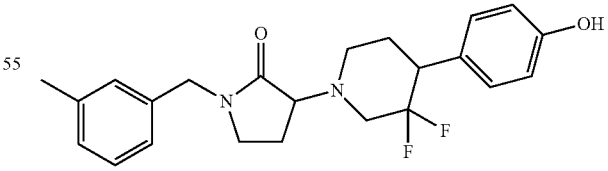

The titled compound of example 93 was prepared as a mixture of diastereomers using the general procedure C. Data for Example 93: LC/MS RT=1.622 min, (M+H)+=401.0 $^1$H NMR (400 MHz, DMSO-d$_6$) δ=9.30 (s, 1H), 7.27-7.20 (m, 1H), 7.09 (d, J=8.0 Hz, 3H), 7.06-6.99 (m, 2H), 6.72 (d, J=8.0 Hz, 2H), 4.40-4.28 (m, 2H), 4.11-4.05 (m, 1H), 3.60 (d, J=8.5 Hz, 1H), 3.39-3.34 (m, 1H), 3.23-2.77 (m, 6H), 2.69-2.54 (m, 1H), 2.45-2.32 (m, 1H), 2.29 (s, 3H), 2.19-2.08 (m, 1H), 2.04-1.85 (m, 2H), 1.79-1.69 (m, 1H).

Example 94

3-(3,3-Difluoro-4-(4-hydroxyphenyl)piperidin-1-yl)-1-(4-(difluoromethoxy)benzyl)-pyrrolidin-2-one

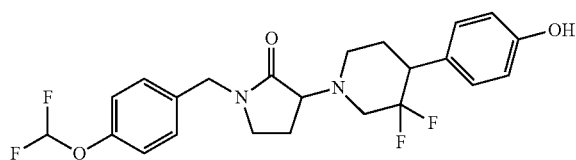 [SMILES: O=C1C(N2CCC(c3ccc(O)cc3)C(F)(F)C2)CCN1Cc1ccc(OC(F)F)cc1]

The titled compound of example 94 was prepared as a mixture of diastereomers using the general procedure C. Data for Example 94: LC/MS RT=1.595 min, (M+H)+=453.0 $^1$H NMR (400 MHz, DMSO-$d_6$) δ=9.30 (d, J=1.0 Hz, 1H), 7.42-7.02 (m, 8H), 6.71 (d, J=8.0 Hz, 2H), 4.43-4.32 (m, 2H), 3.60 (d, J=8.0 Hz, 1H), 3.40-3.33 (m, 1H), 3.24-3.04 (m, 3H), 3.02-2.76 (m, 2H), 2.69-2.54 (m, 1H), 2.43-2.31 (m, 1H), 2.20-2.07 (m, 1H), 2.03-1.85 (m, 1H), 1.79-1.69 (m, 1H).

Example 95

Peak-1

(3S)-1-(4-Chlorobenzyl)-3-(3,3-difluoro-4-(4-hydroxyphenyl)piperidin-1-yl)pyrrolidin-2-one

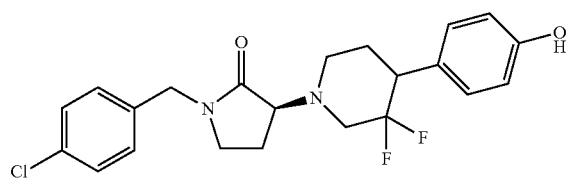 [SMILES: O=C1[C@@H](N2CCC(c3ccc(O)cc3)C(F)(F)C2)CCN1Cc1ccc(Cl)cc1]

and

Example 95

Peak-2

(3R)-1-(4-Chlorobenzyl)-3-(3,3-difluoro-4-(4-hydroxyphenyl)piperidin-1-yl)pyrrolidin-2-one

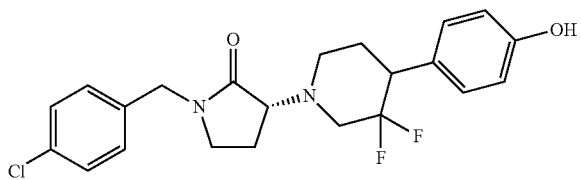 [SMILES: O=C1[C@H](N2CCC(c3ccc(O)cc3)C(F)(F)C2)CCN1Cc1ccc(Cl)cc1]

1-(4-Chlorobenzyl)-3-(3,3-difluoro-4-(4-hydroxyphenyl) piperidin-1-yl)pyrrolidin-2-one was prepared as a mixture of diastereomers using the general procedure C. The mixture of diastereomers was separated into the individual homochiral compounds of example 95 P-1 and P-2 by SFC (method 105). The stereochemical configurations were not determined and are arbitrarily named P-1 and P-2. Data for Example 95, P-1: SFC (Method 105) RT=5.29 min. LC/MS (Method O): RT=2.062 min, (M+H)+=421.2; $^1$H NMR (400 MHz, methanol-$d_4$) δ=7.41-7.35 (m, 2H), 7.32-7.26 (m, 2H), 7.15 (d, J=8.5 Hz, 2H), 6.79-6.73 (m, 2H), 4.55-4.40 (m, 2H), 3.69 (t, J=8.8 Hz, 1H), 3.43-3.37 (m, 1H), 3.31-3.24 (m, 2H), 3.01-2.84 (m, 3H), 2.73-2.58 (m, 1H), 2.28-2.01 (m, 3H), 1.83 (ddd, J=2.0, 1H). Data for Example 95, P-2: SFC (Method 105) RT=8.79 min. LC/MS (Method O): RT=2.059 min, (M+H)+=421.2; $^1$H NMR (400 MHz, methanol-$d_4$) δ=7.40-7.34 (m, 2H), 7.32-7.26 (m, 2H), 7.15 (d, J=8.5 Hz, 2H), 6.78-6.73 (m, 2H), 4.55-4.39 (m, 2H), 3.72 (t, J=8.8 Hz, 1H), 3.62 (s, 1H), 3.30-3.24 (m, 2H), 3.20-3.07 (m, 3H), 2.98-2.86 (m, 1H), 2.53 (s, 1H), 2.30-2.02 (m, 3H), 1.86 (br. s., 1H).

Example 96

Peak-1

(3S)-1-(4-Chloro-3-fluorobenzyl)-3-(3,3-difluoro-4-(4-hydroxyphenyl)piperidin-1-yl)pyrrolidin-2-one

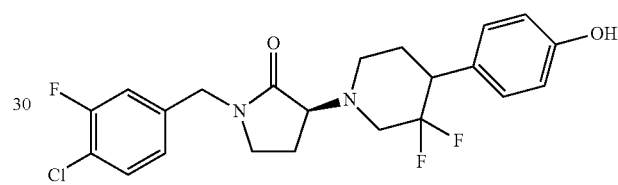

and

Example 96

Peak-2

(3R)-1-(4-Chloro-3-fluorobenzyl)-3-(3,3-difluoro-4-(4-hydroxyphenyl)piperidin-1-yl)pyrrolidin-2-one

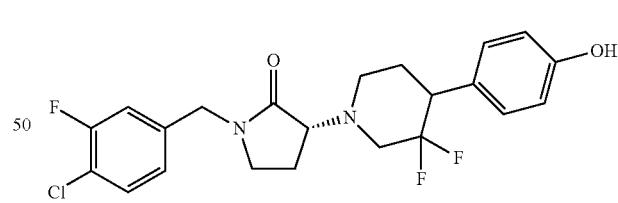

1-(4-Chloro-3-fluorobenzyl)-3-(3,3-difluoro-4-(4-hydroxyphenyl)piperidin-1-yl)pyrrolidin-2-one was prepared as a mixture of diastereomers using the general procedure C. The mixture of diastereomers was separated into the individual homochiral compounds of example 96 P-1 and P-2 by SFC (method 105). The stereochemical configurations were not determined and are arbitrarily named P-1 and P-2. Data for Example 96, P-1: SFC (Method 105) RT=5.13 min. LC/MS (Method O): RT=2.214 min, (M+H)+=439.0; $^1$H NMR (400 MHz, methanol-$d_4$) δ ppm 1.47-1.51 (m, 1H) 1.84 (d, J=13.05 Hz, 1H) 2.05-2.31 (m, 3H) 2.54-2.66 (m, 1H) 2.83-3.02 (m, 3H) 3.29-3.32 (m, 1H) 3.39-3.56 (m, 2H) 3.65-3.74 (m, 1H) 4.41-4.55 (m, 2H) 6.71-6.78 (m, 2H) 7.07-7.35

(m, 4H) 7.46-7.52 (m, 1H). Data for Example 96, P-2: SFC (Method 105) RT=7.15 min. LC/MS (Method O): RT=2.211 min, (M+H)+=439.0; $^1$H NMR (400 MHz, methanol-d4) δ ppm 1.81-1.92 (m, 1H) 2.01-2.30 (m, 3H) 2.46-2.58 (m, 1H) 3.03-3.11 (m, 1H) 3.10-3.21 (m, 2H) 3.24-3.32 (m, 1H) 3.72 (t, J=8.78 Hz, 1H) 4.42-4.56 (m, 2H) 6.72-6.79 (m, 2H) 7.09-7.23 (m, 4H) 7.43-7.51 (m, 1H).

Example 97

3-(3,3-Difluoro-4-(4-hydroxyphenyl)piperidin-1-yl)-1-(3,4-difluorobenzyl)pyrrolidin-2-one

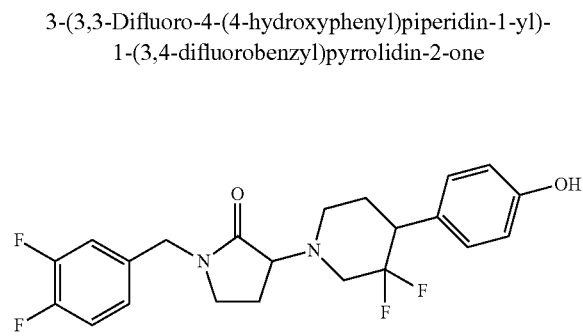

The titled compound of example 97 was prepared as a mixture of diastereomers using the general procedure C. Data for Example 97: LC/MS RT=1.569 min, (M+H)+=423.0; $^1$H NMR (400 MHz, DMSO-d$_6$) δ=9.30 (d, J=1.0 Hz, 1H), 7.46-7.37 (m, 1H), 7.33-7.25 (m, 1H), 7.09 (d, J=8.5 Hz, 3H), 6.71 (d, J=8.5 Hz, 2H), 4.37 (s, 2H), 3.65-3.57 (m, 1H), 3.43-3.35 (m, 1H), 3.27-3.04 (m, 4H), 3.03-2.76 (m, 2H), 2.63-2.58 (m, 1H), 2.44-2.32 (m, 1H), 2.21-2.07 (m, 1H), 2.04-1.87 (m, 2H), 1.79-1.69 (m, 1H).

Example 98

1-(3,4-Dichlorobenzyl)-3-(3,3-difluoro-4-(4-hydroxyphenyl)piperidin-1-yl)pyrrolidin-2-one

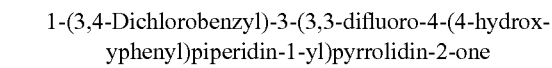

The titled compound of example 98 was prepared as a mixture of diastereomers using the general procedure C. Data for Example 98: LC/MS RT=1.843 min, (M+H)+=454.9; $^1$H NMR (400 MHz, DMSO-d$_6$) δ=9.33-9.28 (m, 1H), 7.62 (dd, J=1.3, 8.3 Hz, 1H), 7.50 (t, J=1.8 Hz, 1H), 7.24 (d, J=2.0 Hz, 1H), 7.09 (d, J=8.5 Hz, 2H), 6.71 (d, J=8.5 Hz, 2H), 4.39 (s, 2H), 4.11-4.05 (m, 1H), 3.65-3.57 (m, 1H), 3.17 (d, J=5.0 Hz, 4H), 3.03-2.76 (m, 2H), 2.42-2.31 (m, 1H), 2.21-2.07 (m, 1H), 1.90 (s, 2H), 1.79-1.69 (m, 1H).

Example 99

Peak-1

(3S)-3-(3,3-Difluoro-4-(4-hydroxyphenyl)piperidin-1-yl)-1-(4-(trifluoromethyl)benzyl)-pyrrolidin-2-one

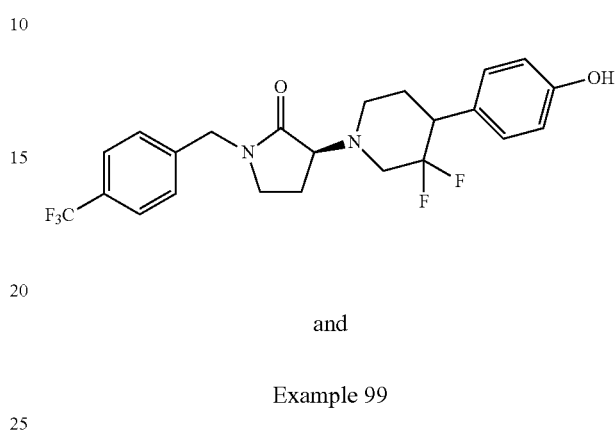

and

Example 99

Peak-2

(3S)-3-(3,3-Difluoro-4-(4-hydroxyphenyl)piperidin-1-yl)-1-(4-(trifluoromethyl)benzyl)-pyrrolidin-2-one

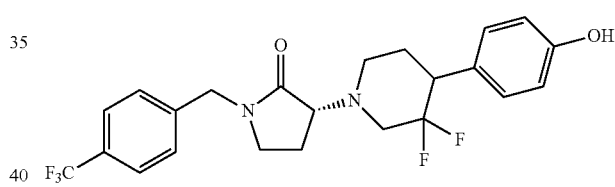

3-(3,3-Difluoro-4-(4-hydroxyphenyl)piperidin-1-yl)-1-(4-(trifluoromethyl)benzyl)-pyrrolidin-2-one was prepared as a mixture of diastereomers using the general procedure C. The mixture of diastereomers was separated into the individual homochiral compounds of example 99 P-1 and P-2 by SFC using method 100. The relative and absolute configurations of were not determined and are arbitrarily named P-1 and P-2 based on the order of elution during the SFC purification. Data for Example 99, P-1: SFC (Method 105) RT=2.8 min. LC/MS (Method O): RT=2.156 min, (M+H)+=455.2; $^1$H NMR (400 MHz, methanol-d$_4$) δ ppm 1.80-1.86 (m, 1H) 2.02-2.32 (m, 3H) 2.61-2.74 (m, 1H) 2.84-3.06 (m, 3H) 3.23-3.30 (m, 1H) 3.38-3.46 (m, 1H) 3.71 (t, J=8.78 Hz, 1H) 4.50-4.64 (m, 2H) 6.71-6.79 (m, 2H) 7.15 (d, J=8.53 Hz, 2H) 7.49 (d, J=8.03 Hz, 2H) 7.68 (d, J=8.53 Hz, 2H). Data for Example 99, P-2: SFC (Method 105) RT=3.36 min. LC/MS (Method O): RT=2.152 min, (M+H)+=455.2; $^1$H NMR (400 MHz, methanol-d$_4$) δ ppm 1.27-1.37 (m, 1H) 2.02-2.30 (m, 3H) 2.54 (t, J=11.04 Hz, 1H) 3.07-3.20 (m, 4H) 3.24-3.30 (m, 2H) 3.35-3.56 (m, 1H) 3.74 (t, J=8.78 Hz, 1H) 4.55-4.60 (m, 2H) 6.72-6.79 (m, 2H) 7.15 (d, J=8.53 Hz, 2H) 7.49 (d, J=8.03 Hz, 2H) 7.68 (d, J=8.03 Hz, 2H).

Example 100

1-(3-Chloro-4-fluorobenzyl)-3-(3,3-difluoro-4-(4-hydroxyphenyl)piperidin-1-yl)pyrrolidin-2-one

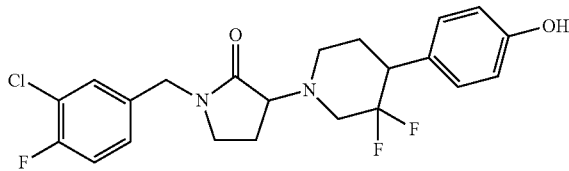 [SMILES: O=C1C(N2CCC(c3ccc(O)cc3)C(F)(F)C2)CCN1Cc1ccc(F)c(Cl)c1]

The titled compound of example 100 was prepared as a mixture of diastereomers using the general procedure C. Data for Example 100: LC/MS RT=1.726 min, (M+H)+=439.0; $^1$H NMR (400 MHz, methanol-$d_4$) δ=7.47-7.42 (m, 1H), 7.30-7.23 (m, 2H), 7.18-7.12 (m, 2H), 6.79-6.72 (m, 2H), 4.52-4.41 (m, 2H), 3.75-3.66 (m, 1H), 3.30-3.26 (m, 1H), 3.20-3.08 (m, 2H), 3.01-2.83 (m, 2H), 2.71-2.49 (m, 1H), 2.33-2.07 (m, 3H), 1.89-1.79 (m, 1H).

General Procedure D

Used for preparation of Examples 101-139.

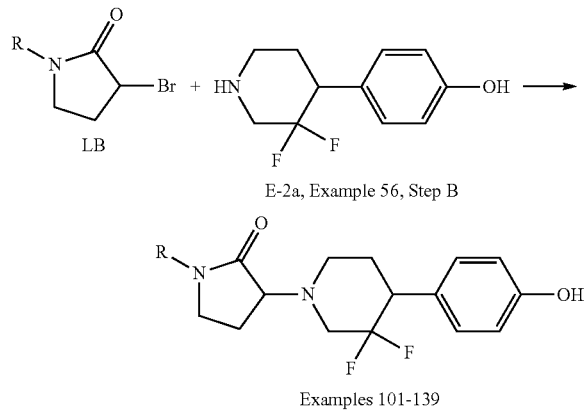

To a microwave vial containing 4-(3,3-difluoropiperidin-4-yl)phenol (25 mg, 0.12 mmol, E-2a, Example 56, step B) and the appropriate lactam bromide (0.29 mmol, LB) was added DMF (1 mL) and triethylamine (0.08 mL, 0.6 mmol). The vial was capped and the reaction mixture was heated to 120° C. using microwave irradiation for 1 h. LC/MS data were collected using method 100. The samples were directly purified by preparative HPLC under conditions B. Products are a mixture of diastereoisomers. In some cases, the diastereoismers were further separated into the individual homochiral components under the conditions reported in the specific examples. Assignment of lactam stereochemistry could be inferred through biological activity, but was not unambiguously determined. Individual compounds are identified by the retention time during SFC. The absolute configuration of the homochiral 4-(3,3-difluoropiperidin-4-yl)phenol used has not been determined.

Example 101

Peak-1

(3S)-1-(3-Chloro-4-(difluoromethoxy)phenyl)-3-(3,3-difluoro-4-(4-hydroxyphenyl)-piperidin-1-yl)pyrrolidin-2-one

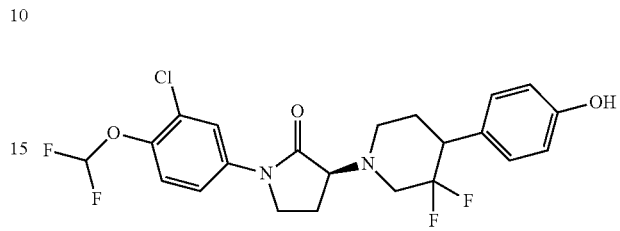

and

Example 101

Peak-2

(3R)-1-(3-Chloro-4-(difluoromethoxy)phenyl)-3-(3,3-difluoro-4-(4-hydroxyphenyl)-piperidin-1-yl)pyrrolidin-2-one

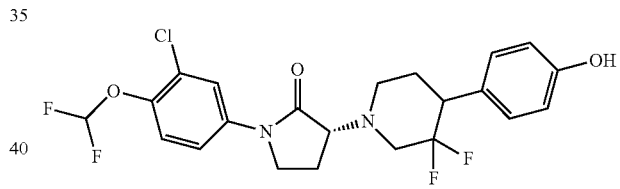

1-(3-Chloro-4-(difluoromethoxy)phenyl)-3-(3,3-difluoro-4-(4-hydroxyphenyl)piperidin-1-yl)pyrrolidin-2-one was prepared as a mixture of diastereomers using the general procedure D. The mixture of diastereomers was separated into the individual homochiral compounds of example 101 P-1 and P-2 by SFC using method 106. The relative and absolute configurations of were not unambiguously determined and are arbitrarily named P-1 and P-2 based on the order of elution during the SFC purification. Data for Example 101, P-1: SFC (Method 106) RT=2.79 min; LC/MS (Method O): RT=2.208 min, (M+H)+=473.0; $^1$H NMR (400 MHz, methanol-$d_4$) δ ppm 1.89 (br. s., 1H) 2.15-2.25 (m, 2H) 2.35-2.47 (m, 2H) 2.58-2.66 (m, 2H) 3.09-3.29 (m, 4H) 3.74-3.92 (m, 3H) 6.65-7.04 (m, 3H) 7.16 (d, J=8.53 Hz, 1H) 7.34 (d, J=9.04 Hz, 1H) 7.57-7.67 (m, 1H) 8.00 (d, J=2.51 Hz, 1H). Data for Example 101, P-2: SFC (Method 106) RT=3.36 min; LC/MS (Method O): RT=2.210 min, (M+H)+=473.0; $^1$H NMR (400 MHz, methanol-$d_4$) δ ppm 1.85 (d, J=13.05 Hz, 1H) 2.12-2.27 (m, 2H) 2.34-2.44 (m, 1H) 2.68-2.82 (m, 2H) 2.87-3.10 (m, 4H) 3.48-3.53 (m, 1H) 3.78-3.89 (m, 3H) 6.61-6.91 (m, 3H) 7.16 (d, J=8.53 Hz, 2H) 7.35 (d, J=9.04 Hz, 1H) 7.61 (dd, J=9.04, 2.51 Hz, 1H) 8.00 (d, J=3.01 Hz, 1H).

Example 102

Peak-1

(3S)-1-Benzyl-3-(3,3-difluoro-4-(4-hydroxyphenyl)piperidin-1-yl)pyrrolidin-2-one

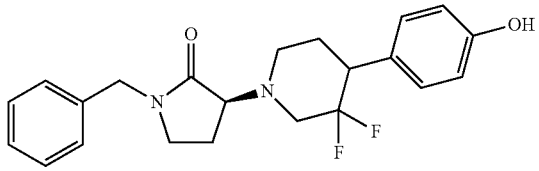 [SMILES: O=C1[C@@H](N2CCC(c3ccc(O)cc3)C(F)(F)C2)CCN1Cc1ccccc1]

and

Example 102

Peak-2

(3R)-1-Benzyl-3-(3,3-difluoro-4-(4-hydroxyphenyl)piperidin-1-yl)pyrrolidin-2-one

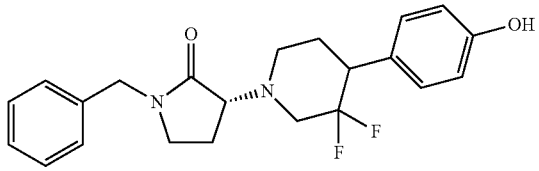 [SMILES: O=C1[C@H](N2CCC(c3ccc(O)cc3)C(F)(F)C2)CCN1Cc1ccccc1]

1-Benzyl-3-(3,3-difluoro-4-(4-hydroxyphenyl)piperidin-1-yl)pyrrolidin-2-one was prepared as a mixture of diastereomers using the general procedure D. The mixture of diastereomers was separated into the individual homochiral compounds of example 102 P-1 and P-2 by SFC using method 105. The relative and absolute configurations of were not unambiguously determined and are arbitrarily named P-1 and P-2 based on the order of elution during the SFC purification. Data for Example 102, P-1: SFC (Method 105) RT=2.62 min; LC/MS (Method O): RT=2.106 min, (M+H)+=387.2; $^1$H NMR (400 MHz, methanol-$d_4$) δ=7.41-7.26 (m, 5H), 7.15 (d, J=8.5 Hz, 2H), 6.79-6.72 (m, 2H), 4.58-4.41 (m, 2H), 3.72 (t, J=8.8 Hz, 1H), 3.30-3.23 (m, 2H), 3.19-3.08 (m, 3H), 3.00-2.86 (m, 1H), 2.54 (t, J=11.5 Hz, 1H), 2.30-2.01 (m, 3H), 1.85 (tdd, J=2.4, 4.6, 13.1 Hz, 1H). Data for Example 102, P-2: LC/MS RT=1.633 min; (M+H)+=401.0 $^1$H NMR (400 MHz, DMSO-$d_6$) δ=9.33-9.28 (m, 1H), 7.19 (d, J=1.5 Hz, 6H), 6.75-6.67 (m, 2H), 4.50-4.41 (m, 1H), 4.35-4.25 (m, 1H), 3.69-3.53 (m, 1H), 3.22-3.02 (m, 3H), 2.94-2.80 (m, 1H), 2.46-2.32 (m, 1H), 2.25 (s, 4H), 2.17-2.06 (m, 1H), 1.99-1.65 (m, 3H).

Example 103

3-(3,3-Difluoro-4-(4-hydroxyphenyl)piperidin-1-yl)-1-(2-methylbenzyl)pyrrolidin-2-one

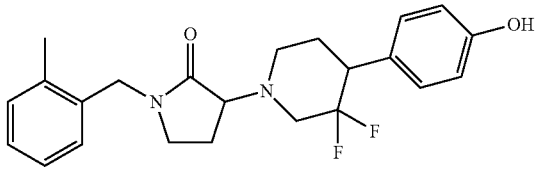

The titled compound of example 100 was prepared as a mixture of diastereomers using the general procedure D. Data for Example 103: LC/MS RT=1.633 min; (M+H)+=401.0 $^1$H NMR (400 MHz, DMSO-$d_6$) δ=9.33-9.28 (m, 1H), 7.19 (d, J=1.5 Hz, 6H), 6.75-6.67 (m, 2H), 4.50-4.41 (m, 1H), 4.35-4.25 (m, 1H), 3.69-3.53 (m, 1H), 3.22-3.02 (m, 3H), 2.94-2.80 (m, 1H), 2.46-2.32 (m, 1H), 2.25 (s, 4H), 2.17-2.06 (m, 1H), 1.99-1.65 (m, 3H).

Example 104

3-(3,3-Difluoro-4-(4-hydroxyphenyl)piperidin-1-yl)-1-(3-methylbenzyl)pyrrolidin-2-one

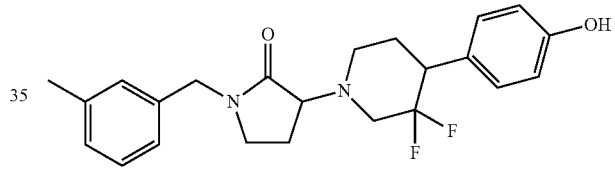

The titled compound of example 104 was prepared as a mixture of diastereomers using the general procedure D. Data for Example 104: LC/MS RT=1.647 min; (M+H)+=401.0 $^1$H NMR (400 MHz, DMSO-$d_6$) δ=9.31 (s, 1H), 7.27-7.19 (m, 1H), 7.12-6.99 (m, 5H), 6.72 (d, J=8.0 Hz, 2H), 4.42-4.24 (m, 2H), 3.60 (d, J=9.0 Hz, 1H), 3.22-3.03 (m, 3H), 2.92-2.56 (m, 2H), 2.29 (s, 3H), 2.13 (br. s., 1H), 1.93 (br. s., 2H), 1.79-1.68 (m, 1H).

Example 105

3-(3,3-Difluoro-4-(4-hydroxyphenyl)piperidin-1-yl)-1-(4-(difluoromethoxy)benzyl)-pyrrolidin-2-one

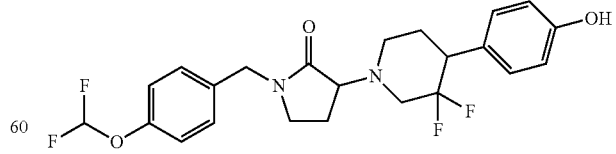

The titled compound of example 105 was prepared as a mixture of diastereomers using the general procedure D. Data for Example 105: LC/MS RT=1.622 min; (M+H)+=453.0 $^1$H NMR (400 MHz, DMSO-$d_6$) δ=9.31 (s, 1H), 7.47-7.24 (m, 3H), 7.22-7.00 (m, 6H), 6.72 (d, J=8.5 Hz, 2H), 4.44-4.31 (m, 2H), 3.60 (d, J=8.0 Hz, 1H), 3.23-3.05 (m, 4H), 3.00-2.77 (m, 2H), 2.44-2.31 (m, 1H), 2.17-2.06 (m, 1H), 1.94 (d, J=17.1 Hz, 2H), 1.79-1.69 (m, 1H).

Example 106

Peak-1

(3S)-1-(4-Chlorobenzyl)-3-(3,3-difluoro-4-(4-hydroxyphenyl)piperidin-1-yl)pyrrolidin-2-one

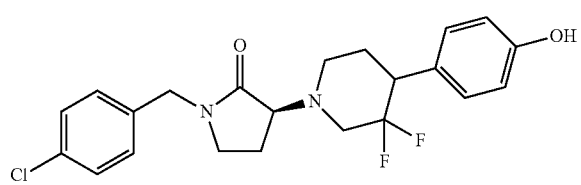 [SMILES: O=C1[C@@H](N2CCC(c3ccc(O)cc3)C(F)(F)C2)CCN1Cc1ccc(Cl)cc1]

and

Example 106

Peak-2

(3R)-1-(4-Chlorobenzyl)-3-(3,3-difluoro-4-(4-hydroxyphenyl)piperidin-1-yl)pyrrolidin-2-one

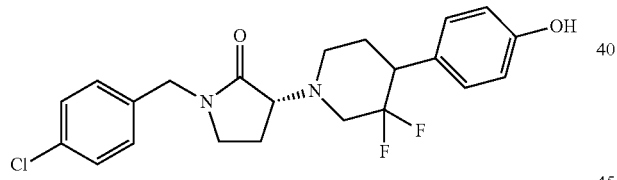

1-(4-Chlorobenzyl)-3-(3,3-difluoro-4-(4-hydroxyphenyl)piperidin-1-yl)pyrrolidin-2-one was prepared as a mixture of diastereomers using the general procedure D. The mixture of diastereomers was separated into the individual homochiral compounds of example 106 P-1 and P-2 by SFC using method 106. The relative and absolute configurations were not determined and are arbitrarily named P-1 and P-2 based on the order of elution during the SFC purification. Data for Example 106, P-1: SFC (Method 106) RT=3.14 min; LC/MS (Method O): RT=2.127 min, (M+H)+=421.2; $^1$H NMR (400 MHz, methanol-d4) δ ppm 7.35-7.41 (m, 2H) 7.26-7.31 (m, 2H) 7.15 (d, J=8.35 Hz, 2H) 6.73-6.78 (m, 2H) 4.40-4.54 (m, 2H) 3.69-3.75 (m, 1H) 3.61-3.62 (m, 0H) 3.45-3.50 (m, 1H) 3.23-3.31 (m, 1H) 3.09-3.20 (m, 3H) 2.86-3.05 (m, 1H) 2.49-2.58 (m, 1H) 2.00-2.31 (m, 3H) 1.79-1.90 (m, 1H). Data for Example 106, P-2: SFC (Method 106) RT=4.29 min; LC/MS (Method O): RT=2.128 min, (M+H)+=421.2; $^1$H NMR (400 MHz, methanol-d4) δ ppm 7.34-7.41 (m, 2H) 7.24-7.30 (m, 2H) 7.15 (d, J=8.35 Hz, 2H) 6.73-6.78 (m, 2H) 4.48 (q, J=14.87 Hz, 2H) 3.69 (t, J=8.85 Hz, 1H) 3.62 (s, 1H) 3.38-

3.49 (m, 1H) 3.23-3.31 (m, 1H) 3.06 (q, J=7.26 Hz, 1H) 2.84-3.01 (m, 2H) 2.60-2.73 (m, 1H) 1.98-2.31 (m, 3H) 1.79-1.89 (m, 1H).

Example 107

Peak-1

(3S)-1-(4-Chloro-3-fluorobenzyl)-3-(3,3-difluoro-4-(4-hydroxyphenyl)piperidin-1-yl)pyrrolidin-2-one

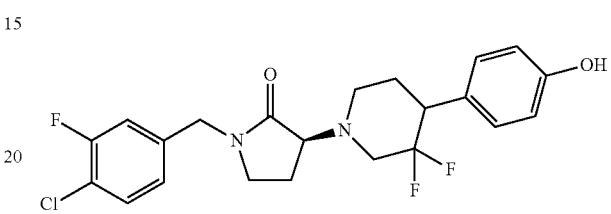

and

Example 107

Peak-2

(3R)-1-(4-Chloro-3-fluorobenzyl)-3-(3,3-difluoro-4-(4-hydroxyphenyl)piperidin-1-yl)pyrrolidin-2-one 1-(4-Chloro-3-fluorobenzyl)-3-(3,3-difluoro-4-(4-hydroxyphenyl)piperidin-1-yl)pyrrolidin-2-one was prepared as a mixture of diastereomers using the general procedure D. The mixture of diastereomers was separated into the individual homochiral compounds of example 107 P-1 and P-2 by SFC using method 105. The relative and absolute configurations were not determined and are arbitrarily named P-1 and P-2 based on the order of elution during the SFC purification. Data for Example 107, P-1: SFC (Method 105) RT=2.85 min; LC/MS (Method O): RT=2.093 min, (M+H)+=439.0; $^1$H NMR (400 MHz, methanol-d$_4$) δ ppm 1.85 (ddt, J=13.18, 4.64, 2.38, 2.38 Hz, 1H) 2.03-2.31 (m, 3H) 2.53 (t, J=11.29 Hz, 1H) 3.05-3.12 (m, 1H) 3.13-3.18 (m, 2H) 3.26-3.31 (m, 2H) 3.72 (t, J=8.78 Hz, 1H) 4.41-4.54 (m, 2H) 6.73-6.79 (m, 2H) 7.08-7.23 (m, 4H) 7.48 (t, J=8.03 Hz, 1H). Data for Example 107, P-2: SFC (Method 105) RT=3.99 min; LC/MS (Method Q): RT=1.648 min, (M+H)+=439.0; $^1$H NMR (400 MHz, methanol-d$_4$) δ ppm 1.85 (ddt, J=13.18, 4.64, 2.38, 2.38 Hz, 1H) 2.03-2.31 (m, 3H) 2.53 (t, J=11.29 Hz, 1H) 3.05-3.12 (m, 1H) 3.13-3.18 (m, 2H) 3.26-3.31 (m, 2H) 3.72

(t, J=8.78 Hz, 1H) 4.41-4.54 (m, 2H) 6.73-6.79 (m, 2H) 7.08-7.23 (m, 4H) 7.48 (t, J=8.03 Hz, 1H).

Example 108

Peak-1

(3S)-3-(3,3-Difluoro-4-(4-hydroxyphenyl)piperidin-1-yl)-1-(3,4-difluorobenzyl)-pyrrolidin-2-one

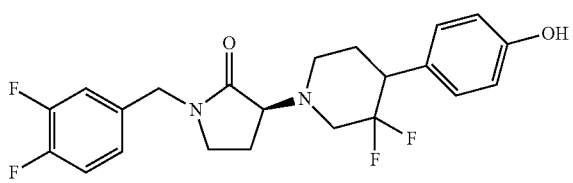 [SMILES: O=C1[C@@H](N2CCC(c3ccc(O)cc3)C(F)(F)C2)CCN1Cc1ccc(F)c(F)c1]

and

Example 108

Peak-2

(3R)-3-(3,3-Difluoro-4-(4-hydroxyphenyl)piperidin-1-yl)-1-(3,4-difluorobenzyl)-pyrrolidin-2-one

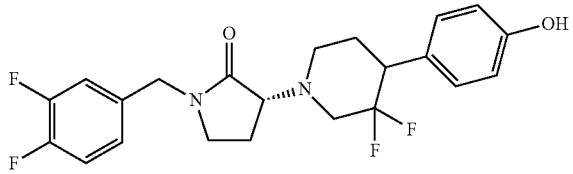 [SMILES: O=C1[C@H](N2CCC(c3ccc(O)cc3)C(F)(F)C2)CCN1Cc1ccc(F)c(F)c1]

3-(3,3-Difluoro-4-(4-hydroxyphenyl)piperidin-1-yl)-1-(3,4-difluorobenzyl)pyrrolidin-2-one was prepared as a mixture of diastereomers using the general procedure D. The mixture of diastereomers was separated into the individual homochiral compounds of example 108 P-1 and P-2 by SFC using method 105. The relative and absolute configurations were not determined and are arbitrarily named P-1 and P-2 based on the order of elution during the SFC purification. Data for Example 108, P-1: SFC (Method 105) RT=2.27 min; LC/MS (Method O): RT=2.149 min, (M+H)+=423.2; $^1$H NMR (400 MHz, methanol-$d_4$) δ=7.32-7.19 (m, 2H), 7.18-7.08 (m, 3H), 6.79-6.72 (m, 2H), 4.60-4.40 (m, 2H), 3.72 (t, J=9.0 Hz, 1H), 3.30-3.24 (m, 2H), 3.20-3.05 (m, 3H), 3.00-2.85 (m, 1H), 2.53 (t, J=11.0 Hz, 1H), 2.30-2.02 (m, 3H), 1.85 (tdd, J=2.4, 4.6, 13.2 Hz, 1H). Data for Example 108, P-2: SFC (Method 105) RT=2.85 min; LC/MS (Method O): RT=2.182 min, (M+H)+=423.2; $^1$H NMR (400 MHz, methanol-$d_4$) δ=7.34-7.07 (m, 5H), 6.76 (d, J=8.5 Hz, 2H), 4.53-4.39 (m, 2H), 3.69 (t, J=9.0 Hz, 1H), 3.46-3.38 (m, 1H), 3.30-3.24 (m, 2H), 3.02-2.83 (m, 3H), 2.73-2.59 (m, 1H), 2.29-2.03 (m, 3H), 1.88-1.79 (m, 1H).

Example 109

1-(3,4-Dichlorobenzyl)-3-(3,3-difluoro-4-(4-hydroxyphenyl)piperidin-1-yl)pyrrolidin-2-one

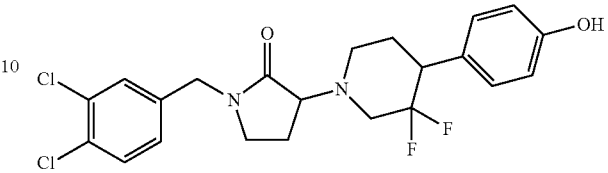

The titled compound of example 109 was prepared as a mixture of diastereomers using the general procedure D. Data for Example 109: LC/MS RT=1.833 min, (M+H)+=454.9; $^1$H NMR (400 MHz, DMSO-$d_6$) δ=9.31 (s, 1H), 7.62 (dd, J=1.5, 8.0 Hz, 2H), 7.51 (d, J=1.5 Hz, 1H), 7.23 (dd, J=2.0, 8.0 Hz, 1H), 7.09 (d, J=8.5 Hz, 2H), 6.72 (d, J=8.5 Hz, 2H), 4.39 (s, 2H), 4.09 (q, J=5.5 Hz, 1H), 3.23-3.13 (m, 4H), 2.94-2.83 (m, 1H), 2.43-2.34 (m, 1H), 2.21-2.09 (m, 2H), 2.01-1.70 (m, 3H).

Example 110

3-(3,3-Difluoro-4-(4-hydroxyphenyl)piperidin-1-yl)-1-(4-(trifluoromethyl)benzyl)-pyrrolidin-2-one

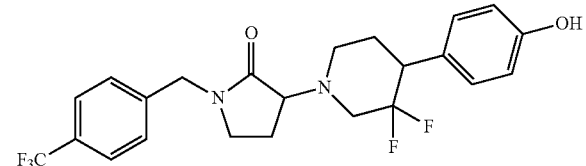

The titled compound of example 110 was prepared as a mixture of diastereomers using the general procedure D. Data for Example 110: LC/MS RT=1.789 min, (M+H)+=455.0; $^1$H NMR (400 MHz, methanol-$d_4$) δ=7.69 (d, J=8.0 Hz, 2H), 7.49 (d, J=8.0 Hz, 2H), 7.15 (d, J=8.5 Hz, 2H), 6.79-6.73 (m, 2H), 4.60 (s, 2H), 3.81 (s, 2H), 3.77-3.68 (m, 1H), 3.46-3.40 (m, 1H), 3.30-3.26 (m, 1H), 3.21-3.09 (m, 2H), 3.02-2.86 (m, 2H), 2.74-2.51 (m, 1H), 2.06 (s, 3H), 1.90-1.80 (m, 1H).

Example 111

1-(3-Chloro-4-fluorobenzyl)-3-(3,3-difluoro-4-(4-hydroxyphenyl)piperidin-1-yl)pyrrolidin-2-one

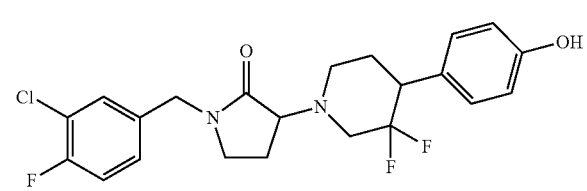 [SMILES: O=C1C(N2CCC(c3ccc(O)cc3)C(F)(F)C2)CCN1Cc1ccc(Cl)c(Cl)c1]

The titled compound of example 110 was prepared as a mixture of diastereomers using the general procedure D. Data for Example 110: LC/MS RT=1.744 min, (M+H)+=439.0; $^1$H NMR (400 MHz, methanol-d₄) δ=7.47-7.41 (m, 1H), 7.28-7.24 (m, 2H), 7.18-7.12 (m, 2H), 6.76 (d, J=9.0 Hz, 2H), 4.52-4.39 (m, 2H), 3.70 (q, J=9.4 Hz, 1H), 3.45-3.37 (m, 1H), 3.30-3.25 (m, 1H), 3.21-3.08 (m, 2H), 3.01-2.85 (m, 2H), 2.69 (d, J=10.5 Hz, 1H), 2.53 (t, J=11.3 Hz, 1H), 2.30-2.03 (m, 3H), 1.85 (tdd, J=2.3, 4.8, 13.2 Hz, 1H).

Example 112

Peak-1

(R)-3-((3S,4R)-3-fluoro-4-(4-hydroxyphenyl)piperidin-1-yl)-1-(4-methylbenzyl)pyrrolidin-2-one

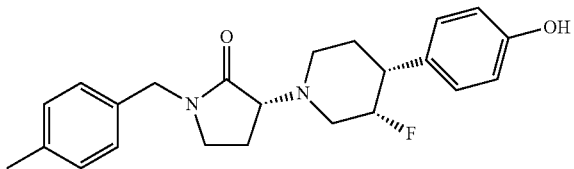 [SMILES: Cc1ccc(CN2CC[C@@H](N3CC[C@H](c4ccc(O)cc4)[C@H](F)C3)C2=O)cc1]

and

Example 112

Peak-2

(R)-3-((3R,4S)-3-fluoro-4-(4-hydroxyphenyl)piperidin-1-yl)-1-(4-methylbenzyl)pyrrolidin-2-one

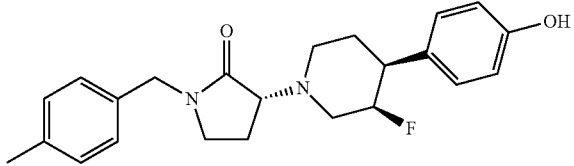 [SMILES: Cc1ccc(CN2CC[C@@H](N3CC[C@@H](c4ccc(O)cc4)[C@@H](F)C3)C2=O)cc1]

Step A. (S)-3-((tert-Butyldimethylsilyl)oxy)pyrrolidin-2-one

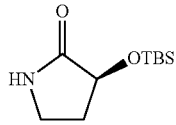

A stirred solution of commercial (S)-3-hydroxypyrrolidin-2-one (5 g, 50 mmol) in DCM (198 ml) was treated with DMAP (0.2 g, 1.63 mmol), imidazole (6.73 g, 99 mmol), and TBDMS-Cl (8.94 g, 59 mmol). The reaction mixture was stirred at rt for 16 h, and then was washed with a satd. NaHCO₃ solution. The organic layer was concentrated and the crude reaction product was purified by silica gel chromatography, eluting with 50% ethyl acetate in petroleum ether. The desired product was isolated as a white solid (8.1 g, 76%). LC/MS (M+H)+=216.2; ¹H NMR (400 MHz, chloroform-d) δ 6.40 (br. s., 1H), 4.26 (t, J=7.8 Hz, 1H), 3.42-3.34 (m, 1H), 3.29-3.21 (m, 1H), 2.36 (dtd, J=12.7, 7.3, 3.3 Hz, 1H), 2.07-1.96 (m, 1H), 0.91 (s, 9H), 0.15 (d, J=7.0 Hz, 6H).

Step B. (S)-3-((tert-Butyldimethylsilyl)oxy)-1-(4-methylbenzyl)pyrrolidin-2-one

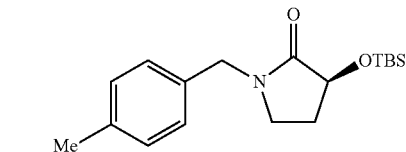 [SMILES: Cc1ccc(CN2CC[C@H](O[Si](C)(C)C(C)(C)C)C2=O)cc1]

(S)-3-((tert-Butyldimethylsilyl)oxy)pyrrolidin-2-one (5 g, 23.22 mmol) was dissolved in anhydrous THF (46.4 ml) and the reaction mixture was cooled to 0° C. under a nitrogen atmosphere. Sodium hydride (1.393 g, 34.8 mmol) was then added in one portion and the reaction mixture was allowed to stir for 5 min before the dropwise addition of 1-(bromomethyl)-4-methylbenzene (5.37 g, 29 mmol) in anhydrous THF (46 ml). The reaction was allowed to stir at 0° C. for 5 min, then the cooling bath was removed and mixture was allowed to warm to rt overnight. The reaction was cautiously quenched with water (100 mL) and then extracted with ethyl acetate (3×100 mL). The combined organic layers were then washed with brine (200 mL) and dried (MgSO4). Evaporation of the solvent in vacuo gave the crude product (9.6 g, oil) which was then purified by silica gel chromatography (330 g of silica) eluting with a gradient of 0% to 20% ethyl acetate in hexanes to provide 6.53 g (88%) of the desired product. LC/MS (Conditions B) RT=4.320 min, (M+H)+=320.3; ¹H NMR (400 MHz, chloroform-d) δ 7.15 (s, 4H), 4.42 (s, 2H), 4.37 (t, J=7.6 Hz, 1H), 3.32-3.18 (m, 1H), 3.10 (dt, J=9.7, 7.5 Hz, 1H), 2.36 (s, 3H), 2.29 (dtd, J=12.6, 7.6, 3.1 Hz, 1H), 1.97-1.84 (m, 1H), 0.95 (s, 9H), 0.20 (d, J=10.3 Hz, 6H).

Step C. (S)-3-Hydroxy-1-(4-methylbenzyl)pyrrolidin-2-one

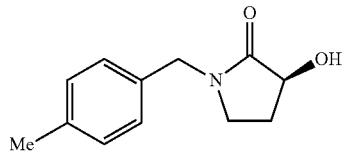 [SMILES: Cc1ccc(CN2CC[C@H](O)C2=O)cc1]

HCl (4 M in 1,4-dioxane, 25.5 ml, 102 mmol) was added in one portion to a solution of (S)-3-((tert-butyldimethylsilyl)oxy)-1-(4-methylbenzyl)pyrrolidin-2-one (6.53 g, 20.4 mmol) in anhydrous DCM (20.44 ml) at rt. A slight exotherm was noted. The reaction mixture was allowed to stir at rt for 2 h and then evaporated in vacuo. The residue was taken up in DCM (100 mL) and washed with a satd. sodium bicarbonate solution (100 mL) and brine (50 mL), and then the solution was dried over MgSO₄ and concentrated to a residue. The crude product was purified by silica gel chromatography (120 g of silica) eluting with a gradient of 40% to 100% ethyl acetate in hexanes to provide 3.73 g (89%) of the desired product. LC/MS (Conditions B) RT=2.338 min, (M+H)+=206.2; ¹H NMR (400 MHz, chloroform-d) δ 7.26-7.02 (m, 4H), 4.43 (d, J=3.5 Hz, 2H), 4.41-4.37 (m, 1H), 3.66 (d, J=2.6

Hz, 1H), 3.34-3.05 (m, 2H), 2.41 (dddd, J=12.8, 8.4, 6.6, 2.2 Hz, 1H), 2.34 (s, 3H), 1.93 (dq, J=12.8, 8.8 Hz, 1H).

Step D. (S)-1-(4-Methylbenzyl)-2-oxopyrrolidin-3-yl methanesulfonate

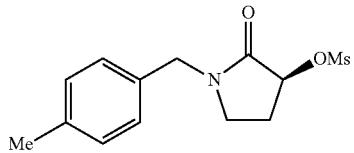 [SMILES: Cc1ccc(CN2CC[C@H](OS(C)(=O)=O)C2=O)cc1]

Triethylamine (0.51 ml, 3.6 mmol) was added to a cooled solution of (S)-3-hydroxy-1-(4-methylbenzyl)pyrrolidin-2-one (0.5 g, 2.4 mmol) in anhydrous DCM (12.2 ml) at 0° C. under a nitrogen atmosphere. Methanesulfonyl chloride (0.2 ml, 2.6 mmol) was then added dropwise and the reaction was allowed to stir at 0° C. for 15 min before quenching with a satd. sodium bicarbonate solution (10 mL). The mixture was allowed to warm to rt and the aqueous layer was separated and extracted with DCM (2×). The combined oranic layers were dried over MgSO$_4$ and evaporated in vacuo to give a white solid (0.73 g) which was then purified by silica gel chromatography (40 g of silica) eluting with a gradient of 0% to 50% ethyl acetate in hexanes to provide 0.63 g (91%) of the desired product as a white solid.

Step E. cis-tert-Butyl 4-(4-(benzyloxy)phenyl)-3-fluoro-4-hydroxypiperidine-1-carboxylate

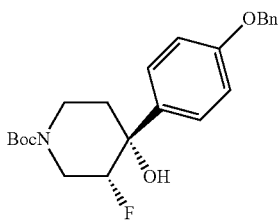 [SMILES: CC(C)(C)OC(=O)N1CC[C@@](O)(c2ccc(OCc3ccccc3)cc2)[C@H](F)C1]

To a cloudy solution of tert-butyl 4-(4-(benzyloxy)phenyl)-5,6-dihydropyridine-1(2H)-carboxylate (Example 50, step C, 2.8 g, 7.7 mmol) in acetonitrile (30 mL) and water (8 mL) was added 1.2 eq. of Selectfluor at rt. After stirring at rt for 1 h, another 0.5 eq. of Selectfluor was added, and the mixture was stirred at 50° C. for 30 min. A saturated NaHCO$_3$ solution (100 mL) was added and the mixture was extracted with 3×150 mL of EtOAc. The combined organic layers were concentrated. The residue was dissolved in 20 mL of CH$_2$Cl$_2$. Triethylamine (3.20 mL, 23 mmol) was added followed by di-tertbutyldicarbonate (4.45 mL, 19.15 mmol). The mixture was stirred at rt for 2 h, and then the mixture was concentrated. The residue was purified via silica gel chromatography (80 g of silica) eluting with a gradient of 0 to 100% ethyl acetate in hexanes. The first eluting spot was isolated to give cis-tert-butyl 4-(4-(benzyloxy)phenyl)-3-fluoro-4-hydroxypiperidine-1-carboxylate (2.0 g, 5 mmol, 65% yield). LC/MS (Conditions CZ-1, M–t-butyl+AcCN+H)$^+$=387.2. (M–t-butyl+AcCN)+=369.25. RT 1.392 min; $^1$H NMR (500 MHz, chloroform-d) δ 7.55-7.31 (m, 7H), 7.09-6.90 (m, 2H), 5.09 (s, 2H), 5.05-4.93 (m, 1H), 4.89 (br. s., 1H), 4.31 (br. s., 1H), 3.92 (br. s., 1H), 3.29 (br. s., 1H), 3.25-3.04 (m, 1H), 2.00-1.86 (m, 1H), 1.83 (br. s., 1H), 1.55-1.45 (m, 9H).

Step F. tert-Butyl 4-(4-(benzyloxy)phenyl)-5-fluoro-5,6-dihydropyridine-1(2H)-carboxylate

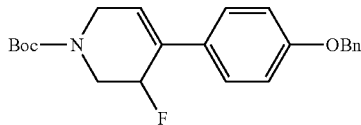 [SMILES: CC(C)(C)OC(=O)N1CC=C(c2ccc(OCc3ccccc3)cc2)C(F)C1]

To a solution of cis-tert-butyl 4-(4-(benzyloxy)phenyl)-3-fluoro-4-hydroxypiperidine-1-carboxylate (2.0 g, 5 mmol) in CH$_2$Cl$_2$ (25 mL) was added 6 mL of TFA dropwise at rt. The mixture was stirred at rt for 2 h. Another 8 mL of TFA was added. After stirring for 1 h, 3 mL more of TFA was added. The mixture was concentrated to dryness in vacuo at rt, then 10 mL of CH$_2$Cl$_2$ and Et$_3$N (4.2 mL, 30 mmol) were added followed by bis-(tert)butyldicarbonate (3.5 mL, 15 mmol) and the resulting mixture was stirred for 16 h. The mixture was concentrated and directly purified via silica gel chromatography (40 g of silica) eluting with a gradient of 0-20% ethyl acetate in hexanes to provide racemic tert-butyl 4-(4-(benzyloxy)phenyl)-5-fluoro-5,6-dihydropyridine-1(2H)-carboxylate (1.35 g, 3.5 mmol, 70.7% yield), LC/MS (Conditions CZ-1, M-Boc+AcCN+H)$^+$=325.25. (M–t-butyl+AcCN+H)$^+$=369.25. RT 1.504 min; $^1$H NMR (500 MHz, chloroform-d) δ 7.48-7.38 (m, 6H), 7.38-7.32 (m, 1H), 6.99 (d, J=8.8 Hz, 2H), 6.34-6.16 (m, 1H), 5.45-5.20 (m, 1H), 5.10 (s, 2H), 4.61-4.37 (m, 2H), 3.81 (br. s., 1H), 3.39-3.24 (m, 1H), 1.59 (s, 3H), 1.52 (s, 9H).

Step G. cis-tert-Butyl 4-(4-(benzyloxy)phenyl)-3-fluoropiperidine-1-carboxylate

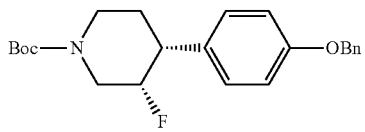 [SMILES: CC(C)(C)OC(=O)N1CC[C@H](c2ccc(OCc3ccccc3)cc2)[C@H](F)C1]

To 10% Pd/C (220 mg) under nitrogen was added a soln of tert-butyl 4-(4-(benzyloxy)-phenyl)-5-fluoro-5,6-dihydropyridine-1(2H)-carboxylate (1.35 g, 3.5 mmol) in ethyl acetate (20 mL). The mixture was stirred at rt under a hydrogen atmosphere at balloon pressure for 45 min. The Pd/C was removed by filtration, and the filtrate was concentrated. The residue was purified via silica gel chromatography (40 g of silica gel) eluting with a gradient of 0-100% ethyl acetate in hexanes to give the product cis-tert-butyl 4-(4-(benzyloxy)phenyl)-3-fluoropiperidine-1-carboxylate (1.05 g, 2.7 mmol, 77% yield). LC/MS (Conditions CZ-1) (M–t-butyl, AcCN+H)$^+$=371.25. RT=1.504 min; $^1$H NMR (500 MHz, chloroform-d) δ 7.45 (d, J=7.6 Hz, 2H), 7.40 (t, J=7.5 Hz, 2H), 7.34 (t, J=7.0 Hz, 1H), 7.22 (d, J=8.4 Hz, 2H), 6.96 (ddd, J=8.9, 2.7, 2.0 Hz, 2H), 5.07 (s, 2H), 4.79-4.60 (m, 1H), 4.55-4.23 (m, 2H), 3.08-2.81 (m, 2H), 2.75 (ddd, J=36.0, 13.4, 3.1 Hz, 1H), 2.21 (qd, J=12.9, 4.3 Hz, 1H), 1.69 (d, J=11.7 Hz, 1H), 1.59 (s, 3H), 1.51 (s, 9H). The structure of this compound was verified by single-crystal X-ray analysis.

Step H.
cis-4-(4-(Benzyloxy)phenyl)-3-fluoropiperidine

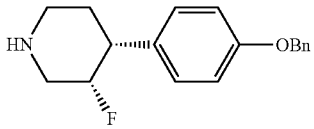 [SMILES: F[C@@H]1CNCC[C@@H]1c1ccc(OCc2ccccc2)cc1]

To a solution of cis-tert-butyl 4-(4-(benzyloxy)phenyl)-3-fluoropiperidine-1-carboxylate (400 mg, 1.04 mmol) in CH$_2$Cl$_2$ (4 mL) was dropwise added TFA (1 mL, 13 mmol) at rt. The mixture was stirred at rt for 2 h and then concentrated. To the residue was added 50 mL of saturated aqueous sodium bicarbonate and the mixture was extracted with 3×60 mL of CH$_2$Cl$_2$. The organic layer was dried over Na$_2$SO$_4$, filtered, and concentrated to dryness to yield 270 mg cis-4-(4-(benzyloxy)phenyl)-3-fluoropiperidine (0.95 mmol, 91%). (M+H)$^+$=286.25. $^1$H NMR (500 MHz, chloroform-d) δ 7.49-7.38 (m, 4H), 7.34 (t, J=7.5 Hz, 1H), 7.26-7.20 (m, J=8.5 Hz, 2H), 7.01-6.93 (m, 2H), 5.08 (s, 2H), 4.70 (d, J=49.0 Hz, 1H), 3.38 (t, J=12.5 Hz, 1H), 3.25 (dt, J=13.4, 2.0 Hz, 1H), 2.93 (d, J=14.3 Hz, 1H), 2.90-2.68 (m, 3H), 2.09 (qd, J=12.9, 4.1 Hz, 1H), 1.69 (d, J=14.3 Hz, 1H).

Step I. cis-4-(3-Fluoropiperidin-4-yl)phenol

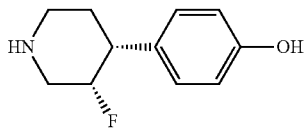 [SMILES: Oc1ccc([C@H]2CCNC[C@H]2F)cc1]

To 10% Pd/C (40 mg) under nitrogen was added a solution of cis-4-(4-(benzyloxy)phenyl)-3-fluoropiperidine (140 mg, 0.49 mmol) in IPA (4 mL). The mixture was stirred under a hydrogen atmosphere using balloon pressure at rt for 2 h. The Pd/C was removed by filtration through a glass fiber filter. The filtrate was concentrated to give cis-4-(3-fluoropiperidin-4-yl)phenol (90 mg, 0.46 mmol, 94% yield). LC/MS (Method J, M+H)$^+$=196.25, RT=0.706 min; $^1$H NMR (500 MHz, methanol-d$_4$) δ 7.14 (d, J=8.4 Hz, 2H), 6.74 (d, J=8.7 Hz, 2H), 4.63 (d, J=48.4 Hz, 1H), 3.30-3.22 (m, 1H), 3.15 (dt, J=13.1, 2.0 Hz, 1H), 2.95-2.66 (m, 3H), 2.12 (qd, J=13.0, 4.2 Hz, 1H), 1.64 (dd, J=13.4, 3.0 Hz, 1H).

Step J. (R)-3-((3S,4R)-3-fluoro-4-(4-hydroxyphenyl)piperidin-1-yl)-1-(4-methylbenzyl)pyrrolidin-2-one and (R)-3-((3R,4S)-3-fluoro-4-(4-hydroxyphenyl)piperidin-1-yl)-1-(4-methylbenzyl)pyrrolidin-2-one

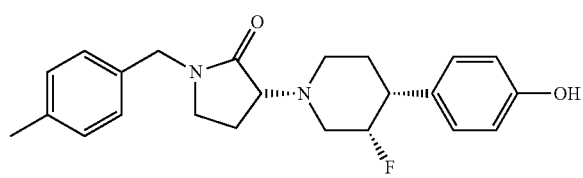

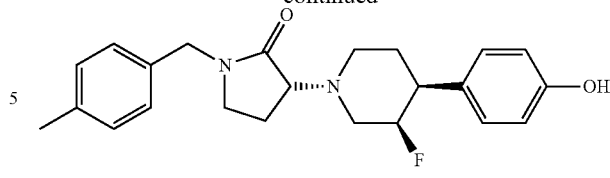

To a solution of cis-4-(3-fluoropiperidin-4-yl)phenol (60 mg, 0.31 mmol) in 1.0 mL of CH$_3$CN and DIPEA (0.2 mL, 1.2 mmol) at 80° C. was added a solution of (S)-1-(4-methylbenzyl)-2-oxopyrrolidin-3-yl methanesulfonate (87 mg, 0.3 mmol) in 0.5 mL of CH$_3$CN over 1.5 h. The mixture was then stirred at 80° C. for 16 h. The mixture was allowed to cool to rt and then concentrated. The residue was purified via silica gel chromatography (4 g of silica) eluting with a gradient of 0-100% EtOAc in hexanes to give a mixture of two diastereomers, which were further separated via chiral HPLC under the following conditions: Chiralcel OD column (21× 250 mm, 10μ) eluting with an isocratic mixture of 30% B where solvent A=0.1% diethylamine in n-heptane and solvent B=100% ethanol. The absolute stereochemistry of the 2 products has not been assigned and is shown and named for convenience. The first eluting isomer (Example 112, P-1) was (R)-3-((3S,4R)-3-fluoro-4-(4-hydroxyphenyl)piperidin-1-yl)-1-(4-methylbenzyl)pyrrolidin-2-one (33.8 mg, 0.086 mmol, 28% yield). $^1$H NMR (500 MHz, methanol-d$_4$) δ 7.21-7.07 (m, 6H), 6.78-6.68 (m, 2H), 4.70 (d, J=48.8 Hz, 1H), 4.41 (dd, J=58.0, 14.5 Hz, 2H), 3.61 (t, J=8.8 Hz, 1H), 3.30-3.03 (m, 5H), 2.77-2.60 (m, 1H), 2.51 (t, J=11.1 Hz, 1H), 2.32 (s, 3H), 2.31-2.15 (m, 2H), 2.01 (dq, J=13.2, 8.4 Hz, 1H), 1.69 (dd, J=13.1, 2.6 Hz, 1H), (M+H)+=383.25. HPLC RT under separation conditions=8.87 min. The second eluting isomer (Example 112, P-2) was (R)-3-((3R,4S)-3-fluoro-4-(4-hydroxyphenyl)piperidin-1-yl)-1-(4-methylbenzyl)pyrrolidin-2-one (35.2 mg, 0.084 mmol, 27.3% yield), $^1$H NMR (500 MHz, methanol-d$_4$) δ 7.19-7.08 (m, 6H), 6.74 (d, J=8.4 Hz, 2H), 4.66 (d, J=47.9 Hz, 1H), 4.41 (dd, J=53.7, 14.8 Hz, 2H), 3.58 (t, J=8.8 Hz, 1H), 3.42 (t, J=10.8 Hz, 1H), 3.30-3.14 (m, 2H), 3.05-2.88 (m, 2H), 2.79-2.51 (m, 2H), 2.33 (s, 3H), 2.31-2.13 (m, 2H), 2.06-1.90 (m, 1H), 1.67 (d, J=10.8 Hz, 1H), (M+H)+=383.25. HPLC RT under separation conditions=11.97 min.

Example 113

1-(4-fluorobenzyl)-3-(4-(4-hydroxyphenyl)piperazin-1-yl)pyrrolidin-2-one

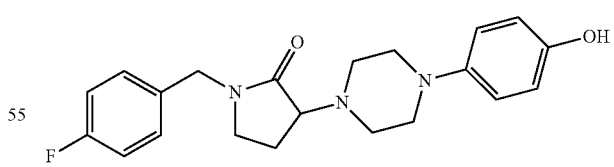

A mixture of intermediate 1 (150 mg), 4-(piperazin-1-yl)phenol (262 mg), and triethylamine (0.820 mL) in acetonitrile (10 mL) was heated in a sealed vial at 145° C. for 1 h. The crude reaction was allowed to cool to rt and was diluted with dichloromethane (2 mL). The crude mixture was purified using silica gel column chromatography (50-100% ethyl acetate/hexanes, then 10% methanol/ethyl acetate) to afford 1-(4-fluorobenzyl)-3-(4-(4-hydroxyphenyl)piperazin-1-yl)pyrrolidin-2-one (300 mg, 54% yield) as a light brown powder. LC/MS (M+H)+=351.3; ¹H NMR (500 MHz, DMSO-d₆) δ 9.10 (s, 1H), 7.77-7.56 (m, 2H), 7.47-7.30 (m, 2H), 7.19-7.08 (m, 1H), 6.94 (d, J=8.4 Hz, 2H), 6.70-6.59 (m, 2H), 3.76-3.66 (m, 2H), 3.58 (t, J=9.0 Hz, 1H), 2.95 (d, J=11.1 Hz, 1H), 2.71 (d, J=11.0 Hz, 1H), 2.58-2.52 (m, 1H), 2.38 (d, J=7.0 Hz, 2H), 2.26-2.10 (m, 2H), 2.05-1.95 (m, 1H), 1.54 (t, J=7.9 Hz, 2H), 1.46-1.30 (m, 1H), 1.21-1.02 (m, 2H).

Example 114

Peak-1

(R)-1-(4-(difluoromethyl)benzyl)-3-((3S,4S)-3-fluoro-4-(4-hydroxyphenyl)piperidin-1-yl)pyrrolidin-2-one

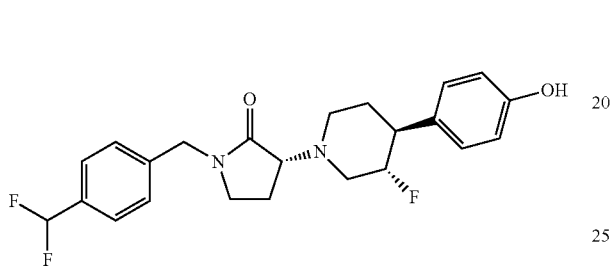

and

Example 114

Peak-2

(S)-1-(4-(difluoromethyl)benzyl)-3-((3S,4S)-3-fluoro-4-(4-hydroxyphenyl)piperidin-1-yl)pyrrolidin-2-one

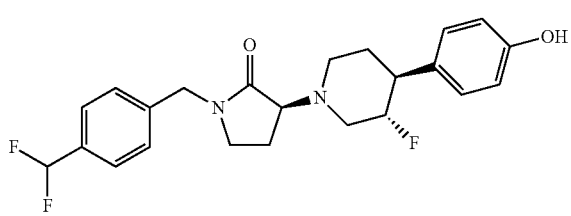 [SMILES: O=C1[C@@H](N2CC[C@@H](c3ccc(O)cc3)[C@H](F)C2)CCN1Cc1ccc(C(F)F)cc1]

Step A.
(S)-3-(tert-Butyldimethylsilyloxy)pyrrolidin-2-one

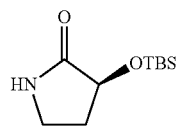

4-Dimethylaminopyridine (0.199 g, 1.63 mmol), imidazole (6.73 g, 99 mmol) and TBDMS-Cl (20.6 ml, 59.3 mmol) was added to a stirred solution of (S)-3-hydroxypyrrolidin-2-one (5.0 g, 49.5 mmol) in DCM (198 ml) at RT. The reaction mixture was stirred for 24 h and then diluted with water. The mixture was extracted with DCM. The combined organic layers were washed with saturated aqueous sodium bicarbonate solution, dried over sodium sulfate, filtered and concentrated in vacuo. The crude product was purified using silica gel column chromatography (50-80% EtOAc/hexanes) to afford (S)-3-((tert-butyldimethylsilyl)oxy)pyrrolidin-2-one (10.4 g, 97% yield) as a white solid: ¹H NMR (500 MHz, chloroform-d) δ 6.15 (br. s., 1H), 4.28 (t, J=7.6 Hz, 1H), 3.40 (dddd, J=9.7, 8.5, 3.1, 1.2 Hz, 1H), 3.28 (dt, J=9.6, 7.4 Hz, 1H), 2.39 (dtd, J=12.7, 7.3, 3.1 Hz, 1H), 2.10-2.02 (m, 1H), 0.97-0.92 (m, 9H), 0.20-0.14 (m, 6H).

Step B. (S)-3-(tert-Butyldimethylsilyloxy)-1-(4-(difluoromethyl)benzyl)pyrrolidin-2-one

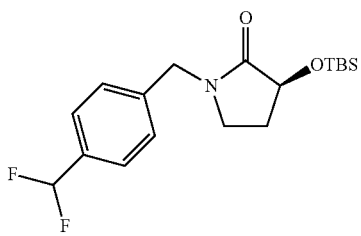 [SMILES: CC(C)(C)[Si](C)(C)O[C@H]1CCN(Cc2ccc(C(F)F)cc2)C1=O]

A 60% dispersion of sodium hydride in mineral oil (232 mg, 5.31 mmol) was added to a stirred solution of (S)-3-((tert-butyldimethylsilyl)oxy)pyrrolidin-2-one (762 mg, 3.54 mmol) in THF (7 mL) at 0° C. After 15 min, a solution of 1-(bromomethyl)-4-(difluoromethyl)benzene (980 mg, 4.43 mmol) in THF (7 mL) was added to the reaction mixture. The resulting mixture was stirred at RT for 6 h. The reaction was quenched with pellets of ice. The resulting mixture was extracted with EtOAc. The combined organic layers were washed with water, dried over sodium sulfate, filtered and concentrated in vacuo. The crude reaction mixture was purified using silica gel column chromatography (0-30% EtOAc/hexanes) to afford (S)-3-((tert-butyldimethylsilyl)oxy)-1-(4-(difluoromethyl)benzyl)pyrrolidin-2-one (440 mg, 35% yield) as a white solid: LCMS (M+H)+356.3; ¹H NMR (500 MHz, chloroform-d) δ 7.49 (d, J=8.1 Hz, 2H), 7.35 (d, J=7.9 Hz, 2H), 6.65 (br. t, J=1.0 Hz, 1H), 4.56-4.44 (m, 2H), 4.38 (t, J=7.5 Hz, 1H), 3.27 (ddd, J=9.7, 8.7, 3.4 Hz, 1H), 3.13 (dt, J=9.7, 7.4 Hz, 1H), 2.36-2.27 (m, 1H), 1.98-1.90 (m, 1H), 0.96 (br. s., 9H), 0.22-0.20 (m, 3H), 0.20-0.18 (m, 3H).

Step C. (S)-1-(4-(Difluoromethyl)benzyl)-3-hydroxypyrrolidin-2-one

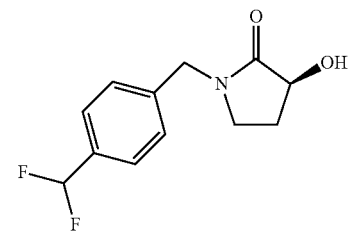 [SMILES: O=C1[C@@H](O)CCN1Cc1ccc(C(F)F)cc1]

A solution of 4 M HCl in dioxane (0.62 mL, 2.5 mmol) was added to a stirred solution of (S)-3-((tert-butyldimethylsilyl)oxy)-1-(4-(difluoromethyl)benzyl)pyrrolidin-2-one (440 mg, 1.24 mmol) in dichloromethane (1.24 mL) at RT. The reaction mixture was stirred for 2 h. The reaction mixture was concentrated in vacuo to afford (S)-1-(4-(difluoromethyl)benzyl)-3-hydroxypyrrolidin-2-one (368 mg, quantitative yield): LC-MS (M+H)+242.1.

Step D. (S)-1-(4-(Difluoromethyl)benzyl)-2-oxopyrrolidin-3-yl methanesulfonate

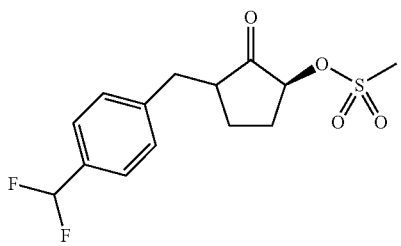 [SMILES: CS(=O)(=O)O[C@H]1CCC(Cc2ccc(C(F)F)cc2)C1=O]

Triethylamine (0.319 mL, 2.29 mmol) and methansulfonyl chloride (0.131 mL, 1.68 mmol) was added to a stirred solution of (S)-1-(4-(difluoromethyl)benzyl)-3-hydroxypyrrolidin-2-one (368 mg, 1.53 mmol) in dichloromethane (7.63 mL) at 0° C. The reaction mixture was stirred at 0° C. for 1 h. The resulting mixture was diluted with water and the aqueous mixture was extracted with dichloromethane. The combined organic layers were washed with 10% sodium bicarbonate solution, dried over sodium sulfate, filtered, and concentrated in vacuo. The crude material was purified using silica gel column chromatography (0-100% EtOAc). The pure fractions were combined and concentrated in vacuo to afford 1-(4-(difluoromethyl)benzyl)-2-oxopyrrolidin-3-yl methanesulfonate (322 mg, 66% yield) as a white solid: LC-MS (M+H)+320.1; $^1$H NMR (500 MHz, chloroform-d) δ 7.53 (d, J=7.9 Hz, 2H), 7.38-7.33 (m, 2H), 6.67 (br. t, J=1.0 Hz, 1H), 5.27 (dd, J=8.2, 7.5 Hz, 1H), 4.60-4.49 (m, 2H), 3.41-3.35 (m, 1H), 3.33 (s, 3H), 3.27 (dt, J=9.9, 7.3 Hz, 1H), 2.64-2.55 (m, 1H), 2.27 (ddt, J=13.9, 8.9, 7.1 Hz, 1H).

Step E. (R)-1-(4-(Difluoromethyl)benzyl)-3-((3S,4S)-3-fluoro-4-(4-hydroxyphenyl)piperidin-1-yl)pyrrolidin-2-one (Peak 1) and (S)-1-(4-(Difluoromethyl)benzyl)-3-((3S,4S)-3-fluoro-4-(4-hydroxyphenyl)piperidin-1-yl)pyrrolidin-2-one (Peak 2)

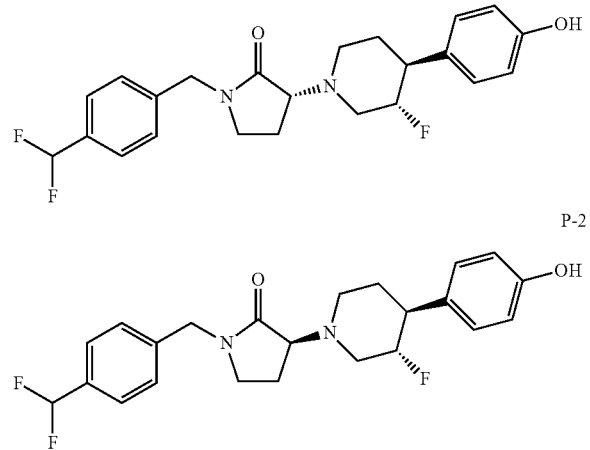

P-1

P-2

A solution of (S)-1-(4-(difluoromethyl)benzyl)-2-oxopyrrolidin-3-yl methanesulfonate (500 mg, 1.57 mmol) in 5.0 mL of acetonitrile was added dropwise over 1.5 h to a stirred mixture of 4-((3S,4S)-3-fluoropiperidin-4-yl)phenol, hydrochloride (363 mg, 1.57 mmol, from example 46, step M) and N,N-diisopropylethylamine (1.09 mL, 6.26 mmol) in 5.0 mL of acetonitrile maintained at 85° C. After complete addition, the reaction mixture was stirred at 85° C. for 16 h. The resulting mixture was concentrated in vacuo. The residue was purified using silica gel column chromatography (0-100% EtOAc/hexanes) to afford a diasteromeric mixture of 1-(4-(difluoromethyl)benzyl)-3-((3S,4S)-3-fluoro-4-(4-hydroxyphenyl)piperidin-1-yl)pyrrolidin-2-one (235 mg, 35% yield) due to partial epimerization. A sample of the diastereomeric mixture (780 mg) was separated by preparative chiral SFC (column=Lux Cellulose-2 (21×250 mm, 5 µm); isocratic solvent=20% methanol (with 15 mM ammonia)/80% $CO_2$; temp=35° C.; flow rate=60 mL/min; injection volumn=1.0 mL (~20 mg/mL in MeOH) stacked @ 13 min intervals; λ=210 nM; Peak 1=19.6 min, Peak 2=24.5 min) to afford 389 mg of Example 114, P-1 and 242 mg of Example 114, P-2. Data for Example 114, P-1: LC-MS m/z 419.3 (M+H$^+$); $^1$H NMR (500 MHz, chloroform-d) δ 7.50 (d, J=7.9 Hz, 2H), 7.34 (d, J=7.9 Hz, 2H), 7.15 (d, J=8.5 Hz, 2H), 6.91-6.80 (m, 2H), 6.65 (t, J=56.4 Hz, 1H), 4.96 (s, 1H), 4.77-4.43 (m, 3H), 3.68 (t, J=8.8 Hz, 1H), 3.42-3.33 (m, 1H), 3.29-3.14 (m, 2H), 2.85 (d, J=10.4 Hz, 1H), 2.78-2.69 (m, 1H), 2.69-2.57 (m, 1H), 2.48 (td, J=9.9, 4.9 Hz, 1H), 2.21-2.11 (m, 1H), 2.04 (dq, J=13.0, 8.6 Hz, 1H), 1.94-1.82 (m, 2H)). The relative and absolute configuration of Example 114, P-1 was confirmed by single crystal X-ray analysis. Data for Example 114, P-2: LC-MS m/z 419.3 (M+H$^+$); $^1$H NMR (500 MHz, chloroform-d) δ 7.50 (d, J=7.9 Hz, 2H), 7.35 (d, J=7.9 Hz, 2H), 7.15 (d, J=8.4 Hz, 2H), 6.87-6.81 (m, 2H), 6.65 (t, J=56.5 Hz, 1H), 4.95 (s, 1H), 4.74-4.42 (m, 3H), 3.66 (t, J=8.9 Hz, 1H), 3.28-3.15 (m, 3H), 3.07-2.99 (m, 1H), 2.72-2.58 (m, 2H), 2.49-2.40 (m, 1H), 2.20-2.12 (m, 1H), 2.04 (dq, J=13.0, 8.7 Hz, 1H), 1.93-1.87 (m, 2H).

Example 115

(R)-3-((3S,4S)-3-fluoro-4-(3-fluoro-4-hydroxyphenyl)piperidin-1-yl)-1-(4-methylbenzyl)pyrrolidin-2-one

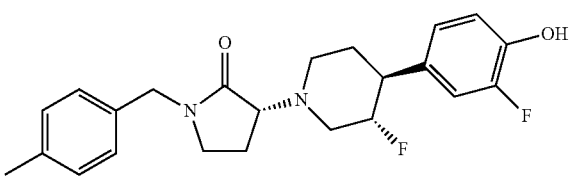 [SMILES: Cc1ccc(CN2CC[C@@H](N3CC[C@@H](c4ccc(O)c(F)c4)[C@H](F)C3)C2=O)cc1]

Step A. tert-Butyl 4-(4-(benzyloxy)-3-fluorophenyl)-5,6-dihydropyridine-1(2H)-carboxylate

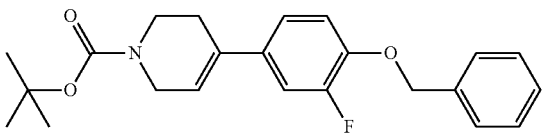 [SMILES: CC(C)(C)OC(=O)N1CC=C(c2ccc(OCc3ccccc3)c(F)c2)CC1]

A solution of 1-(benzyloxy)-4-bromo-2-fluorobenzene (5.0 g, 17.8 mmol) and tert-butyl 4-(4,4,5,5-tetramethyl-1,3,2-dioxaborolan-2-yl)-5,6-dihydropyridine-1(2H)-carboxylate (6.60 g, 21.3 mmol) in acetonitrile (50 mL) was degassed for 5 min. To this was added water (50 mL), $Na_2CO_3$ (5.66 g, 53.4 mmol) and Pd(Ph$_3$P)$_4$ (1.23 g, 1.07 mmol) and the reaction was further degassed for 10 min. It was then heated to 80° C. for 16 h. The reaction cooled to rt, poured into water, and extracted with EtOAc. The combined organic layers were, dried with magnesium sulfate, filtered through celite, and concentrated in vacuo to afford a brown oil. The oil was purified using silica gel column chromatography (0-30% EtOAc/hexanes) to afford 1-butyl 4-(4-(benzyloxy)-3-fluorophenyl)-5,6-dihydropyridine-1(2H)-carboxylate (5.63 g, 83% yield): LC-MS [M+H]$^+$–tBu+ACN=369.2; $^1$H NMR (500 MHz, DMSO-d$_6$) δ 7.51-7.27 (m, 6H), 7.25-7.13 (m, 2H), 6.12 (br. s., 1H), 5.19 (s, 2H), 3.97 (br. s., 2H), 3.51 (t, J=5.6 Hz, 2H), 2.41 (d, J=1.5 Hz, 2H), 1.42 (s, 9H).

Step B. (±)-rel-(3R,4R)-tert-Butyl 4-(4-(benzyloxy)-3-fluorophenyl)-3-hydroxypiperidine-1-carboxylate

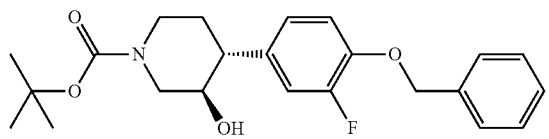 [SMILES: CC(C)(C)OC(=O)N1CC[C@H](c2ccc(OCc3ccccc3)c(F)c2)[C@@H](O)C1]

To sodium borohydride (2.282 g, 60.3 mmol) in THF (81 ml) at 0° C. was added boron trifluoride diethyl etherate (9.86 ml, 78 mmol) dropwise via addition funnel. The ice bath was removed and the solution was allowed to warm to rt and stir for 1 h. The reaction was chilled to 0° C., then tert-butyl 4-(4-(benzyloxy)-3-fluorophenyl)-5,6-dihydropyridine-1 (2H)-carboxylate (7.46 g, 19.5 mmol) in THF (8.11 ml) was added dropwise via additional funnel. After complete additional, the reaction was allowed to warm to rt and was stirred for 2 h. The reaction was cooled to 0° C. and quenched with water (16.2 ml) until the effervescence subsided. To this mixture was sequentially added aqueous 10% sodium hydroxide (14.2 ml, 38.9 mmol), aqueous 30% hydrogen peroxide (13.91 ml, 136 mmol) and EtOH (16.2 ml). The resulting mixture was stirred at rt for 16 h. The mixture was diluted with ice water and extracted with dichloromethane. The combined organic layers were dried with magnesium sulfate, filtered, and concentrated in vacuo to afford (±)-rel-(3R,4R)-tert-butyl 4-(4-(benzyloxy)-3-fluorophenyl)-3-hydroxypiperidine-1-carboxylate (7.32 g, 94% yield) as a white solid: LC-MS [M+H]$^+$=328.2; $^1$H NMR (500 MHz, DMSO-d$_6$) δ 7.53-7.28 (m, 5H), 7.18-7.07 (m, 2H), 6.97 (d, J=8.2 Hz, 1H), 5.14 (s, 2H), 4.82 (d, J=5.6 Hz, 1H), 4.10 (br. s., 1H), 3.95 (br. s., 1H), 3.40 (tt, J=10.2, 5.2 Hz, 1H), 2.81-2.60 (m, 1H), 2.46-2.35 (m, 1H), 1.66 (dd, J=13.4, 3.1 Hz, 1H), 1.59-1.46 (m, 1H), 1.42 (s, 9H).

Step C. (3R,4R)-tert-Butyl 4-(4-(benzyloxy)-3-fluorophenyl)-3-hydroxypiperidine-1-carboxylate and (3S,4S)-tert-Butyl 4-(4-(benzyloxy)-3-fluorophenyl)-3-hydroxypiperidine-1-carboxylate

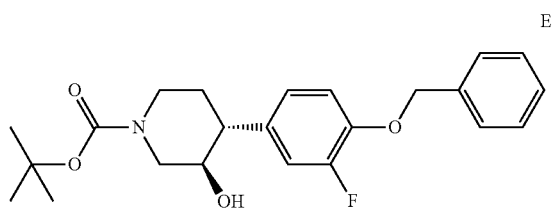

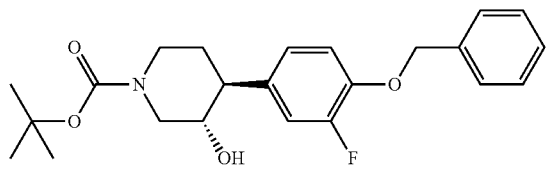

(±)-rel-(3R,4R)-tert-Butyl 4-(4-(benzyloxy)-3-fluorophenyl)-3-hydroxypiperidine-1-carboxylate (17.1 g, from step B) was subjected to chiral SFC separation (column=Chiralpak AD-H; isocratic solvent=30% methanol/ 70% CO$_2$; temp=40° C.; flow rate=3 mL/min; λ=220 nM; Peak 1 (E-1)=3.8 min, Peak 2 (E-2)=7.7 min) to yield enantiomers E-1 (7.2 g, 42% yield) and E-2 (7.5 g, 44% yield). Data for E-1: LC-MS [M+H]$^+$–t-Bu=346.1; $^1$H NMR (500 MHz, DMSO-d$_6$) δ 7.52-7.26 (m, 5H), 7.18-7.06 (m, 2H), 6.97 (d, J=8.4 Hz, 1H), 5.14 (s, 2H), 4.81 (d, J=5.6 Hz, 1H), 4.09 (br. s., 1H), 3.95 (br. s., 1H), 3.39 (td, J=10.3, 5.3 Hz, 1H), 2.47-2.30 (m, 3H), 1.72-1.62 (m, 1H), 1.59-1.45 (m, 1H), 1.42 (s, 9H). Data for E-2: LC-MS [M+H]$^+$–t-Bu=346.1; $^1$H NMR (500 MHz, DMSO-d$_6$) δ 7.52-7.27 (m, 5H), 7.19-7.06 (m, 2H), 6.97 (dd, J=8.4, 1.1 Hz, 1H), 5.14 (s, 2H), 4.81 (d, J=5.6 Hz, 1H), 4.10 (br. s., 1H), 3.95 (br. s., 1H), 3.49-3.35 (m, 1H), 2.46-2.33 (m, 3H), 1.72-1.63 (m, 1H), 1.59-1.46 (m, 1H), 1.46-1.32 (m, 9H).

Step D. (3S,4S)-tert-Butyl 4-(3-fluoro-4-hydroxyphenyl)-3-hydroxypiperidine-1-carboxylate

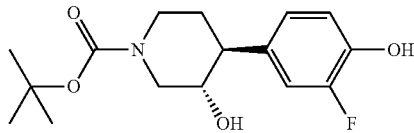 [SMILES: CC(C)(C)OC(=O)N1CC[C@@H](c2ccc(O)c(F)c2)[C@H](O)C1]

To (3S,4S)-tert-butyl 4-(4-(benzyloxy)-3-fluorophenyl)-3-hydroxypiperidine-1-carboxylate (4.0 g, 9.96 mmol, E-2 from step C) in degassed MeOH (100 mL) was added 10% Pd/C (0.191 g, 1.79 mmol) and the reaction was repeated evacuated and flushed with hydrogen gas. Then placed under 1 atm of hydrogen for 4 h. The reaction solution was purged with nitrogen and filtered through celite. The filtrated was concentrated to afford (3S,4S)-tert-butyl 4-(3-fluoro-4-hydroxyphenyl)-3-hydroxypiperidine-1-carboxylate (2.99 g, 96% yield) as a grey oil. LC-MS [M+H]$^+$–tBu=256.05; $^1$H NMR (500 MHz, DMSO-d$_6$) δ 7.03-6.95 (m, 1H), 6.89-6.78 (m, 2H), 4.78 (d, J=4.6 Hz, 1H), 4.09 (br. s., 2H), 3.94 (br. s., 1H), 3.36 (dd, J=9.5, 4.7 Hz, 1H), 3.17 (s, 1H), 2.80-2.58 (m, 1H), 2.42-2.27 (m, 1H), 1.65 (dd, J=13.4, 3.4 Hz, 1H), 1.56-1.33 (m, 10H).

Step E. (3S,4S)-tert-Butyl 3-fluoro-4-(3-fluoro-4-hydroxyphenyl)piperidine-1-carboxylate

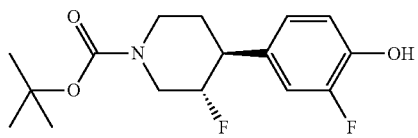

To (3S,4S)-tert-butyl 4-(3-fluoro-4-hydroxyphenyl)-3-hydroxypiperidine-1-carboxylate (2.99 g, 9.60 mmol) in DCM (75 mL) at 0° C. was added DAST (6.34 mL, 48.0 mmol) dropwise. The reaction was then allowed to warm to room temperature and stir for 2 h. The reaction was slowly quenched with ice water. The reaction was then extracted with dichloromethane, washed with additional water, dried with magnesium sulfate, filtered and concentrated in vacuo to afford (3S,4S)-tert-butyl 3-fluoro-4-(3-fluoro-4-hydroxyphenyl)piperidine-1-carboxylate (3.88 g, quantitative yield) as a yellow viscous oil: LC-MS [M–H]+ 312.2; 1H NMR (500 MHz, DMSO-$d_6$) δ 7.22-7.10 (m, 1H), 7.00-6.76 (m, 3H), 5.76 (s, 2H), 4.60 (td, J=10.1, 5.2 Hz, 1H), 4.50 (td, J=10.1, 5.2 Hz, 1H), 4.27 (br. s., 1H), 4.07-3.78 (m, 2H), 3.66-3.50 (m, 1H), 3.00-2.65 (m, 4H), 1.81-1.69 (m, 1H), 1.63-1.50 (m, 1H), 1.46-1.30 (m, 14H), 1.20-1.01 (m, 2H).

Step E. (3S,4S)-tert-Butyl 3-fluoro-4-(3-fluoro-4-hydroxyphenyl)piperidine-1-carboxylate

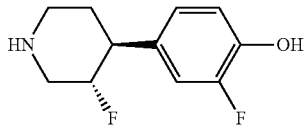 [SMILES: Oc1ccc([C@@H]2CCNC[C@H]2F)cc1F]

To (3S,4S)-tert-butyl 3-fluoro-4-(3-fluoro-4-hydroxyphenyl)piperidine-1-carboxylate (3.01 g, 9.61 mmol) in dioxane (10 mL) was added HCl (4 M in Dioxane) (24 mL, 96 mmol) and the reaction was allowed to stir at room temperature for 5 h. The reaction was concentrated to an oil. The oil was taken up in saturated aqueous sodium bicarbonate and extracted with EtOAc/5% MeOH. The combined organic layers were concentrated in vacuo to afford 2-fluoro-4-((3S,4S)-3-fluoropiperidin-4-yl)phenol (2.15 g, quantitative yield): LC-MS [M+H]+=214.1; 1H NMR (500 MHz, DMSO-$d_6$) δ 6.93 (d, J=12.4 Hz, 1H), 6.85-6.72 (m, 2H), 4.49 (td, J=9.9, 4.9 Hz, 1H), 4.39 (td, J=10.0, 5.0 Hz, 1H), 3.27-3.19 (m, 3H), 2.85 (d, J=11.4 Hz, 2H), 2.62-2.54 (m, 2H), 2.46-2.37 (m, 4H), 1.76-1.64 (m, 2H), 1.57-1.37 (m, 3H).

Step F. (R)-3-((3S,4S)-3-Fluoro-4-(3-fluoro-4-hydroxyphenyl) piperidin-1-yl)-1-(4-methylbenzyl) pyrrolidin-2-one

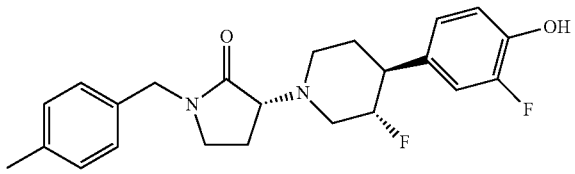 [SMILES: Cc1ccc(CN2CC[C@@H](N3CC[C@@H](c4ccc(O)c(F)c4)[C@H](F)C3)C2=O)cc1]

A solution of (S)-1-(4-methylbenzyl)-2-oxopyrrolidin-3-yl methanesulfonate (0.106 g, 0.375 mmol, from example 112, step D) in acetonitrile (1 mL) was added to a mixture of 2-fluoro-4-((3S,4S)-3-fluoropiperidin-4-yl)phenol (0.04 g, 0.188 mmol, from step E) and DIPEA (0.098 mL, 0.563 mmol) in acetonitrile (2 mL) heated at 80° C. The reaction mixture was stirred at 80° C. for 16 h. The mixture was allowed to cool to rt and then concentrated in vacuo. The residue was purified using preparative LC/MS (Waters XBridge C18, 19×150 mm, 5 μm; Guard Column: Waters XBridge C18, 19×10 mm, 5 μm; Mobile Phase A: 5:95 acetonitrile:water with 10 mM NH$_4$OAc; Mobile Phase B: 95:5 acetonitrile:water with 10 mM NH$_4$OAc; Gradient: 15-60% B over 25 min, followed by a 10 min hold at 60% B and 5 min hold at 100% B; Flow: 15 mL/min). Fractions containing the desired product were combined concentrated in vacuo using a Genevac centrifugal evaporator to the titled compound of Example 115 (31 mg, 0.077 mmol, 41% yield) as pale yellow solid. LC-MS (M+H)+ 401; 1H NMR: (400 MHz, DMSO-$d_6$) d=7.19-7.06 (m, 5H), 6.95-6.84 (m, 2H), 4.70-4.48 (m, 1H), 4.41-4.24 (m, 2H), 3.55 (s, 1H), 3.48-3.29 (m, 3H), 2.76-2.63 (m, 2H), 2.62-2.52 (m, 1H), 2.28 (s, 4H), 2.16-2.03 (m, 1H), 1.89 (s, 3H), 1.79-1.54 (m, 2H).

Example 116

(R)-1-(4-chlorobenzyl)-3-((3S,4S)-3-fluoro-4-(3-fluoro-4-hydroxyphenyl)piperidin-1-yl)pyrrolidin-2-one

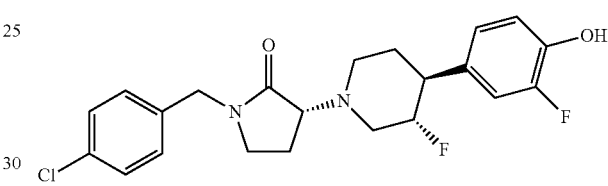

Step A. (S)-3-(tert-Butyldimethylsilyloxy)-1-(4-chlorobenzyl)pyrrolidin-2-one

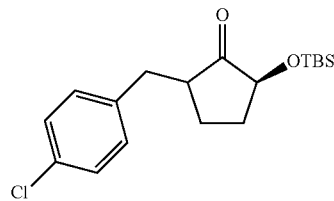 [SMILES: CC(C)(C)[Si](C)(C)O[C@H]1CCC(Cc2ccc(Cl)cc2)C1=O]

A 60% dispersion of sodium hydride in mineral oil (0.608 g, 13.9 mmol) was added to a stirred solution of (S)-3-((tert-butyldimethylsilyl)oxy)pyrrolidin-2-one (2.0 g, 9.29 mmol, from example 114, step A) in THF (7 mL) at 0° C. After 15 min, a solution of 1-(bromomethyl)-4-chlorobenzene (1.72 g, 8.37 mmol) in THF (7 mL) was added to the reaction mixture. The resulting mixture was stirred at RT for 6 h. The reaction was quenched with pellets of ice. The resulting mixture was extracted with EtOAc. The combined organic layers were washed with water, dried over sodium sulfate, filtered and concentrated in vacuo. The crude reaction mixture was purified using silica gel column chromatography (0-15% EtOAc/hexanes) to afford (S)-3-((tert-butyldimethylsilyl)oxy)-1-(4-chlorobenzyl)pyrrolidin-2-one (1.34 g, 42% yield): LCMS (M+H)+ 340.2; 1H NMR (500 MHz, chloroform-d) δ 1H NMR (500 MHz, chloroform-d) δ 7.36-7.29 (m, J=8.4 Hz, 2H), 7.23-7.16 (m, J=8.4 Hz, 2H), 4.51-4.33 (m, 3H), 3.31-3.22 (m, 1H), 3.11 (dt, J=9.7, 7.4 Hz, 1H), 2.37-2.25 (m, 1H), 1.97-1.84 (m, 1H), 0.95 (s, 9H), 0.21 (s, 3H), 0.18 (s, 3H).

Step B. (S)-1-(4-Chlorobenzyl)-3-hydroxypyrrolidin-2-one

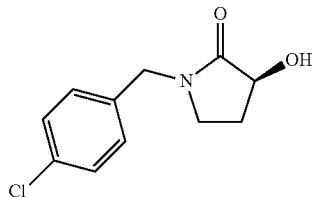 [SMILES: O=C1[C@@H](O)CCN1Cc1ccc(Cl)cc1]

A solution of 4 M HCl in dioxane (4.93 ml, 19.7 mmol) was added to a stirred solution of (S)-3-((tert-butyldimethylsilyl)oxy)-1-(4-chlorobenzyl)pyrrolidin-2-one (1.34 g, 3.94 mmol) in dichloromethane (4 mL) at RT. The reaction mixture was stirred for 2 h. The reaction mixture was concentrated in vacuo to afford (S)-1-(4-chlorobenzyl)-3-hydroxypyrrolidin-2-one (910 mg, 4.03 mmol, quantitative yield): LC-MS (M+H)$^+$ 226.1; $^1$H NMR (500 MHz, methanol-d$_4$) δ 7.37-7.33 (m, J=8.5 Hz, 2H), 7.27-7.23 (m, J=8.5 Hz, 2H), 4.52-4.37 (m, 2H), 4.34 (t, J=8.2 Hz, 1H), 3.30-3.18 (m, 2H), 1.84 (dq, J=12.8, 8.5 Hz, 1H).

Step C. (S)-1-(4-Chlorobenzyl)-2-oxopyrrolidin-3-yl methanesulfonate

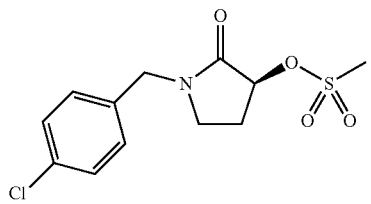 [SMILES: CS(=O)(=O)O[C@H]1CCN(Cc2ccc(Cl)cc2)C1=O]

Triethylamine (0.825 mL, 5.92 mmol) and methansulfonyl chloride (0.338 mL, 4.34 mmol) was added to a stirred solution of (S)-1-(4-chlorobenzyl)-3-hydroxypyrrolidin-2-one (890 mg, 3.94 mmol) in dichloromethane (20 mL) at 0° C. The reaction mixture was stirred at 0° C. for 1 h. The resulting mixture was diluted with water and the aqueous mixture was extracted with dichloromethane. The combined organic layers were washed with 10% sodium bicarbonate solution, dried over sodium sulfate, filtered, and concentrated in vacuo. The crude material was purified using silica gel column chromatography (0-100% EtOAc). The pure fractions were combined and concentrated in vacuo to afford (S)-1-(4-chlorobenzyl)-2-oxopyrrolidin-3-yl methanesulfonate (1.1 g, 3.62 mmol, 92% yield) as a white solid: LC-MS (M+H)$^+$ 304.1; $^1$H NMR (500 MHz, chloroform-d) δ 7.38-7.33 (m, 2H), 7.22-7.17 (m, 2H), 5.25 (dd, J=8.2, 7.6 Hz, 1H), 4.52-4.41 (m, 2H), 3.40-3.31 (m, 4H), 3.25 (dt, J=10.0, 7.3 Hz, 1H), 2.58 (dddd, J=13.7, 8.4, 7.5, 3.3 Hz, 1H), 2.33-2.20 (m, 1H).

Step D. (S)-1-(4-Chlorobenzyl)-2-oxopyrrolidin-3-yl methanesulfonate

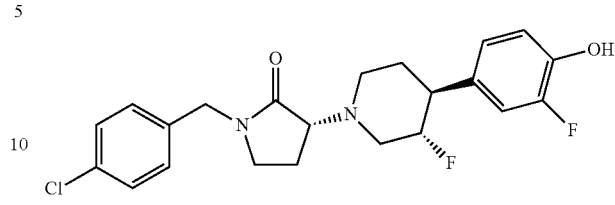

To a solution of 2-fluoro-4-((3S,4S)-3-fluoropiperidin-4-yl)phenol (1.0 g, 4.7 mmol, from example 114, step E) in acetonitrile (25 mL) was added diisopropylethylamine (2.5 mL, 14 mmol) and it was heated to 60° C. for 30 min. To this preheated mixture was then added (S)-1-(4-chlorobenzyl)-2-oxopyrrolidin-3-yl methanesulfonate (1.710 g, 5.63 mmol, from step C) in acetonitrile (15 mL). The reaction mixture was heated at 90° C. for 16 h. The reaction was diluted with sat. aqueous sodium bicarbonate and extracted with EtOAc. The organic layers were combined and concentrated to a black oil. The oil was purified using silica gel column chromatography (20-100% EtOAc/hexanes then 0-20% MeOH/dichloromethane) to afford 1-(4-chlorobenzyl)-3-((3S,4S)-3-fluoro-4-(3-fluoro-4-hydroxyphenyl)piperidin-1-yl)pyrrolidin-2-one (752 mg, 38% yield). Chiral HPLC analysis revealed that the final product was a (3:1) mixture of diastereomers, due to partial epimerization. The diastereomeric mixture (750 mg) was separated by preparative chiral SFC (column=Lux Cellulose-2 (21×250 mm, 5 μm); isocratic solvent=35% methanol in CO$_2$, 150 bar; temp=35° C.; flow rate=40 mL/min; injection volumn=0.75 mL (~42 mg/mL in MeOH) stacked intervals; λ=220 nM; Peak 1=5.5 min, Peak 2=7.9 min) to afford the titled compound (482 mg) of Example 116 (the second peak to elute). Data for Example 116: LC-MS m/z 421 (M+H); $^1$H NMR (400 MHz, DMSO-d$_6$) δ 9.63 (s, 1H), 7.42 (d, J=8.5 Hz, 2H), 7.26 (d, J=8.5 Hz, 2H), 7.17-7.03 (m, 1H), 6.88 (s, 2H), 4.78-4.46 (m, 1H), 4.38 (d, J=11.5 Hz, 2H), 3.70-3.48 (m, 1H), 3.45-3.37 (m, 1H), 3.28-3.03 (m, 2H), 2.82-2.63 (m, 2H), 2.61-2.53 (m, 1H), 2.40-2.21 (m, 1H), 2.18-2.02 (m, 1H), 1.98-1.84 (m, 1H), 1.82-1.50 (m, 2H).

Example 117

Peak-1

(S)-1-(4-(difluoromethyl)benzyl)-3-((3S,4S)-3-fluoro-4-(3-fluoro-4-hydroxyphenyl)piperidin-1-yl)pyrrolidin-2-one

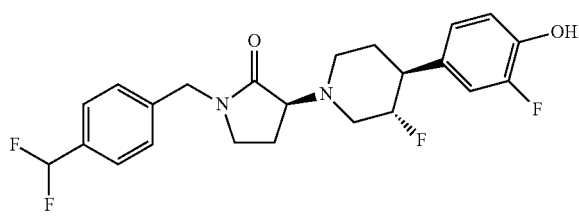 [SMILES: O=C1[C@@H](N2CC[C@@H](c3ccc(O)c(F)c3)[C@H](F)C2)CCN1Cc1ccc(C(F)F)cc1]

and

Example 117

Peak-2

(R)-1-(4-(difluoromethyl)benzyl)-3-((3S,4S)-3-fluoro-4-(3-fluoro-4-hydroxyphenyl)piperidin-1-yl)pyrrolidin-2-one

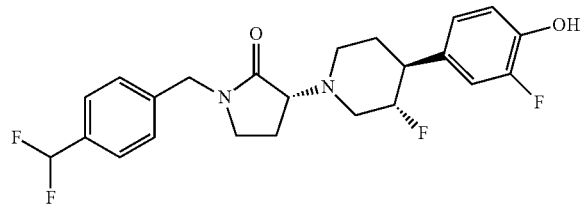 [SMILES: O=C1[C@H](N2CC[C@@H](c3ccc(O)c(F)c3)[C@H](F)C2)CCN1Cc1ccc(C(F)F)cc1]

A stirred mixture of 3-bromo-1-(4-(difluoromethyl)benzyl)pyrrolidin-2-one (100 mg, 0.328 mmol, intermediate 2a), 2-fluoro-4-((3S,4S)-3-fluoropiperidin-4-yl)phenol (70 mg, 0.328 mmol, from example 114, step E), and triethylamine (0.137 mL, 0.985 mmol) in acetonitrile (2 mL) was heated at 120° C. in a CEM microwave for one hour. The reaction mixture was diluted with water and extracted with ethyl acetate (100 mL). The organic layer was washed with brine solution, dried over sodium sulfate, and evaporated under reduced pressure to give a crude residue. The crude residue was purified via preparative LC/MS (column: Waters Xbridge C18, 19×150 mm, 5 μm; guard column: Waters XBridge C18, 19×10 mm, 5 μm; mobile phase A: 5:95 methanol:water with 10 mM $NH_4OAc$; mobile Phase B: 95:5 methanol:water with 10 mM $NH_4OAc$; Gradient: 15-50% B over 25 min, followed by a 10 min hold at 50% B and 5 min hold at 100% B; flow: 15 ml/min) to afford 1-(4-(difluoromethyl)benzyl)-3-((3S,4S)-3-fluoro-4-(3-fluoro-4-hydroxyphenyl)piperidin-1-yl)pyrrolidin-2-one (68 mg, 46%). The diastereomeric mixture was separated by preparative chiral SFC (column=Chiralpak AD-H (250 mm×21 mm, 5 μm); isocratic solvent=40% methanol (w/0.25% DEA) in $CO_2$, 100 bar; temp=25° C.; flow rate=75 g/min; injection volumn=1.1 mL (~6 mg/mL in MeOH); λ=220 nM; Peak 1=3.2 min, Peak 2=5.0 min) to afford the titled compounds of example 117 (18 mg of peak-1, and 20 mg of peak-2). Data for example 117, P-1: LC-MS m/z 437 $(M+H)^+$; $^1H$ NMR (400 MHz, methanol-$d_4$) δ ppm 7.55 (d, J=8.03 Hz, 2H) 7.42 (s, 2H) 6.97-7.04 (m, 1H) 6.62-6.95 (m, 3H) 4.48-4.68 (m, 3H) 3.76 (t, J=8.78 Hz, 1H) 3.50 (dt, J=3.31, 1.64 Hz, 0H) 3.25-3.31 (m, 0H) 3.11-3.18 (m, 0H) 2.99-3.05 (m, 0H) 2.41-2.71 (m, 3H) 2.16-2.26 (m, 1H) 2.08 (dq, J=12.91, 8.79 Hz, 1H) 1.78-1.91 (m, 2H). Data for example 117, P-2: LC-MS m/z 437 $(M+H)^+$; $^1H$ NMR (400 MHz, methanol-$d_4$) δ ppm 7.55 (d, J=8.03 Hz, 2H) 7.41 (d, J=8.28 Hz, 2H) 7.00 (dd, J=12.39, 1.91 Hz, 1H) 6.62-6.93 (m, 3H) 4.47-4.70 (m, 3H) 3.69-3.77 (m, 1H) 3.38-3.55 (m, 1H) 3.24-3.30 (m, 1H) 3.15 (dt, J=3.31, 1.64 Hz, 1H) 2.74-2.83 (m, 2H) 2.52-2.72 (m, 2H) 2.44 (td, J=10.02, 4.80 Hz, 1H) 2.03-2.27 (m, 2H) 1.76-1.90 (m, 2H).

Biological Methods

Radioligand Binding Assay.

Binding experiments to determine binding to NR2B-subtype NMDA receptors were performed on forebrains of 8-10 weeks old male Sprague Dawley rats (Harlan, Netherlands) using $^3H$ Ro 25-6981 (Mutel V; Buchy D; Klingelschmidt A; Messer J; Bleuel Z; Kemp J A; Richards J G. *Journal of Neurochemistry*, 1998, 70(5):2147-2155. Rats were decapitated without anesthesia using a Guillotine (approved by animal ethics committee) and the harvested brains were snap-frozen and stored at −80° C. for 3-6 months for membrane preparation.

For membrane preparation, rat forebrains were thawed on ice for 20 minutes in homogenization buffer composed of 50 mM $KH_2PO_4$ (pH adjusted to 7.4 with KOH), 1 mM EDTA, 0.005% Triton X 100 and protease inhibitor cocktail (Sigma Aldrich). Thawed brains were homogenized using a Dounce homogenizer and centrifuged at 48000×g for 20 min. The pellet was resuspended in cold buffer and homogenized again using a Dounce homogenizer. Subsequently, the homogenate was aliquoted, snap-frozen and stored at −80° C. for not more than 3-4 months.

To perform the competition binding assay, thawed membrane homogenate was added to each well of a 96-well plate (20 μg/well). The experimental compounds were serially diluted in 100% DMSO and added to each row of the assay plate to achieve desired compound concentrations, keeping the DMSO concentration in the assay plate at 1.33% of the final reaction volume. Next, $^3H$ Ro 25-6981 (4 nM) was added to the assay plate. After incubation for 1 hr at room temperature, the membrane bound radioligand was harvested on to GF/B filter plates (treated with 0.5% PEI for 1 hr at room temperature). The filter plates were dried at 50° C. for 20 mins, incubated with microscint 20 for 10 minutes and finally, the counts were read on TopCount (Perkin Elmer). Non-specific binding was determined using MK-0657 (the preparation of this compound is described as example 1 in WO 2004 108705 (40 μM). CPM values were converted to % inhibition and the concentration response curves were plotted using custom made software. Each experiment was repeated at least twice to obtain the final binding $K_i$ values for experimental compounds. Using this assay, the compound of example 1 shows a binding Ki of 4 nM.

| Example | Structure | NR2B Binding Ki, nM |
|---|---|---|
| 1 | 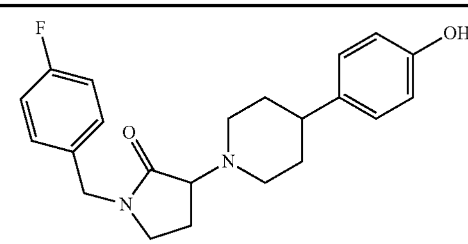 | 3 |

-continued
| Example | Structure | NR2B Binding Ki, nM |
|---|---|---|
| 2a | 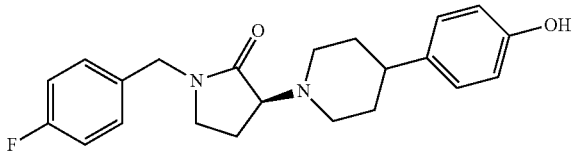 [SMILES: O=C1[C@@H](N2CCC(c3ccc(O)cc3)CC2)CCN1Cc1ccc(F)cc1] | 740 |
| 2b | 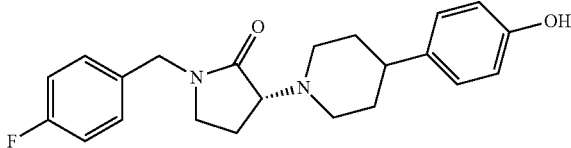 | 1.4 |
| 3 | 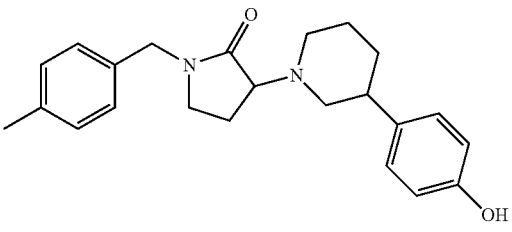 [SMILES: Cc1ccc(CN2CCC(N3CCCC(c4ccc(O)cc4)C3)C2=O)cc1] | 1320 |
| 4 | 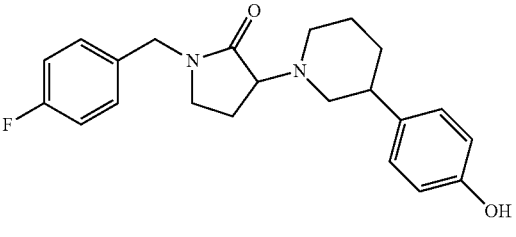 [SMILES: O=C1C(N2CCCC(c3ccc(O)cc3)C2)CCN1Cc1ccc(F)cc1] | 5000 |
| 5 | 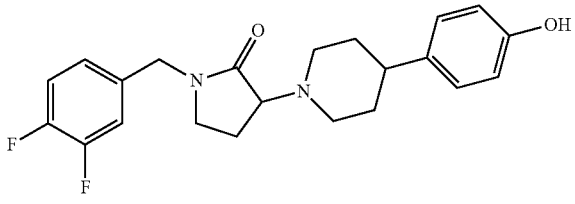 [SMILES: O=C1C(N2CCC(c3ccc(O)cc3)CC2)CCN1Cc1ccc(F)c(F)c1] | 4.4 |
| 6a | 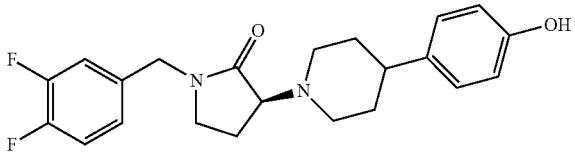 [SMILES: O=C1[C@@H](N2CCC(c3ccc(O)cc3)CC2)CCN1Cc1ccc(F)c(F)c1] | 850 |
| 6b | 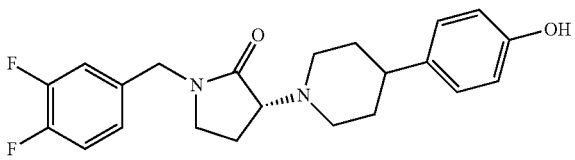 [SMILES: O=C1[C@H](N2CCC(c3ccc(O)cc3)CC2)CCN1Cc1ccc(F)c(F)c1] | 4.7 |
| 7 | 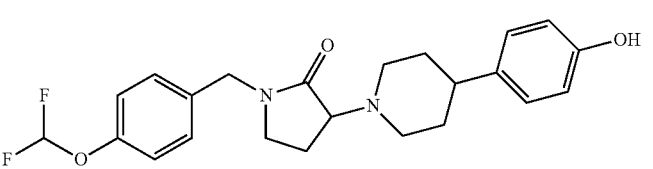 [SMILES: O=C1C(N2CCC(c3ccc(O)cc3)CC2)CCN1Cc1ccc(OC(F)F)cc1] | 37 |

-continued

| Example | Structure | NR2B Binding Ki, nM |
|---|---|---|
| 8 | 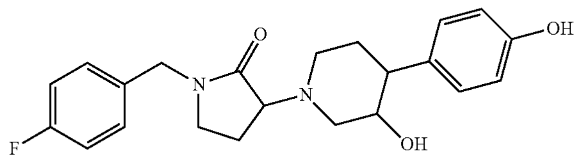 [SMILES: O=C1C(N2CCC(c3ccc(O)cc3)C(O)C2)CCN1Cc1ccc(F)cc1] | 420 |
| 9a | 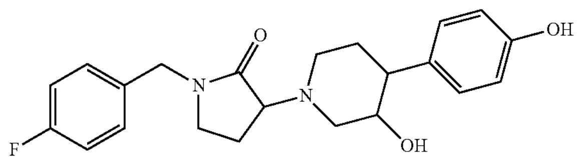 [SMILES: O=C1C(N2CCC(c3ccc(O)cc3)C(O)C2)CCN1Cc1ccc(F)cc1] | 180 |
| 9b | 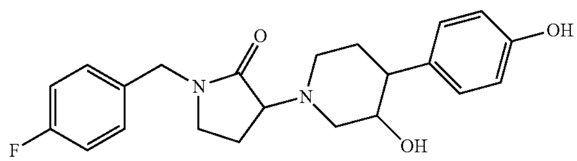 [SMILES: O=C1C(N2CCC(c3ccc(O)cc3)C(O)C2)CCN1Cc1ccc(F)cc1] | 1400 |
| 9c | 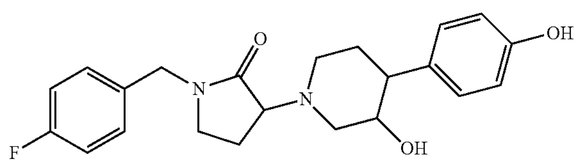 [SMILES: O=C1C(N2CCC(c3ccc(O)cc3)C(O)C2)CCN1Cc1ccc(F)cc1] | 5000 |
| 9d | 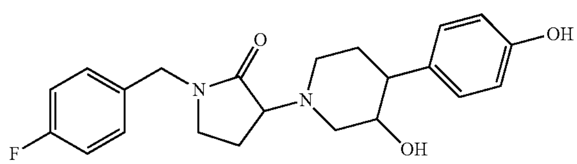 [SMILES: O=C1C(N2CCC(c3ccc(O)cc3)C(O)C2)CCN1Cc1ccc(F)cc1] | 160 |
| 10 | 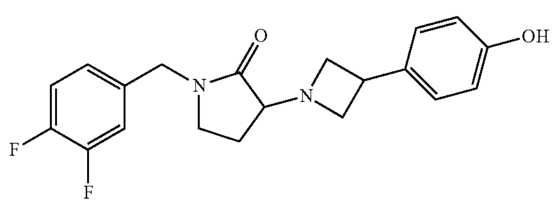 [SMILES: O=C1C(N2CC(c3ccc(O)cc3)C2)CCN1Cc1ccc(F)c(F)c1] | 1020 |
| 11 | 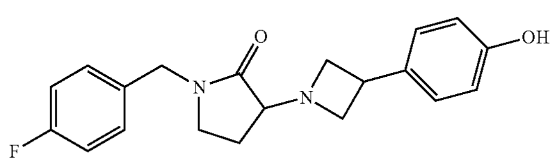 [SMILES: O=C1C(N2CC(c3ccc(O)cc3)C2)CCN1Cc1ccc(F)cc1] | 510 |
| 12 | 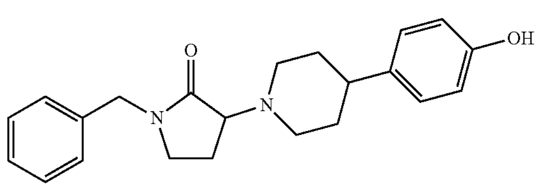 [SMILES: O=C1C(N2CCC(c3ccc(O)cc3)CC2)CCN1Cc1ccccc1] | 4 |
| 13a | 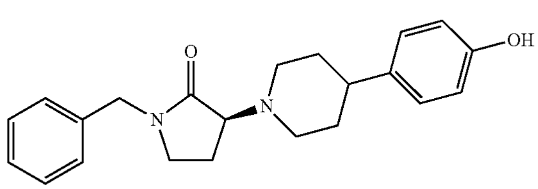 [SMILES: O=C1[C@@H](N2CCC(c3ccc(O)cc3)CC2)CCN1Cc1ccccc1] | 41 |

-continued

| Example | Structure | NR2B Binding Ki, nM |
|---|---|---|
| 13b | 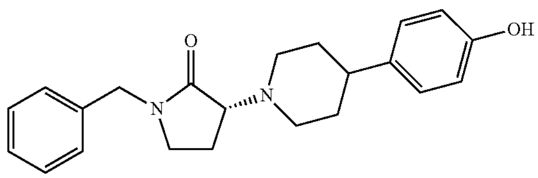 | 1.6 |
| 14 | 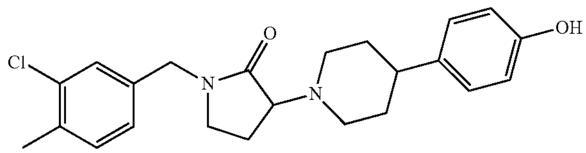 [SMILES: Cc1ccc(CN2CCC(N3CCC(c4ccc(O)cc4)CC3)C2=O)cc1Cl] | |
| 15 | 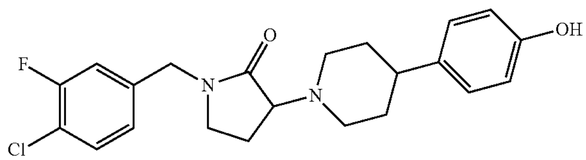 [SMILES: O=C1C(N2CCC(c3ccc(O)cc3)CC2)CCN1Cc1ccc(Cl)c(F)c1] | 12 |
| 16 | 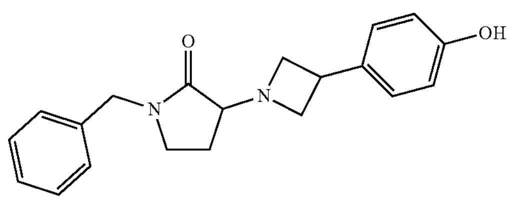 [SMILES: O=C1C(N2CC(c3ccc(O)cc3)C2)CCN1Cc1ccccc1] | 560 |
| 17 | 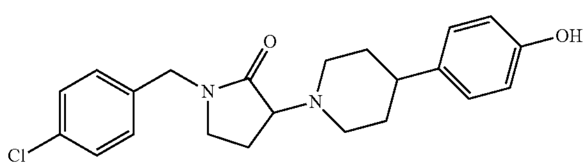 | 1.6 |
| 18a | 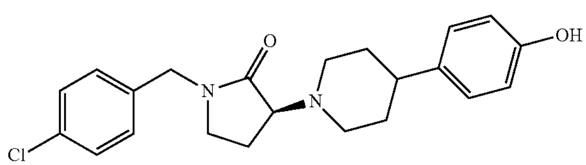 [SMILES: O=C1[C@@H](N2CCC(c3ccc(O)cc3)CC2)CCN1Cc1ccc(Cl)cc1] | 170 |
| 18b | 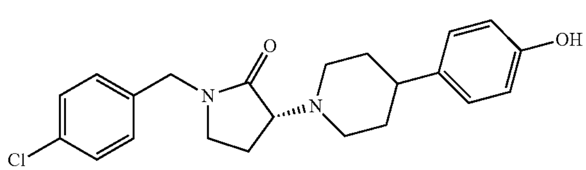 | 1.5 |
| 19 | 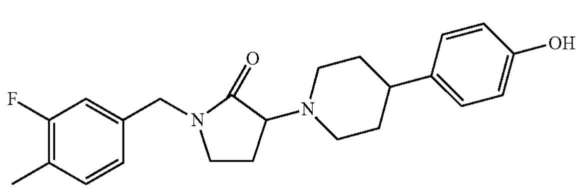 [SMILES: Cc1ccc(CN2CCC(N3CCC(c4ccc(O)cc4)CC3)C2=O)cc1F] | 3.9 |

| Example | Structure | NR2B Binding Ki, nM |
|---|---|---|
| 20 | 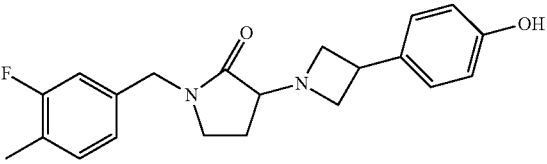 [SMILES: Cc1ccc(CN2CCC(N3CC(c4ccc(O)cc4)C3)C2=O)cc1F] | 43 |
| 21a | 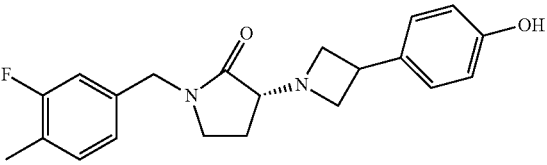 [SMILES: Cc1ccc(CN2CC[C@@H](N3CC(c4ccc(O)cc4)C3)C2=O)cc1F] | 37 |
| 21b | 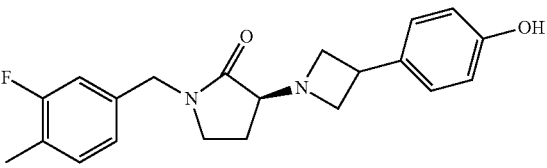 [SMILES: Cc1ccc(CN2CC[C@H](N3CC(c4ccc(O)cc4)C3)C2=O)cc1F] | 410 |
| 22 | 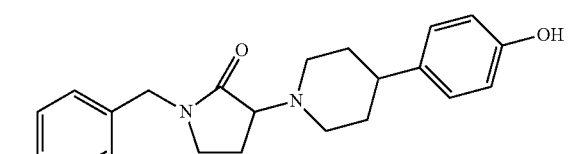 | 2.9 |
| 23a | 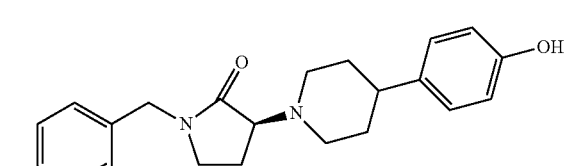 | 11 |
| 23b | 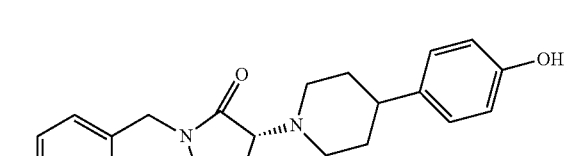 | 1.4 |
| 24 | 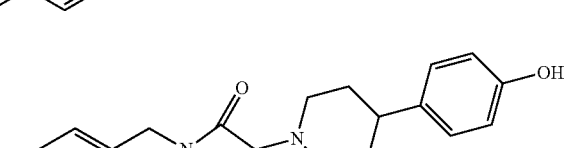 | 4.7 |
| 25a | 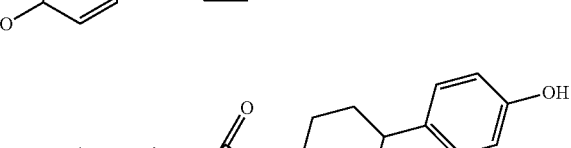 | 1200 |

-continued

| Example | Structure | NR2B Binding Ki, nM |
|---|---|---|
| 25b | 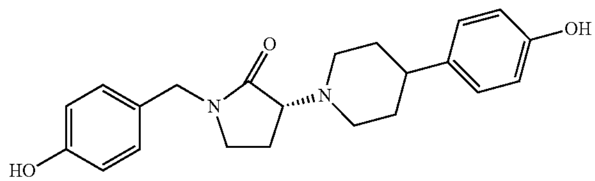 [SMILES: O=C1[C@H](N2CCC(c3ccc(O)cc3)CC2)CCN1Cc1ccc(O)cc1] | 5.3 |
| 26 | 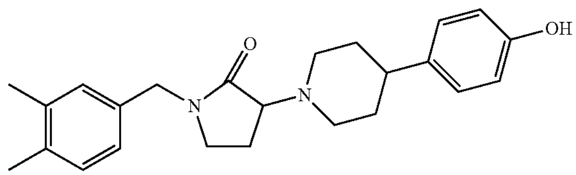 [SMILES: Cc1ccc(CN2CCC(N3CCC(c4ccc(O)cc4)CC3)C2=O)cc1C] | 31 |
| 27 | 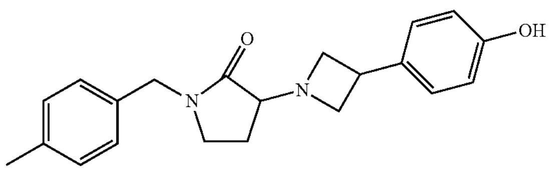 [SMILES: Cc1ccc(CN2CCC(N3CC(c4ccc(O)cc4)C3)C2=O)cc1] | 20 |
| 28a | 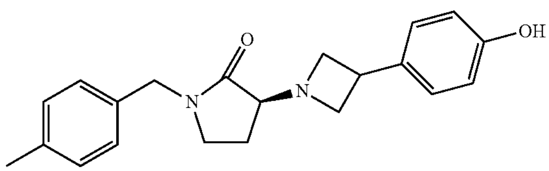 [SMILES: Cc1ccc(CN2CC[C@H](N3CC(c4ccc(O)cc4)C3)C2=O)cc1] | 420 |
| 28b | 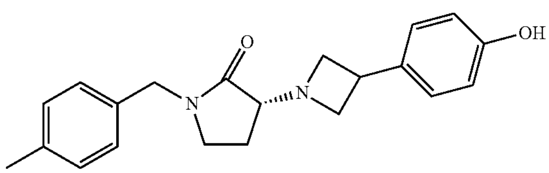 [SMILES: Cc1ccc(CN2CC[C@@H](N3CC(c4ccc(O)cc4)C3)C2=O)cc1] | 10 |
| 29 | 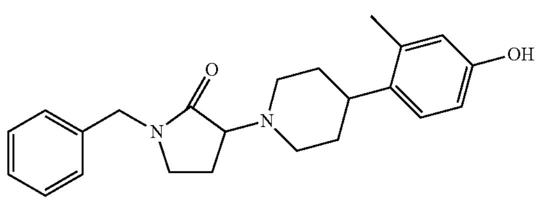 [SMILES: Cc1cc(O)ccc1C1CCN(C2CCN(Cc3ccccc3)C2=O)CC1] | 78 |
| 30 | 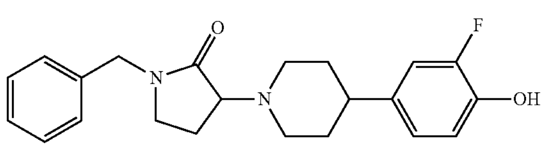 [SMILES: O=C1C(N2CCC(c3ccc(O)c(F)c3)CC2)CCN1Cc1ccccc1] | 4.7 |
| 31 | 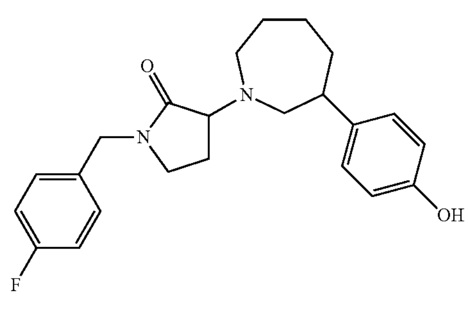 [SMILES: O=C1C(N2CCCCC(c3ccc(O)cc3)C2)CCN1Cc1ccc(F)cc1] | 800 |

-continued

| Example | Structure | NR2B Binding Ki, nM |
|---------|-----------|---------------------|
| 32 | 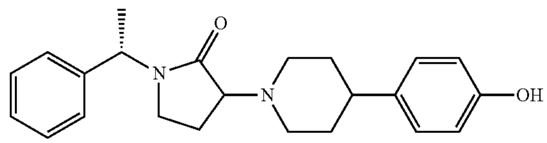 [SMILES: C[C@@H](c1ccccc1)N1CCC(N2CCC(c3ccc(O)cc3)CC2)C1=O] | 100 |
| 33a | 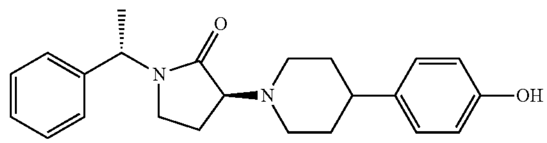 [SMILES: C[C@@H](c1ccccc1)N1CC[C@H](N2CCC(c3ccc(O)cc3)CC2)C1=O] | 5000 |
| 33b | 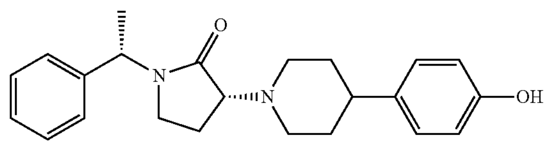 [SMILES: C[C@@H](c1ccccc1)N1CC[C@@H](N2CCC(c3ccc(O)cc3)CC2)C1=O] | 44 |
| 34 | 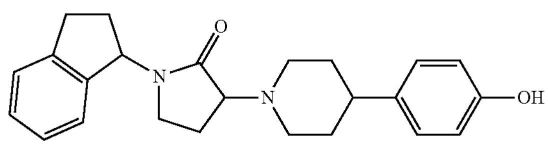 [SMILES: O=C1C(N2CCC(c3ccc(O)cc3)CC2)CCN1C1CCc2ccccc21] | 670 |
| 35 | 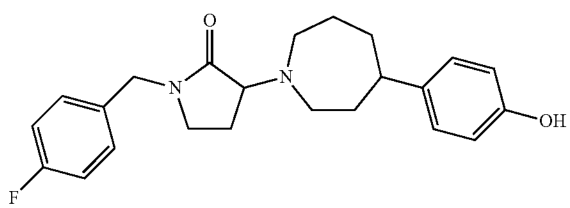 [SMILES: O=C1C(N2CCCC(c3ccc(O)cc3)CC2)CCN1Cc1ccc(F)cc1] | 17 |
| 36 | 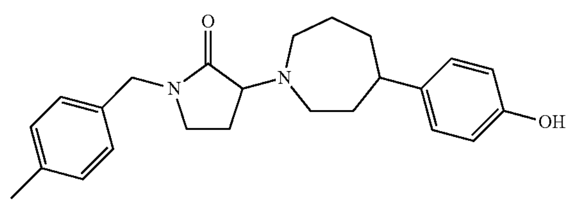 [SMILES: Cc1ccc(CN2CCC(N3CCCC(c4ccc(O)cc4)CC3)C2=O)cc1] | 34 |
| 37 | 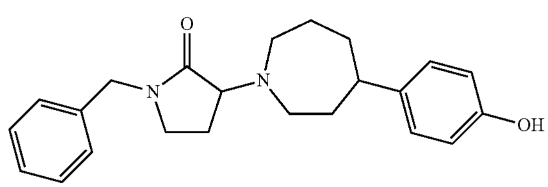 [SMILES: O=C1C(N2CCCC(c3ccc(O)cc3)CC2)CCN1Cc1ccccc1] | 21 |
| 38 | 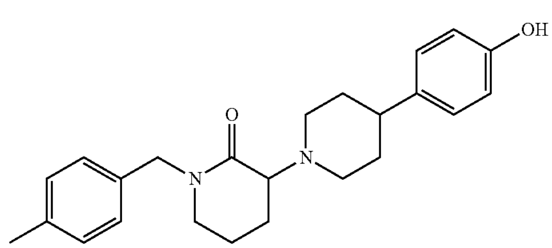 [SMILES: Cc1ccc(CN2CCCC(N3CCC(c4ccc(O)cc4)CC3)C2=O)cc1] | 150 |

-continued

| Example | Structure | NR2B Binding Ki, nM |
|---|---|---|
| 39 | 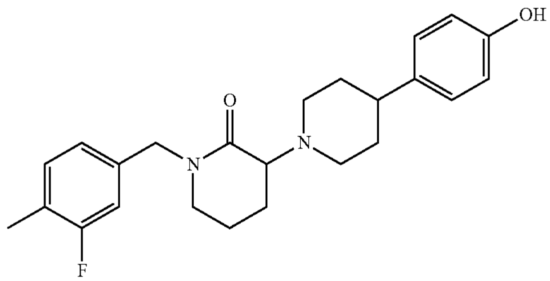 [SMILES: Cc1ccc(CN2CCCC(N3CCC(c4ccc(O)cc4)CC3)C2=O)cc1F] | 300 |
| 40 | 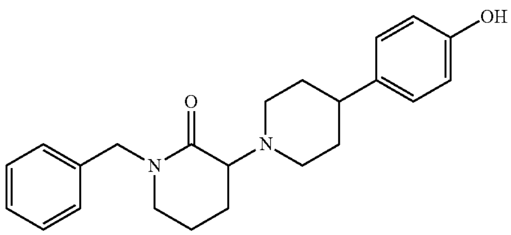 [SMILES: O=C1C(N2CCC(c3ccc(O)cc3)CC2)CCCN1Cc1ccccc1] | 480 |
| 41a | 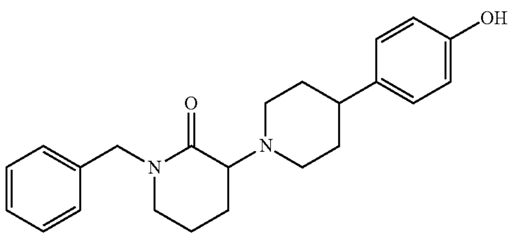 [SMILES: O=C1C(N2CCC(c3ccc(O)cc3)CC2)CCCN1Cc1ccccc1] | 990 |
| 41b | 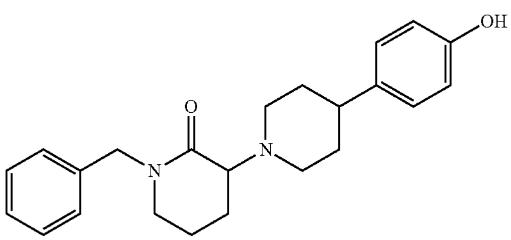 [SMILES: O=C1C(N2CCC(c3ccc(O)cc3)CC2)CCCN1Cc1ccccc1] | 200 |
| 42 | 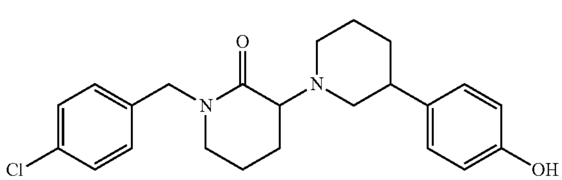 [SMILES: O=C1C(N2CCCC(c3ccc(O)cc3)C2)CCCN1Cc1ccc(Cl)cc1] | 720 |
| 43 | 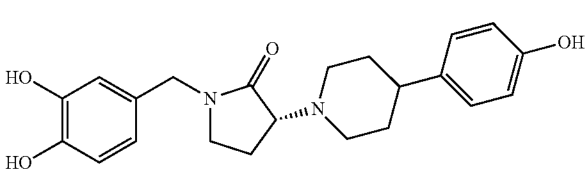 [SMILES: O=C1[C@H](N2CCC(c3ccc(O)cc3)CC2)CCN1Cc1ccc(O)c(O)c1] | 150 |
| 44, E-1 | 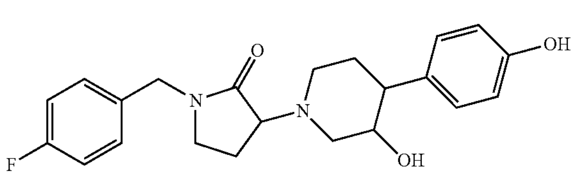 [SMILES: O=C1C(N2CCC(c3ccc(O)cc3)C(O)C2)CCN1Cc1ccc(F)cc1] | 650 |

-continued

| Example | Structure | NR2B Binding Ki, nM |
|---|---|---|
| 44, E-2 | 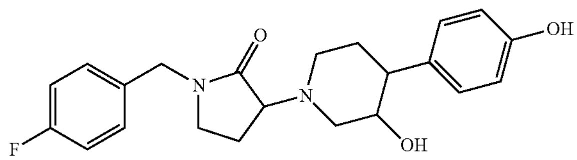 [SMILES: O=C1C(N2CCC(c3ccc(O)cc3)C(O)C2)CCN1Cc1ccc(F)cc1] | 5.7 |
| 45, P-1 | 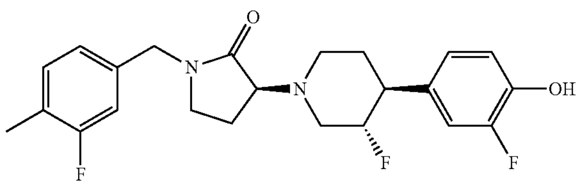 [SMILES: Cc1ccc(CN2CC[C@H](N3CC[C@@H](c4ccc(O)c(F)c4)[C@H](F)C3)C2=O)cc1F] | 260 |
| 45, P-2 | 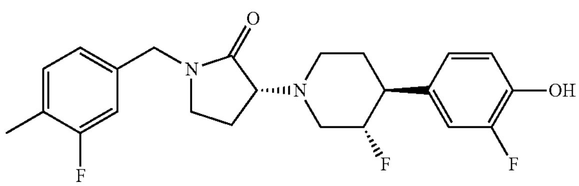 | 3.1 |
| 45, P-3 | 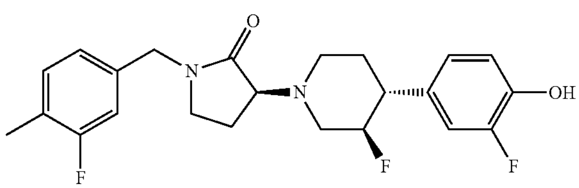 [SMILES: Cc1ccc(CN2CC[C@H](N3CC[C@H](c4ccc(O)c(F)c4)[C@@H](F)C3)C2=O)cc1F] | 380 |
| 45, P-4 | 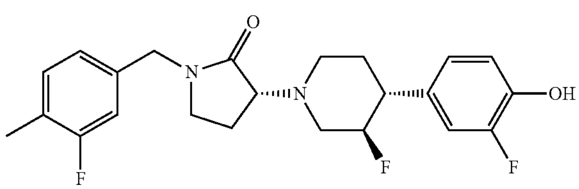 | 2.5 |
| 46, P-1 | 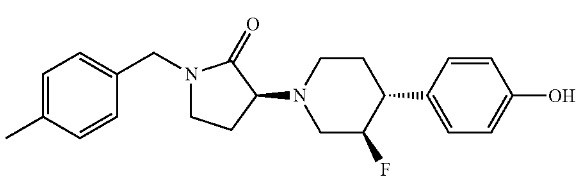 [SMILES: Cc1ccc(CN2CC[C@H](N3CC[C@H](c4ccc(O)cc4)[C@@H](F)C3)C2=O)cc1] | 430 |
| 46, P-2 | 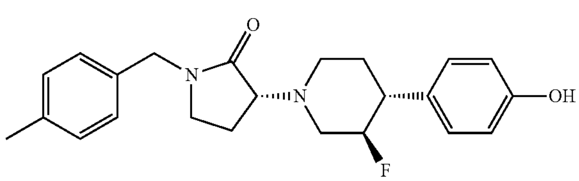 [SMILES: Cc1ccc(CN2CC[C@@H](N3CC[C@H](c4ccc(O)cc4)[C@@H](F)C3)C2=O)cc1] | 4.3 |
| 46, P-3 | 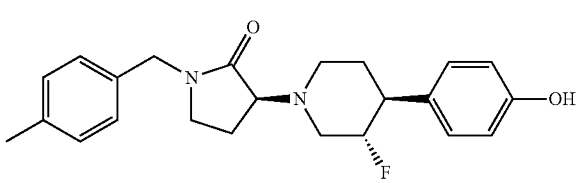 [SMILES: Cc1ccc(CN2CC[C@H](N3CC[C@@H](c4ccc(O)cc4)[C@H](F)C3)C2=O)cc1] | 340 |

| Example | Structure | NR2B Binding Ki, nM |
|---|---|---|
| 46, P-4 | 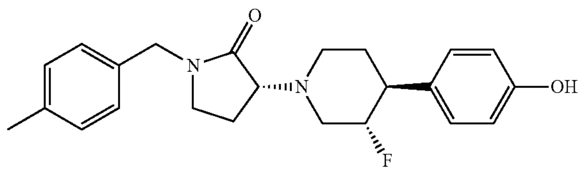 [SMILES: Cc1ccc(CN2CC[C@@H](N3CC[C@@H](c4ccc(O)cc4)[C@H](F)C3)C2=O)cc1] | 4.0 |
| 47, P-1 | 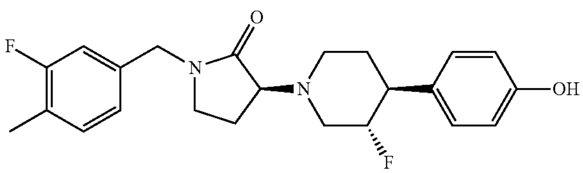 [SMILES: Cc1ccc(CN2CC[C@H](N3CC[C@@H](c4ccc(O)cc4)[C@H](F)C3)C2=O)cc1F] | 470 |
| 47, P-2 | 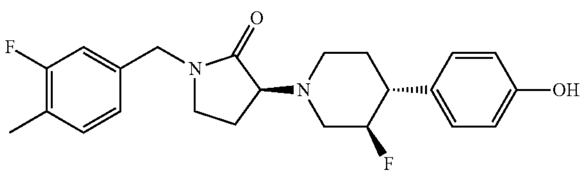 | 470 |
| 47, P-3 | 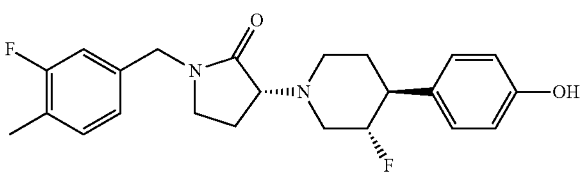 | 3.8 |
| 47, P-4 | 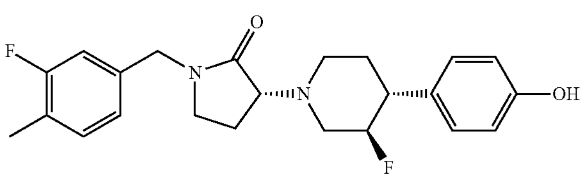 | 3.4 |
| 48, P-1 | 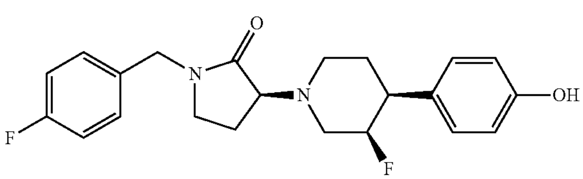 [SMILES: O=C1[C@@H](N2CC[C@@H](c3ccc(O)cc3)[C@@H](F)C2)CCN1Cc1ccc(F)cc1] | 760 |
| 48, P-2 | 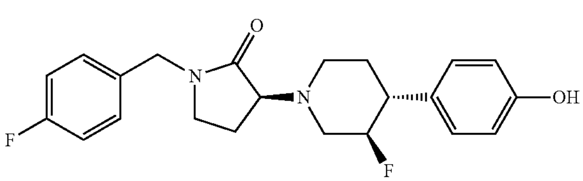 [SMILES: O=C1[C@@H](N2CC[C@H](c3ccc(O)cc3)[C@@H](F)C2)CCN1Cc1ccc(F)cc1] | 1700 |
| 48, P-3 | 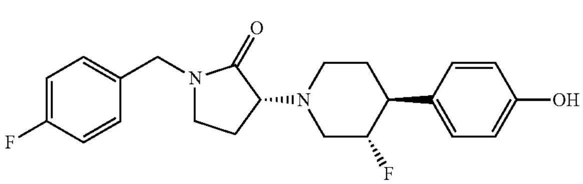 [SMILES: O=C1[C@H](N2CC[C@@H](c3ccc(O)cc3)[C@H](F)C2)CCN1Cc1ccc(F)cc1] | 11 |

-continued

| Example | Structure | NR2B Binding Ki, nM |
|---|---|---|
| 48, P-4 | 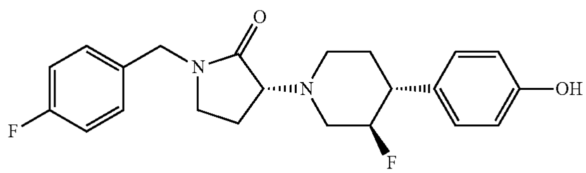 [SMILES: O=C1[C@H](N2CC[C@H](c3ccc(O)cc3)[C@@H](F)C2)CCN1Cc1ccc(F)cc1] | 13 |
| 49, P-1 | 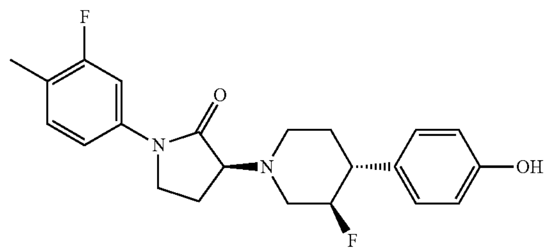 [SMILES: Cc1ccc(N2CC[C@H](N3CC[C@H](c4ccc(O)cc4)[C@@H](F)C3)C2=O)cc1F] | 420 |
| 49, P-2 | 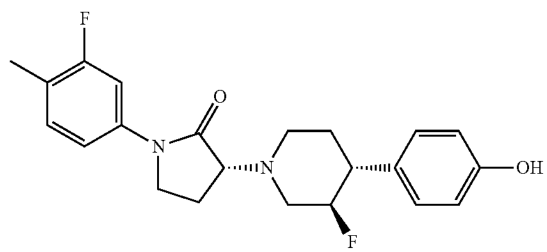 [SMILES: Cc1ccc(N2CC[C@@H](N3CC[C@H](c4ccc(O)cc4)[C@@H](F)C3)C2=O)cc1F] | 73 |
| 50, P-1 | 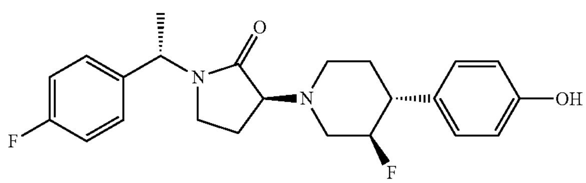 [SMILES: C[C@@H](c1ccc(F)cc1)N1CC[C@H](N2CC[C@H](c3ccc(O)cc3)[C@@H](F)C2)C1=O] | 5000 |
| 50, P-2 | 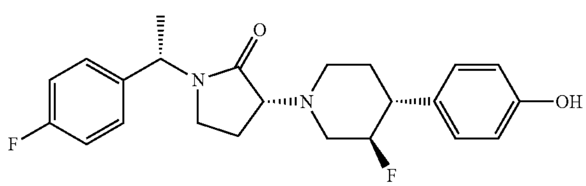 [SMILES: C[C@@H](c1ccc(F)cc1)N1CC[C@@H](N2CC[C@H](c3ccc(O)cc3)[C@@H](F)C2)C1=O] | 890 |
| 50, P-3 | 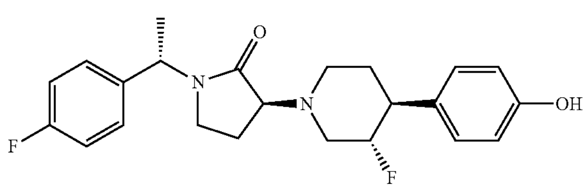 [SMILES: C[C@@H](c1ccc(F)cc1)N1CC[C@H](N2CC[C@@H](c3ccc(O)cc3)[C@H](F)C2)C1=O] | 5000 |
| 50, P-4 | 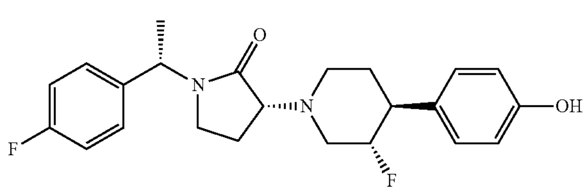 [SMILES: C[C@@H](c1ccc(F)cc1)N1CC[C@@H](N2CC[C@@H](c3ccc(O)cc3)[C@H](F)C2)C1=O] | 1300 |

-continued

| Example | Structure | NR2B Binding Ki, nM |
|---|---|---|
| 51, P-1 | First eluting product | 660 |
| 51, P-2 | Second eluting product | 7.6 |
| 51, P-3 | Third eluting product | 30 |
| 51, P-4 | Fourth eluting product | 11 |
| 52, P-1 | First eluting product | 690 |
| 52, P-2 | Second eluting product | 6.2 |
| 52, P-3 | Third eluting product | 89 |

-continued

| Example | Structure | NR2B Binding Ki, nM |
|---|---|---|
| 52, P-4 | Fourth eluting product | 6.7 |
| 53, P-1 | First eluting product | 1100 |
| 53, P-2 | Second eluting product | 5.8 |
| 54, P-1 | First eluting product | 530 |
| 54, P-2 | Second eluting product | 8.5 |
| 54, P-3 | Third eluting product | 110 |
| 54, P-4 | Fourth eluting product | 26 |

-continued
| Example | Structure | NR2B Binding Ki, nM |
|---|---|---|
| 55, P-1 | 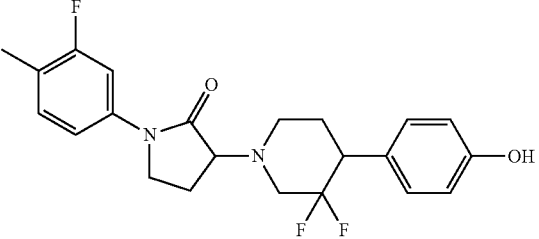 [SMILES: Cc1ccc(N2CCC(N3CCC(c4ccc(O)cc4)C(F)(F)C3)C2=O)cc1F]<br>First eluting product | 280 |
| 55, P-2 | 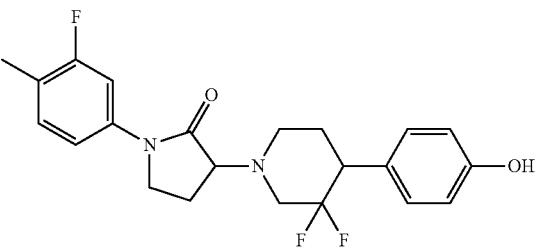 [SMILES: Cc1ccc(N2CCC(N3CCC(c4ccc(O)cc4)C(F)(F)C3)C2=O)cc1F]<br>Second eluting product | 32 |
| 55, P-3 | 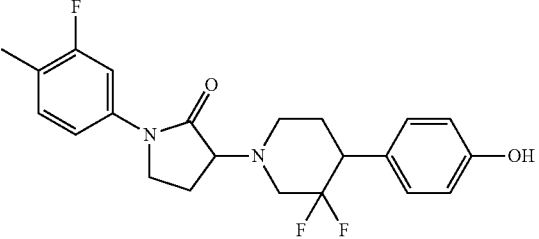 [SMILES: Cc1ccc(N2CCC(N3CCC(c4ccc(O)cc4)C(F)(F)C3)C2=O)cc1F]<br>Third eluting product | 130 |
| 55, P-4 | 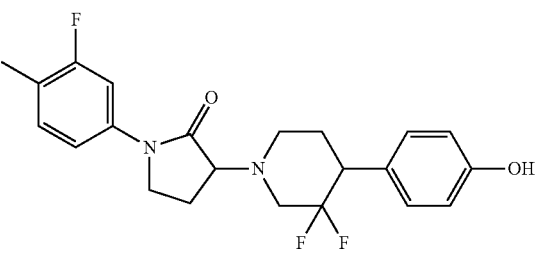 [SMILES: Cc1ccc(N2CCC(N3CCC(c4ccc(O)cc4)C(F)(F)C3)C2=O)cc1F]<br>Fourth eluting product | 430 |
| 56, P-1 | 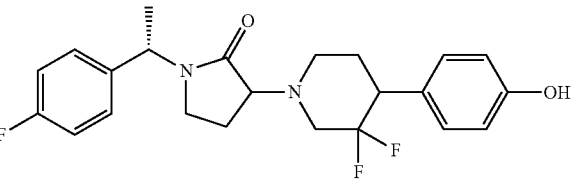<br>First eluting product | 5000 |
| 56, P-2 | 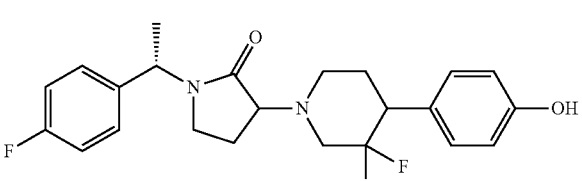<br>Second eluting product | 1400 |

| Example | Structure | NR2B Binding Ki, nM |
|---------|-----------|---------------------|
| 56, P-3 | 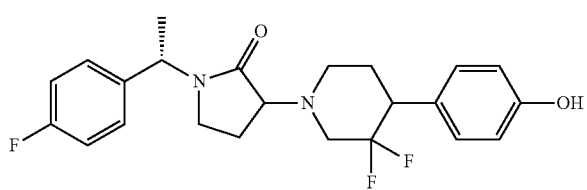 [SMILES: C[C@@H](c1ccc(F)cc1)N1CCC(N2CCC(c3ccc(O)cc3)C(F)(F)C2)C1=O]<br>Third eluting product | 5000 |
| 56, P-4 | 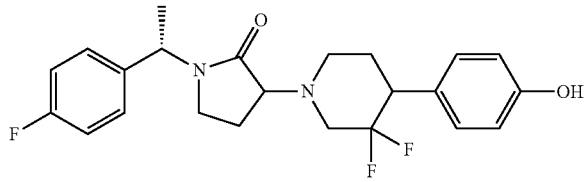 [SMILES: C[C@@H](c1ccc(F)cc1)N1CCC(N2CCC(c3ccc(O)cc3)C(F)(F)C2)C1=O]<br>Fourth eluting product | 660 |
| 57 | 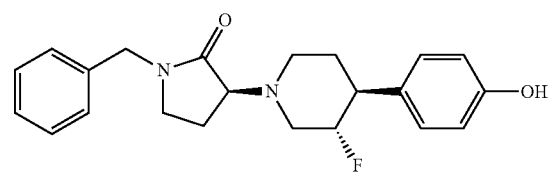 [SMILES: O=C1[C@@H](N2CC[C@@H](c3ccc(O)cc3)[C@H](F)C2)CCN1Cc1ccccc1] | 490 |
| 58 | 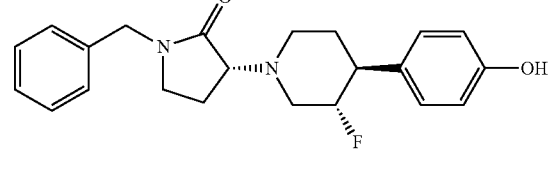 | 8.7 |
| 59 | 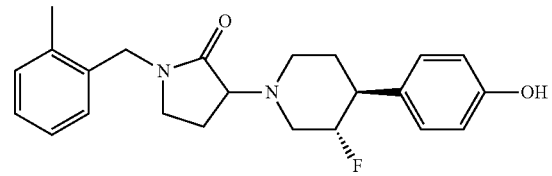 | 81 |
| 60 | 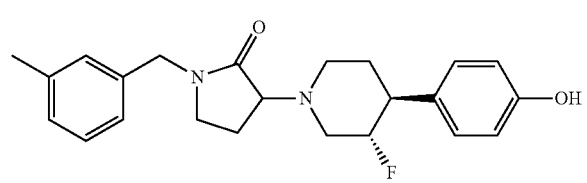 [SMILES: Cc1cccc(CN2CCC(N3CC[C@@H](c4ccc(O)cc4)[C@H](F)C3)C2=O)c1] | 110 |
| 61 | 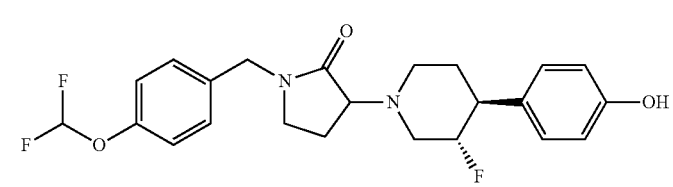 [SMILES: O=C1C(N2CC[C@@H](c3ccc(O)cc3)[C@H](F)C2)CCN1Cc1ccc(OC(F)F)cc1] | 46 |

| Example | Structure | NR2B Binding Ki, nM |
|---|---|---|
| 62 | 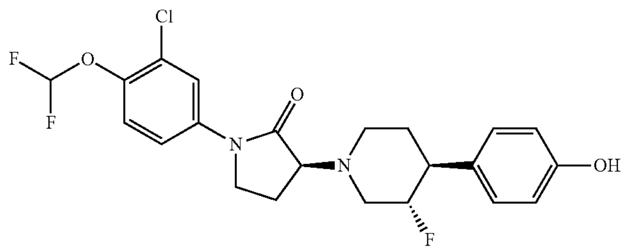 [SMILES: O=C1[C@@H](N2CC[C@@H](c3ccc(O)cc3)[C@H](F)C2)CCN1c1ccc(OC(F)F)c(Cl)c1] | 6.7 |
| 63 | 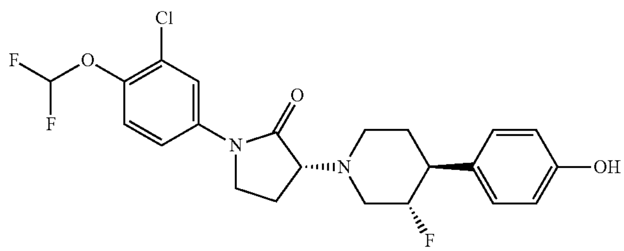 [SMILES: O=C1[C@H](N2CC[C@@H](c3ccc(O)cc3)[C@H](F)C2)CCN1c1ccc(OC(F)F)c(Cl)c1] | 10 |
| 64 | 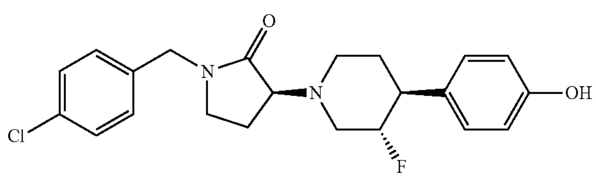 [SMILES: O=C1[C@@H](N2CC[C@@H](c3ccc(O)cc3)[C@H](F)C2)CCN1Cc1ccc(Cl)cc1] | 490 |
| 65 | 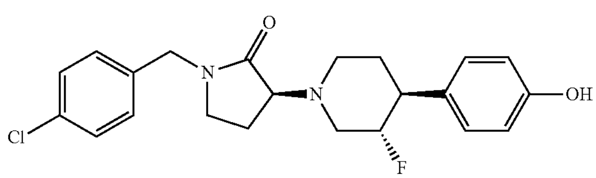 [SMILES: O=C1[C@@H](N2CC[C@@H](c3ccc(O)cc3)[C@H](F)C2)CCN1Cc1ccc(Cl)cc1] | 3.6 |
| 66 | 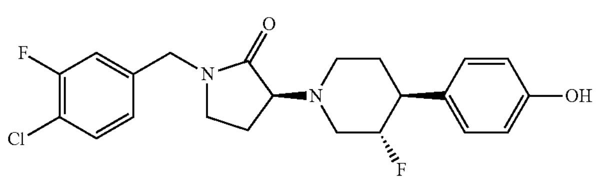 [SMILES: O=C1[C@@H](N2CC[C@@H](c3ccc(O)cc3)[C@H](F)C2)CCN1Cc1ccc(Cl)c(F)c1] | 1500 |
| 67 | 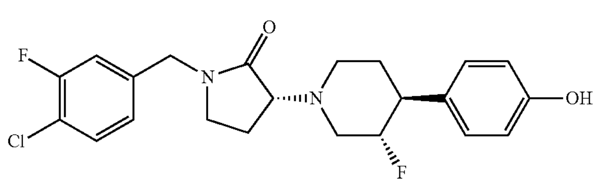 [SMILES: O=C1[C@H](N2CC[C@@H](c3ccc(O)cc3)[C@H](F)C2)CCN1Cc1ccc(Cl)c(F)c1] | 6.5 |
| 68 | 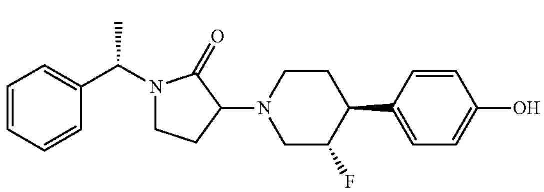 [SMILES: C[C@@H](c1ccccc1)N1CCC(N2CC[C@@H](c3ccc(O)cc3)[C@H](F)C2)C1=O] | 710 |

-continued

| Example | Structure | NR2B Binding Ki, nM |
|---|---|---|
| 69 | 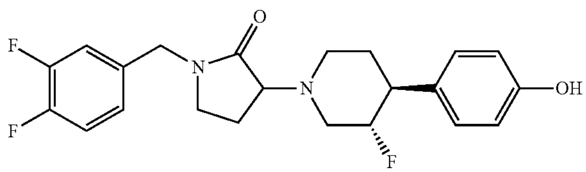 [SMILES: O=C1C(N2CC[C@@H](c3ccc(O)cc3)[C@H](F)C2)CCN1Cc1ccc(F)c(F)c1] | 34 |
| 70 | 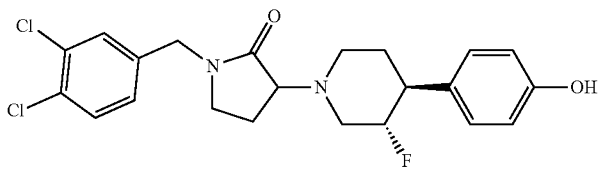 [SMILES: O=C1C(N2CC[C@@H](c3ccc(O)cc3)[C@H](F)C2)CCN1Cc1ccc(Cl)c(Cl)c1] | 180 |
| 71 | 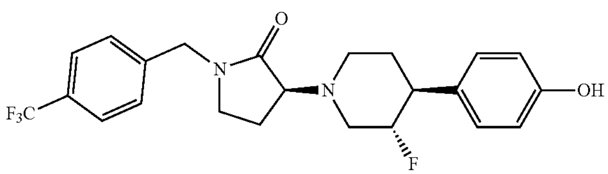 | 560 |
| 72 | 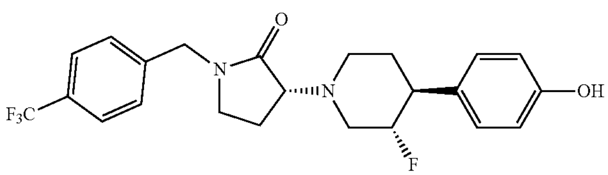 [SMILES: O=C1[C@H](N2CC[C@@H](c3ccc(O)cc3)[C@H](F)C2)CCN1Cc1ccc(C(F)(F)F)cc1] | 6.0 |
| 73 | 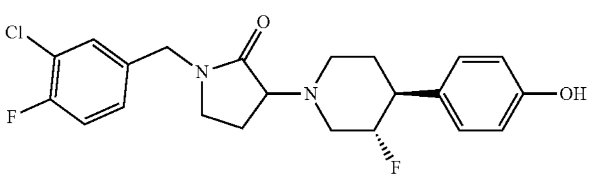 [SMILES: O=C1C(N2CC[C@@H](c3ccc(O)cc3)[C@H](F)C2)CCN1Cc1ccc(F)c(Cl)c1] | 330 |
| 74 | 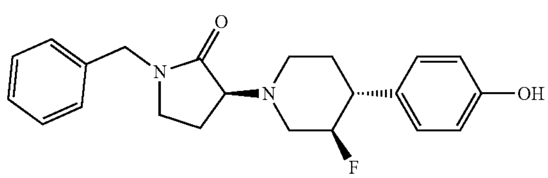 [SMILES: O=C1[C@@H](N2CC[C@H](c3ccc(O)cc3)[C@@H](F)C2)CCN1Cc1ccccc1] | 680 |
| 75 | 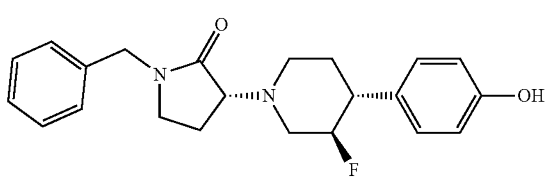 [SMILES: O=C1[C@H](N2CC[C@H](c3ccc(O)cc3)[C@@H](F)C2)CCN1Cc1ccccc1] | 8.0 |
| 76 | 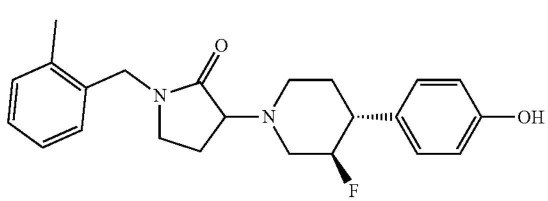 [SMILES: Cc1ccccc1CN1CCC(N2CC[C@H](c3ccc(O)cc3)[C@@H](F)C2)C1=O] | 33 |

| Example | Structure | NR2B Binding Ki, nM |
|---|---|---|
| 77 | 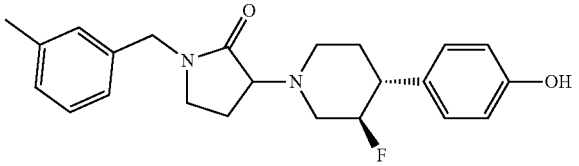 [SMILES: Cc1cccc(CN2CCC(N3CC[C@H](c4ccc(O)cc4)[C@@H](F)C3)C2=O)c1] | 27 |
| 78 | 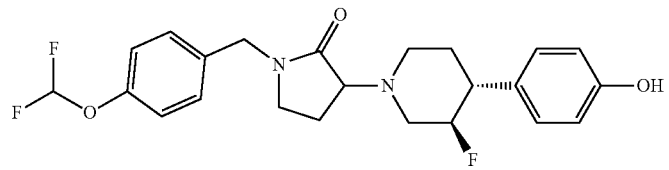 [SMILES: O=C1C(N2CC[C@H](c3ccc(O)cc3)[C@@H](F)C2)CCN1Cc1ccc(OC(F)F)cc1] | 190 |
| 79 | 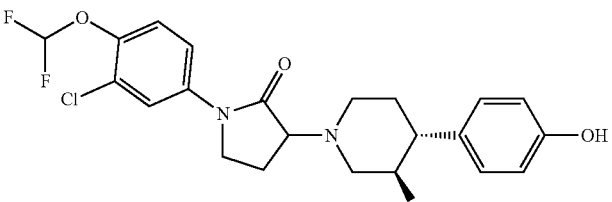 | 40 |
| 80 | 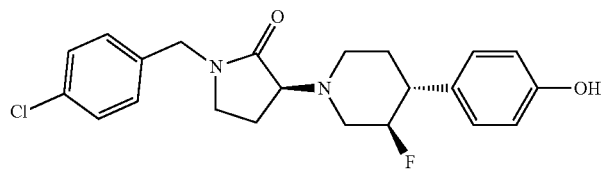 | 560 |
| 81 | 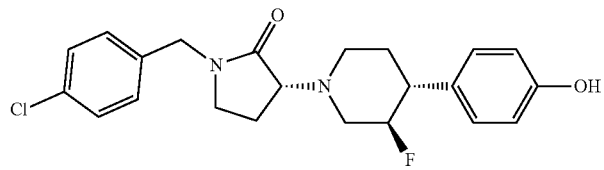 [SMILES: O=C1[C@H](N2CC[C@H](c3ccc(O)cc3)[C@@H](F)C2)CCN1Cc1ccc(Cl)cc1] | 3.8 |
| 82 | 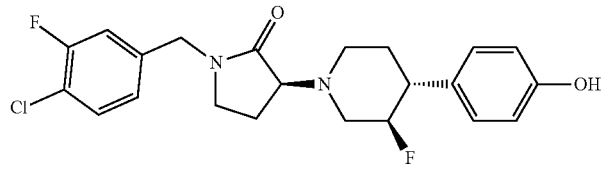 [SMILES: O=C1[C@@H](N2CC[C@H](c3ccc(O)cc3)[C@@H](F)C2)CCN1Cc1ccc(Cl)c(F)c1] | 860 |
| 83 | 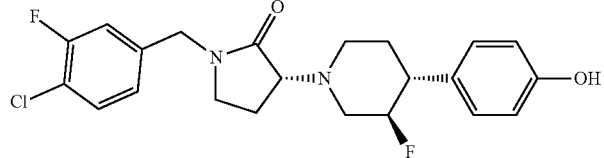 [SMILES: O=C1[C@H](N2CC[C@H](c3ccc(O)cc3)[C@@H](F)C2)CCN1Cc1ccc(Cl)c(F)c1] | 5.0 |
| 84 | 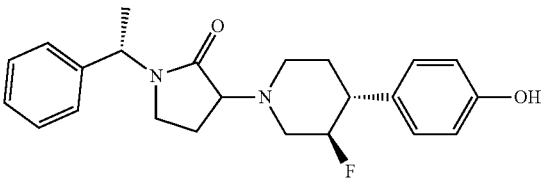 [SMILES: C[C@@H](c1ccccc1)N1CCC(N2CC[C@H](c3ccc(O)cc3)[C@@H](F)C2)C1=O] | 950 |

-continued

| Example | Structure | NR2B Binding Ki, nM |
|---|---|---|
| 85 | 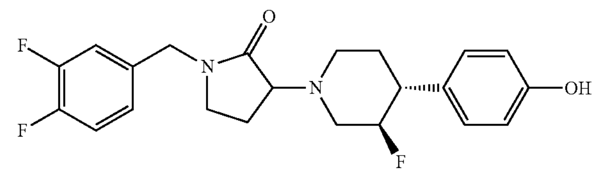 | 23 |
| 86 | 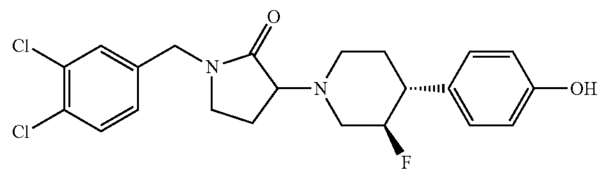 [SMILES: O=C1C(N2CC[C@H](c3ccc(O)cc3)[C@@H](F)C2)CCN1Cc1ccc(Cl)c(Cl)c1] | 78 |
| 87 | 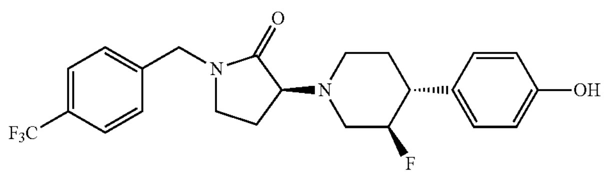 [SMILES: O=C1[C@@H](N2CC[C@H](c3ccc(O)cc3)[C@@H](F)C2)CCN1Cc1ccc(C(F)(F)F)cc1] | 540 |
| 88 | 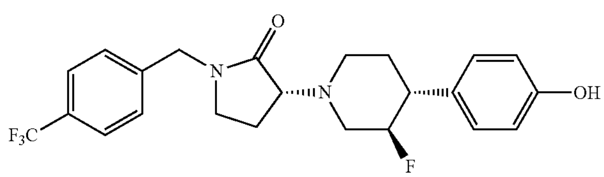 [SMILES: O=C1[C@H](N2CC[C@H](c3ccc(O)cc3)[C@@H](F)C2)CCN1Cc1ccc(C(F)(F)F)cc1] | 5.3 |
| 89 | 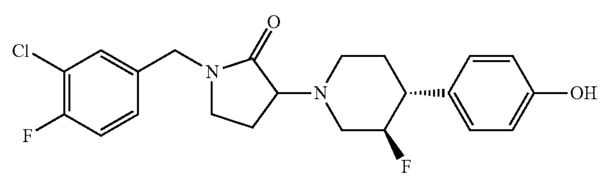 [SMILES: O=C1C(N2CC[C@H](c3ccc(O)cc3)[C@@H](F)C2)CCN1Cc1ccc(F)c(Cl)c1] | 200 |
| 90 | 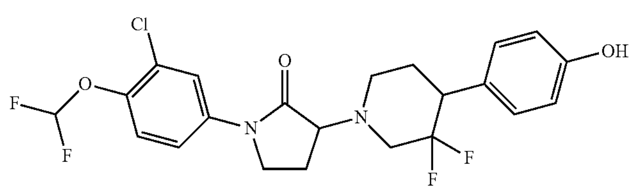 | 77 |
| 91, P-1 | 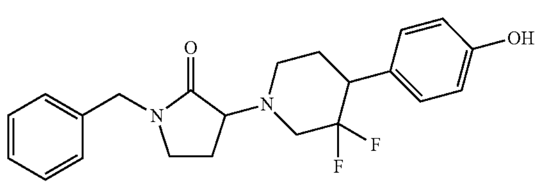 | 76 |
| 91, P-2 | 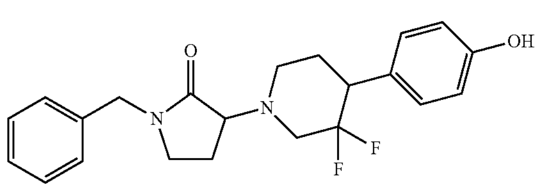 | 14 |

| Example | Structure | NR2B Binding Ki, nM |
|---|---|---|
| 92 | 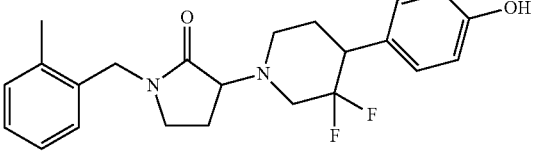 | 59 |
| 93 | 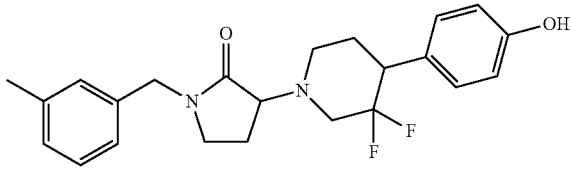 [SMILES: Cc1cccc(CN2CCC(N3CCC(c4ccc(O)cc4)C(F)(F)C3)C2=O)c1] | 67 |
| 94 | 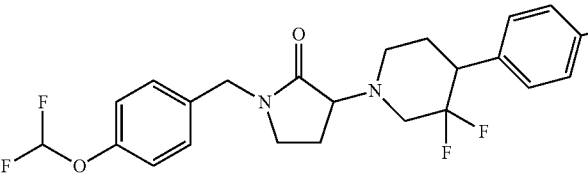 | 390 |
| 95, P-1 | 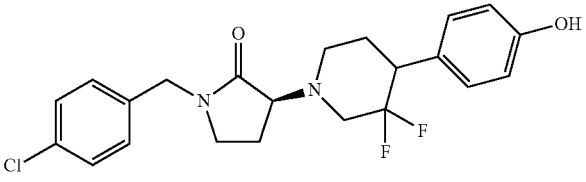 [SMILES: O=C1[C@@H](N2CCC(c3ccc(O)cc3)C(F)(F)C2)CCN1Cc1ccc(Cl)cc1] | 54 |
| 95, P-2 | 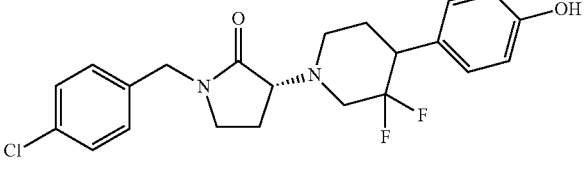 | 12 |
| 96, P-1 | 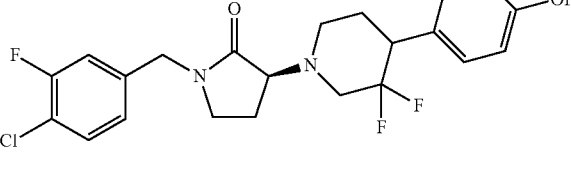 | 490 |
| 96, P-2 | 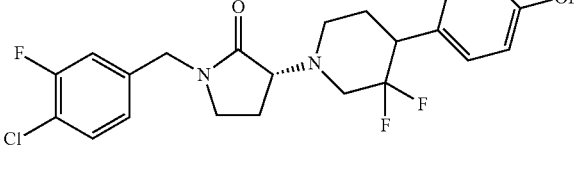 | 18 |
| 97 | 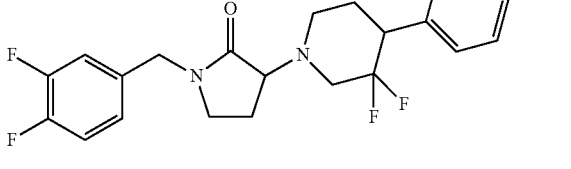 | 45 |

-continued

| Example | Structure | NR2B Binding Ki, nM |
|---|---|---|
| 98 | 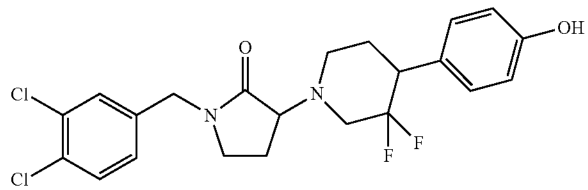 [SMILES: O=C1C(N2CCC(c3ccc(O)cc3)C(F)(F)C2)CCN1Cc1ccc(Cl)c(Cl)c1] | 230 |
| 99, P-1 | 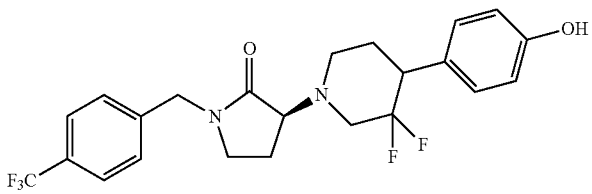 [SMILES: O=C1[C@@H](N2CCC(c3ccc(O)cc3)C(F)(F)C2)CCN1Cc1ccc(C(F)(F)F)cc1] | 380 |
| 99, P-2 | 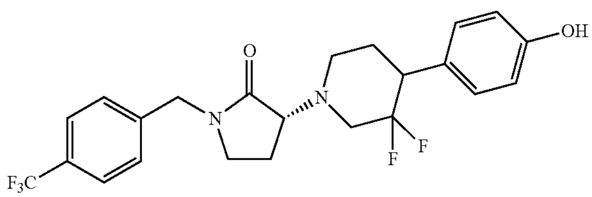 [SMILES: O=C1[C@H](N2CCC(c3ccc(O)cc3)C(F)(F)C2)CCN1Cc1ccc(C(F)(F)F)cc1] | 22 |
| 100 | 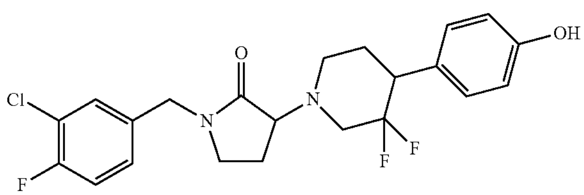 [SMILES: O=C1C(N2CCC(c3ccc(O)cc3)C(F)(F)C2)CCN1Cc1ccc(F)c(Cl)c1] | 570 |
| 101, P-1 | 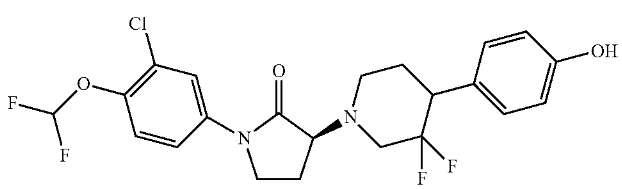 [SMILES: O=C1[C@@H](N2CCC(c3ccc(O)cc3)C(F)(F)C2)CCN1c1ccc(OC(F)F)c(Cl)c1] | 13 |
| 101, P-2 | 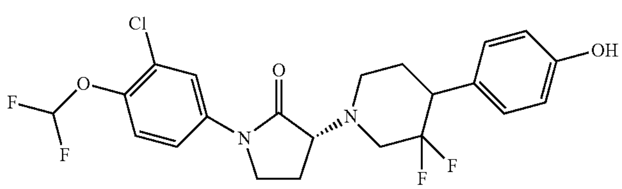 [SMILES: O=C1[C@H](N2CCC(c3ccc(O)cc3)C(F)(F)C2)CCN1c1ccc(OC(F)F)c(Cl)c1] | 11 |
| 102, P-1 | 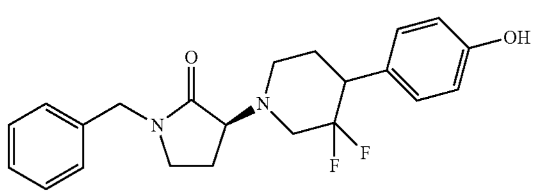 [SMILES: O=C1[C@@H](N2CCC(c3ccc(O)cc3)C(F)(F)C2)CCN1Cc1ccccc1] | 740 |
| 102, P-2 | 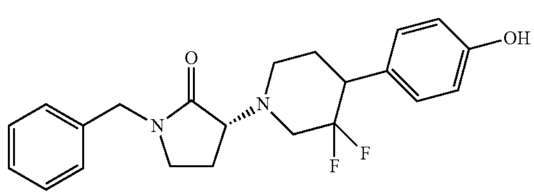 [SMILES: O=C1[C@H](N2CCC(c3ccc(O)cc3)C(F)(F)C2)CCN1Cc1ccccc1] | 30 |

| Example | Structure | NR2B Binding Ki, nM |
|---|---|---|
| 103 | 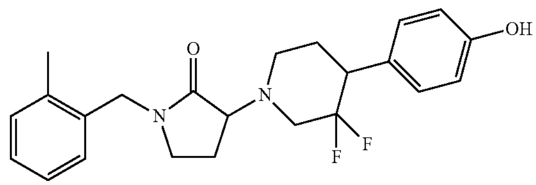 [SMILES: Cc1ccccc1CN1CCC(N2CCC(c3ccc(O)cc3)C(F)(F)C2)C1=O] | 81 |
| 104 | 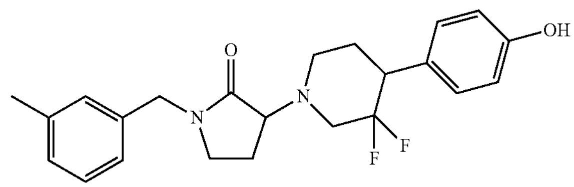 [SMILES: Cc1cccc(CN2CCC(N3CCC(c4ccc(O)cc4)C(F)(F)C3)C2=O)c1] | 130 |
| 105 | 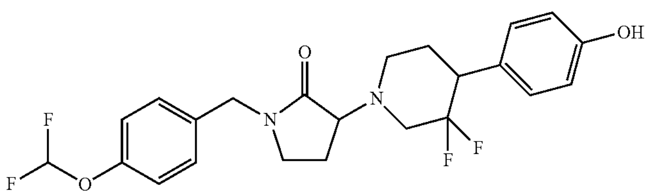 [SMILES: O=C1C(N2CCC(c3ccc(O)cc3)C(F)(F)C2)CCN1Cc1ccc(OC(F)F)cc1] | 180 |
| 106, P-1 | 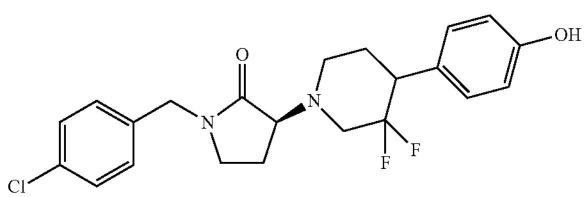 [SMILES: O=C1[C@@H](N2CCC(c3ccc(O)cc3)C(F)(F)C2)CCN1Cc1ccc(Cl)cc1] | 990 |
| 106, P-2 | 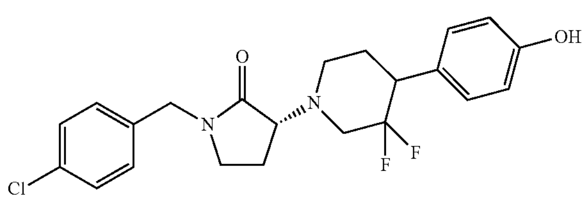 [SMILES: O=C1[C@H](N2CCC(c3ccc(O)cc3)C(F)(F)C2)CCN1Cc1ccc(Cl)cc1] | 4.6 |
| 107, P-1 | 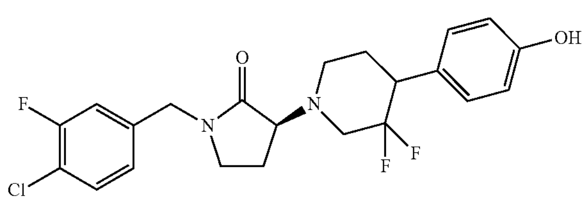 [SMILES: O=C1[C@@H](N2CCC(c3ccc(O)cc3)C(F)(F)C2)CCN1Cc1ccc(Cl)c(F)c1] | 1200 |
| 107, P-2 | 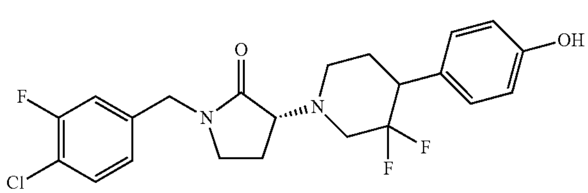 [SMILES: O=C1[C@H](N2CCC(c3ccc(O)cc3)C(F)(F)C2)CCN1Cc1ccc(Cl)c(F)c1] | 7.7 |

| Example | Structure | NR2B Binding Ki, nM |
|---|---|---|
| 108, P-1 | 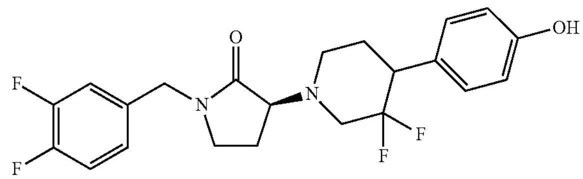 [SMILES: O=C1[C@@H](N2CCC(c3ccc(O)cc3)C(F)(F)C2)CCN1Cc1ccc(F)c(F)c1] | 1200 |
| 108, P-2 | 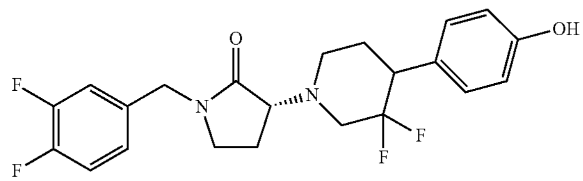 | 15 |
| 109 | 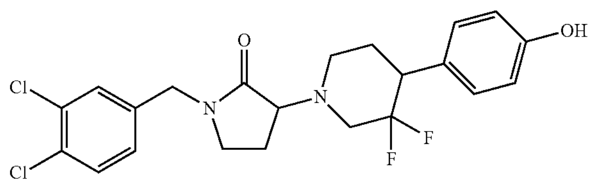 | 290 |
| 110 | 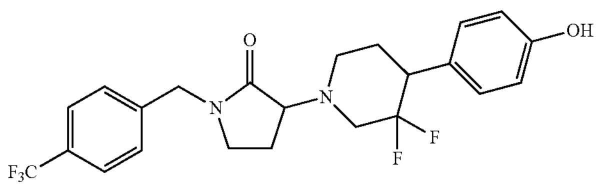 [SMILES: O=C1C(N2CCC(c3ccc(O)cc3)C(F)(F)C2)CCN1Cc1ccc(C(F)(F)F)cc1] | 36 |
| 111 | 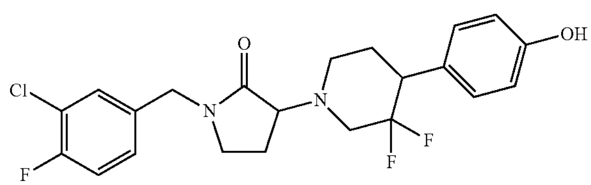 [SMILES: O=C1C(N2CCC(c3ccc(O)cc3)C(F)(F)C2)CCN1Cc1ccc(F)c(Cl)c1] | 590 |
| 112, P-1 | 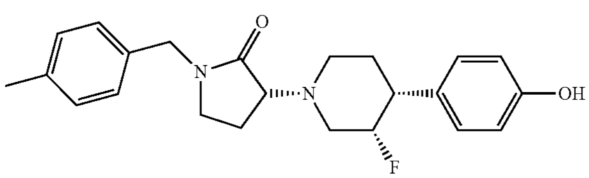 | 4.4 |
| 112, P-2 | 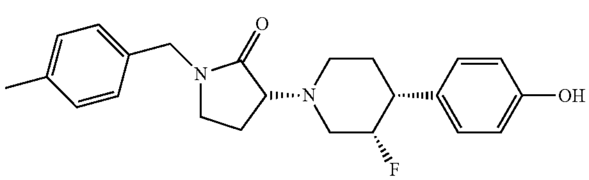 | 8.4 |
| 113 | 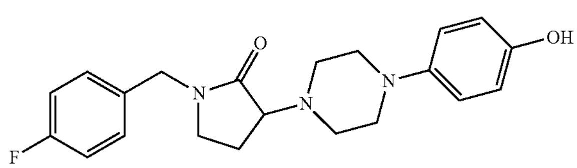 [SMILES: O=C1C(N2CCN(c3ccc(O)cc3)CC2)CCN1Cc1ccc(F)cc1] | 33 |

-continued

| Example | Structure | NR2B Binding Ki, nM |
|---|---|---|
| 114, P-1 | 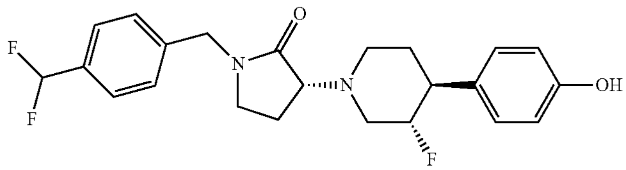 [SMILES: O=C1[C@H](N2CC[C@@H](c3ccc(O)cc3)[C@H](F)C2)CCN1Cc1ccc(C(F)F)cc1] | 3.5 |
| 114, P-2 | 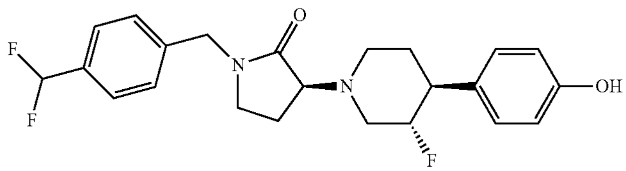 [SMILES: O=C1[C@@H](N2CC[C@@H](c3ccc(O)cc3)[C@H](F)C2)CCN1Cc1ccc(C(F)F)cc1] | 180 |
| 115 | 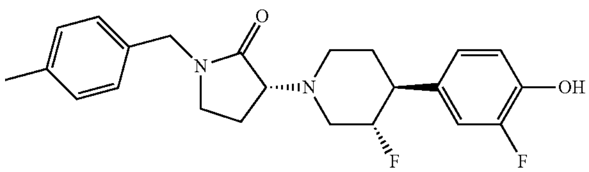 [SMILES: Cc1ccc(CN2CC[C@@H](N3CC[C@@H](c4ccc(O)c(F)c4)[C@H](F)C3)C2=O)cc1] | 2.7 |
| 116 | 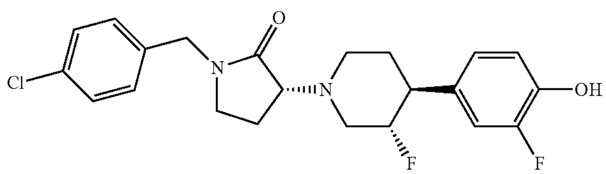 | 2.0 |
| 117, P-1 | 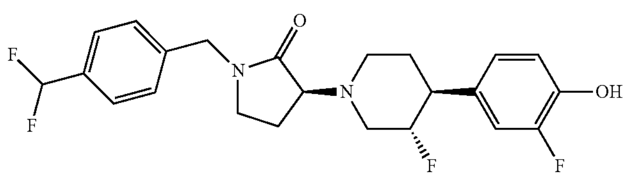 [SMILES: O=C1[C@@H](N2CC[C@@H](c3ccc(O)c(F)c3)[C@H](F)C2)CCN1Cc1ccc(C(F)F)cc1] | 79 |
| 117, P-2 | 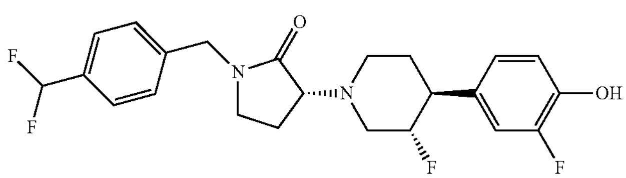 [SMILES: O=C1[C@H](N2CC[C@@H](c3ccc(O)c(F)c3)[C@H](F)C2)CCN1Cc1ccc(C(F)F)cc1] | 2.9 |

Ex Vivo Occupancy Assay.

This assay demonstrates that the compound of example 1 occupies brain-resident NR2B-subtype receptors in animals after closing. 7-9 weeks old male CD-1 mice were dosed intravenously in a vehicle consisting of 10% dimethylacetamide, 40% PEG-400, 30% hydroxypropyl betacyclodextrin, and 30% water with experimental compounds and the forebrains were harvested 15 minutes post-closing by decapitation. The brain samples were immediately snap-frozen and stored at −80° C. On the following day, the dosed brain samples were thawed on ice for 15-20 minutes followed by homogenization using Polytron for 10 seconds in cold homogenization buffer composed of 50 mM $KH_2PO_4$ (pH adjusted to 7.4 with KOH), 1 mM EDTA, 0.005% Triton X 100 and protease inhibitor cocktail (Sigma Aldrich). The crude homogenates were further homogenized using a Dounce homogenizer and the homogenized membrane aliquots from all animals were flash-frozen and stored at −80° C. until further use. The whole homogenization process was performed on ice.

For determining occupancy, the membrane homogenates were first thawed on ice and then needle-homogenized using a 25 gauge needle. The homogenized membrane (6.4 mg/ml) was added to a 96-well plate followed by addition of $^3$H Ro 25-6981 (6 nM). The reaction mixture was incubated for 5 minutes on a shaker at 4° C. and then harvested onto GF/B filter plates (treated with 0.5% PEI for 1 hr at room temperature). The filter plates were dried at 50° C. for 20 mins, incubated with microscint 20 for 10 minutes and read on TopCount (Perkin Elmer). Each close or compound group consisted of 4-5 animals. The control group of animals was dosed with vehicle alone. Membrane from each animal was added in triplicates to the assay plate. Non-specific binding was determined using 10 μM Ro 25-6981 added to the wells containing membrane homogenates from vehicle-dosed animals. Specific counts/minute was converted to % occupancy at each close of a compound for each animal using the following equation:

$$\% \text{ Occupancy (animal } A) = 100 - \left( \frac{\text{specific CPM of animal } A}{\text{Average CPM from control group}} \times 100 \right)$$

Using this procedure, the compound of example 46, P-4 shows 95% NR2B receptor occupancy after a 3 mg/Kg i.v. close. Drug levels were determined by mass spectroscopy in the usual manner. Drug levels in the blood plasma were 1106 nM in at this close, and drug levels in the homogonized brain tissue were 1984 nM. The compound of example 114, P-1 showed 97% NR2B receptor occupancy after a 3 mg/Kg i.v. close. Drug levels in the blood plasma were 1800 nM in at this close, and drug levels in the homogonized brain tissue were 2200 nM.

hERG Electrophysiology Assay.

The experimental compounds were assessed for hERG activity on HEK 293 cells stably expressing hERG channels using patch clamp technique. Coverslips plated with hERG expressing cells were placed in the experimental chamber and were perfused with a solution composed of (in mM): 140 NaCl, 4 KCl, 1.8 CaCl$_2$, 1 MgCl$_2$, 10 Glucose, 10 HEPES (pH 7.4, NaOH) at room temperature. Borosilicate patch pipettes had tip resistances of 2-4 Mohms when filled with an internal solution containing: 130 KCl, 1 MgCl$_2$, 1 CaCl$_2$, 10 EGTA, 10 HEPES, 5 ATP-K$_2$ (pH 7.2, KOH). The cells were clamped at −80 mV in whole cell configuration using an Axopatch 200B (Axon instruments, Union City, Calif.) patch clamp amplifier controlled by pClamp (Axon instruments) software. Upon formation of a gigaseal, the following voltage protocol was repeatedly (0.05 Hz) applied to record tail currents: depolarization step from −80 mV to +20 mV for 2 seconds followed by a hyperpolarization step to −65 mV (3 seconds) to elicit tail currents and then, back to the holding potential. Compounds were applied after stabilization of tail current. First, tail currents were recorded in presence of extracellular solution alone (control) and subsequently, in extracellular solution containing increasing compound concentrations. Each compound concentration was applied for 2-5 minutes. The percentage inhibition at each concentration was calculated as reduction in peak tail current with respect to the peak tail current recorded in the presence of control solution. Data analysis was performed in custom made software. The percent inhibitions at different concentrations were plotted to obtain a concentration response curve, which was subsequently fitted with a four parameter equation to calculate the hERG IC$_{50}$ value. Using this procedure, the compound of example 46, P-4 is a poor inhibitor of the hERG channel, with an IC$_{50}$=28 µM. The compound of example 114, P-1 is a poor inhibitor of the hERG channel, with an IC$_{50}$=13.5 µM.

Mouse Forced Swim Test (mFST).

Forced Swim Test (FST) is an animal model used to assess antidepressant compounds in preclinical studies. The FST was performed similar to the method of Porsolt et al. with modifications (Porsolt R D, Bertin A, Jalfre M. Behavioral despair in mice: a primary screening test for antidepressants. Arch Int Pharmacodyn Thér 1977; 229:327-36). In this paradigm, mice are forced to swim in an inescapable cylinder filled with water. Under these conditions, mice will initially try to escape and eventually develop immobility behavior; this behavior is interpreted as a passive stress-coping strategy or depression-like behavior. Swim tanks were positioned inside a box made of plastic. Each tank was separated from each other by opaque plastic sheets to the height of cylinders. Three mice were subjected to test at a time. Swim sessions were conducted for 6 min by placing mice in individual glass cylinders (46 cm height×20 cm diameter) containing water (20-cm deep, maintained at 24-25° C.). At this water level, the mouse tail does not touch the bottom of the container. The mouse was judged to be immobile whenever it remained floating passively without struggling in the water and only making those movements necessary to keep its nose/head above the water and to keep it afloat. The duration of immobility was evaluated during the total 6 min of the test and expressed as duration (sec) of immobility. Each mouse was tested only once. At the end of each session, mice were dried with a dry cloth and returned to their home cage placed on a thermal blanket to prevent hypothermia. Water was replaced after each trial. All testing sessions were recorded with a video camera (Sony Handicam, Model: DCR—HC38E; PAL) and scoring was done using the Forced Swim Scan, Version 2.0 software (Clever Systems Inc., Reston, Va., USA; see Hayashi E, Shimamura M, Kuratani K, Kinoshita M, Hara H. Automated experimental system capturing three behavioral components during murine forced swim test. Life Sci. 2011 Feb. 28; 88(9-10):411-7 and Yuan P, Tragon T, Xia M, Leclair C A, Skoumbourdis A P, Zheng W, Thomas C J, Huang R, Austin C P, Chen G, Guitart X. Phosphodiesterase 4 inhibitors enhance sexual pleasure-seeking activity in rodents. Pharmacol Biochem Behay. 2011; 98(3):349-55). For NCE testing: Test compound was administered in mice 15 min before swim session by i.v. route and immobility time was recorded for next 6 min. At the end of FST, the mouse were euthanized by rapid decapitation method and plasma and brain samples were collected and stored under −80° C. fill further analysis. In the mouce forced swim assay, the compound of example 1 was dosed intraveneously in a vehicle of 30% hydroxypropyl betacyclodextrin/70% citrate buffer pH 4 at a 5 mL/Kg closing volume. The compound of example 46, P-4 demonstrated a statistically significant decrease in immobility time at 1 mg/Kg under these conditions. Drug levels were 268 +/−128 nM in the plasma and 749 +/−215 nM in the brain at this close. The NR2B receptor occupancy was determined as reported above and was determined to be 73%. The compound of example 224, P-2 demonstrated a statistically significant decrease in immobility time at 1 mg/Kg under these same conditions. Drug levels were 360 nM in the plasma. The NR2B receptor occupancy was determined to be 79%.

We claim:

1. A compound of the formula I

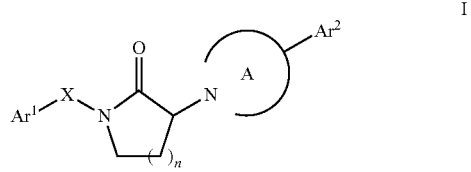

where:
Ar$^1$ is phenyl or indanyl and is substituted with 0-3 substituents selected from cyano, halo, alkyl, haloalkyl, and haloalkoxy;
Ar$^2$ is phenyl substituted with 1 OH substituent and also substituted with 0-3 substituents selected from cyano, halo, alkyl, haloalkyl, and haloalkoxy;
X is a bond or C$_1$-C$_3$ alkylene;
n is 1 or 2; and
ring A is azetidinyl, pyrrolidinyl, piperidinyl, piperazinyl, homopiperidinyl, or homopiperazinyl and is substituted with 0-4 substituents selected from halo, alkyl, hydroxy, or alkoxy;
or a pharmaceutically acceptable salt thereof.

2. A compound of claim 1 where n is 1 and ring A is piperidinyl substituted with 0-2 halo substituents.

3. A compound of claim 1 where Ar$^1$ is phenyl substituted with 0-3 substituents selected from cyano, halo, alkyl, haloalkyl, and haloalkoxy.

4. A compound of claim 1 where Ar$^2$ is p-hydroxyphenyl.

5. A compound of claim 1 where X is methylene.

6. A compound of claim 1 selected from the group consisting of (R)-3-((3S,4R)-3-fluoro-4-(4-hydroxyphenyl)piperidin-1-yl)-1-(4-methylbenzyl)pyrrolidin-2-one

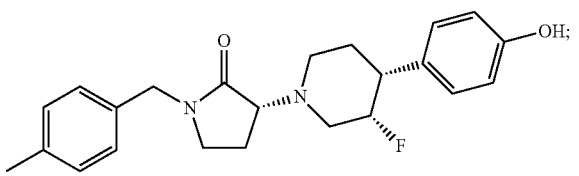 [SMILES: Cc1ccc(CN2CC[C@@H](N3CC[C@H](c4ccc(O)cc4)[C@H](F)C3)C2=O)cc1]

(R)-1-(4-(difluoromethyl)benzyl)-3-((3S,4S)-3-fluoro-4-(4-hydroxyphenyl)piperidin-1-yl)pyrrolidin-2-one

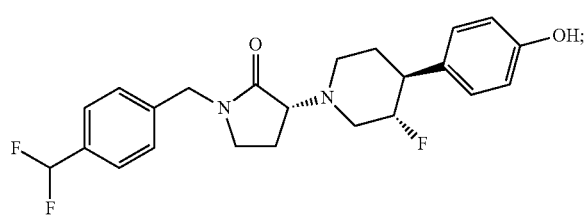 [SMILES: O=C1[C@H](N2CC[C@@H](c3ccc(O)cc3)[C@H](F)C2)CCN1Cc1ccc(C(F)F)cc1]

(R)-1-(4-chlorobenzyl)-3-(3S,4S)-3-fluoro-4-(3-fluoro-4-hydroxyphenyl)piperidin-1-yl)pyrrolidin-2-one

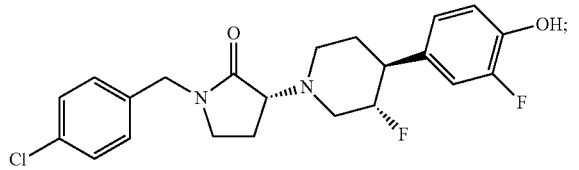 [SMILES: O=C1[C@H](N2CC[C@@H](c3ccc(O)c(F)c3)[C@H](F)C2)CCN1Cc1ccc(Cl)cc1]

(R)-1-(4-fluorobenzyl)-3-(4-(4-hydroxyphenyl)piperidin-1-yl)pyrrolidin-2-one

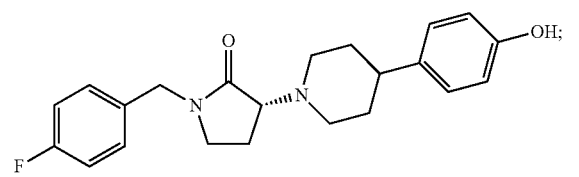 [SMILES: O=C1[C@H](N2CCC(c3ccc(O)cc3)CC2)CCN1Cc1ccc(F)cc1]

3-(3,3-difluoro-4-(4-hydroxyphenyl)piperidin-1-yl)-1-(4-methylbenzyl)pyrrolidin-2-one

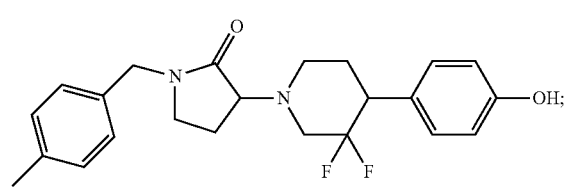 [SMILES: Cc1ccc(CN2CCC(N3CCC(c4ccc(O)cc4)C(F)(F)C3)C2=O)cc1]

(R)-3-((3S,4S)-3-fluoro-4-(4-hydroxyphenyl)piperidin-1-yl)-1-(3-fluoro-4-methylbenzyl)pyrrolidin-2-one

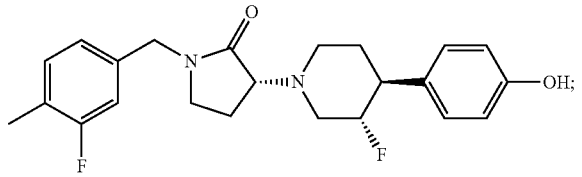 [SMILES: Cc1ccc(CN2CC[C@@H](N3CC[C@@H](c4ccc(O)cc4)[C@H](F)C3)C2=O)cc1F]

(R)-3-((3R,4R)-3-fluoro-4-(4-hydroxyphenyl)piperidin-1-yl)-1-(3-fluoro-4-methylbenzyl)pyrrolidin-2-one.

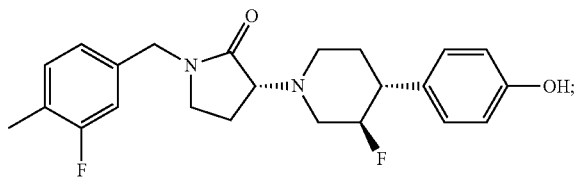 [SMILES: Cc1ccc(CN2CC[C@@H](N3CC[C@H](c4ccc(O)cc4)[C@@H](F)C3)C2=O)cc1F]

(R)-3-((3R,4R)-3-fluoro-4-(4-hydroxyphenyl)piperidin-1-yl)-1-(4-methyl)benzyl)pyrrolidin-2-one

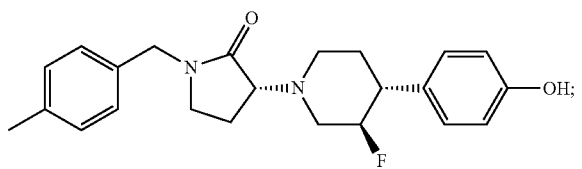 [SMILES: Cc1ccc(CN2CC[C@@H](N3CC[C@H](c4ccc(O)cc4)[C@@H](F)C3)C2=O)cc1]

(R)-3-((3S,4S)-3-fluoro-4-(3-fluoro-4-hydroxyphenyl)piperidin-1-yl)-1-(4-methylbenzyl)pyrrolidin-2-one

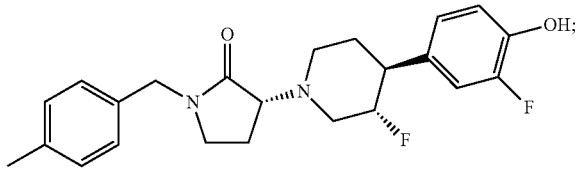 [SMILES: Cc1ccc(CN2CC[C@@H](N3CC[C@@H](c4ccc(O)c(F)c4)[C@H](F)C3)C2=O)cc1]

(R)-1-(4-(difluoromethyl)benzyl)-3-((3S,4S)-3-fluoro-4-(3-fluoro-4-hydroxyphenyl)piperidin-1-yl)pyrrolidin-2-one

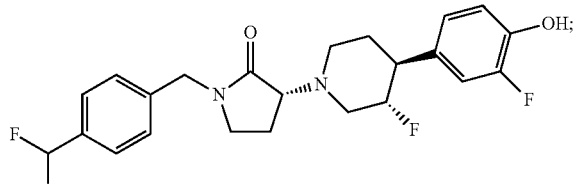

and
(R)-1-(4-fluorobenzyl)-3-((3S,4S)-3-hydroxy-4-(4-methoxyphenyl)piperidin-1-yl)pyrrolidin-2-one

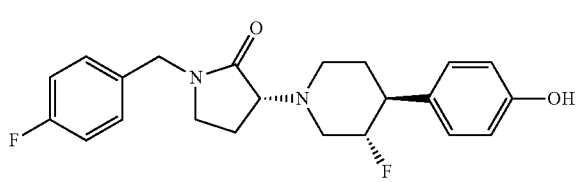

or a pharmaceutically acceptable salt thereof.

7. The compound of claim 1: (R)-3-((3S,4S)-3-fluoro-4-(4-hydroxyphenyl)piperidin-1-yl)-1-(4-methylbenzyl)pyrrolidin-2-one or a pharmaceutically acceptable salt thereof

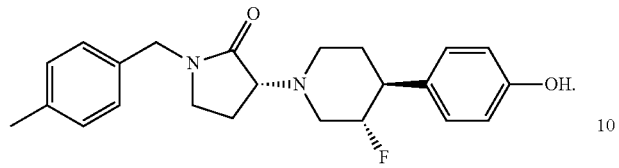

8. A pharmaceutical composition comprising a compound of claim 1 or a pharmaceutically acceptable salt thereof and a pharmaceutically acceptable carrier.

9. A method for the treatment of depression, Alzheimer's disease, neuropathic pain, or Parkinson's disease, which comprises administering to a patient a therapeutically affective amount of a compound of claim 1.

10. The method of claim 9 directed to the treatment of depression.

11. The method of claim 9 directed to the treatment of Alzheimer's disease.

12. The method of claim 9 directed to the treatment of neuropathic pain.

* * * * *